US009358003B2

(12) United States Patent
Hall et al.

(10) Patent No.: US 9,358,003 B2
(45) Date of Patent: Jun. 7, 2016

(54) ELECTROMECHANICAL SURGICAL DEVICE WITH SIGNAL RELAY ARRANGEMENT

(71) Applicant: Ethicon Endo-Surgery, Inc., Cincinnati, OH (US)

(72) Inventors: Steven G. Hall, Cincinnati, OH (US); Daniel L. Baber, Liberty Township, OH (US); Richard L. Leimbach, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 596 days.

(21) Appl. No.: 13/782,499

(22) Filed: Mar. 1, 2013

(65) Prior Publication Data
US 2014/0246474 A1 Sep. 4, 2014

(51) Int. Cl.
| G05B 15/00 | (2006.01) |
| G05B 19/00 | (2006.01) |
| A61B 17/068 | (2006.01) |
| A61B 17/072 | (2006.01) |
| A61B 18/14 | (2006.01) |
| A61B 17/00 | (2006.01) |

(52) U.S. Cl.
CPC ......... *A61B 17/068* (2013.01); *A61B 17/07207* (2013.01); *A61B 18/1445* (2013.01); *A61B 2017/00017* (2013.01); *A61B 2017/00022* (2013.01); *A61B 2017/00115* (2013.01); *A61B 2017/00221* (2013.01); *A61B 2017/00398* (2013.01); *A61B 2017/00482* (2013.01); *A61B 2017/00734* (2013.01)

(58) Field of Classification Search
USPC .............. 700/251, 250, 245, 258; 227/175.1, 227/156; 606/130
See application file for complete search history.

(56) References Cited

U.S. PATENT DOCUMENTS

| 66,052 A | 6/1867 | Smith |
| 662,587 A | 11/1900 | Blake |
| 670,748 A | 3/1901 | Weddeler |
| 951,393 A | 3/1910 | Hahn |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

International Search Report for PCT/US2014/018241, dated Aug. 7, 2014 (6 pages).

(Continued)

*Primary Examiner* — Ronnie Mancho

(57) ABSTRACT

A surgical instrument configured to relay a low-power signal from an end effector to a remote device is disclosed. The surgical instrument may comprise a handle, a shaft extending distally from the handle, and an end effector attached to the distal end of the shaft. A sensor may be disposed in the end effector. The sensor may generate a signal indicative of a condition at the end effector. A transmitter may be located in the end effector. The transmitter may transmit the signal from the sensor at a first power level. The signal may be received by a relay station located proximally to the shaft. The relay station is configured to retransmit the signal at a second power level, wherein the second power level is higher than the first power level.

20 Claims, 99 Drawing Sheets

(56) References Cited

U.S. PATENT DOCUMENTS

| | | |
|---|---|---|
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,441,096 A | 5/1948 | Happe |
| 2,526,902 A | 10/1950 | Rublee |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,959,974 A | 11/1960 | Emrick |
| 3,032,769 A | 5/1962 | Palmer |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,551,987 A | 1/1971 | Wilkinson |
| 3,568,675 A | 3/1971 | Harvey |
| 3,572,159 A | 3/1971 | Tschanz |
| 3,598,943 A | 8/1971 | Barrett |
| 3,608,549 A | 9/1971 | Merrill |
| 3,640,317 A | 2/1972 | Panfili |
| 3,643,851 A | 2/1972 | Green et al. |
| 3,661,666 A | 5/1972 | Foster et al. |
| 3,662,939 A | 5/1972 | Bryan |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,841,474 A | 10/1974 | Maier |
| 3,851,196 A | 11/1974 | Hinds |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| 3,955,581 A | 5/1976 | Spasiano et al. |
| RE28,932 E | 8/1976 | Noiles et al. |
| 3,981,051 A | 9/1976 | Brumlik |
| 4,054,108 A | 10/1977 | Gill |
| 4,060,089 A | 11/1977 | Noiles |
| 4,106,446 A | 8/1978 | Yamada et al. |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |
| 4,305,539 A | 12/1981 | Korolkov et al. |
| 4,312,685 A | 1/1982 | Riedl |
| 4,317,451 A | 3/1982 | Cerwin et al. |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,454,887 A | 6/1984 | Krüger |
| 4,467,805 A | 8/1984 | Fukuda |
| 4,473,077 A | 9/1984 | Noiles et al. |
| 4,475,679 A | 10/1984 | Fleury, Jr. |
| 4,485,816 A | 12/1984 | Krumme |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |

(56) References Cited

U.S. PATENT DOCUMENTS

| | | |
|---|---|---|
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,873,977 A | 10/1989 | Avant et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,951,860 A | 8/1990 | Peters et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A | 7/1991 | Pruitt |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |

(56) References Cited

U.S. PATENT DOCUMENTS

| | | |
|---|---|---|
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller et al. |
| 5,314,466 A | 5/1994 | Stern et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,409,498 A | 4/1995 | Braddock et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Schichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,417 A | 9/1995 | Kuhl et al. |

(56) References Cited

U.S. PATENT DOCUMENTS

| | | |
|---|---|---|
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |

(56) References Cited

U.S. PATENT DOCUMENTS

| | | |
|---|---|---|
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |

(56) References Cited

U.S. PATENT DOCUMENTS

| | | |
|---|---|---|
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,010,054 A | 1/2000 | Johnson et al. |
| 6,010,513 A | 1/2000 | Törmälä et al. |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,097 A | 5/2000 | Oi et al. |
| 6,063,098 A | 5/2000 | Houser et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |

(56) References Cited

U.S. PATENT DOCUMENTS

| | | |
|---|---|---|
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,117 B1 | 6/2001 | Blatter |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,447,518 B1 | 9/2002 | Krause et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,478,210 B2 | 11/2002 | Adams et al. |
| 6,482,200 B2 | 11/2002 | Shippert |
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |

(56) References Cited

U.S. PATENT DOCUMENTS

| | | |
|---|---|---|
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,588,643 B2 | 7/2003 | Bolduc et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,777,838 B2 | 8/2004 | Miekka et al. |
| 6,780,151 B2 | 8/2004 | Grabover et al. |
| 6,780,180 B2 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |

(56) References Cited

U.S. PATENT DOCUMENTS

| | | |
|---|---|---|
| 6,846,309 B2 | 1/2005 | Whitman et al. |
| 6,849,071 B2 | 2/2005 | Whitman et al. |
| 6,850,817 B1 | 2/2005 | Green |
| 6,858,005 B2 | 2/2005 | Ohline et al. |
| RE38,708 E | 3/2005 | Bolanos et al. |
| 6,861,142 B1 | 3/2005 | Wilkie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,899,538 B2 | 5/2005 | Matoba |
| 6,905,057 B2 | 6/2005 | Swayze et al. |
| 6,905,497 B2 | 6/2005 | Truckai et al. |
| 6,908,472 B2 | 6/2005 | Wiener et al. |
| 6,911,033 B2 | 6/2005 | de Guillebon et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,994,708 B2 | 2/2006 | Manzo |
| 6,995,729 B2 | 2/2006 | Govari et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |

(56) References Cited

U.S. PATENT DOCUMENTS

| | | |
|---|---|---|
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,202,653 B2 | 4/2007 | Pai |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,213,736 B2 | 5/2007 | Wales et al. |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,287,682 B1 | 10/2007 | Ezzat et al. |
| 7,293,685 B2 | 11/2007 | Ehrenfels et al. |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,730 B2 | 6/2008 | Uchikubo |
| 7,388,217 B2 | 6/2008 | Buschbeck et al. |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |

(56) References Cited

U.S. PATENT DOCUMENTS

| | | | |
|---|---|---|---|
| 7,448,525 | B2 | 11/2008 | Shelton, IV et al. |
| 7,451,904 | B2 | 11/2008 | Shelton, IV |
| 7,455,208 | B2 | 11/2008 | Wales et al. |
| 7,455,676 | B2 | 11/2008 | Holsten et al. |
| 7,455,682 | B2 | 11/2008 | Viola |
| 7,461,767 | B2 | 12/2008 | Viola et al. |
| 7,462,187 | B2 | 12/2008 | Johnston et al. |
| 7,464,846 | B2 | 12/2008 | Shelton, IV et al. |
| 7,464,847 | B2 | 12/2008 | Viola et al. |
| 7,464,849 | B2 | 12/2008 | Shelton, IV et al. |
| 7,467,740 | B2 | 12/2008 | Shelton, IV et al. |
| 7,467,849 | B2 | 12/2008 | Silverbrook et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,473,253 | B2 | 1/2009 | Dycus et al. |
| 7,473,263 | B2 | 1/2009 | Johnston et al. |
| 7,479,608 | B2 | 1/2009 | Smith |
| 7,481,347 | B2 | 1/2009 | Roy |
| 7,481,348 | B2 | 1/2009 | Marczyk |
| 7,481,349 | B2 | 1/2009 | Holsten et al. |
| 7,481,824 | B2 | 1/2009 | Boudreaux et al. |
| 7,485,133 | B2 | 2/2009 | Cannon et al. |
| 7,485,142 | B2 | 2/2009 | Milo |
| 7,487,899 | B2 | 2/2009 | Shelton, IV et al. |
| 7,490,749 | B2 | 2/2009 | Schall et al. |
| 7,494,039 | B2 | 2/2009 | Racenet et al. |
| 7,494,499 | B2 | 2/2009 | Nagase et al. |
| 7,494,501 | B2 | 2/2009 | Ahlberg et al. |
| 7,500,979 | B2 | 3/2009 | Hueil et al. |
| 7,501,198 | B2 | 3/2009 | Barlev et al. |
| 7,503,474 | B2 | 3/2009 | Hillstead et al. |
| 7,506,790 | B2 | 3/2009 | Shelton, IV |
| 7,506,791 | B2 | 3/2009 | Omaits et al. |
| 7,507,202 | B2 | 3/2009 | Schoellhorn |
| 7,510,107 | B2 | 3/2009 | Timm et al. |
| 7,510,566 | B2 | 3/2009 | Jacobs et al. |
| 7,513,408 | B2 | 4/2009 | Shelton, IV et al. |
| 7,517,356 | B2 | 4/2009 | Heinrich |
| 7,524,320 | B2 | 4/2009 | Tierney et al. |
| 7,530,984 | B2 | 5/2009 | Sonnenschein et al. |
| 7,530,985 | B2 | 5/2009 | Takemoto et al. |
| 7,533,906 | B2 | 5/2009 | Luettgen et al. |
| 7,534,259 | B2 | 5/2009 | Lashinski et al. |
| 7,546,939 | B2 | 6/2009 | Adams et al. |
| 7,546,940 | B2 | 6/2009 | Milliman et al. |
| 7,547,312 | B2 | 6/2009 | Bauman et al. |
| 7,549,563 | B2 | 6/2009 | Mather et al. |
| 7,549,564 | B2 | 6/2009 | Boudreaux |
| 7,549,998 | B2 | 6/2009 | Braun |
| 7,552,854 | B2 | 6/2009 | Wixey et al. |
| 7,556,185 | B2 | 7/2009 | Viola |
| 7,556,186 | B2 | 7/2009 | Milliman |
| 7,556,647 | B2 | 7/2009 | Drews et al. |
| 7,559,449 | B2 | 7/2009 | Viola |
| 7,559,450 | B2 | 7/2009 | Wales et al. |
| 7,559,452 | B2 | 7/2009 | Wales et al. |
| 7,559,937 | B2 | 7/2009 | de la Torre et al. |
| 7,563,862 | B2 | 7/2009 | Sieg et al. |
| 7,565,993 | B2 | 7/2009 | Milliman et al. |
| 7,566,300 | B2 | 7/2009 | Devierre et al. |
| 7,567,045 | B2 | 7/2009 | Fristedt |
| 7,568,603 | B2 | 8/2009 | Shelton, IV et al. |
| 7,568,604 | B2 | 8/2009 | Ehrenfels et al. |
| 7,568,619 | B2 | 8/2009 | Todd et al. |
| 7,575,144 | B2 | 8/2009 | Ortiz et al. |
| 7,588,174 | B2 | 9/2009 | Holsten et al. |
| 7,588,175 | B2 | 9/2009 | Timm et al. |
| 7,588,176 | B2 | 9/2009 | Timm et al. |
| 7,588,177 | B2 | 9/2009 | Racenet |
| 7,591,783 | B2 | 9/2009 | Boulais et al. |
| 7,597,229 | B2 | 10/2009 | Boudreaux et al. |
| 7,597,230 | B2 | 10/2009 | Racenet et al. |
| 7,600,663 | B2 | 10/2009 | Green |
| 7,604,150 | B2 | 10/2009 | Boudreaux |
| 7,604,151 | B2 | 10/2009 | Hess et al. |
| 7,607,557 | B2 | 10/2009 | Shelton, IV et al. |
| 7,611,038 | B2 | 11/2009 | Racenet et al. |
| 7,611,474 | B2 | 11/2009 | Hibner et al. |
| 7,615,003 | B2 | 11/2009 | Stefanchik et al. |
| 7,615,067 | B2 | 11/2009 | Lee et al. |
| 7,617,961 | B2 | 11/2009 | Viola |
| 7,624,902 | B2 | 12/2009 | Marczyk et al. |
| 7,624,903 | B2 | 12/2009 | Green et al. |
| 7,625,370 | B2 | 12/2009 | Hart et al. |
| 7,631,793 | B2 | 12/2009 | Rethy et al. |
| 7,631,794 | B2 | 12/2009 | Rethy et al. |
| 7,635,074 | B2 | 12/2009 | Olson et al. |
| 7,637,409 | B2 | 12/2009 | Marczyk |
| 7,637,410 | B2 | 12/2009 | Marczyk |
| 7,638,958 | B2 | 12/2009 | Philipp et al. |
| 7,641,091 | B2 | 1/2010 | Olson et al. |
| 7,641,092 | B2 | 1/2010 | Kruszynski et al. |
| 7,641,093 | B2 | 1/2010 | Doll et al. |
| 7,641,095 | B2 | 1/2010 | Viola |
| 7,644,783 | B2 | 1/2010 | Roberts et al. |
| 7,644,848 | B2 | 1/2010 | Swayze et al. |
| 7,645,230 | B2 | 1/2010 | Mikkaichi et al. |
| 7,648,519 | B2 | 1/2010 | Lee et al. |
| 7,651,017 | B2 | 1/2010 | Ortiz et al. |
| 7,651,498 | B2 | 1/2010 | Shifrin et al. |
| 7,654,431 | B2 | 2/2010 | Hueil et al. |
| 7,655,288 | B2 | 2/2010 | Bauman et al. |
| 7,656,131 | B2 | 2/2010 | Embrey et al. |
| 7,658,311 | B2 | 2/2010 | Boudreaux |
| 7,658,312 | B2 | 2/2010 | Vidal et al. |
| 7,659,219 | B2 | 2/2010 | Biran et al. |
| 7,662,161 | B2 | 2/2010 | Briganti et al. |
| 7,665,646 | B2 | 2/2010 | Prommersberger |
| 7,665,647 | B2 | 2/2010 | Shelton, IV et al. |
| 7,669,746 | B2 | 3/2010 | Shelton, IV |
| 7,669,747 | B2 | 3/2010 | Weisenburgh, II et al. |
| 7,670,334 | B2 | 3/2010 | Hueil et al. |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,674,253 | B2 | 3/2010 | Fisher et al. |
| 7,674,255 | B2 | 3/2010 | Braun |
| 7,674,263 | B2 | 3/2010 | Ryan |
| 7,674,270 | B2 | 3/2010 | Layer |
| 7,682,307 | B2 | 3/2010 | Danitz et al. |
| 7,686,201 | B2 | 3/2010 | Csiky |
| 7,686,826 | B2 | 3/2010 | Lee et al. |
| 7,688,028 | B2 | 3/2010 | Phillips et al. |
| 7,691,098 | B2 | 4/2010 | Wallace et al. |
| 7,691,106 | B2 | 4/2010 | Schenberger et al. |
| 7,694,865 | B2 | 4/2010 | Scirica |
| 7,695,485 | B2 | 4/2010 | Whitman et al. |
| 7,699,204 | B2 | 4/2010 | Viola |
| 7,699,835 | B2 | 4/2010 | Lee et al. |
| 7,699,844 | B2 | 4/2010 | Utley et al. |
| 7,699,846 | B2 | 4/2010 | Ryan |
| 7,699,856 | B2 | 4/2010 | Van Wyk et al. |
| 7,699,859 | B2 | 4/2010 | Bombard et al. |
| 7,699,860 | B2 | 4/2010 | Huitema et al. |
| 7,703,653 | B2 | 4/2010 | Shah et al. |
| 7,708,180 | B2 | 5/2010 | Murray et al. |
| 7,708,181 | B2 | 5/2010 | Cole et al. |
| 7,708,758 | B2 | 5/2010 | Lee et al. |
| 7,714,239 | B2 | 5/2010 | Smith |
| 7,717,312 | B2 | 5/2010 | Beetel |
| 7,717,313 | B2 | 5/2010 | Criscuolo et al. |
| 7,717,846 | B2 | 5/2010 | Zirps et al. |
| 7,718,180 | B2 | 5/2010 | Karp |
| 7,718,556 | B2 | 5/2010 | Matsuda et al. |
| 7,721,930 | B2 | 5/2010 | McKenna et al. |
| 7,721,931 | B2 | 5/2010 | Shelton, IV et al. |
| 7,721,933 | B2 | 5/2010 | Ehrenfels et al. |
| 7,721,934 | B2 | 5/2010 | Shelton, IV et al. |
| 7,721,936 | B2 | 5/2010 | Shelton, IV et al. |
| 7,722,527 | B2 | 5/2010 | Bouchier et al. |
| 7,722,607 | B2 | 5/2010 | Dumbauld et al. |
| 7,722,610 | B2 | 5/2010 | Viola et al. |

(56) References Cited

U.S. PATENT DOCUMENTS

| | | |
|---|---|---|
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,886 B2 | 10/2010 | Whitfield et al. |
| 7,823,592 B2 | 11/2010 | Bettuchi et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,838,789 B2 | 11/2010 | Stoffers et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,891,531 B1 | 2/2011 | Ward |
| 7,891,532 B2 | 2/2011 | Mastri et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,895 B2 | 3/2011 | Boudreaux et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,931,660 B2 | 4/2011 | Aranyi et al. |
| 7,931,695 B2 | 4/2011 | Ringeisen |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |

(56) References Cited

U.S. PATENT DOCUMENTS

| | | |
|---|---|---|
| 7,955,257 B2 | 6/2011 | Frasier et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Franischelli et al. |
| 7,963,964 B2 | 6/2011 | Santilli et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,034,363 B2 | 10/2011 | Li et al. |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,047,236 B2 | 11/2011 | Perry |
| 8,048,503 B2 | 11/2011 | Farnsworth et al. |
| 8,056,787 B2 | 11/2011 | Boudreaux et al. |
| 8,056,788 B2 | 11/2011 | Mastri et al. |
| 8,057,508 B2 | 11/2011 | Shelton, IV |
| 8,058,771 B2 | 11/2011 | Giordano et al. |
| 8,061,576 B2 | 11/2011 | Cappola |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,743 B2 | 12/2011 | Kagan et al. |
| 8,075,571 B2 | 12/2011 | Vitali et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,085,013 B2 | 12/2011 | Wei et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,100,872 B2 | 1/2012 | Patel |
| 8,102,278 B2 | 1/2012 | Deck et al. |
| 8,105,350 B2 | 1/2012 | Lee et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,766 B2 | 2/2012 | Bauman et al. |
| 8,123,767 B2 | 2/2012 | Bauman et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,136,713 B2 | 3/2012 | Hathaway et al. |
| 8,140,417 B2 | 3/2012 | Shibata |
| 8,141,762 B2 | 3/2012 | Bedi et al. |
| 8,141,763 B2 | 3/2012 | Milliman |
| 8,146,790 B2 | 4/2012 | Milliman |
| 8,147,485 B2 | 4/2012 | Wham et al. |
| 8,152,041 B2 | 4/2012 | Kostrzewski |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,170,241 B2 * | 5/2012 | Roe ............... B25J 19/023 381/122 |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,180,458 B2 | 5/2012 | Kane et al. |
| 8,181,840 B2 | 5/2012 | Milliman |
| 8,186,555 B2 | 5/2012 | Shelton, IV et al. |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,205,779 B2 | 6/2012 | Ma |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,226,715 B2 | 7/2012 | Hwang et al. |
| 8,227,946 B2 | 7/2012 | Kim |
| 8,231,040 B2 | 7/2012 | Zemlok et al. |
| 8,231,041 B2 | 7/2012 | Marczyk et al. |
| 8,231,042 B2 | 7/2012 | Hessler et al. |

(56) References Cited

U.S. PATENT DOCUMENTS

| | | |
|---|---|---|
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,281,974 B2 | 10/2012 | Hessler et al. |
| 8,286,845 B2 | 10/2012 | Perry et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,388,633 B2 | 3/2013 | Rousseau et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Oakamoto et al. |
| 8,409,174 B2 | 4/2013 | Omori |
| 8,409,222 B2 | 4/2013 | Whitfield et al. |
| 8,409,223 B2 | 4/2013 | Sorrentino et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,892 B2 | 4/2013 | Bindra et al. |
| 8,430,898 B2 | 4/2013 | Wiener et al. |
| 8,439,246 B1 | 5/2013 | Knodel et al. |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,502 B2 | 6/2013 | Zergiebel |
| 8,469,973 B2 | 6/2013 | Meade et al. |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |

(56) References Cited

U.S. PATENT DOCUMENTS

| | | |
|---|---|---|
| 8,521,273 B2 | 8/2013 | Kliman |
| 8,523,881 B2 | 9/2013 | Cabiri et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,551,076 B2 | 10/2013 | Duval et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,579,176 B2 | 11/2013 | Smith et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,662,370 B2 | 3/2014 | Takei |
| 8,663,192 B2 | 3/2014 | Hester et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,678,263 B2 | 3/2014 | Viola |
| 8,679,093 B2 | 3/2014 | Farra |
| 8,679,137 B2 | 3/2014 | Bauman et al. |
| 8,679,454 B2 | 3/2014 | Guire et al. |
| 8,684,250 B2 | 4/2014 | Bettuchi et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,211 B2 | 4/2014 | Zemlok et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,728,119 B2 | 5/2014 | Cummins |
| 8,733,613 B2 | 5/2014 | Huitema et al. |
| 8,733,614 B2 | 5/2014 | Ross et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,771,169 B2 | 7/2014 | Whitman et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,808,294 B2 | 8/2014 | Fox et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,911,426 B2 | 12/2014 | Coppeta et al. |
| 8,911,471 B2 | 12/2014 | Spivey et al. |
| 8,920,438 B2 | 12/2014 | Aranyi et al. |
| 8,925,782 B2 | 1/2015 | Shelton, IV |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,960,520 B2 | 2/2015 | McCuen |

(56) References Cited

U.S. PATENT DOCUMENTS

| | | |
|---|---|---|
| 8,960,521 B2 | 2/2015 | Kostrzewski |
| 8,967,443 B2 | 3/2015 | McCuen |
| 8,967,446 B2 | 3/2015 | Beardsley et al. |
| 8,968,337 B2 | 3/2015 | Whitfield et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,996,165 B2 * | 3/2015 | Wang ........................ B25J 5/00 348/14.02 |
| 8,998,058 B2 | 4/2015 | Moore et al. |
| 9,005,230 B2 | 4/2015 | Yates et al. |
| 9,016,542 B2 | 4/2015 | Shelton, IV et al. |
| 9,023,014 B2 | 5/2015 | Chowaniec et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,044,227 B2 | 6/2015 | Shelton, IV et al. |
| 9,044,228 B2 | 6/2015 | Woodard, Jr. et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,089,330 B2 | 7/2015 | Widenhouse et al. |
| 9,095,339 B2 | 8/2015 | Moore et al. |
| 9,096,033 B2 | 8/2015 | Holop et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,957 B2 | 9/2015 | Shelton, IV et al. |
| 9,123,286 B2 | 9/2015 | Park |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,138,225 B2 | 9/2015 | Huang et al. |
| 9,149,274 B2 | 10/2015 | Spivey et al. |
| 9,168,038 B2 | 10/2015 | Shelton, IV et al. |
| 9,186,143 B2 | 11/2015 | Timm et al. |
| 2001/0025183 A1 | 9/2001 | Shahidi |
| 2001/0044637 A1 | 11/2001 | Jacobs et al. |
| 2002/0022836 A1 | 2/2002 | Goble et al. |
| 2002/0029036 A1 | 3/2002 | Goble et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128552 A1 | 9/2002 | Nowlin et al. |
| 2002/0134811 A1 | 9/2002 | Napier et al. |
| 2002/0143340 A1 | 10/2002 | Kaneko |
| 2002/0165541 A1 | 11/2002 | Whitman |
| 2002/0193808 A1 | 12/2002 | Belef et al. |
| 2003/0023316 A1 | 1/2003 | Brown et al. |
| 2003/0078647 A1 | 4/2003 | Vallana et al. |
| 2003/0084983 A1 | 5/2003 | Rangachari et al. |
| 2003/0093103 A1 | 5/2003 | Malacowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin, III et al. |
| 2004/0108357 A1 | 6/2004 | Milliman et al. |
| 2004/0110439 A1 | 6/2004 | Chaikof et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254566 A1 | 12/2004 | Plicchi et al. |
| 2004/0254590 A1 | 12/2004 | Hoffman et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0010213 A1 | 1/2005 | Stad et al. |
| 2005/0032511 A1 | 2/2005 | Malone et al. |
| 2005/0033352 A1 | 2/2005 | Zeph et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |

(56) References Cited

U.S. PATENT DOCUMENTS

| | | |
|---|---|---|
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |
| 2005/0154258 A1 | 7/2005 | Tartaglia et al. |
| 2005/0154406 A1 | 7/2005 | Bombard et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010838 A1 | 1/2007 | Shelton, IV et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0034668 A1 | 2/2007 | Holsten et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0066981 A1 | 3/2007 | Meagher |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0093869 A1 | 4/2007 | Bloom et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135686 A1 | 6/2007 | Pruitt, Jr. et al. |
| 2007/0135803 A1 | 6/2007 | Belson |
| 2007/0155010 A1 | 7/2007 | Farnsworth et al. |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0219571 A1 | 9/2007 | Balbierz et al. |

(56) References Cited

U.S. PATENT DOCUMENTS

| | | |
|---|---|---|
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |
| 2007/0299427 A1 | 12/2007 | Yeung et al. |
| 2008/0003196 A1 | 1/2008 | Jonn et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0051833 A1 | 2/2008 | Gramuglia et al. |
| 2008/0065153 A1 | 3/2008 | Allard et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0114315 A1 | 5/2008 | Voegele et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Linvneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0200949 A1 | 8/2008 | Hiles et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0287988 A1 | 11/2008 | Smith et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2008/0315829 A1 | 12/2008 | Jones et al. |
| 2009/0001121 A1 | 1/2009 | Hess et al. |
| 2009/0001122 A1 | 1/2009 | Prommersberger et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0076506 A1 | 3/2009 | Baker |
| 2009/0078736 A1 | 3/2009 | Van Lue |
| 2009/0082789 A1 | 3/2009 | Milliman et al. |
| 2009/0088774 A1 | 4/2009 | Swarup et al. |
| 2009/0090763 A1 | 4/2009 | Zemlok et al. |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0137952 A1 | 5/2009 | Ramamurthy et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0242610 A1 | 10/2009 | Shelton, IV et al. |
| 2009/0247901 A1 | 10/2009 | Zimmer |
| 2009/0248038 A1* | 10/2009 | Blumenkranz .... A61B 19/2203 606/130 |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0270895 A1 | 10/2009 | Churchill et al. |
| 2009/0277949 A1 | 11/2009 | Viola et al. |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1 | 1/2010 | Tarinelli Racenet et al. |
| 2010/0016852 A1 | 1/2010 | Manzo et al. |
| 2010/0016888 A1 | 1/2010 | Calabrese et al. |
| 2010/0023024 A1 | 1/2010 | Zeiner et al. |
| 2010/0036370 A1 | 2/2010 | Mirel et al. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076483 A1 | 3/2010 | Imuta |
| 2010/0076489 A1 | 3/2010 | Stopek et al. |
| 2010/0087835 A1* | 4/2010 | Blumenkranz .... A61B 19/2203 606/130 |
| 2010/0087840 A1 | 4/2010 | Ebersole et al. |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |

(56) References Cited

U.S. PATENT DOCUMENTS

| | | |
|---|---|---|
| 2010/0108741 A1 | 5/2010 | Hessler et al. |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0186219 A1 | 7/2010 | Smith |
| 2010/0193566 A1 | 8/2010 | Schieb et al. |
| 2010/0198220 A1* | 8/2010 | Boudreaux ...... A61B 17/07207 606/52 |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249519 A1 | 9/2010 | Park et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0298636 A1 | 11/2010 | Casto et al. |
| 2010/0305552 A1 | 12/2010 | Shelton, IV et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0011916 A1 | 1/2011 | Levine |
| 2011/0017799 A1 | 1/2011 | Whitman et al. |
| 2011/0017801 A1 | 1/2011 | Zemlok et al. |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0046666 A1 | 2/2011 | Sorrentino et al. |
| 2011/0046667 A1 | 2/2011 | Culligan et al. |
| 2011/0060363 A1 | 3/2011 | Hess et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0118754 A1 | 5/2011 | Dachs, II et al. |
| 2011/0118778 A1 | 5/2011 | Burbank |
| 2011/0125176 A1 | 5/2011 | Yates et al. |
| 2011/0144640 A1 | 6/2011 | Heinrich et al. |
| 2011/0147433 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0174099 A1 | 7/2011 | Ross et al. |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0210156 A1 | 9/2011 | Smith et al. |
| 2011/0253765 A1 | 10/2011 | Nicholas et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0282446 A1 | 11/2011 | Schulte et al. |
| 2011/0288573 A1 | 11/2011 | Yates et al. |
| 2011/0290851 A1 | 12/2011 | Shelton, IV |
| 2011/0290856 A1 | 12/2011 | Shelton, IV et al. |
| 2011/0293690 A1 | 12/2011 | Griffin et al. |
| 2011/0295269 A1 | 12/2011 | Swensgard et al. |
| 2011/0295270 A1* | 12/2011 | Giordano ............... A61B 19/00 606/130 |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0018326 A1 | 1/2012 | Racenet et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0074200 A1 | 3/2012 | Schmid et al. |
| 2012/0080336 A1 | 4/2012 | Shelton, IV et al. |
| 2012/0080338 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080488 A1 | 4/2012 | Shelton, IV et al. |
| 2012/0080498 A1 | 4/2012 | Shelton, IV et al. |
| 2012/0089131 A1 | 4/2012 | Zemlok et al. |
| 2012/0110810 A1 | 5/2012 | Houser et al. |
| 2012/0116395 A1 | 5/2012 | Madan et al. |
| 2012/0125792 A1 | 5/2012 | Cassivi |
| 2012/0138658 A1 | 6/2012 | Ullrich et al. |
| 2012/0150192 A1 | 6/2012 | Dachs, II et al. |
| 2012/0175398 A1 | 7/2012 | Sandborn et al. |
| 2012/0187179 A1 | 7/2012 | Gleiman |
| 2012/0199632 A1 | 8/2012 | Spivey et al. |
| 2012/0209289 A1 | 8/2012 | Duque et al. |
| 2012/0223123 A1 | 9/2012 | Baxter, III et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0238823 A1 | 9/2012 | Hagerty et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0253329 A1 | 10/2012 | Zemlok et al. |
| 2012/0265176 A1 | 10/2012 | Braun |
| 2012/0271285 A1 | 10/2012 | Sholev et al. |
| 2012/0273550 A1 | 11/2012 | Scirica |
| 2012/0283707 A1 | 11/2012 | Giordano et al. |
| 2012/0283748 A1 | 11/2012 | Ortiz et al. |
| 2012/0286021 A1 | 11/2012 | Kostrzewski et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0012983 A1 | 1/2013 | Kleyman |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |

(56) References Cited

U.S. PATENT DOCUMENTS

| | | |
|---|---|---|
| 2013/0026210 A1 | 1/2013 | Shelton, IV et al. |
| 2013/0032626 A1 | 2/2013 | Smith et al. |
| 2013/0037596 A1 | 2/2013 | Bear et al. |
| 2013/0048697 A1 | 2/2013 | Shelton, IV et al. |
| 2013/0056518 A1 | 3/2013 | Swensgard |
| 2013/0060278 A1 | 3/2013 | Bozung et al. |
| 2013/0062391 A1 | 3/2013 | Boudreaux et al. |
| 2013/0075446 A1 | 3/2013 | Wang et al. |
| 2013/0075449 A1 | 3/2013 | Schmid et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0098970 A1 | 4/2013 | Racenet et al. |
| 2013/0103024 A1 | 4/2013 | Monson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0126582 A1 | 5/2013 | Shelton, IV et al. |
| 2013/0131651 A1 | 5/2013 | Strobl et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214025 A1 | 8/2013 | Zemlok et al. |
| 2013/0214030 A1 | 8/2013 | Aronhalt et al. |
| 2013/0221059 A1 | 8/2013 | Racenet et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0233908 A1 | 9/2013 | Knodel et al. |
| 2013/0248576 A1 | 9/2013 | Laurent et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |
| 2013/0277412 A1 | 10/2013 | Gresham et al. |
| 2013/0310873 A1 | 11/2013 | Stopek et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0319706 A1 | 12/2013 | Nicholas et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005679 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005702 A1 | 1/2014 | Timm et al. |
| 2014/0005703 A1 | 1/2014 | Stulen et al. |
| 2014/0005708 A1 | 1/2014 | Shelton, IV |
| 2014/0005718 A1 | 1/2014 | Shelton, IV et al. |
| 2014/0008414 A1 | 1/2014 | Shelton, IV et al. |
| 2014/0012237 A1 | 1/2014 | Pribanic et al. |
| 2014/0014705 A1 | 1/2014 | Baxter, III |
| 2014/0015782 A1 | 1/2014 | Kim et al. |
| 2014/0018832 A1 | 1/2014 | Shelton, IV |
| 2014/0042205 A1 | 2/2014 | Baxter, III et al. |
| 2014/0048582 A1 | 2/2014 | Shelton, IV et al. |
| 2014/0061279 A1 | 3/2014 | Laurent et al. |
| 2014/0061280 A1 | 3/2014 | Ingmanson et al. |
| 2014/0097227 A1 | 4/2014 | Aronhalt et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0128850 A1 | 5/2014 | Kerr et al. |
| 2014/0151431 A1 | 6/2014 | Hodgkinson et al. |
| 2014/0151433 A1 | 6/2014 | Shelton, IV et al. |
| 2014/0151434 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175155 A1 | 6/2014 | Shelton, IV et al. |
| 2014/0191014 A1 | 7/2014 | Shelton, IV |
| 2014/0191015 A1 | 7/2014 | Shelton, IV |
| 2014/0205637 A1 | 7/2014 | Widenhouse et al. |
| 2014/0207166 A1 | 7/2014 | Shelton, IV et al. |
| 2014/0224686 A1 | 8/2014 | Aronhalt et al. |
| 2014/0224857 A1 | 8/2014 | Schmid |
| 2014/0236184 A1 | 8/2014 | Leimbach et al. |
| 2014/0239036 A1 | 8/2014 | Zerkle et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |

(56) References Cited

U.S. PATENT DOCUMENTS

| | | |
|---|---|---|
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263537 A1 | 9/2014 | Leimbach et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263571 A1 | 9/2014 | Morgan et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291381 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0305995 A1 | 10/2014 | Shelton, IV et al. |
| 2014/0309665 A1 | 10/2014 | Parihar et al. |
| 2014/0309666 A1 | 10/2014 | Shelton, IV et al. |
| 2014/0326777 A1 | 11/2014 | Zingman |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0353359 A1 | 12/2014 | Hall et al. |
| 2014/0367447 A1 | 12/2014 | Woodard, Jr. et al. |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0090765 A1 | 4/2015 | Hess et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0144678 A1 | 5/2015 | Hall et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |

(56) References Cited

U.S. PATENT DOCUMENTS

| | | | |
|---|---|---|---|
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289870 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0327853 A1 | 11/2015 | Aronhalt et al. |

FOREIGN PATENT DOCUMENTS

| | | | |
|---|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101541251 A | 9/2009 |
| CN | 101675898 A | 3/2010 |
| CN | 101683280 A | 3/2010 |
| CN | 102188270 A | 9/2011 |
| CN | 101534723 B | 1/2012 |
| CN | 101507633 B | 2/2013 |
| CN | 101023879 B | 3/2013 |
| CN | 101401736 B | 6/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |

(56) References Cited

FOREIGN PATENT DOCUMENTS

| | | |
|---|---|---|
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1806103 B1 | 9/2007 |
| EP | 1837041 A1 | 9/2007 |

(56) References Cited

FOREIGN PATENT DOCUMENTS

| | | |
|---|---|---|
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000102 A2 | 12/2008 |
| EP | 2005894 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090244 B1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110084 A2 | 10/2009 |
| EP | 2111803 A2 | 10/2009 |
| EP | 1762190 B8 | 11/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 2353545 A1 | 8/2011 |
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2399538 A2 | 12/2011 |
| EP | 1785102 B1 | 1/2012 |
| EP | 2090253 B1 | 3/2012 |
| EP | 2430986 A2 | 3/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2005895 B1 | 8/2012 |
| EP | 2090248 B1 | 8/2012 |
| EP | 2481359 A1 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 B1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 1884206 B1 | 3/2013 |
| EP | 2090238 B1 | 4/2013 |
| EP | 1982657 B1 | 7/2013 |

(56) References Cited

FOREIGN PATENT DOCUMENTS

| | | |
|---|---|---|
| EP | 2614782 A2 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 1772105 B1 | 5/2014 |
| EP | 2446835 B1 | 1/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| FR | 2815842 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 93100110 A | 11/1993 |
| JP | 50-33988 U | 4/1975 |
| JP | S 58500053 A | 1/1983 |
| JP | S 58-501360 A | 8/1983 |
| JP | S 59-174920 A | 3/1984 |
| JP | 60-100955 A | 6/1985 |
| JP | 60-212152 A | 10/1985 |
| JP | 61-98249 A | 5/1986 |
| JP | S 61502036 A | 9/1986 |
| JP | S 62-170011 U | 10/1987 |
| JP | S 63-59764 A | 3/1988 |
| JP | S 63-147449 A | 6/1988 |
| JP | 63-203149 | 8/1988 |
| JP | H 02-279149 A | 11/1990 |
| JP | 3-12126 A | 1/1991 |
| JP | H 04-215747 A | 8/1992 |
| JP | H 4-131860 U | 12/1992 |
| JP | H 05-084252 A | 4/1993 |
| JP | H 05-123325 A | 5/1993 |
| JP | 5-212039 A | 8/1993 |
| JP | 6007357 A | 1/1994 |
| JP | H 6-30945 A | 2/1994 |
| JP | H 06-54857 A | 3/1994 |
| JP | H 06-26812 U | 4/1994 |
| JP | H 6-121798 A | 5/1994 |
| JP | H 6-125913 A | 5/1994 |
| JP | H 06-197901 A | 7/1994 |
| JP | H 06-237937 A | 8/1994 |
| JP | H 06-327684 A | 11/1994 |
| JP | 7-31623 A | 2/1995 |
| JP | 7051273 A | 2/1995 |
| JP | H 7-47070 A | 2/1995 |
| JP | 7-124166 A | 5/1995 |
| JP | H 7-163574 A | 6/1995 |
| JP | 07-171163 | 7/1995 |
| JP | 7-255735 A | 10/1995 |
| JP | H 7-285089 A | 10/1995 |
| JP | 8-33642 A | 2/1996 |
| JP | 8033641 | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 8-336540 A | 12/1996 |
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H 10-113352 A | 5/1998 |
| JP | H 10-118090 A | 5/1998 |
| JP | 10-512469 A | 12/1998 |
| JP | 2000-14632 | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-204801 A | 7/2002 |
| JP | 2002-528161 A | 9/2002 |
| JP | 2002-314298 A | 10/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 A | 5/2003 |
| JP | 2003-164066 | 6/2003 |
| JP | 2003-521301 A | 7/2003 |
| JP | 2003-523251 A | 8/2003 |
| JP | 2003-523254 A | 8/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344663 A | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005-505334 A | 2/2005 |
| JP | 2005505322 T | 2/2005 |
| JP | 2005-80702 A | 3/2005 |
| JP | 2005-103280 A | 4/2005 |
| JP | 2005-103281 A | 4/2005 |
| JP | 2005-511131 A | 4/2005 |
| JP | 2005-511137 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |

(56) References Cited

FOREIGN PATENT DOCUMENTS

| | | | |
|---|---|---|---|
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |
| JP | 2006-334417 A | 12/2006 |
| JP | 2006-346445 A | 12/2006 |
| JP | 2007-61628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203057 A | 8/2007 |
| JP | 2007-524435 A | 8/2007 |
| JP | 2007-229448 A | 9/2007 |
| JP | 4001860 B2 | 10/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-259860 A | 10/2008 |
| JP | 2008-264535 A | 11/2008 |
| JP | 2008-283459 A | 11/2008 |
| JP | 2009-502351 A | 1/2009 |
| JP | 2009-506799 A | 2/2009 |
| JP | 2009-507526 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-536082 A | 10/2009 |
| JP | 2009-261944 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-505524 A | 2/2010 |
| JP | 2010-069310 A | 4/2010 |
| JP | 2010-088876 A | 4/2010 |
| JP | 2010-098844 A | 4/2010 |
| JP | 4549018 B2 | 9/2010 |
| JP | 2010-540192 A | 12/2010 |
| JP | 4783373 B2 | 7/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| KR | 20110003229 A | 1/2011 |
| RU | 1814161 A1 | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |

(56) References Cited

FOREIGN PATENT DOCUMENTS

| | | |
|---|---|---|
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A2 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |

(56) References Cited

FOREIGN PATENT DOCUMENTS

| | | |
|---|---|---|
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/124748 A1 | 10/2008 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2010/028332 A2 | 3/2010 |
| WO | WO 2010/030434 A1 | 3/2010 |
| WO | WO 2010/050771 A2 | 5/2010 |
| WO | WO 2010/054404 A1 | 5/2010 |
| WO | WO 2010/063795 A1 | 6/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/143913 A2 | 10/2012 |
| WO | WO 2012/148667 A2 | 11/2012 |
| WO | WO 2012/148703 A2 | 11/2012 |
| WO | WO 2013/009699 A2 | 1/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/148762 A2 | 10/2013 |
| WO | WO 2013/167427 A1 | 11/2013 |

OTHER PUBLICATIONS

Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/ abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print. cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications:

(56) References Cited

OTHER PUBLICATIONS

Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.
U.S. Appl. No. 12/031,573, filed Feb. 14, 2008.
U.S. Appl. No. 14/498,070, filed Sep. 26, 2014.
U.S. Appl. No. 14/498,087, filed Sep. 26, 2014.
U.S. Appl. No. 14/498,105, filed Sep. 26, 2014.
U.S. Appl. No. 14/498,107, filed Sep. 26, 2014.
U.S. Appl. No. 14/498,121, filed Sep. 26, 2014.
U.S. Appl. No. 14/498,145, filed Sep. 26, 2014.
U.S. Appl. No. 14/847,804, filed Sep. 8, 2015.
U.S. Appl. No. 14/848,591, filed Sep. 9, 2015.
U.S. Appl. No. 14/850,570, filed Sep. 10, 2015.

* cited by examiner

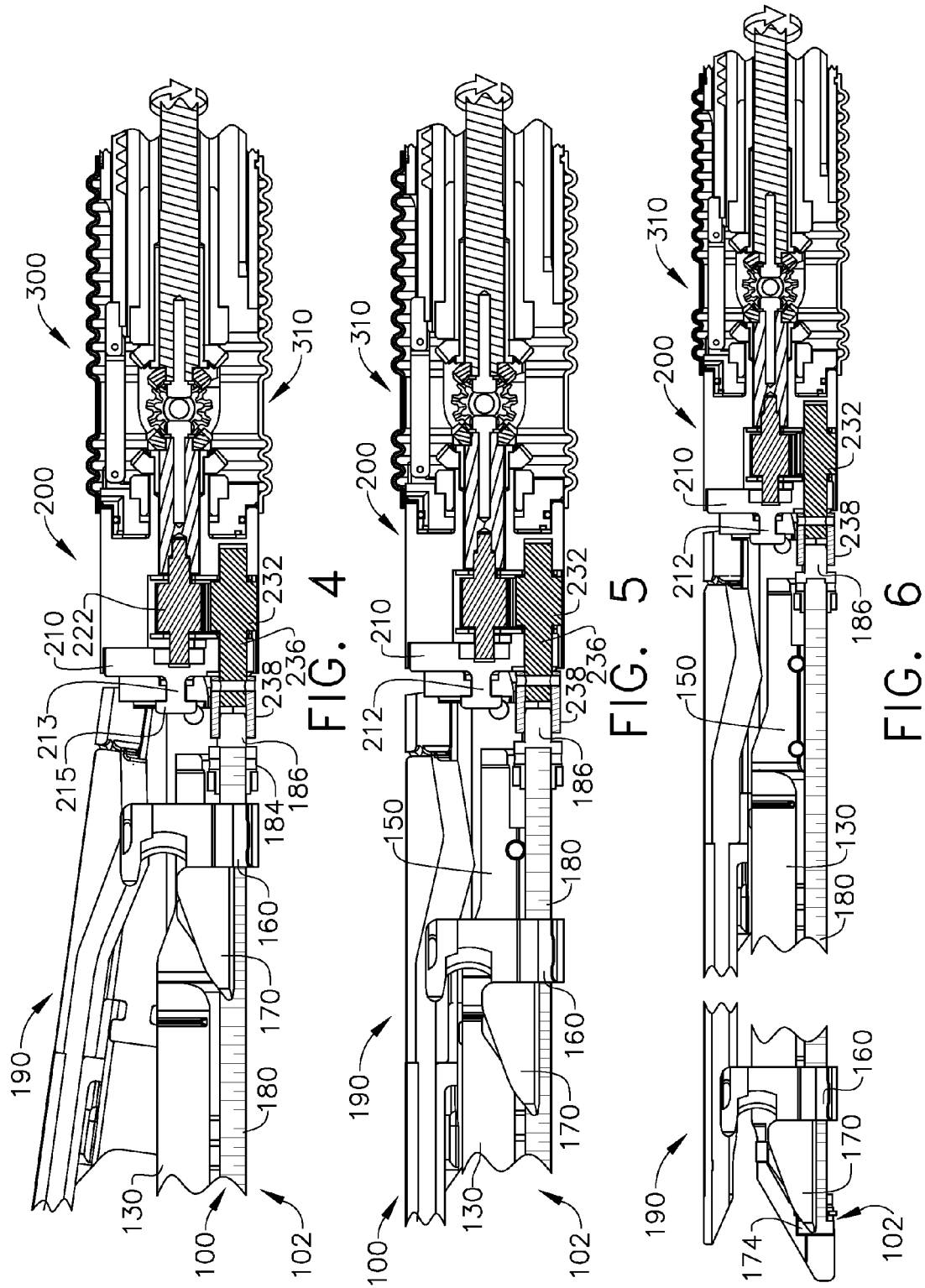

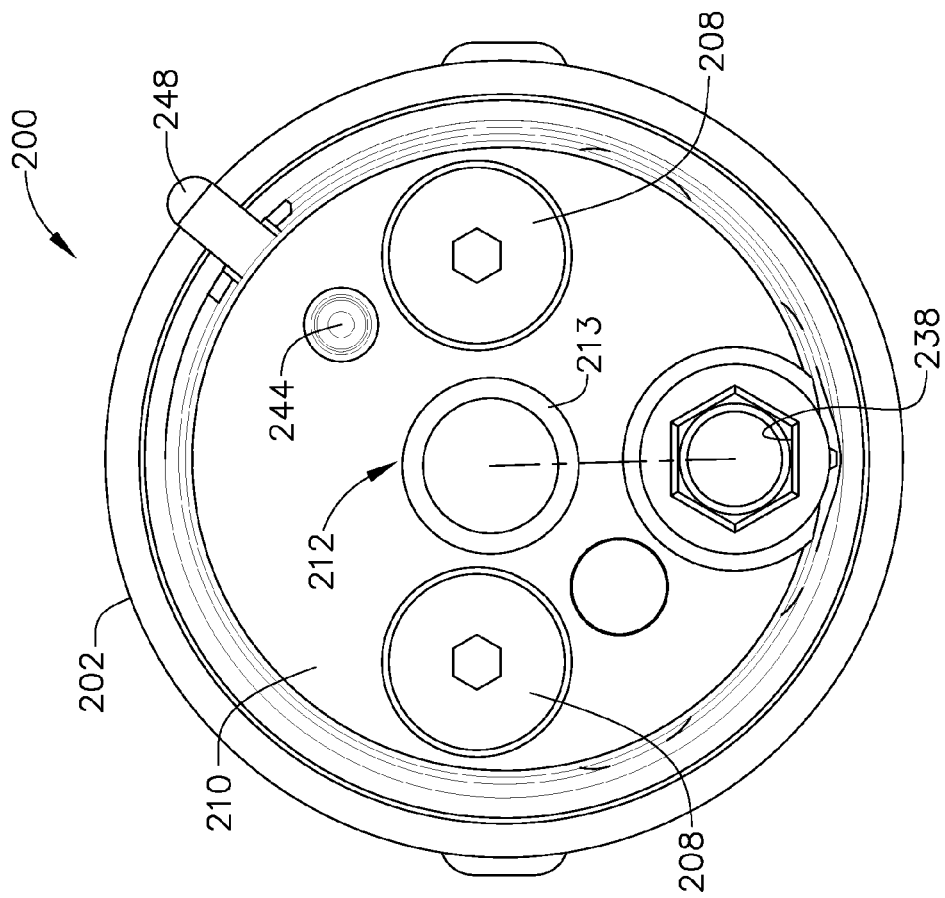
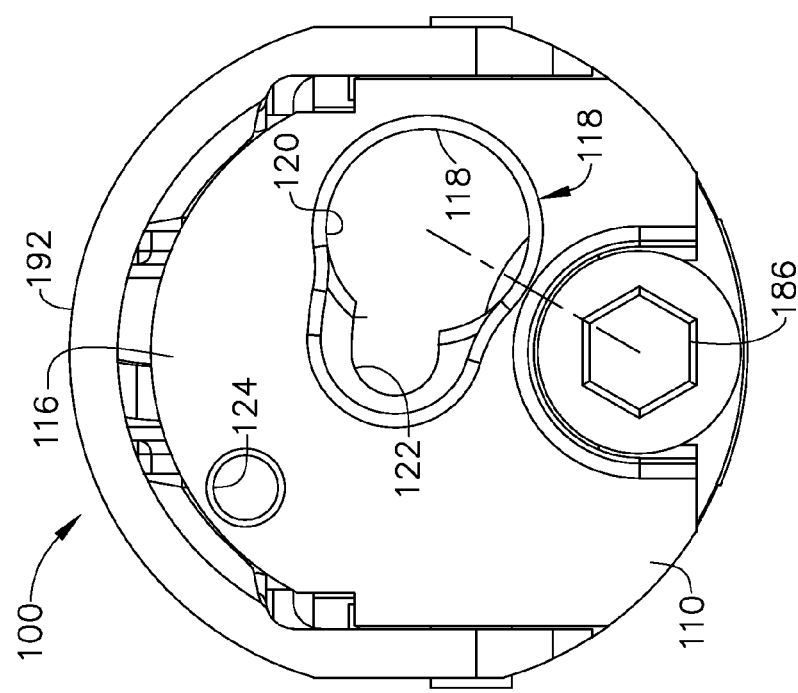
FIG. 11
FIG. 10

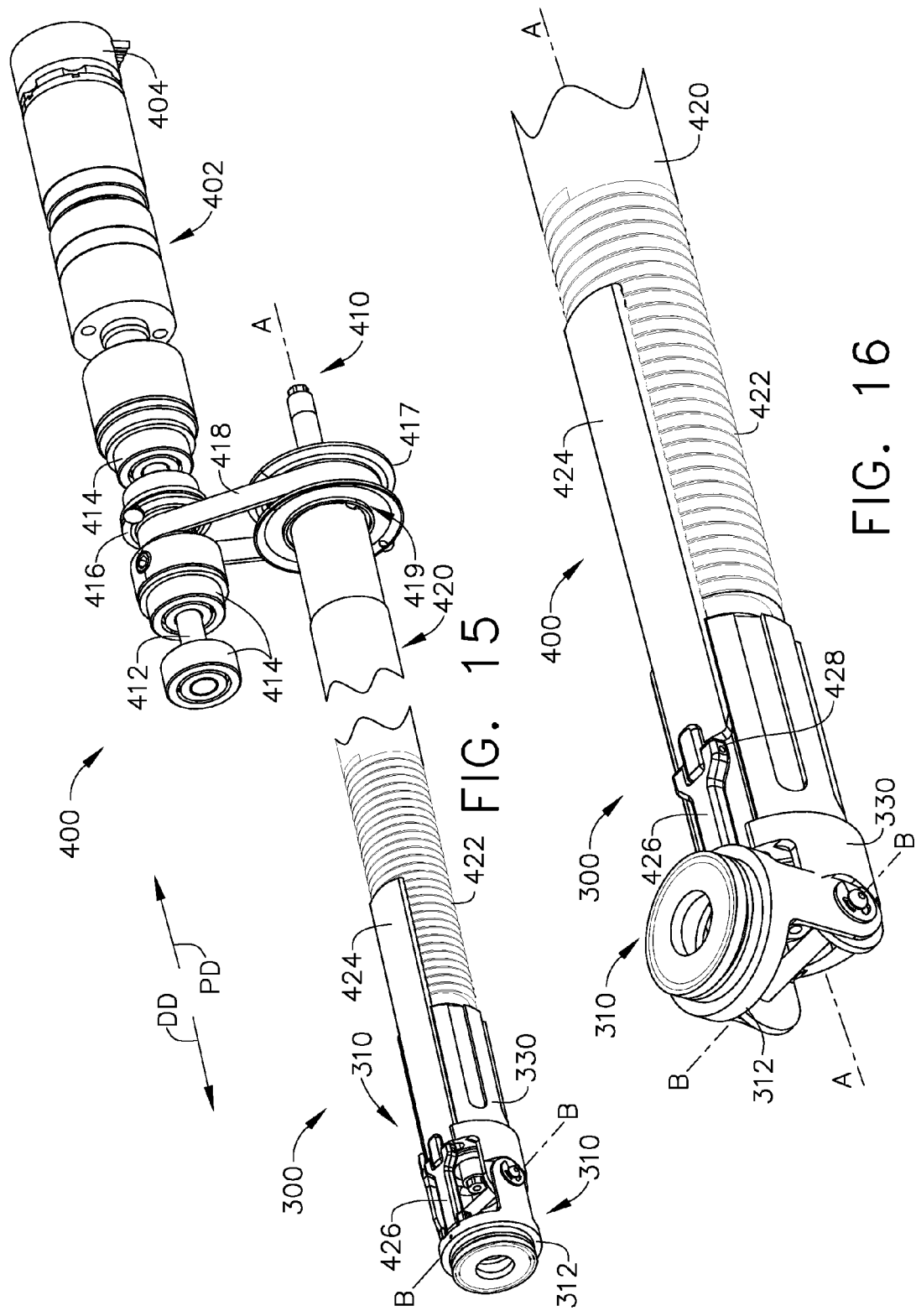

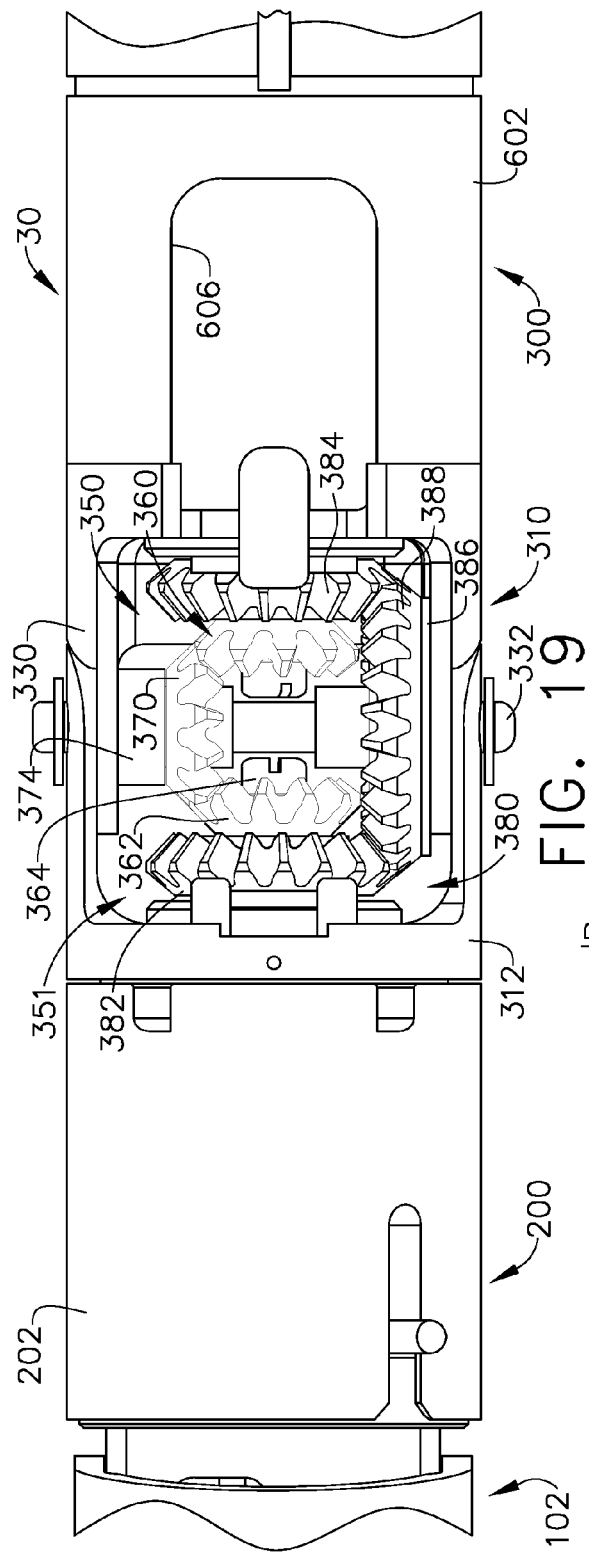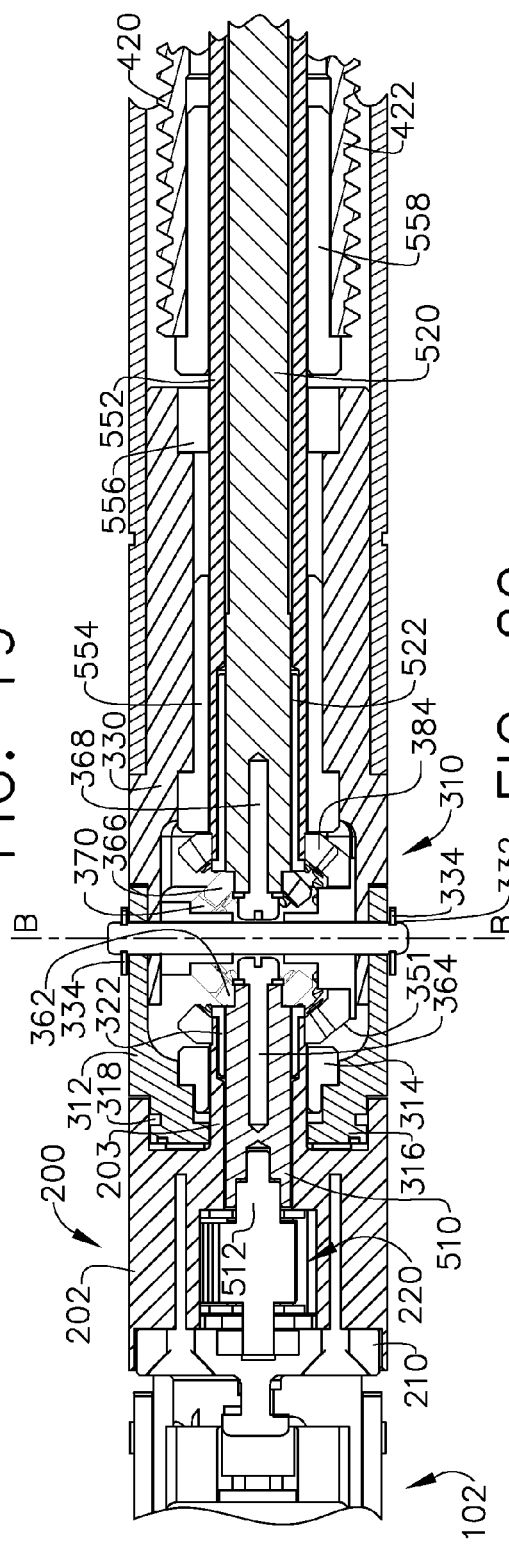

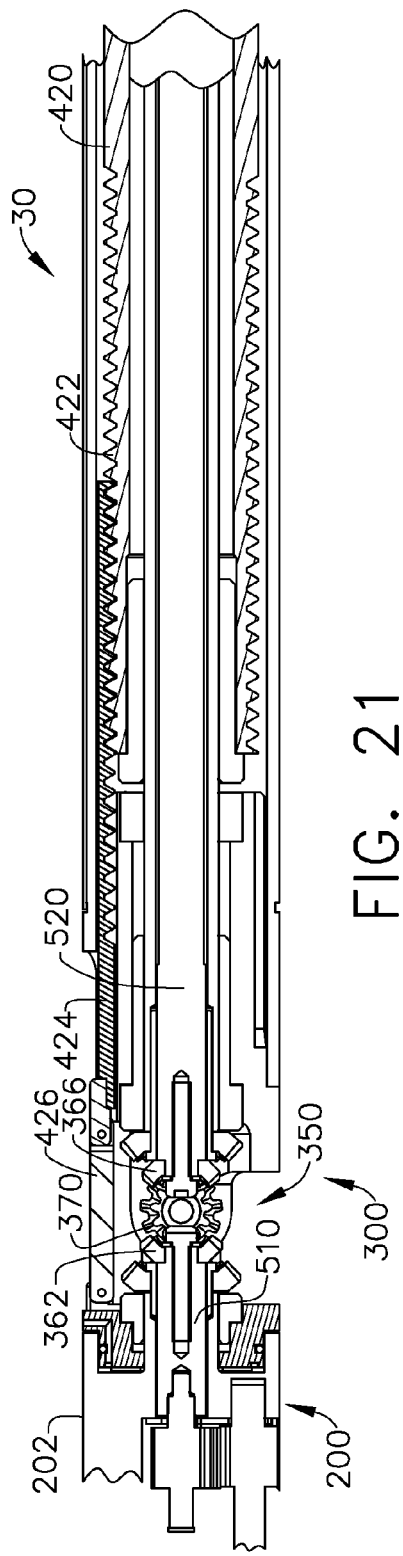
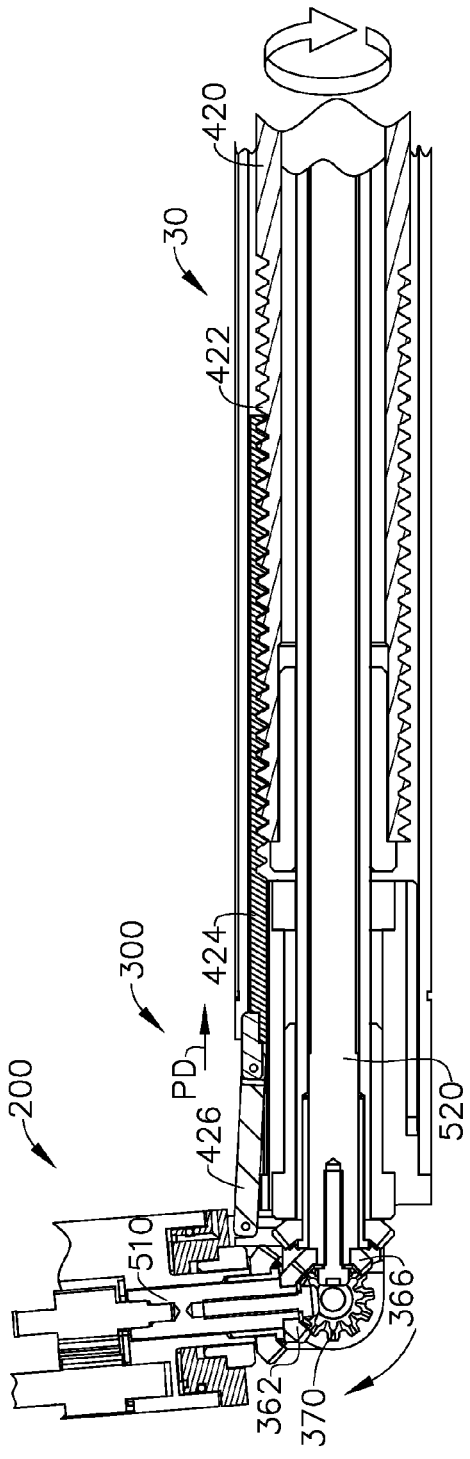

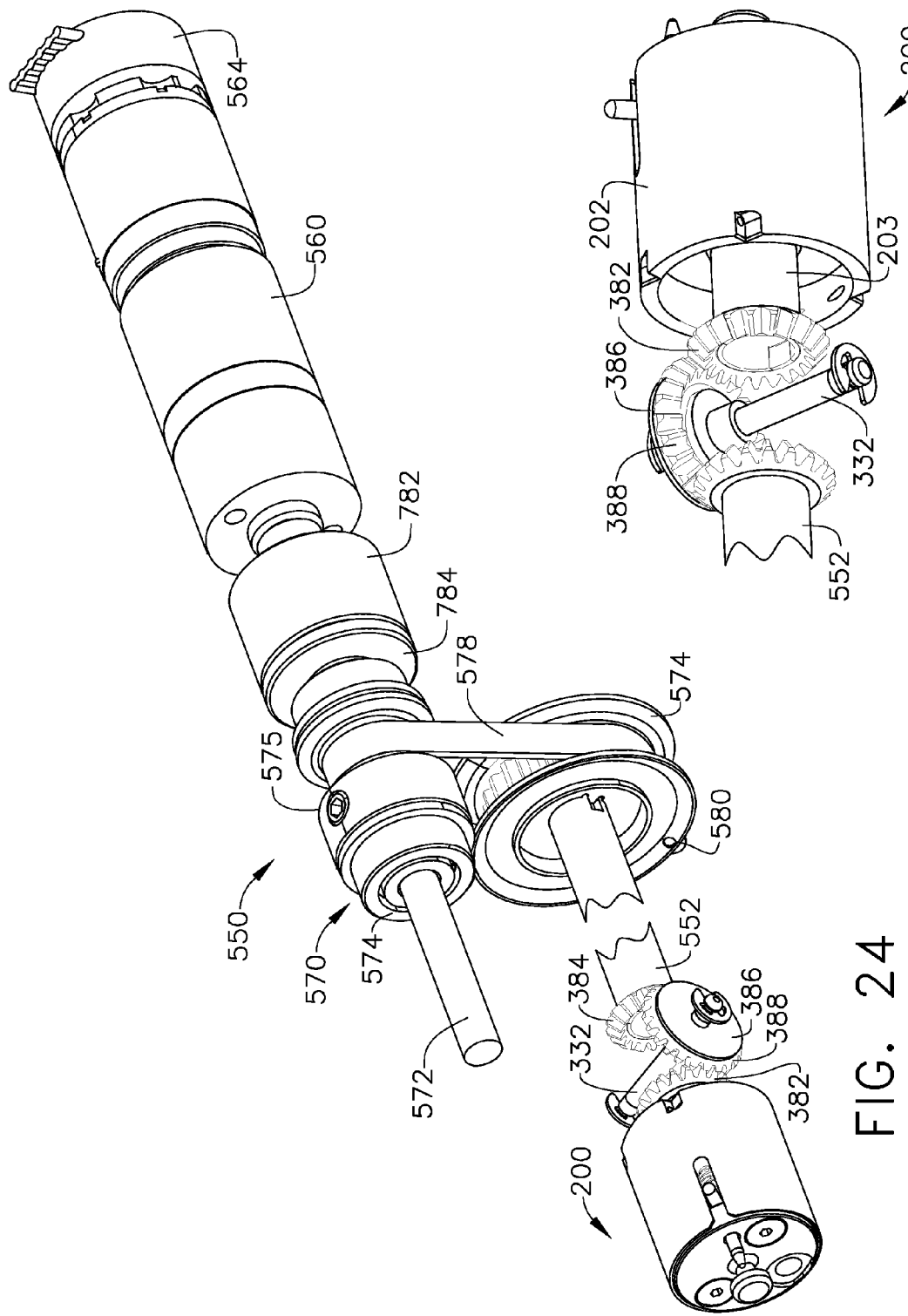

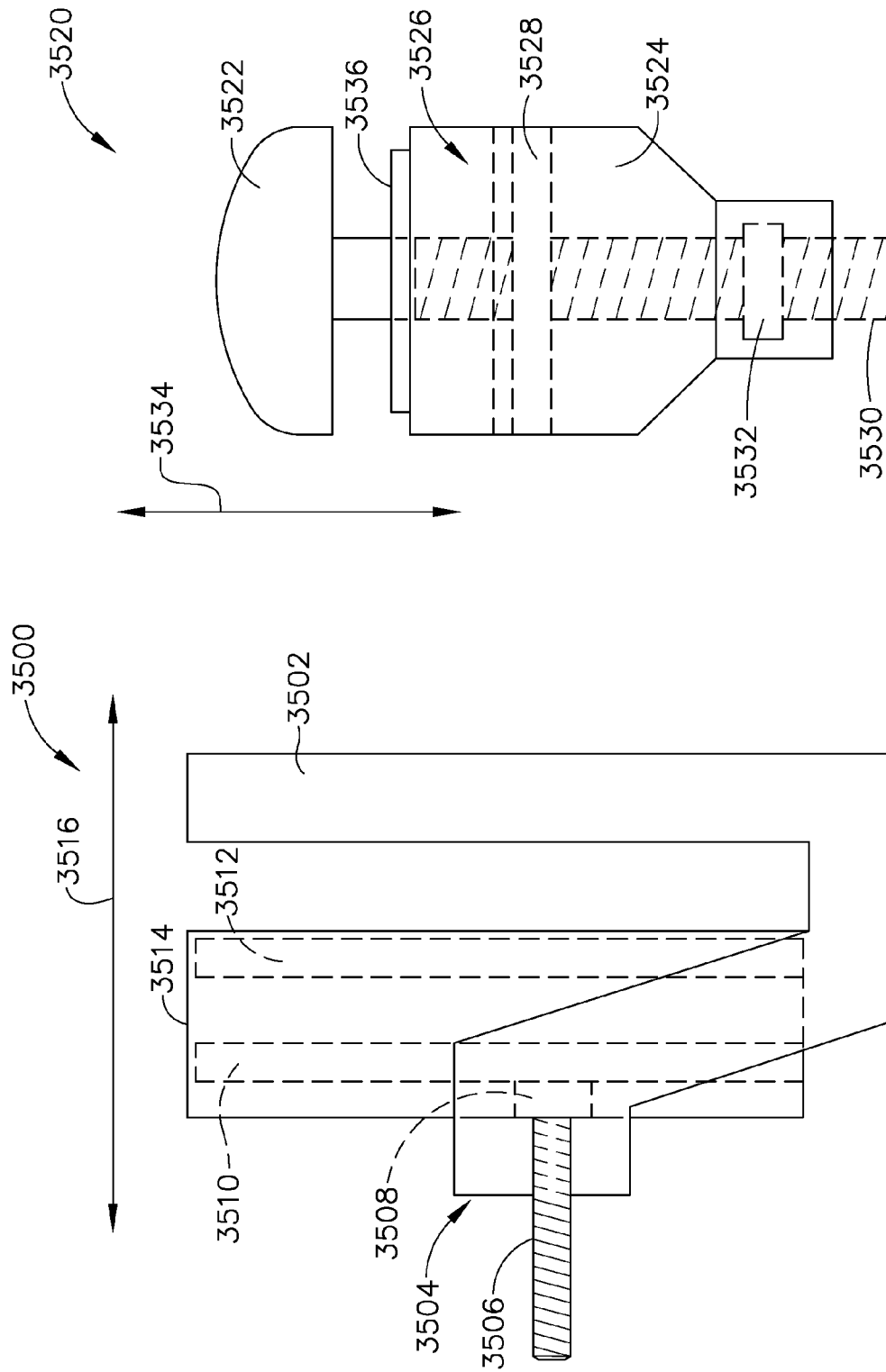

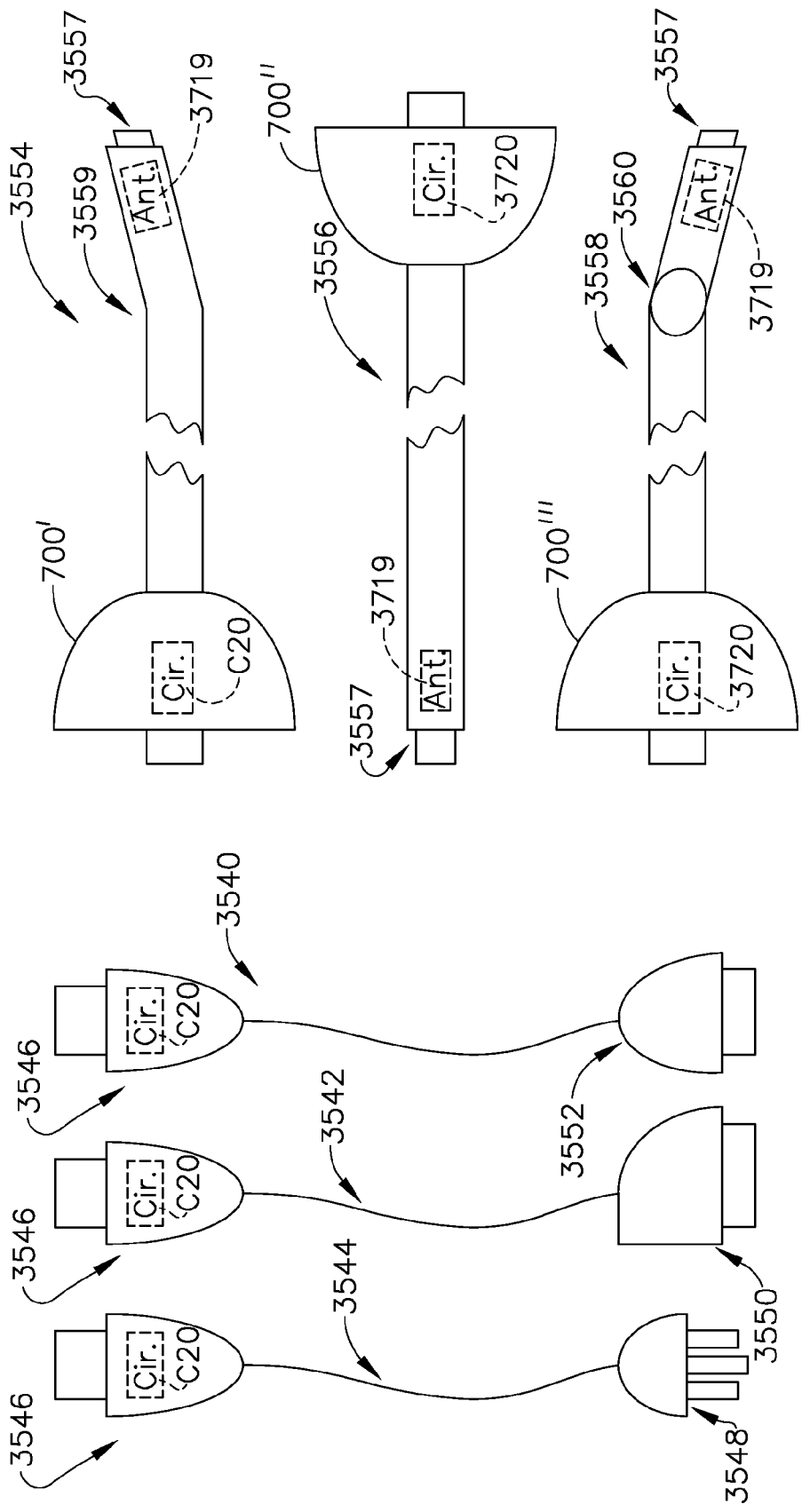

ELECTROMECHANICAL SURGICAL DEVICE WITH SIGNAL RELAY ARRANGEMENT

FIELD OF THE INVENTION

The present invention relates to surgical instruments and, in various arrangements, to surgical cutting and stapling instruments and staple cartridges therefor that are designed to cut and staple tissue.

BACKGROUND

Surgical staplers are often used to deploy staples into soft tissue to reduce or eliminate bleeding from the soft tissue, especially as the tissue is being transected, for example. Surgical staplers, such as an endocutter, for example, can comprise an end effector which can be moved, or articulated, with respect to an elongate shaft assembly. End effectors are often configured to secure soft tissue between first and second jaw members where the first jaw member often includes a staple cartridge which is configured to removably store staples therein and the second jaw member often includes an anvil. Such surgical staplers can include a closing system for pivoting the anvil relative to the staple cartridge.

Surgical staplers, as outlined above, can be configured to pivot the anvil of the end effector relative to the staple cartridge in order to capture soft tissue therebetween. In various circumstances, the anvil can be configured to apply a clamping force to the soft tissue in order to hold the soft tissue tightly between the anvil and the staple cartridge. If a surgeon is unsatisfied with the position of the end effector, however, the surgeon must typically activate a release mechanism on the surgical stapler to pivot the anvil into an open position and then reposition the end effector. Thereafter, staples are typically deployed from the staple cartridge by a driver which traverses a channel in the staple cartridge and causes the staples to be deformed against the anvil and secure layers of the soft tissue together. Often, as known in the art, the staples are deployed in several staple lines, or rows, in order to more reliably secure the layers of tissue together. The end effector may also include a cutting member, such as a knife, for example, which is advanced between two rows of the staples to resect the soft tissue after the layers of the soft tissue have been stapled together.

Such surgical staplers and effectors may be sized and configured to be inserted into a body cavity through a trocar or other access opening. The end effector is typically coupled to an elongate shaft that is sized to pass through the trocar or opening. The elongate shaft assembly is often operably coupled to a handle that supports control systems and/or triggers for controlling the operation of the end effector. To facilitate proper location and orientation of the end effector within the body, many surgical instruments are configured to facilitate articulation of the end effector relative to a portion of the elongate shaft.

The foregoing discussion is intended only to illustrate various aspects of the related art in the field of the invention at the time, and should not be taken as a disavowal of claim scope.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 4 is a partial cross-sectional view of a portion of the end effector and the elongate shaft assembly of the surgical instrument of FIGS. 1 and 2 with the anvil assembly in an open position;

FIG. 5 is another partial cross-sectional view of the end effector and elongate shaft assembly of FIG. 4 with the anvil assembly in a closed position prior to firing;

FIG. 6 is another partial cross-sectional view of the end effector and elongate shaft assembly of FIGS. 4 and 5 after the tissue cutting member has been advanced to a distal-most position within the end effector;

FIG. 10 is an elevational view of the proximal end of the end effector of FIG. 9;

FIG. 11 is an elevational view of the distal end of the coupler assembly of FIG. 9;

FIG. 15 is a perspective view of an articulation control arrangement of the present invention;

FIG. 16 is a perspective view of a portion of an articulation shaft segment arrangement;

FIG. 19 is a top view of the articulation joint arrangement of FIGS. 17 and 18;

FIG. 20 is a cross-sectional view of the components illustrated in FIG. 19;

FIG. 21 is another cross-sectional view of the articulation joint of FIGS. 19 and 20;

FIG. 22 is another cross-sectional view of the articulation joint of FIG. 21 in an articulated configuration;

FIG. 24 is a perspective view of an end effector rotation system arrangement of the present invention;

FIG. 25 is a perspective view of a portion of an articulation joint and coupler assembly of the present invention;

FIG. 78 illustrates one form of a linear staple end effector that may be used with the surgical instrument;

FIG. 79 illustrates one form of a circular staple end effector that may be used with the surgical instrument;

FIG. 80 illustrates several example power cords for use with the surgical instrument;

FIG. 81 illustrates several example shafts that can be used with the surgical instrument;

DETAILED DESCRIPTION

Figure 1:
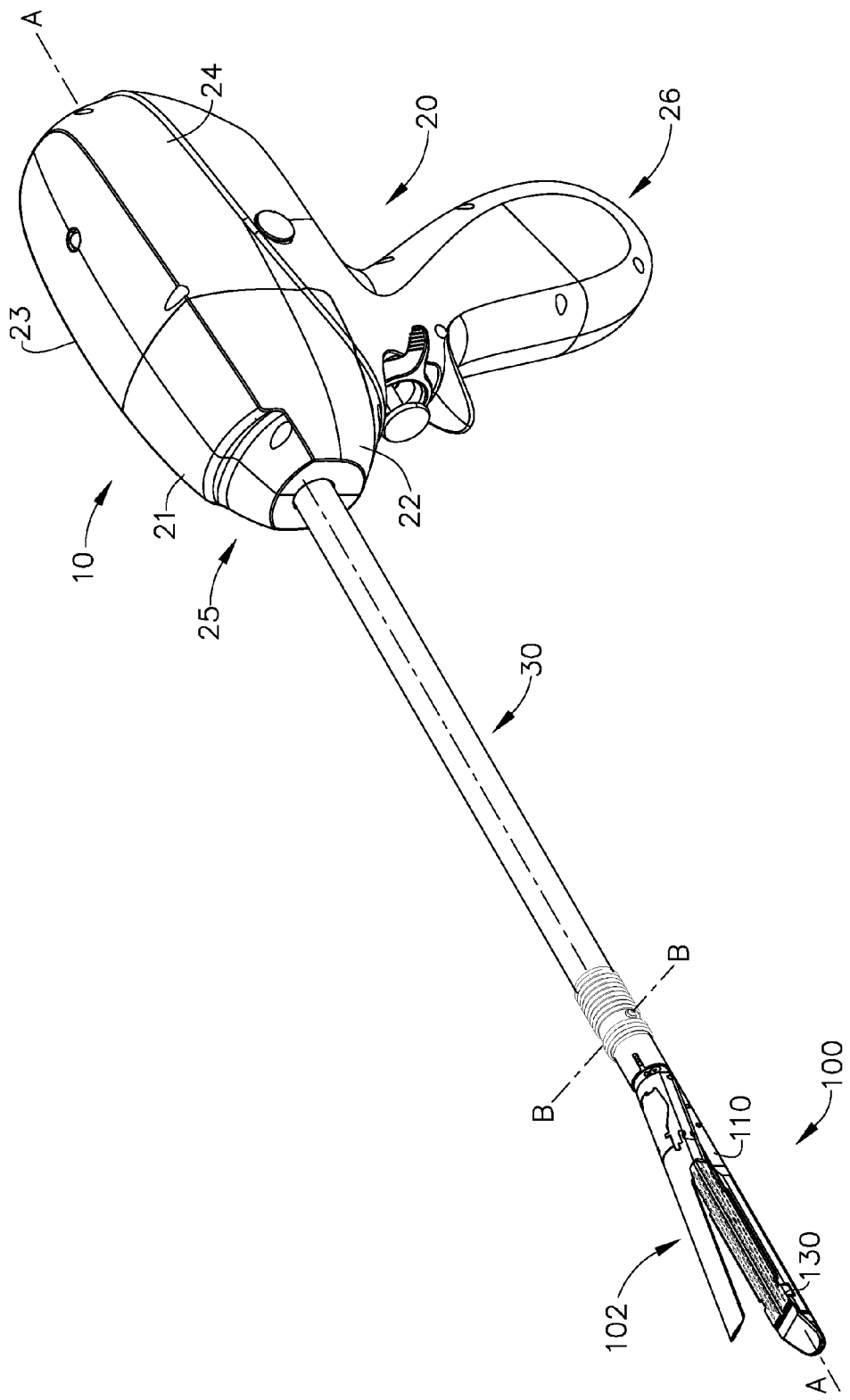
FIG. 1 is a perspective view of a surgical stapling instrument of one form of the present invention.

Applicant of the present application also owns the following patent applications that were filed on Mar. 1, 2013 and which are each herein incorporated by reference in their respective entireties:

U.S. patent application Ser. No. 13/782,375, entitled "Rotary Powered Surgical Instruments Wth Multiple Degrees of Freedom", now U.S. Patent Application Publication No. 2014/0246473;

U.S. patent application Ser. No. 13/782,323, entitled "Rotary Powered Articulation Joints For Surgical Instruments", now U.S. Patent Application Publication No. 2014/0246472;

U.S. patent application Ser. No. 13/782,295, entitled "Articulatable Surgical Instruments With Conductive Pathways For Signal Communication", now U.S. Patent Application Publication No. 2014/0246471;

U.S. patent application Ser. No. 13/782,338, entitled "Thumbwheel Switch Arrangements For Surgical Instruments", now U.S. Patent Application Publication No. 2014/0249557;

U.S. patent application Ser. No. 13/782,358, entitled "Joystick Switch Assemblies For Surgical Instruments", now U.S. Patent Application Publication No. 2014/0246477;

U.S. patent application Ser. No. 13/782,536, entitled "Electromechanical Soft Stops For Surgical Instruments", now U.S. Patent Application Publication No. 2014/0246476;

U.S. patent application Ser. No. 13/782,481, entitled "Sensor Straightened End Effector During removal Through Trocar", now U.S. Patent Application Publication No. 2014/0246479;

U.S. patent application Ser. No. 13/782,460, entitled "Multiple Processor Motor Control For Modular Surgical Device", now U.S. Patent Application Publication No. 2014/0246478; and U.S. patent application Ser. No. 13/782,518, entitled "Control Methods for Surgical Instruments with Removable Implement Portions", now U.S. Patent Application Publication No. 2014/0246475.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Figure 2:
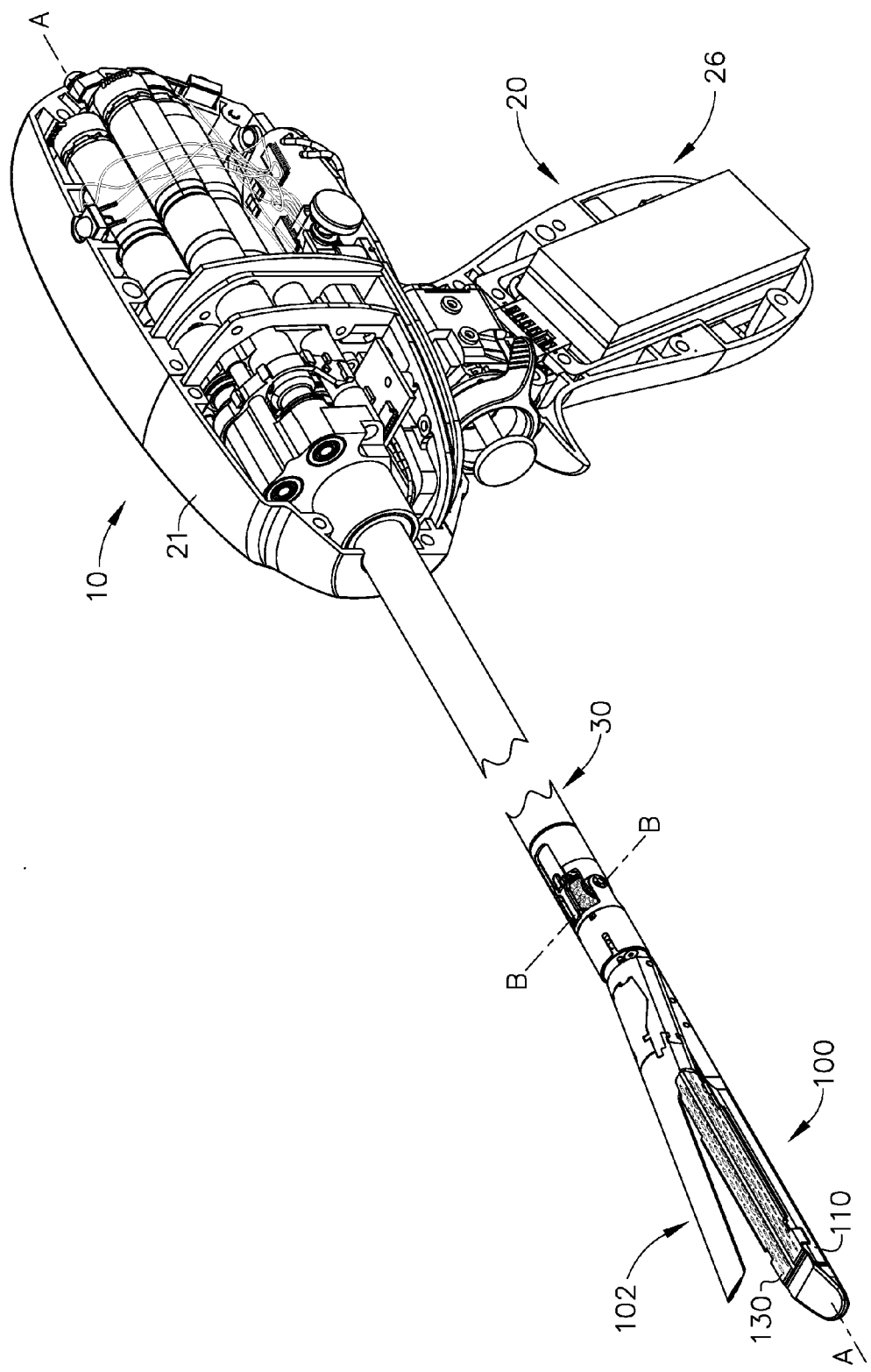
FIG. 2 is another perspective view of the surgical instrument of FIG. 1 with a portion of the handle housing removed.
Figure 3:
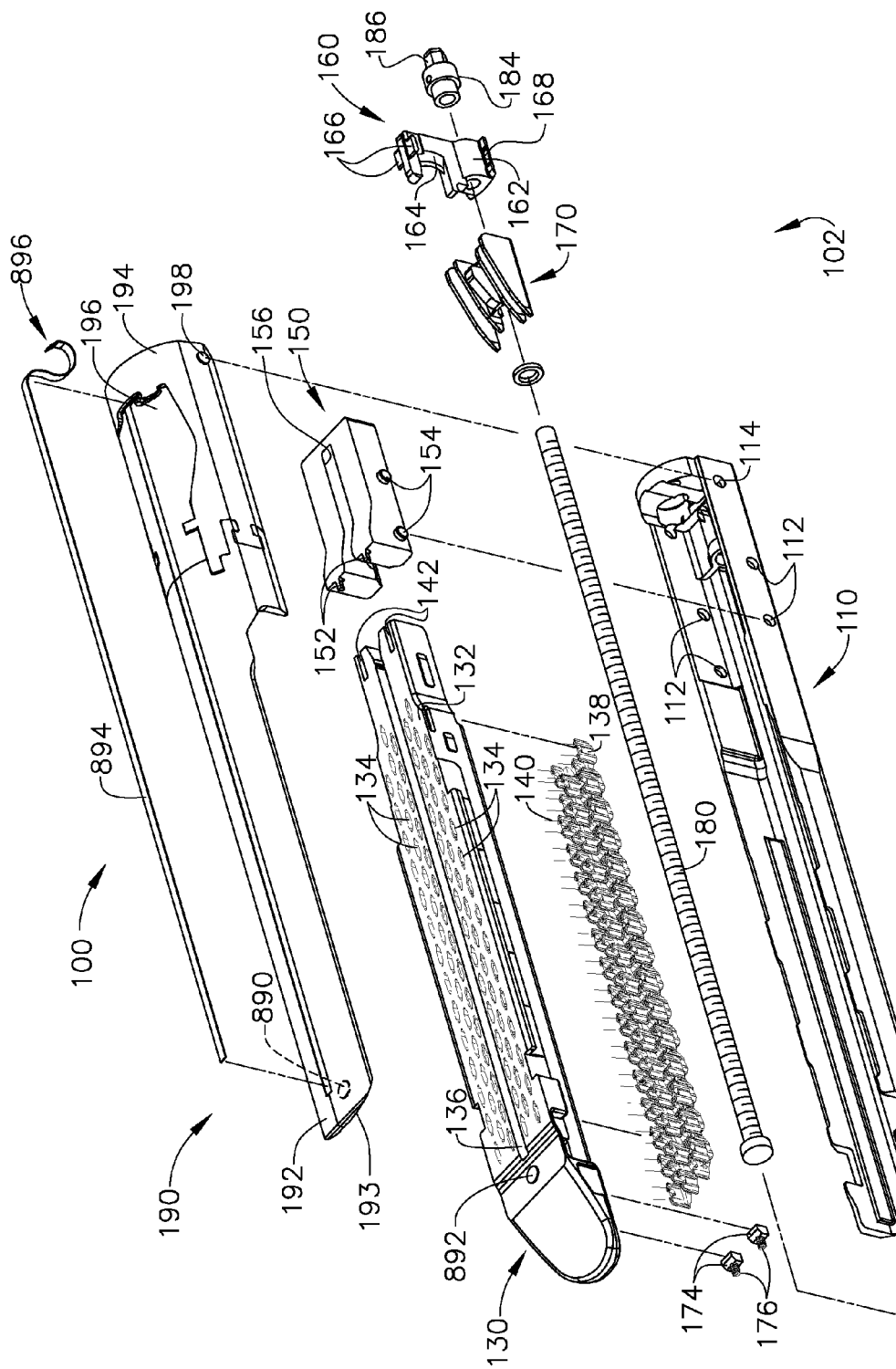
FIG. 3 is an exploded assembly view of one effector arrangement of the present invention
Figure 7:
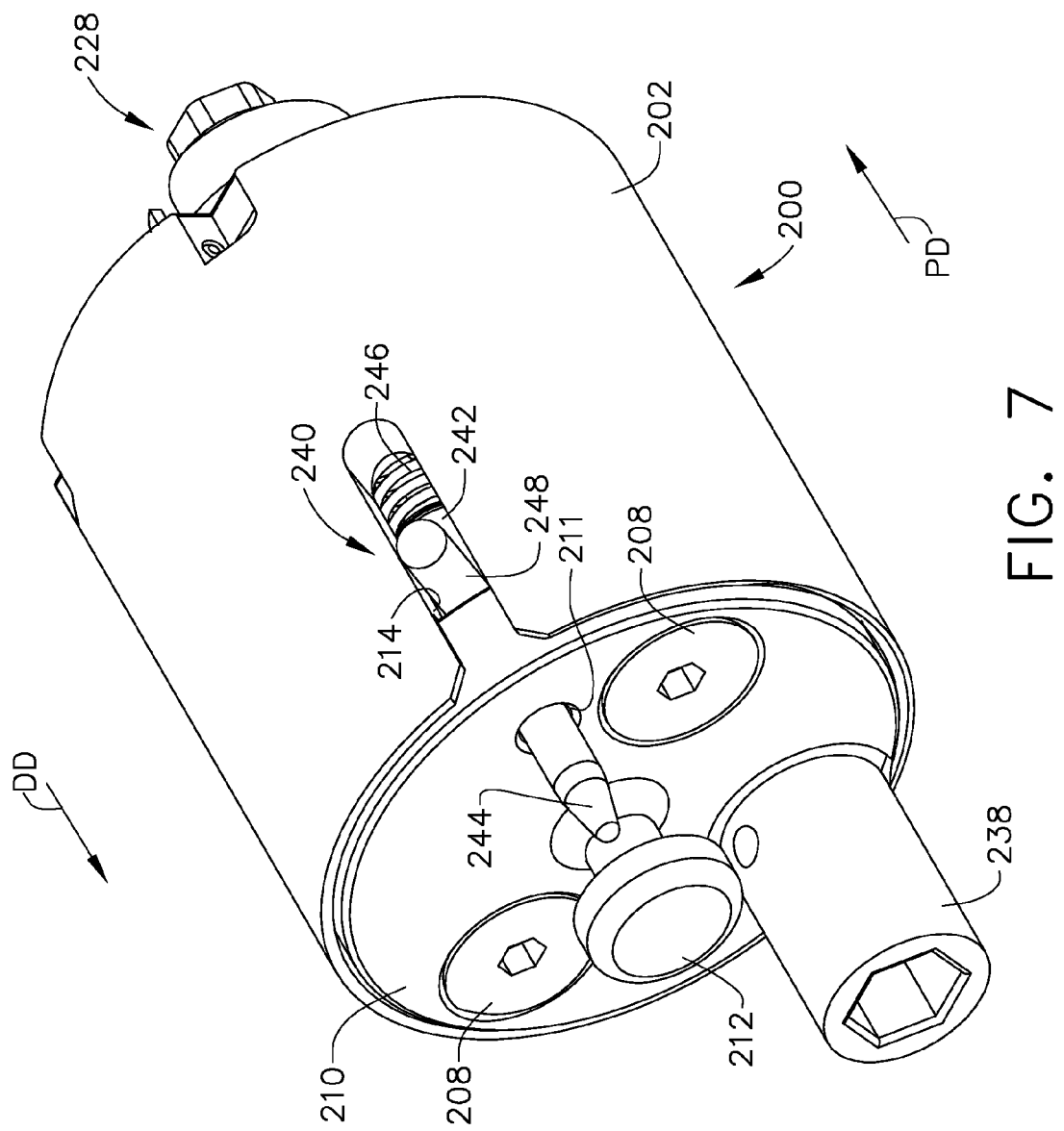
FIG. 7 is a perspective view of a coupler assembly arrangement of the present invention.

Turning to the Drawings wherein like numerals denote like components throughout the several views, FIGS. 1-3 depict a surgical instrument 10 that is capable of applying rotary actuation motions to an implement portion 100 operably coupled thereto. As will be discussed in further detail below, the instrument 10 may be effectively employed with a variety of different implements that may be interchangeably coupled to the instrument 10. The arrangement of FIGS. 1 and 2, for example, is shown coupled to an end effector 102 that is configured to cut and staple tissue. However, other implement arrangements may also be operated by the instrument 10.

End Effector

The end effector 102 depicted in FIGS. 1-6 includes an elongate channel member 110 that may be configured to operably and removably support a staple cartridge 130. The staple cartridge 130 may include an upper surface or cartridge deck 132 that includes a plurality of staple pockets 134 that are arranged in lines in a staggered fashion on each side of an elongate slot 136. See FIG. 3. A plurality of surgical staples 140 are supported on corresponding staple drivers 138 that are operably supported within the staple pockets 134. As can also be seen in FIG. 3, in one form, the end effector 102 includes an end base 150 that is configured to be coupled to a proximal end of the staple cartridge 130 and seated within a proximal end of the elongate channel 110. For example, the end base 150 may be formed with distally-extending latch tabs 152 that are configured to be received in corresponding latch slots 142 in the cartridge deck 132. In addition, the end base 150 may be provided with laterally-extending attachment lugs 154 for attaching the end base 150 to the elongate channel 110. For example, the attachment lugs 154 may be configured to be received in corresponding attachment holes 112 in the elongate channel 110.

In one form, the end base 150 includes a centrally disposed slot 156 that is configured to support a tissue cutting member 160 and sled 170. The tissue cutting member 160 may include a body portion 162 that has a tissue cutting portion 164 thereon or otherwise attached thereto. The body portion 162 may be threadably journaled on an end effector drive screw 180 that is rotatably mounted within the elongate channel 110. The sled 170 is supported for axial travel relative to the end effector drive screw 180 and may be configured to interface with the body portion 162 of the tissue cutting member 160. As the tissue cutting member 160 is driven distally, the sled 170 is driven distally by the tissue cutting member 160. As the sled 170 is driven distally, the wedges 172 formed thereon serve to advance the drivers 138 upward within the staple cartridge 130.

The end effector 102 may further include an anvil assembly 190 that is supported for selective movement relative to the staple cartridge 130. In at least one form, the anvil assembly 190 may comprise a first anvil portion 192 that is coupled to a rear anvil portion 194 and a top anvil portion 196. The rear anvil portion 194 may have a pair of laterally protruding trunnions 198 that are configured to be received in corresponding trunnions holes or cavities 114 in the elongate channel 110 to facilitate movable or pivotal travel of the anvil assembly 190 relative to the elongate channel 110 and the staple cartridge 130 supported therein.

The tissue cutting member 160 may be provided with a pair of laterally-protruding actuator tabs 166 that are configured to be slidably received within slots 199 in the anvil assembly 190. In addition, the tissue cutting member 160 may further have a foot 168 that is sized to engage a bottom portion of the elongate channel 110 such that, as the tissue cutting member 160 is driven distally, the tabs 166 and foot 168 cause the anvil assembly 190 to move to a closed position. The tabs 166 and foot 168 may serve to space the anvil assembly 190 relative to the staple cartridge 130 at a desired spacing as the tissue is cut and stapled. The first anvil portion 192 may have a staple forming underside 193 thereon to form the surgical staples 140 as they are driven into contact therewith. FIG. 4 illustrates the position of the anvil assembly 190 and the cutting member 160 when the anvil assembly 190 is in an open position. FIG. 5 illustrates the position of the anvil assembly 190 and the cutting member 160 after the anvil assembly 190 has been closed, but before the tissue cutting member 160 has been advanced distally or "fired". FIG. 6 illustrates the position of the tissue cutting member 160 after it has been advanced to its distal-most position within the staple cartridge 130.

The end effector drive screw 180 may be rotatably supported within the elongate channel 110. In one form, for example, the end effector drive screw 180 may have a proximal end 182 that is coupled to a drive shaft attachment member 184 that is configured to interface with a coupler assembly 200. The drive shaft attachment member 184 may be configured to be attached to the proximal end 182 of the end effector drive screw 180. For example, the drive shaft attachment member 184 may have a hexagonally-shaped protrusion 186 extending therefrom that is adapted to be non-rotatably received in a correspond hexagonal socket that comprises a portion of a firing system generally designated as 500. Rotation of the end effector drive screw 180 in a first direction causes the tissue cutting member 160 to move in the distal direction. In various forms, the staple cartridge 130 may be fitted with a pair of bumpers 174 that that serve to cushion the sled 170 as it reaches its distal-most position within the elongate channel 110. The bumpers 174 may each have a spring 176 to provide the bumper with a desired amount of cushion.

End Effector Coupler Assembly

Various forms of implements 100 may be operably coupled to the surgical instrument 10 by means of a coupler assembly 200. One form of coupler assembly 200 is shown in FIGS. 7-14. The coupler assembly 200 may include a coupler housing segment 202 that is configured to operably support a drive gear assembly collectively designated as 220. In at least one form, the drive gear assembly 220 includes an input gear 222, a transfer gear 228, and an output gear 232. See FIG. 8. The input gear 222 is mounted to or formed on an input shaft 224 that is rotatably supported by first and second bulkhead members 204, 206. The input shaft 224 has a proximal end 226 that is configured to mate with a distal firing shaft segment 510 that comprises a portion of a unique and novel firing system 500 which will be described in further detail below. For example, the proximal end 226 may be configured with a hexagonal cross-sectional shape for non-rotatable insertion into a hexagonal-shaped socket 512 formed in a distal end of a distal firing shaft segment 510. The transfer gear 228 may be mounted to or formed on a transfer shaft 230 that is rotatably supported by the baffle members 204, 206. The output gear 232 may be mounted to or formed on an output drive shaft 234 that is rotatably supported by the baffle members 204, 206. For assembly purposes, the distal end 236 of the output drive shaft 234 may be configured to be non-rotatably attached to an output socket 238 that protrudes distally out through a distal end cap 210. In one arrangement, the distal end cap 210 may be attached to the coupler housing 202 by fasteners 208 or any other suitable fastener arrangements. The output socket 238 may be pinned to the distal end 236 of the output drive shaft 234. The output socket 238 may be configured to non-rotatably mate with the drive shaft attachment member 184. For example, the output socket 238 may be configured with a hexagonal shape so that it can mate with the hexagonal protrusion 186 on the drive shaft attachment member 184. In addition, to facilitate operable attachment of the implement 100 to the coupler assembly 200, an attachment lug may be formed or attached to the end cap 210.

One arrangement of the coupler assembly 200 may further include a locking assembly generally designated as 240. In at least one form, the locking assembly 240 includes a spring-biased locking member or pin 242 that is movably supported in a locking slot 214 formed in the coupler housing segment 202. The locking pin 242 may be configured to axially move within the locking slot 214 such that its locking end 244 protrudes out through a hole 211 in the end cap 210. See FIG. 8. A locking spring 246 is journaled on the locking pin 242 to bias the locking pin 242 within the locking slot 214 in the distal direction "DD". An actuator arm 248 may be formed on or attached to the locking pin 242 to enable the user to apply an unlocking motion to the locking pin 242 in the proximal direction "PD".

Figure 9:
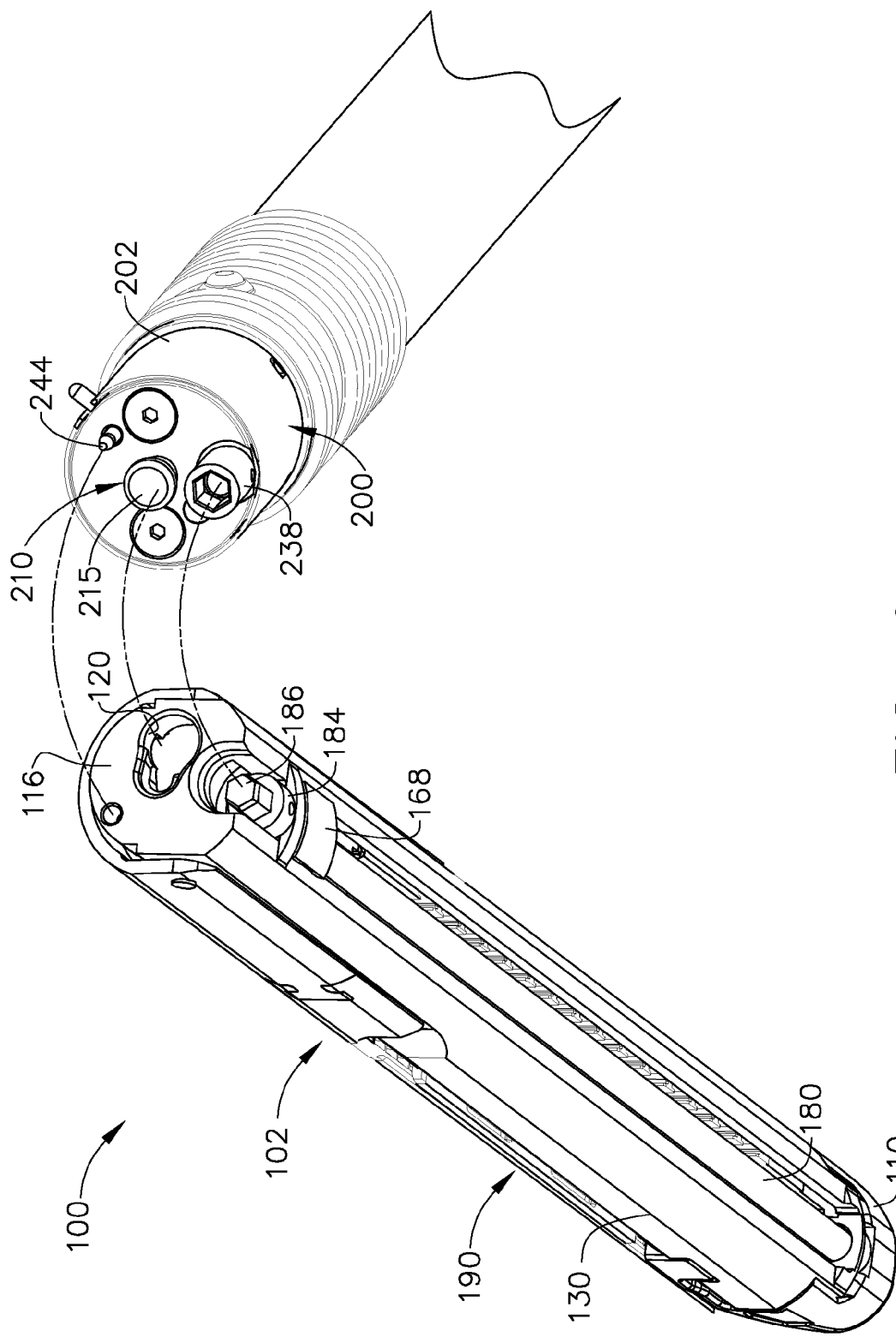
FIG. 9 is a perspective view of the proximal end of the end effector and the distal end of the elongate shaft assembly and coupler assembly attached thereto.

As can be seen in FIGS. 3, 9, and 10, the elongate channel 110 of the end effector 102 may have a proximal end wall 116 that has a coupling opening 118 formed therein for receipt of the attachment lug 212 therein. In one arrangement, for example, the attachment lug 212 may include a neck portion 213 that has a mushroomed attachment head 215 formed thereon. The coupling opening 118 may have a first circular portion 120 sized to enable the attachment head 215 to be inserted therein. The coupling opening 118 may further have a narrow slot 122 formed therein that is sized to enable the neck 213 to be received therein. The proximal end wall 116 may further have a locking hole 124 for receiving the distal end 244 of the locking pin 242 therein.

Figure 12:
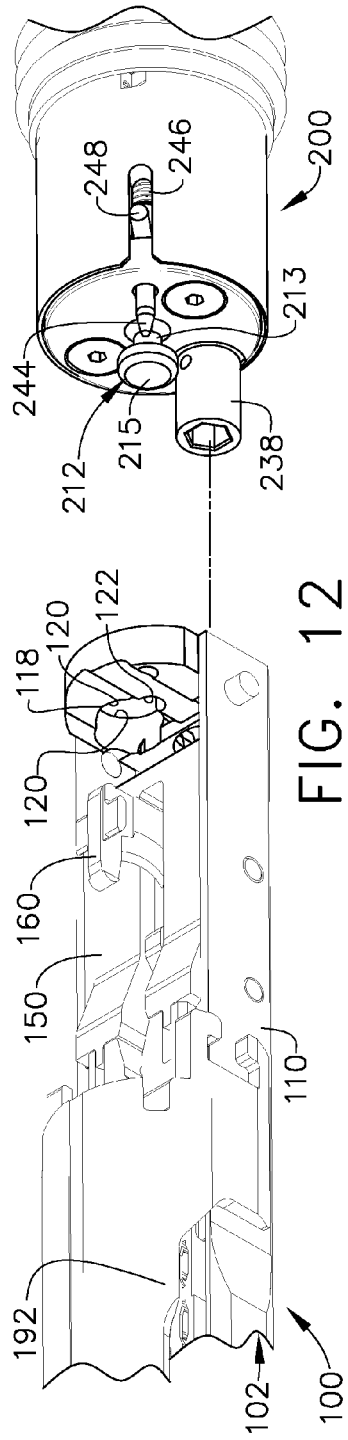
FIG. 12 is a perspective assembly view of a portion of the end effector and elongate shaft assembly prior to coupling the end effector thereto.
Figure 13:
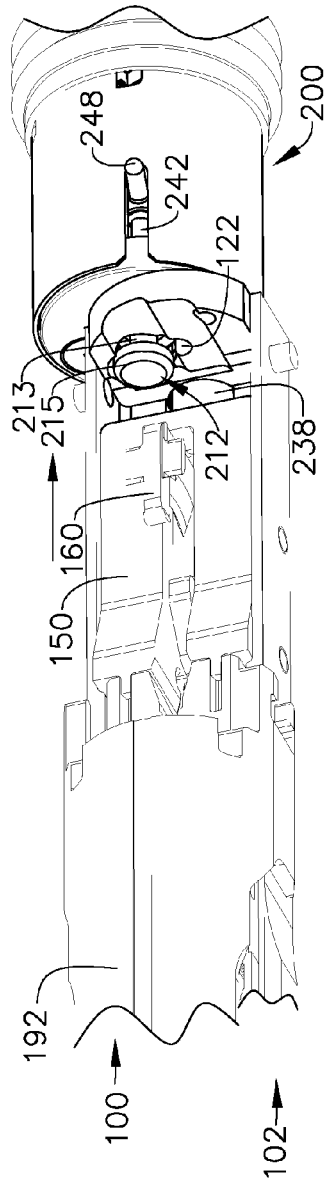
FIG. 13 is another perspective view of a portion of an end effector and elongate shaft assembly arrangement after the end effector has been initially engaged with a coupler assembly portion of the elongate shaft assembly.
Figure 14:
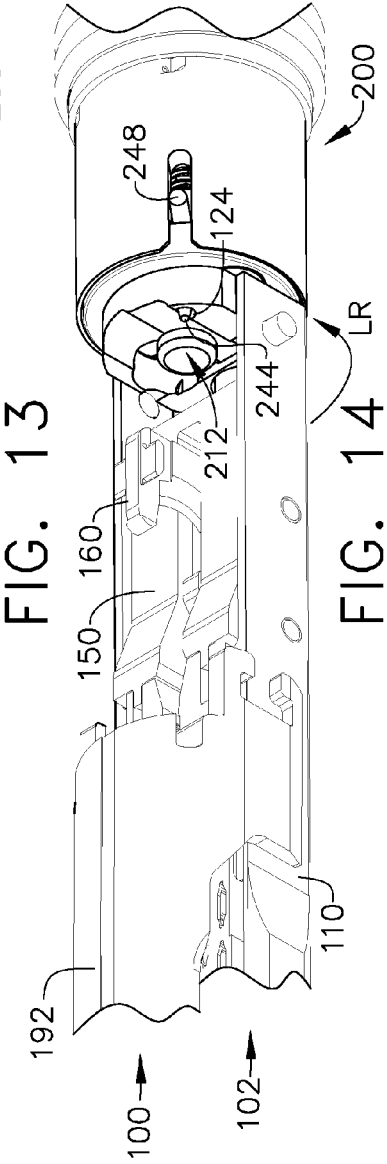
FIG. 14 is another perspective view of the components depicted in FIG. 13 after the end effector has been coupled to the coupler assembly portion of the elongate shaft assembly.

One method of attaching an end effector 102 to the coupling assembly 200 of the surgical instrument 10 may be understood from reference to FIGS. 12-14. For example, to attach the end effector 102 to the coupling assembly 200, the user may align the hexagonal protrusion 186 on the drive shaft attachment member 184 with the hexagonal output socket 238. Likewise, the mushroom head 215 may be aligned with the circular opening portion 120 of the coupling opening 118 as illustrated in FIGS. 9 and 12. The user may then axially insert the protrusion 186 into the socket 238 and the attachment head 215 into the coupling opening 118 as shown in FIG. 13. Thereafter, the user may rotate the end effector 102 (represented by arrow "R" in FIG. 14) to cause the neck 213 to enter the slot 122 and enable the distal end 244 of the locking pin 242 to snap into the locking hole 124 to prevent further relative rotation between the end effector 102 and the coupling assembly 200. Such arrangement serves to operably couple the end effector 102 to the surgical instrument 10.

To detach the end effector 102 from the coupling assembly 200, the user may apply an unlocking motion to the actuator arm 246 to bias the locking pin the proximal direction "PD". Such movement of the locking pin 242 causes the distal end 244 of the locking pin 242 to move out of the locking hole 124 in the end wall 116 of the elongate channel 110. The user is then free to rotate the end effector 102 relative to the coupling assembly in an opposite direction to move the neck portion 213 of the attachment button 212 out of the slot 122 to enable the attachment head 215 to be axially pulled out of the coupling opening 118 in the end effector 102 to thereby detach the end effector 102 from the coupling assembly 200. As can be appreciated from above, the coupling assembly 200 provides a unique and novel arrangement for operably coupling a surgical implement 100 that is operable through application of rotary drive motion(s) to the surgical instrument 10. In particular, the coupling assembly 200 enables a variety of different surgical implements 100 or end effectors 102 to be operably coupled to the elongate shaft assembly 30 of the surgical instrument 10.

Articulation System

Figure 18:
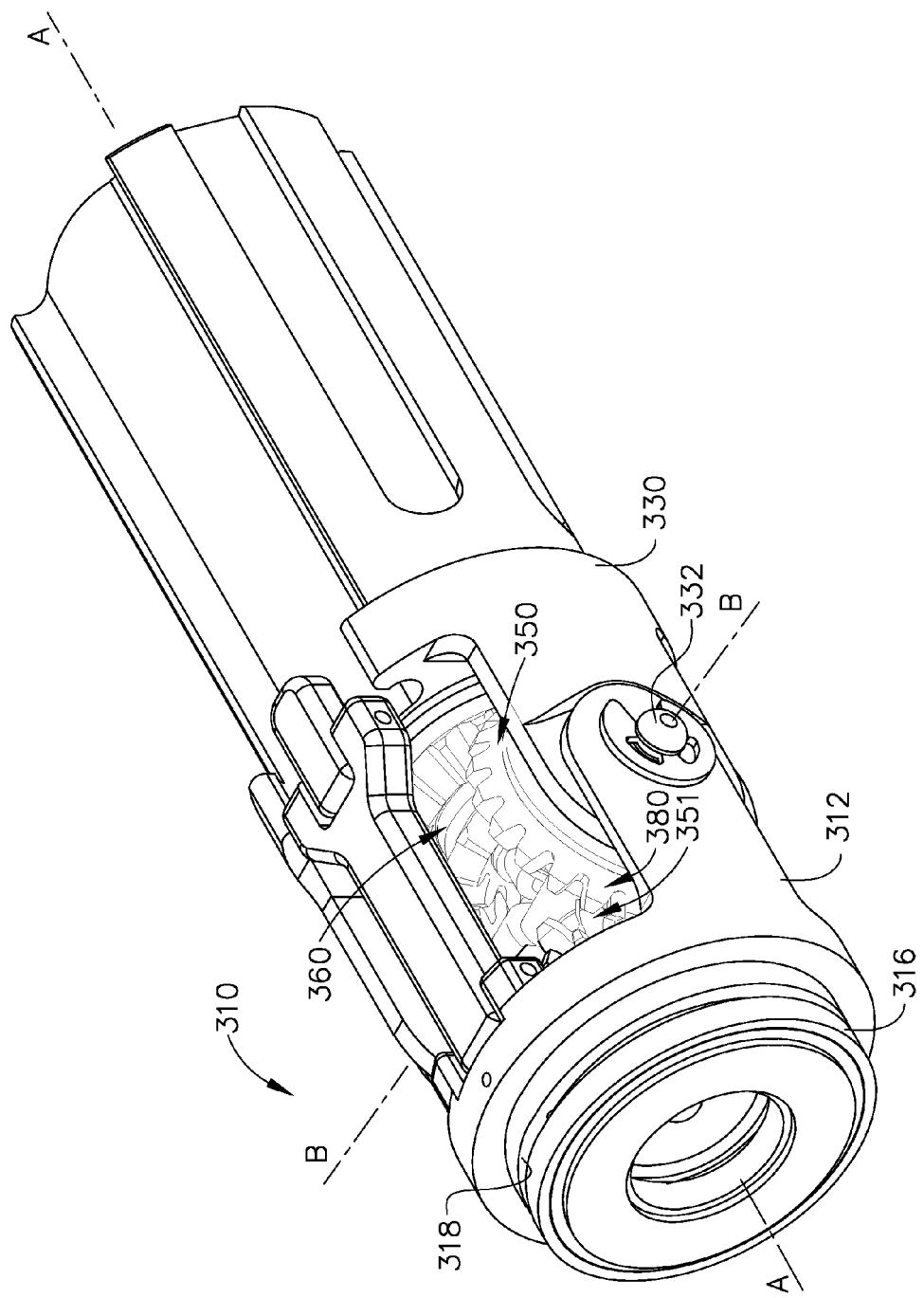
FIG. 18 is a perspective view of the articulation joint arrangement of FIG. 17.

As can be seen in FIGS. 1 and 2, the elongate shaft assembly 30 may define a shaft axis A-A. In at least one form, the elongate shaft assembly 30 may include an articulation system 300 for selectively articulating the end effector 102 about an articulation axis B-B that is substantially transverse to the shaft axis A-A. One form of articulation system 300 is shown in FIGS. 15 and 16. As can be seen in those Figures, the articulation system 300 may include a powered articulation joint 310. In at least one arrangement, the articulation joint 310 includes a distal joint portion or a distal clevis 312 that is rotatably supported on a proximally-extending hub portion 203 of the coupler housing segment 202 by a distal housing bearing 314. See FIG. 20. The distal clevis 312 may be pivotally attached to a proximal joint portion or proximal clevis 330 by an articulation pin 332 that defines articulation axis B-B. See FIG. 18. The distal clevis 312 may include a distally-protruding attachment hub 316 that is sized to be received within the proximal end of the coupler housing segment 202. The attachment hub 316 may have an annular groove 318 therein that is configured to receive attachment pins 320 therein. See FIG. 8. The attachment pins 320 serve to attach the coupler housing segment 202 to the distal clevis 312 such that the coupler housing segment 202 may rotate relative to the distal clevis 312 about the shaft axis A-A. As can be seen in FIG. 20, the distal firing shaft segment 510 extends through the hub portion 203 of the coupler housing segment 202 and is rotatably supported relative thereto by a distal firing shaft bearing 322 mounted within the hub portion 203.

To facilitate the application of a rotary drive or firing motion to the end effector 102, as well as to facilitate rotation of the end effector 102 relative to the elongate shaft 30 about the shaft axis A-A while maintaining the ability to articulate the end effector 102 relative to the elongate shaft assembly 30 about articulation axis B-B, the articulation joint 310 may include a unique and novel "nested" gear assembly, generally designated as 350 and which is located within a gear area 351 between the distal clevis 312 and the proximal clevis 330. See FIGS. 18-20. In at least one form, for example, the nested gear assembly 350 may include an inner drive shaft gear train or "first gear train" 360 that is "nested" with an outer end effector gear train or "second gear train" 380. As used herein, the term "nested" may mean that no portion of the first gear train 360 extends radially outward beyond any portion of the second gear train 380. Such unique and novel gear arrangement is compact and facilitates the transfer of rotary control motions to the end effector while also enabling the distal clevis portion to pivot relative to the proximal clevis portion. As will be discussed in further detail below, the inner drive shaft gear train 360 facilitates the application of rotary drive or firing motions from a proximal firing shaft segment 520 to the distal firing shaft segment 510 through the articulation joint 310. Likewise, the outer end effector gear train 380 facilitates the application of rotary control motions to the coupler assembly 200 from an end effector rotation system 550 as will be discussed in further detail below.

Figure 17:
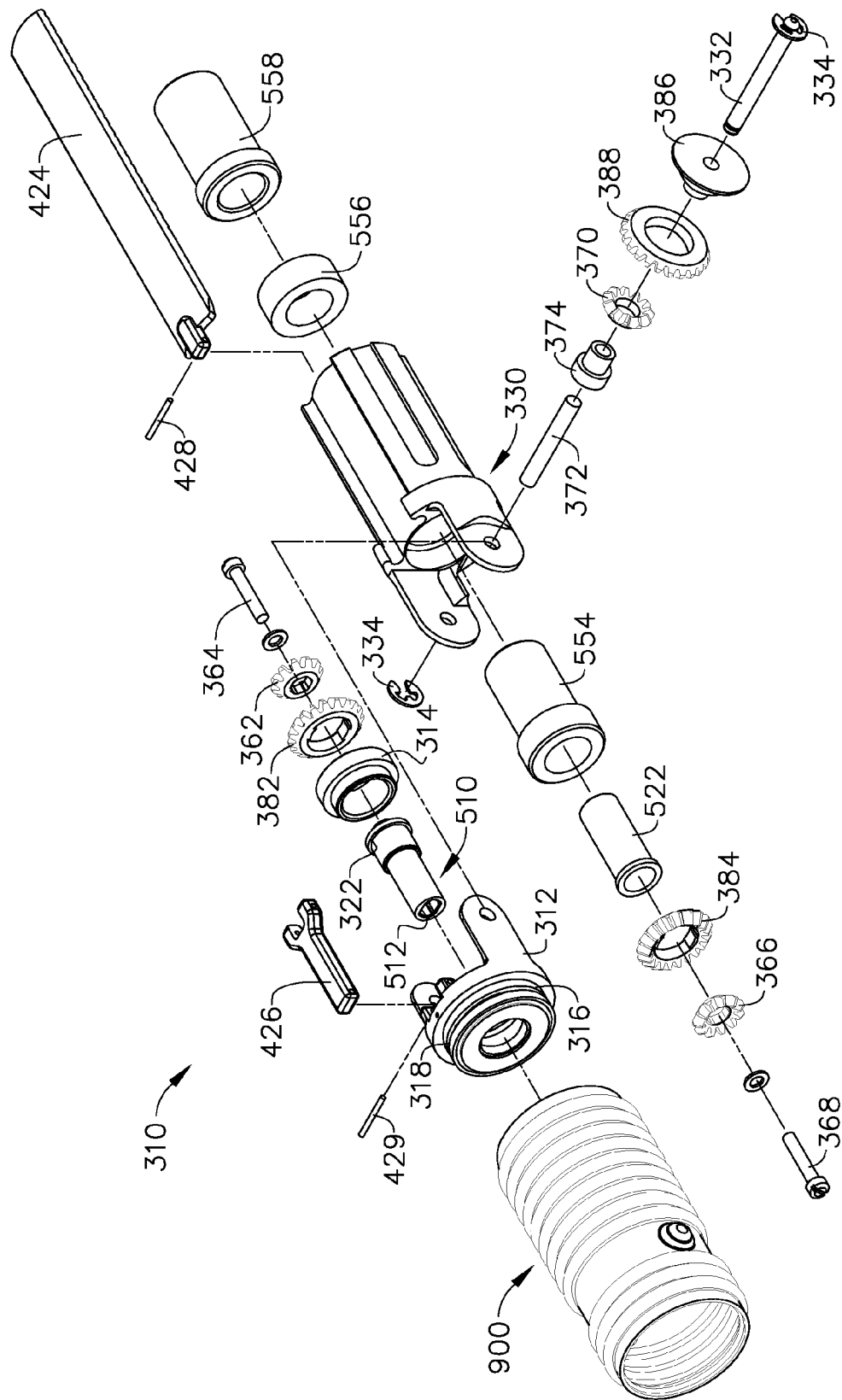
FIG. 17 is an exploded perspective view of an articulation joint arrangement of the present invention.

In at least one form, for example, the inner drive shaft gear train 360 may include a a distal drive shaft bevel gear 362 that may be attached to the proximal end of the distal firing shaft segment 510 by a screw 364. See FIG. 17. The inner drive shaft gear train 360 may also include a proximal drive shaft bevel gear 366 that is attached to the proximal firing shaft segment 520 by a screw 368. See FIG. 20. In addition, the inner drive shaft gear train 360 may further include a drive shaft transfer gear 370 that is mounted on a transfer gear bearing 374 that is mounted on a transverse gear shaft 372. See FIG. 17. Such inner drive shaft gear train 360 may facilitate the transfer of rotary drive motions from the proximal firing shaft segment 520 through the articulation joint 310 to the distal firing shaft segment 510.

As indicated above, the nested gear assembly 350 also includes an outer end effector gear train 380 that facilitates the application of rotary control motions to the coupler assembly 200 from the end effector rotation system 550 through the articulation joint 310. In at least one form, the outer end effector gear train 380 may, for example, include an output bevel gear 382 that is non-rotatably (e.g., keyed) onto the proximally-extending hub portion 203 of the coupler housing segment 202. The outer end effector gear train 380 may further include an input bevel gear 384 that is non-rotatably attached (e.g., keyed onto) to a proximal rotation shaft segment 552 of the end effector rotation system 550. In addition, the outer end effector gear train 380 may further include a rotation shaft transfer gear 388 that is mounted on an outer transfer gear bearing 386 that is supported on the transversely-extending articulation pin 332. See FIG. 17. Articulation pin 332 extends through the hollow transverse gear shaft 372 and serves to pin the distal clevis 312 to the proximal clevis 330 for articulation about the transverse articulation axis B-B. The articulation shaft 332 may be retained in position by spring clips 334. The unique and novel articulation joint 310 and nested gear assembly 350 facilitate the transfer of various control motions from the handle assembly 20 through the elongate shaft assembly 30 to the end effector 102 while enabling the end effector 102 to rotate about the elongate shaft axis A-A and articulate about the articulation axis B-B.

Figure 27:
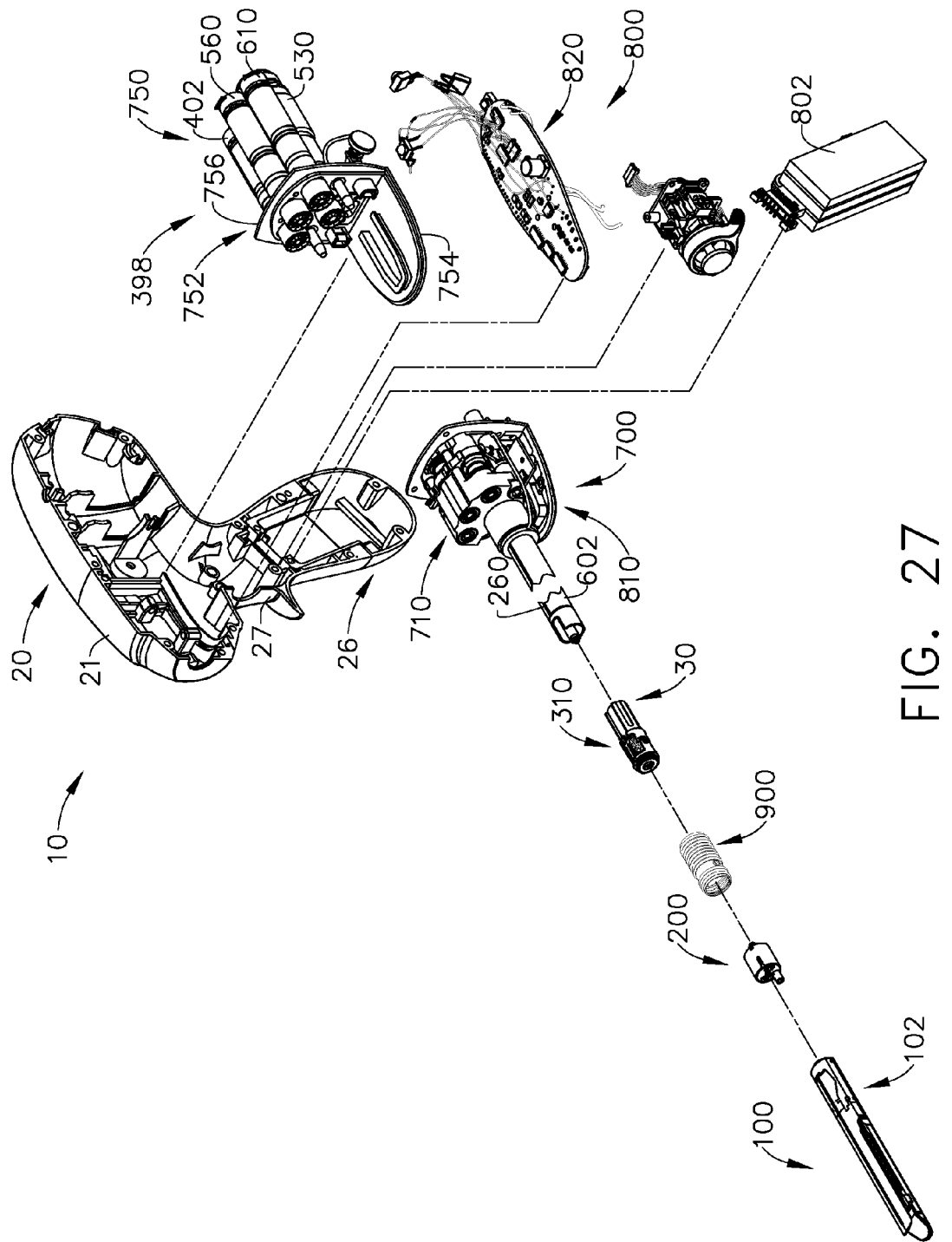
FIG. 27 is an exploded perspective view of the surgical instrument of FIGS. 1 and 2.

Articulation of the end effector 102 about the articulation axis B-B relative to the elongate shaft assembly 30 may be accomplished by an articulation control system 400. In various forms, the articulation control system 400 may include an articulation control motor 402 that is operably supported in the handle assembly 20. See FIG. 15. The articulation control motor 402 may be coupled to an articulation drive assembly 410 that is operably supported on a detachable drive mount 700 that is removably supported in the handle assembly 20 as will be discussed in further detail below. In at least one form, the articulation drive assembly 410 may include a proximal articulation drive shaft segment 412 that is rotatably supported in a shaft housing assembly 710 of the detachable drive mount 700. See FIGS. 27 and 28. For example, the proximal articulation drive shaft segment 412 may be rotatably supported within a distal shaft housing portion 712 by articulation bearings 414. In addition, the proximal articulation drive shaft segment 412 may be rotatably supported in a proximal shaft housing portion 714 by bearings 415. See FIG. 28. The articulation control system 400 may further comprise a proximal articulation shaft segment 420 that is rotatably driven about the shaft axis A-A by the articulation control motor 402. As can also be seen in FIG. 15, the articulation drive assembly 410 may also include a pair of articulation drive pulleys 416, 417 that serve to drive articulation drive belt 418. Thus, actuation of the articulation control motor 402 may result in the rotation of the proximal articulation shaft segment 420 about the shaft axis A-A. See FIG. 15.

As can be seen in FIGS. 15 and 16, the proximal articulation shaft segment 420 has a threaded portion 422 that is adapted to threadably mate with an articulation drive link 424. Rotation of the distal articulation drive shaft segment 420 in a first direction may axially drive the articulation drive link 424 in the distal direction "DD" and rotation of the distal articulation drive shaft segment 420 in an opposite or second direction may cause the articulation drive link 424 to move axially in the proximal direction "PD". The articulation drive link 424 may be pinned to an articulation bar 426 by a pin 428. The articulation bar 426 may, in turn, be pinned to the distal clevis 312 by pin 429. See FIG. 17. Thus, when the clinician wishes to articulate the end effector 102 or implement 100 about the articulation axis B-B relative to the elongate shaft assembly 30, the clinician actuates the articulation control motor 402 to cause the articulation control motor 402 to rotate the proximal articulation shaft segment 420 to thereby actuate the articulation bar 426 in the desired direction to pivot the distal clevis 312 (and end effector 102 attached thereto) in the desired direction. See FIGS. 21 and 22.

Firing System

Figure 23:
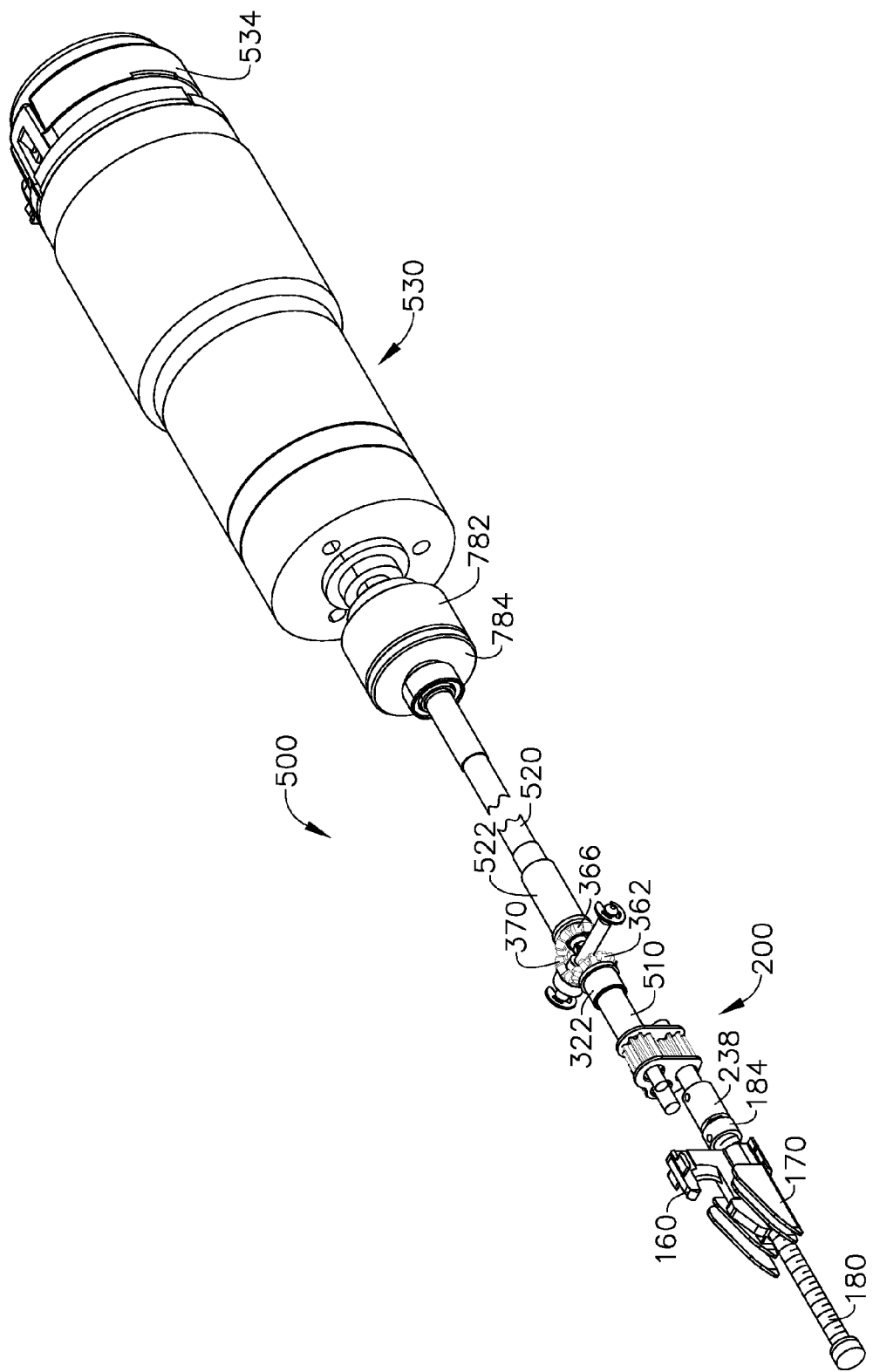
FIG. 23 is a perspective view of a firing system arrangement of the present invention.
Figure 30:
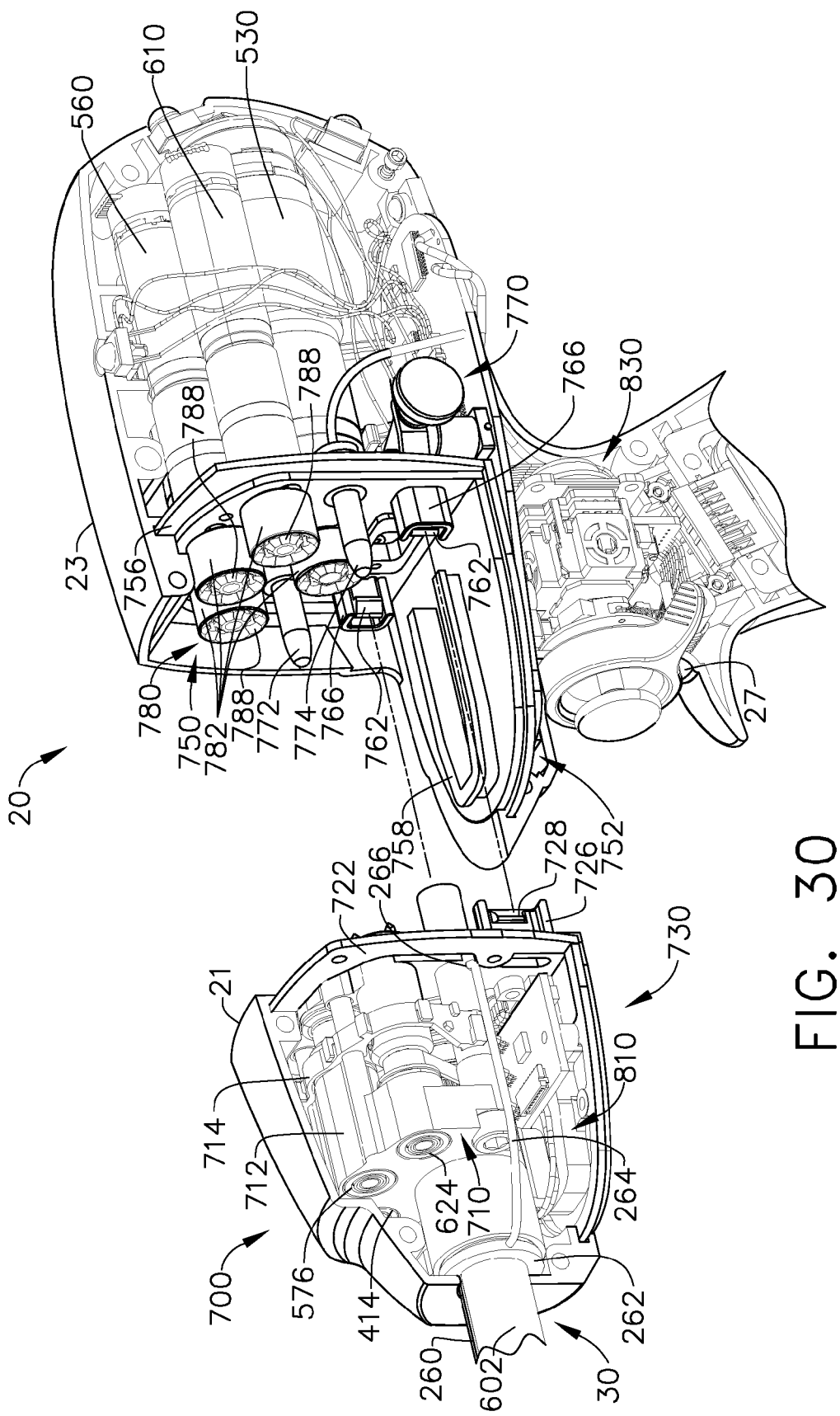
FIG. 30 is an exploded assembly view of a detachable drive mount and motor mounting assembly within the handle housing portions.

As indicated above, the end effector 102 may be operated by rotary controlled motions applied to the end effector drive screw 180 by a firing system 500 which includes the distal firing shaft segment 510 and the proximal firing shaft segment 520. See FIG. 23. The proximal firing shaft segment 520 comprises a portion of the elongate shaft assembly 30 and may be rotatably supported within a hollow proximal rotation shaft segment 552 by a distal bearing sleeve 522. See FIG. 20. Referring again to FIG. 23, in at least one form, the firing system 500 includes a firing motor 530 that is operably supported in the handle assembly 20. A proximal end of the proximal firing shaft segment 520 may be rotatably supported within the detachable drive mount 700 and be configured to be coupled to the firing motor 530 in a manner discussed in further detail below. As can be seen in FIG. 30, the proximal end of the proximal firing shaft segment 520 may be rotatably supported in a thrust bearing 524 mounted with the distal bulkhead plate 722 of the drive mount bulkhead assembly 720. Actuation of the firing motor 530 will ultimately result in the rotation of the end effector drive screw 180 to apply the rotary control motion to the end effector 102.

End Effector Rotation System

In various forms, the surgical instrument 10 may also include an end effector rotation system or "distal roll system" 550 for selectively rotating the end effector 102 relative to the elongate shaft assembly 30 about the shaft axis A-A. The end effector rotation system 550 may include the proximal rotation shaft segment 552 which also comprises a portion of the elongate shaft assembly 30. As can be seen in FIG. 20, the proximal rotation shaft segment 552 may be rotatably supported within the proximal clevis 330 by a distal bearing 554 and a proximal bearing 556. In addition, the proximal rotation shaft segment 552 may be rotatably supported within the proximal articulation shaft segment 420 by a distal bearing sleeve 558 and a proximal bearing 559. See FIGS. 20 and 30. The proximal end of the proximal rotation shaft segment 552 may also be rotatably supported within a drive mount bulkhead assembly 720 by a proximal bearing 555 as can be seen in FIG. 30.

Figure 28:
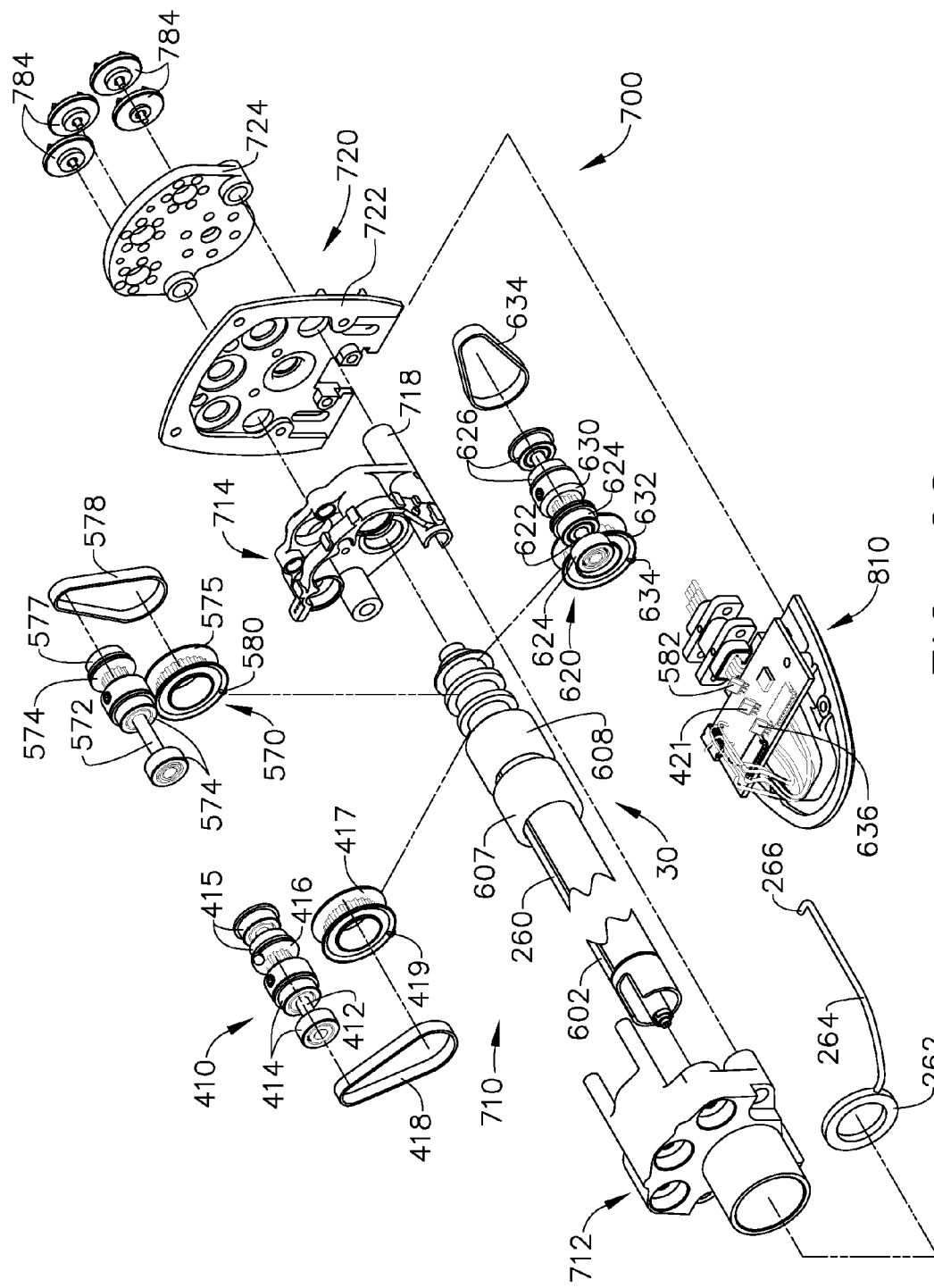
FIG. 28 is an exploded perspective view of a detachable drive mount arrangement of the present invention.
Figure 28A:
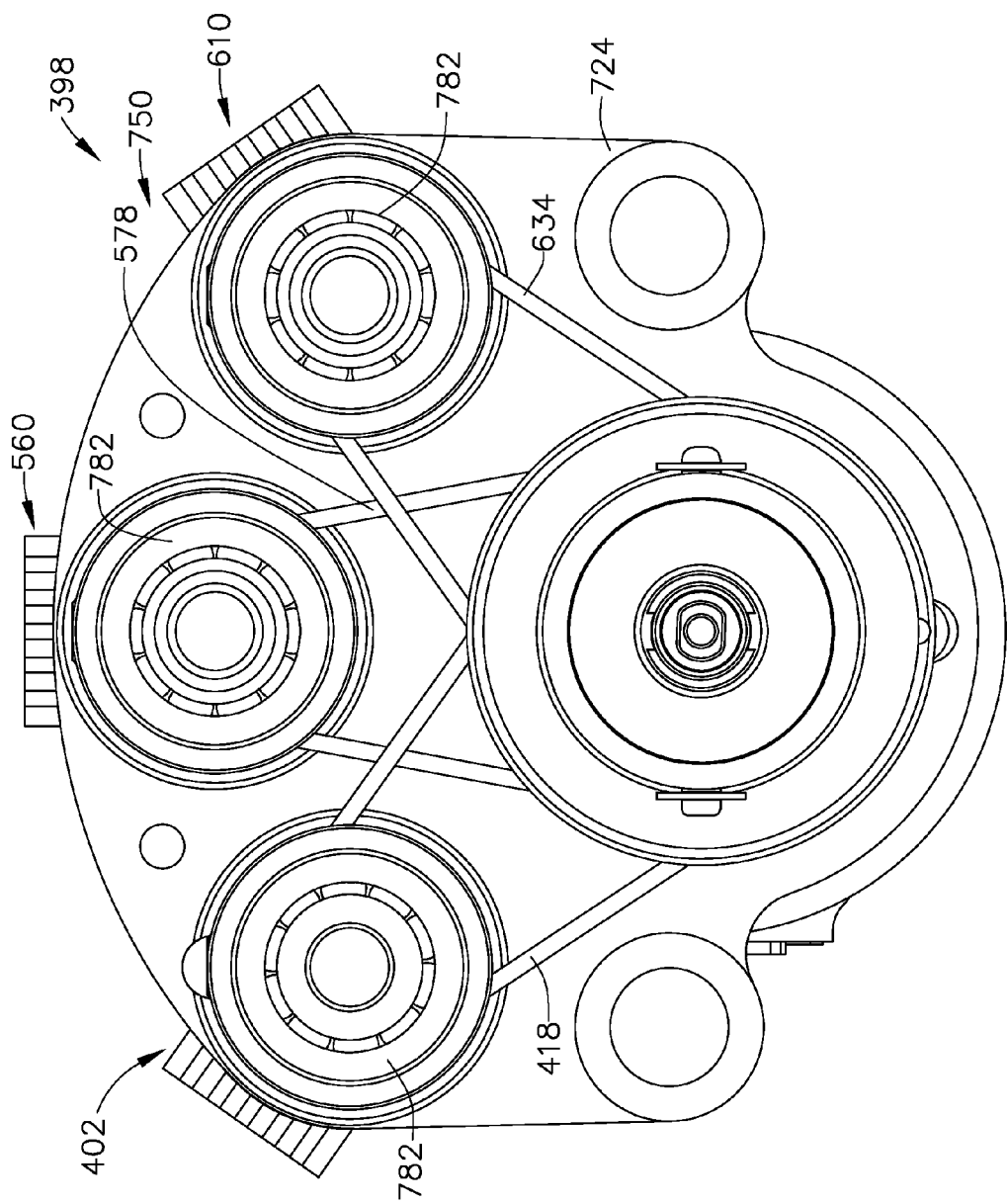
FIG. 28A is an end elevational view of a portion of the detachable drive mount arrangement of FIG. 28 attached to a motor mounting assembly arrangement.
Figure 28B:
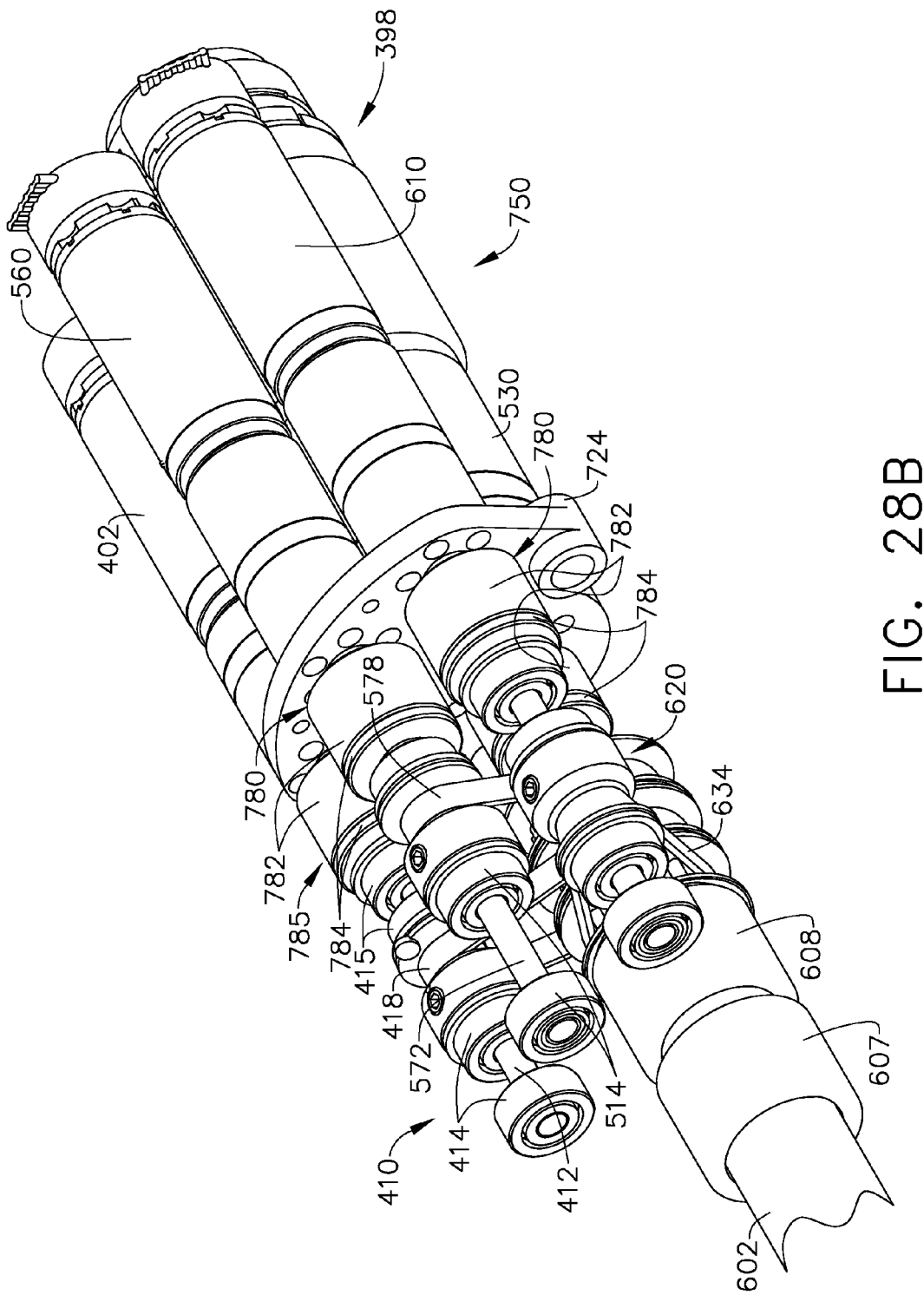
FIG. 28B is a perspective view of a portion of the detachable drive mount arrangement and motor mounting assembly arrangement of FIG. 28A.

In at least one form, the end effector rotation system 550 may include an end effector rotation or "distal roll" motor 560 that is operably supported in the handle assembly 20. See FIG. 24. The end effector rotation motor 560 may be coupled to a rotation drive assembly 570 that is operably supported on the detachable drive mount 700. In at least one form, the rotation drive assembly 570 includes a proximal rotation drive shaft segment 572 that is rotatably supported in the shaft housing assembly 710 of the detachable drive mount 700. See FIG. 27. For example, the proximal rotation drive shaft segment 572 may be rotatably supported within the distal shaft housing portion 712 by bearings 576. In addition, the proximal rotation drive shaft segment 572 is rotatably supported in the proximal housing portion 714 by bearing 577. See FIG. 28. As can be seen in FIGS. 24 and 28, the rotation drive assembly 570 may also include a pair of rotation drive pulleys 574, 575 that serve to drive a rotation drive belt 578. Thus, actuation of the end effector rotation motor 560 will result in the rotation of the proximal rotation shaft segment 552 about the shaft axis A-A. Rotation of the proximal rotation shaft segment 552 results in rotation of the coupler assembly 200 and ultimately of the end effector 102 coupled thereto.

Shaft Rotation System

Figure 26:
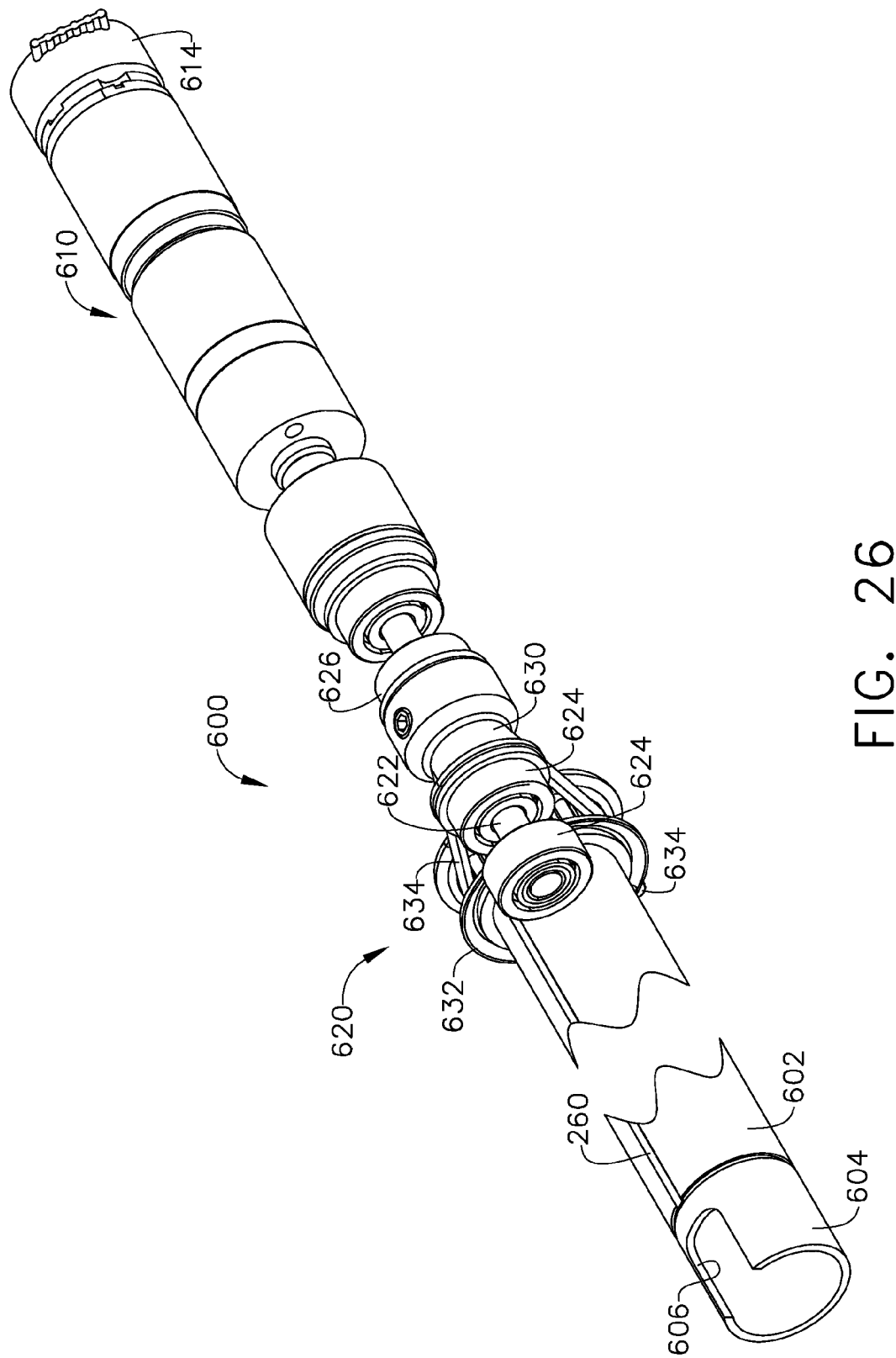
FIG. 26 is a perspective view of a shaft rotation system arrangement of the present invention.

Various forms of the surgical instrument 10 may also include a shaft rotation system generally designated as 600. The shaft rotation system may also be referred to herein as the "proximal roll system". In at least one form, the shaft rotation system 600 includes a proximal outer shaft segment 602 that also comprises a portion of the elongate shaft assembly 30. The proximal outer shaft segment 602 has a distal end 604 that is non-rotatably coupled to the proximal clevis 330. As can be seen in FIGS. 19 and 26, the distal end 604 has a clearance notch 606 therein for permitting actuation of the articulation bar 426 relative thereto. The shaft rotation system 600 may include a shaft rotation or "proximal roll" motor 610 that is operably supported in the handle assembly 20. The shaft rotation motor 610 may be coupled to a shaft drive assembly 620 that is operably supported on the detachable drive mount 700. In at least one form, the shaft drive assembly 620 includes a proximal drive shaft segment 622 that is rotatably supported in the distal shaft housing portion 712 of the detachable drive mount 700 by bearings 624. See FIG. 28. In addition, the proximal drive shaft segment 622 is rotatably supported in the proximal drive shaft housing portion 714 by bearing 626. As can be seen in FIGS. 26 and 28, the shaft drive assembly 620 may also include a pair of rotation drive pulleys 630, 632 that serve to drive a shaft drive belt 634. The drive pulley 632 is non-rotatably attached to the proximal drive shaft segment 602 such that rotation of the drive pulley 632 results in rotation of the proximal drive shaft segment 602 and the end effector 102 attached thereto about the shaft axis A-A. As can be further seen in FIGS. 28 and 30, the proximal drive shaft segment 602 is rotatably supported within the distal shaft housing portion 712 by a pair of sleeve bearings 607 and 608.

The unique and novel articulation system arrangements of the present invention afford multiple degrees of freedom to the end effector while facilitating the application of rotary control motions thereto. For example, in connection with some surgical operations, positioning of the end effector into a position that is coplanar with the target tissue may be necessary. Various arrangements of the present invention offer at least three degrees of freedom to an end effector while meeting size limitations often encountered when performing surgical procedures laparoscopically, for example.

Various forms of the present surgical instrument facilitate improved user dexterity, precision, and efficiency in positioning the end effector relative to the target tissue. For example, conventional shaft articulation joints commonly used for power transmission frequently employ universal joints(s), hinged vertebral and flexurally compliant couplings. All of those methods may tend to suffer from performance limitations including limits in bend radius and excessive length characteristics. Various forms of the unique and novel elongate shaft assemblies and drive systems disclosed herein, for example, allow the distance between the articulation axis and the end effector to be minimized when compared to other conventional articulation arrangements. The elongate shaft assemblies and articulation joint arrangements disclosed herein facilitate transfer of at least one rotary control motion to the end effector while also affording multiple degrees of freedom to the end effector to enable the end effector to be precisely positioned relative to the target tissue.

After the end effector 102 or implement 100 has been used, it may be detached from the coupler assembly 200 of the surgical instrument 10 and either disposed of or separately reprocessed and sterilized utilizing appropriate sterilization methods. The surgical instrument 10 may be used multiple times in connection with fresh end effectors/implements. Depending upon the particular application, it may be desirable for the surgical instrument 10 to be resterilized. For example, the instrument 10 may be resterilized before it is used to complete another surgical procedure.

Surgical instruments must be sterile prior to use. One popular method for sterilizing medical devices involves exposing the device to wet steam at a desired temperature for a desired time period. Such sterilization procedures, while effective, are generally ill-suited for sterilizing surgical instruments that employ electrical components due to the high temperatures generated when using steam sterilization methods. Such devices are commonly sterilized by exposing them to a gas such as, for example, Ethylene Oxide.

Various forms of the surgical instrument 10 may be sterilized utilizing conventional sterilization methods. In at least one form, for example, the elongated shaft assembly 30 may be fabricated from components and materials that may be effectively sterilized utilizing methods that employ relatively high sterilization temperatures. It may be desirable, however, to use sterilization methods that have lower operating temperatures when sterilizing the handle assembly, for example, to avoid possibly damaging the electrical components. Thus, it may be desirable to sterilize the handle assembly 20, which houses various electrical components, apart from the elongate shaft assembly 30. To facilitate use of such separate sterilization procedures, the elongate shaft assembly 30, in at least one form, is detachable from the handle assembly 20.

Detachable Drive Mount Assembly

More specifically and with reference to FIG. 28, the detachable drive mount assembly 700 is operably supported within a portion of the handle assembly 20. In one form, for example, the detachable drive mount assembly 700 may be mounted within distal handle housing segments 21 and 22 that may be interconnected by means of snap features, screws or other fastener arrangements. The distal handle housing segments 21 and 22 when coupled together may be referred to herein as a "distal handle housing portion" or "housing" 25. The detachable drive mount assembly 700 may, for example, include a shaft housing assembly 710 that comprises a distal shaft housing 712 and a proximal shaft housing 714. The detachable drive mount assembly 700 may further comprise a drive mount bulkhead assembly 720 that includes a distal bulkhead plate 722 and a proximal coupler bulkhead plate 724. As was described above, in at least one form, the detachable drive mount assembly 700 may operably support the articulation drive assembly 410, the proximal end of the proximal firing shaft segment 520, the rotation drive assembly 570, and the shaft drive assembly 620. To facilitate quick coupling of the firing shaft segment 520, the articulation drive assembly 410, the rotation drive assembly 570, and the shaft drive assembly 620 to the firing motor 530, the articulation control motor 402, the end effector rotation motor 560 and the shaft rotation motor 610, respectively, a unique and novel coupler arrangement may be employed.

Motor Mounting Assembly

In at least one form, for example, the detachable drive mount assembly 700 may be configured to be removably coupled to a motor mounting assembly generally designated as 750. The motor mounting assembly 750 may be supported within handle housing segments 23 and 24 that are couplable together by snap features, screws, etc. and serve to form a pistol grip portion 26 of the handle assembly 20. See FIG. 1. The handle housing segments 23 and 24, when coupled together, may be referred to herein as a "proximal handle housing portion" or "housing" 28. Referring to FIGS. 29-32, the motor mounting assembly 750 may comprise a motor mount 752 that is removably supported within the handle housing segments 23 and 24. In at least one form, for example, the motor mount 752 may have a bottom plate 754 and a vertically extending motor bulkhead assembly 756. The bottom plate 754 may have a fastener tab 758 formed thereon that is configured to retainingly mate to be received with a bottom plate portion 730 of the detachable drive mount 700. In addition, a right locator pin 772 and a left locator pin 774 are mounted in the motor bulkhead assembly 756 and protrude distally therethrough in corresponding right and left socket tubes 716, 718 formed in the proximal shaft housing portion 714. See FIG. 32.

Figure 31:
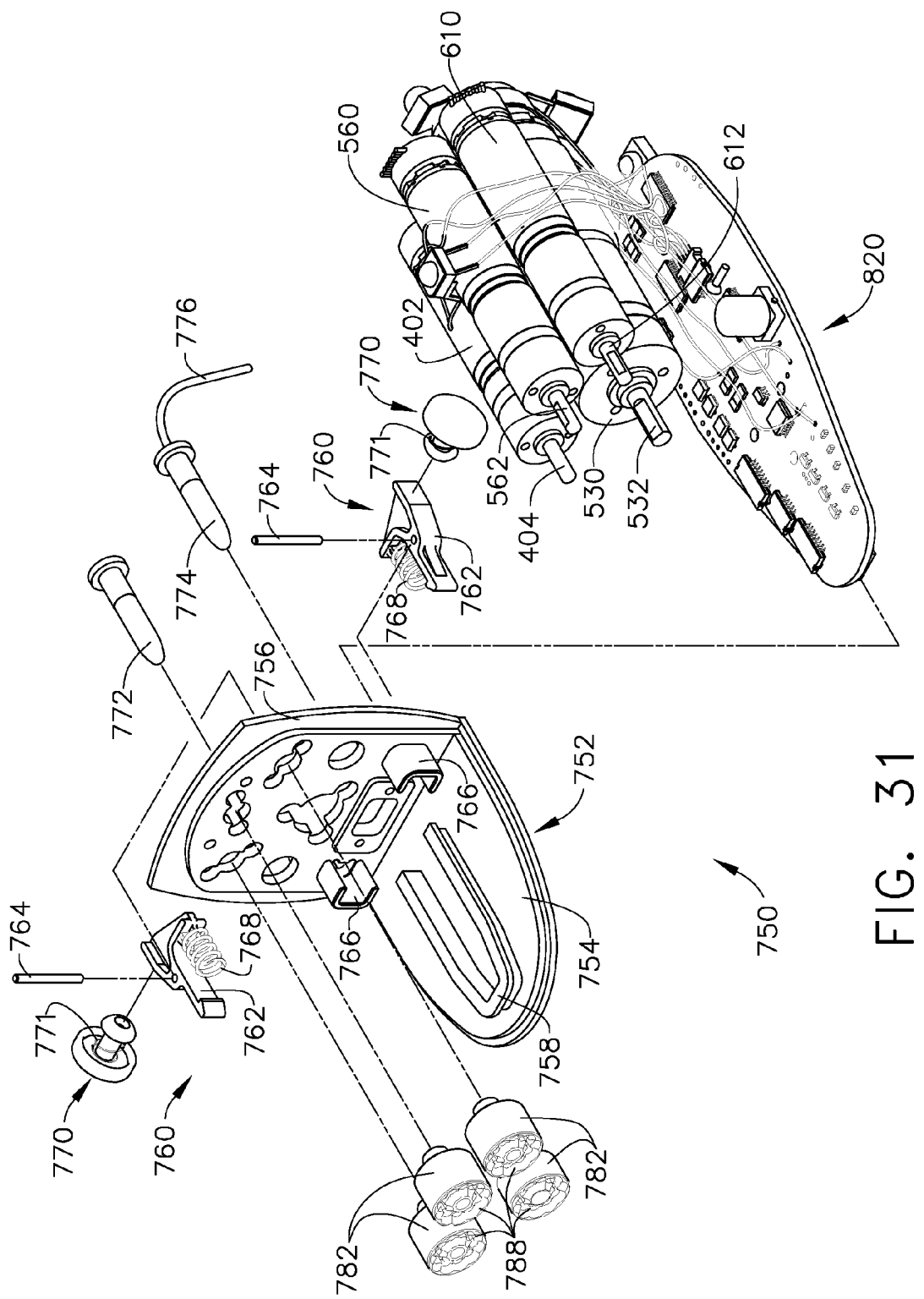
FIG. 31 is an exploded assembly view of a motor mounting assembly arrangement.
Figure 32:
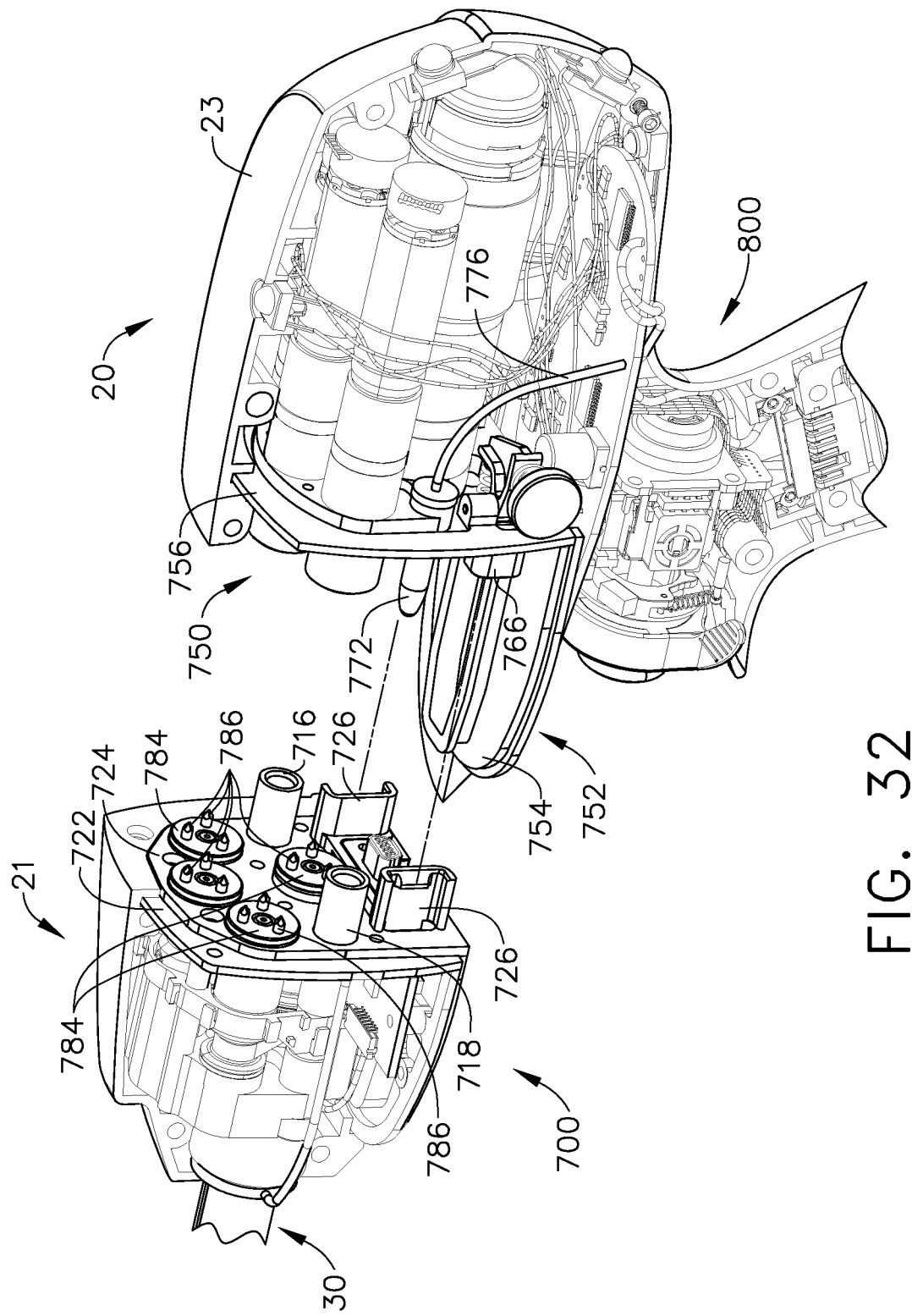
FIG. 32 is another an exploded cross-sectional assembly view of the detachable drive mount and motor mounting assembly within the handle housing portions.
Figure 33:
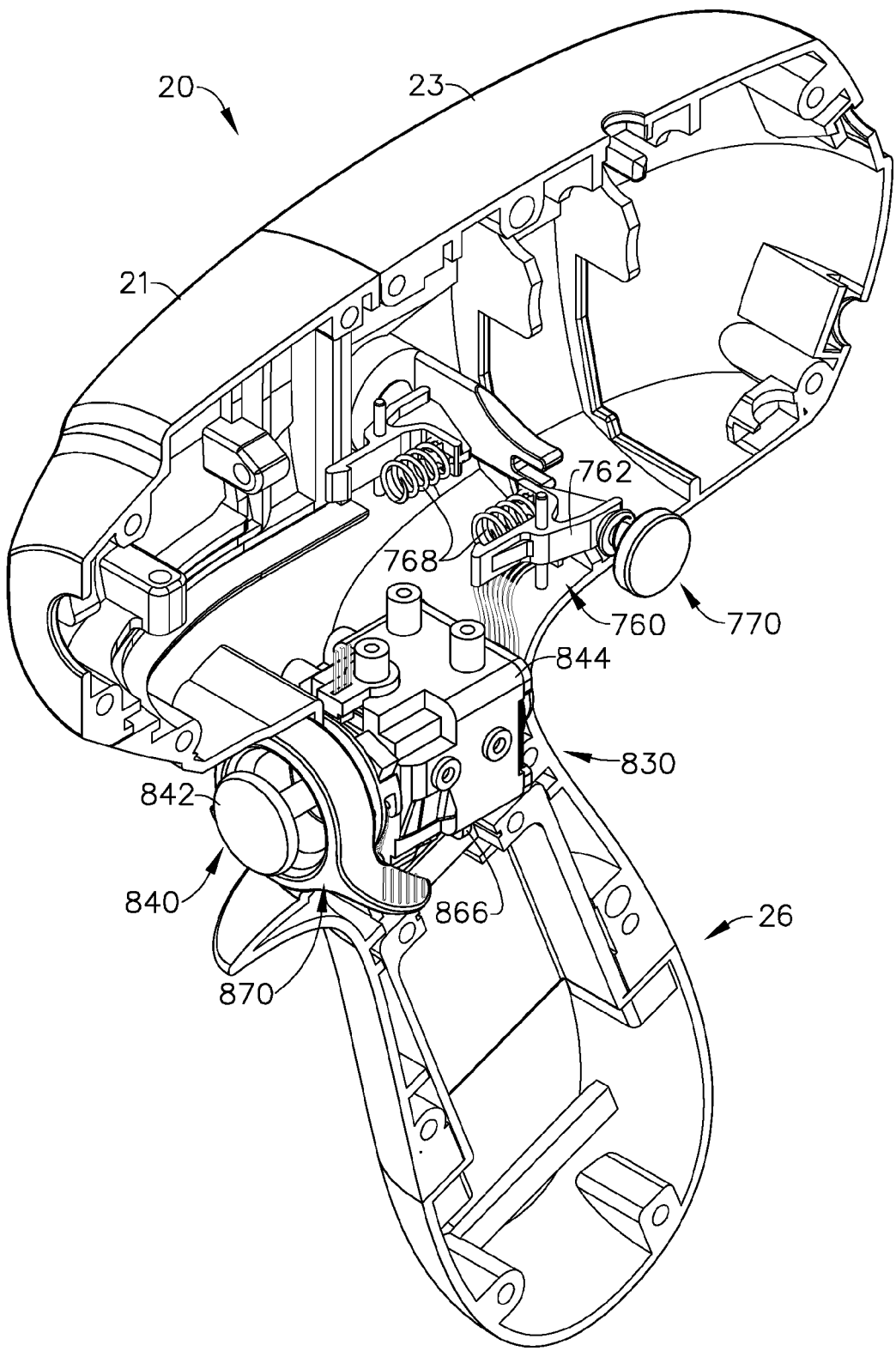
FIG. 33 is a side elevational view of a portion of the handle assembly with various components omitted for clarity.
Figure 34:
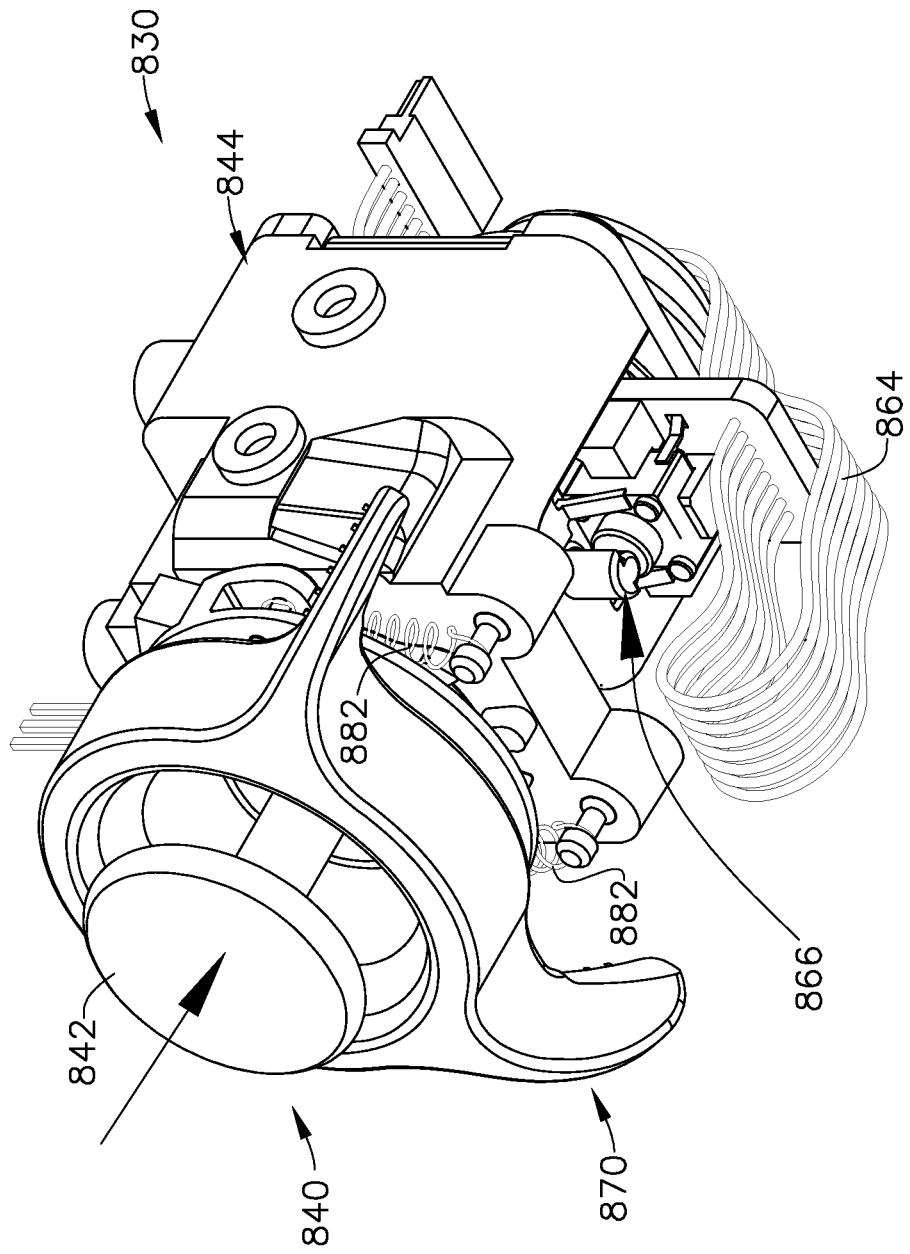
FIG. 34 is a bottom perspective view of a switch arrangement of the present invention.
Figure 35:
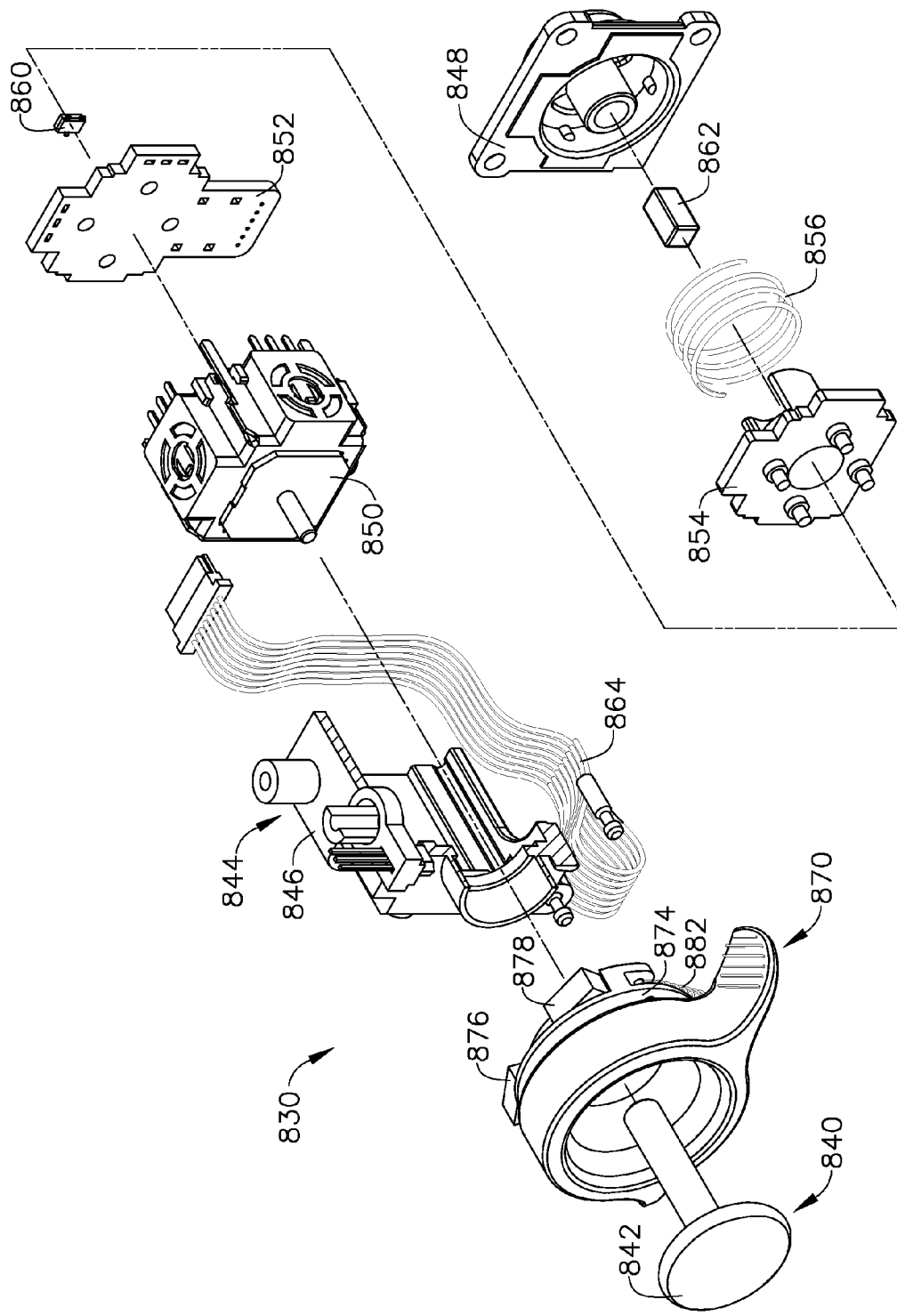
FIG. 35 is an exploded assembly view of the switch arrangement of FIG. 34.

In at least one configuration, the detachable drive mount assembly 700 may be removably coupled to the motor mounting assembly 750 by releasable latch arrangements 760. As can be seen in FIG. 31, for example, a releasable latch arrangement 760 may be located on each lateral side of the motor mounting assembly 750. Each releasable latch arrangement 760 may include a latch arm 762 that is pivotally attached to the motor bulkhead assembly 756 by a corresponding pin 764. Each latch arm 762 may protrude out through a corresponding fastener lug 766 formed on the distal side of the motor bulkhead assembly 756. The fastener lugs 766 may be configured to be slidably received within corresponding receiver members 726 that protrude proximally from the proximal coupler bulkhead plate 724. See FIGS. 30 and 32. When the drive mount assembly 700 is brought into mating engagement with the motor mounting assembly 750, the fastener lugs 766 are slid into the corresponding receiver members 726 such that the latch arms 762 retainingly engage a latch portion 728 of the corresponding receiver member 726. Each latch arm 762 has a corresponding latch spring 768 associated therewith to bias the latch arm 762 into retaining engagement with the corresponding latch portion 728 to retain the detachable drive mount assembly 700 coupled to the motor mounting assembly 750. In addition, in at least one form, each latch arrangement 760 further includes a release button 770 that is movably coupled to the motor bulkhead 756 and is oriented for selective contact therewith. Each release button 770 may include a release spring 771 that biases the button 770 out of contact with its corresponding latch arm 762. When the clinician desires to detach the detachable drive mount assembly 700 from the motor mounting assembly 750, the clinician simply pushes each button 770 inwardly to bias the latch arms 762 out of retaining engagement with the latch portions 728 on the receiver members 726 and then pulls the detachable drive mount assembly 700 out of mating engagement with the motor mounting assembly 750. Other releasable latch arrangements may be employed to releasably couple the detachable drive mount assembly 700 may be removably coupled to the motor mounting assembly 750.

At least one form of the surgical instrument 10 may also employ coupler assemblies for coupling the control motors to their respective drive assemblies that are operably supported mounted on the detachable drive mount 700. More specifically and with reference to FIGS. 28-32, a coupler assembly 780 is employed to removably couple the articulation drive assembly 410 to the articulation control motor 402. The coupler assembly 780 may include a proximal coupler portion 782 that is operably coupled to the drive shaft 404 of articulation control motor 402. In addition, the coupler assembly 780 may further include a distal coupler portion 784 that is attached to the proximal articulation drive shaft 412. See FIGS. 28 and 32. Each distal coupler portion 784 may have a plurality of (three are shown) coupler protrusions 786 that are designed to non-rotatably seat with corresponding scalloped areas 788 formed in the proximal coupler portion 782. See FIG. 30. Similarly, another distal coupler portion 784 may be attached to the proximal rotation drive shaft 572 of the rotation drive assembly 570 and a corresponding proximal coupler portion 782 is attached to the rotation motor drive shaft 562. In addition, another distal coupler portion 784 may be attached to the proximal firing shaft segment 520 and a corresponding proximal coupler portion 782 is attached to the firing motor drive shaft 532. Still another distal coupler portion 784 may be attached to the proximal drive shaft segment 622 of the shaft drive assembly 620 and a corresponding proximal coupler portion 782 is attached to the drive shaft 612 of the shaft rotation motor 610. Such coupler assemblies 780 facilitate coupling of the control motors to their respective drive assemblies regardless of the positions of the drive shafts and the motor shafts.

The various forms of the unique and novel handle assembly arrangement described above enable the elongate shaft assembly 30 to be easily detached from the remaining portion of the handle assembly 20 that houses the motors 402, 530, 560 and 610 and the various electrical components comprising a control system, generally designated as 800. As such, the elongate shaft assembly 30 and the detachable drive mount portion 700 may be sterilized apart from the remaining portion of handle assembly housing the motors and control system which may be damaged utilizing sterilization methods that employ high temperatures. Such unique and novel detachable drive mount arrangement may also be employed in connection with arrangements wherein the drive system (motors and control components) comprise a portion of a robotic system that may or may not be hand held.

Gear Driven Drive Mount Arrangement

Figure 100:
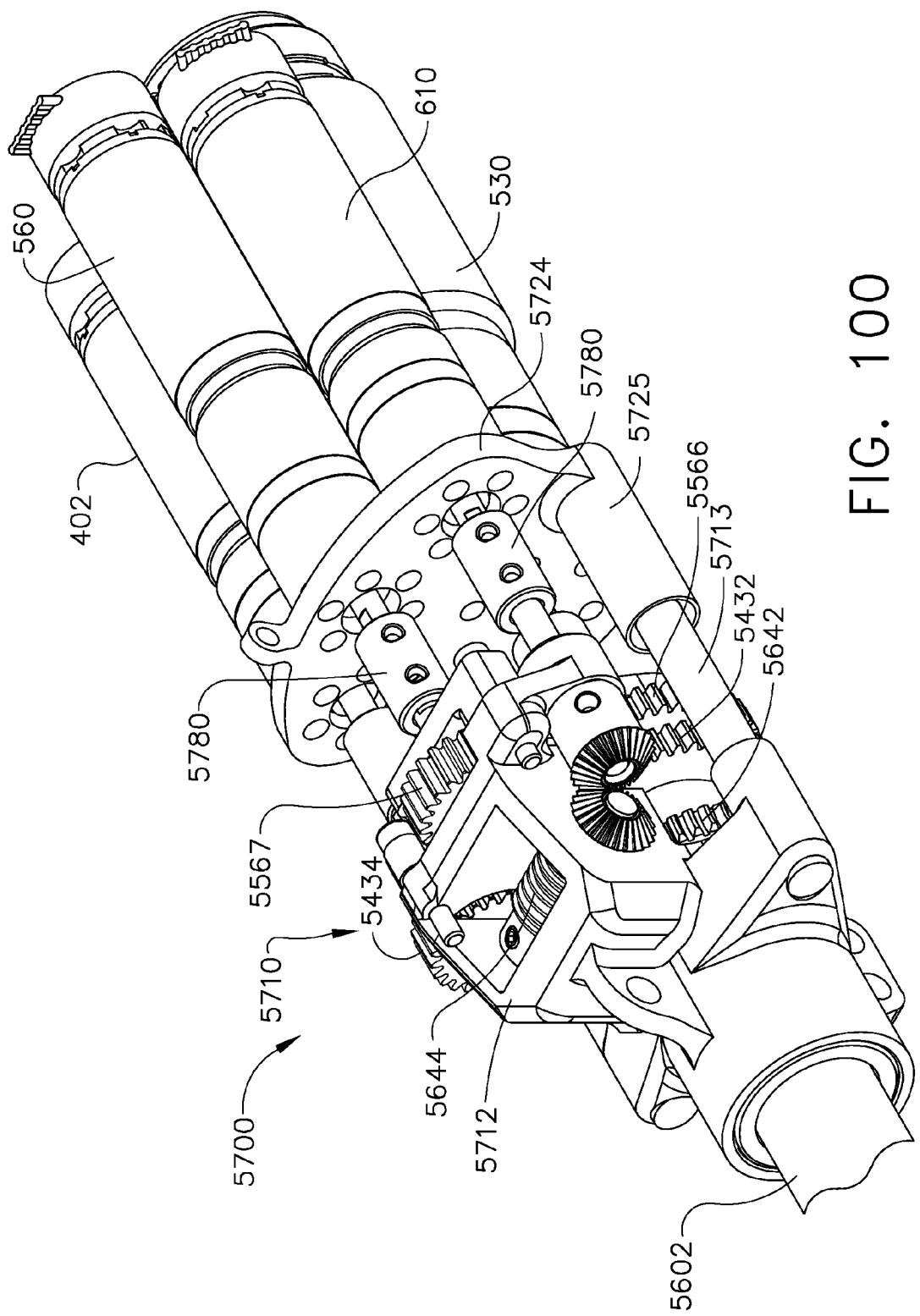
FIG. 100 is a perspective view of an alternative motor mounting assembly that employs a gear driven drive mount assembly.
Figure 101:
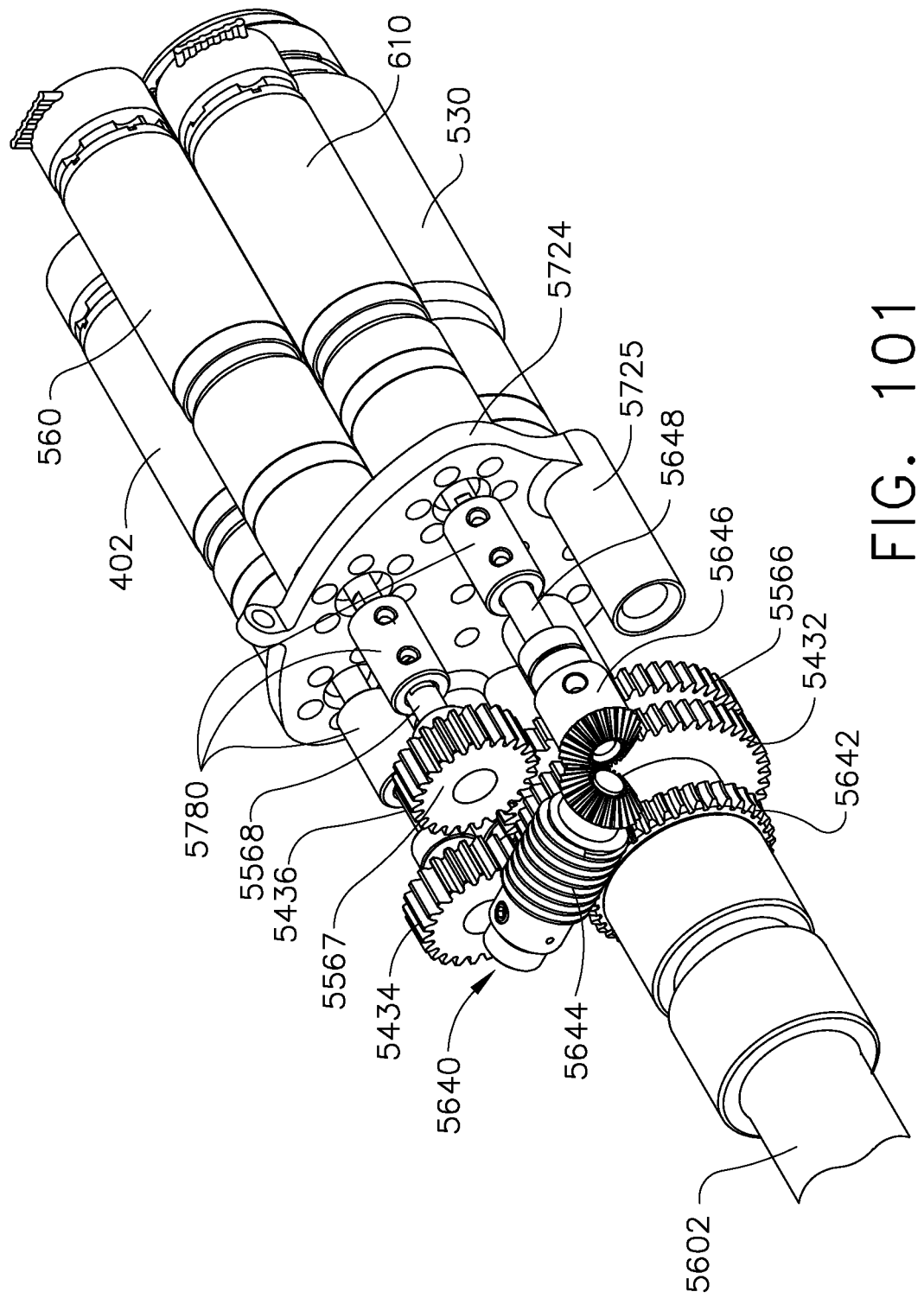
FIG. 101 is another perspective view of the motor mounting assembly of FIG. 100 with the distal shaft housing omitted for clarity.
Figure 102:
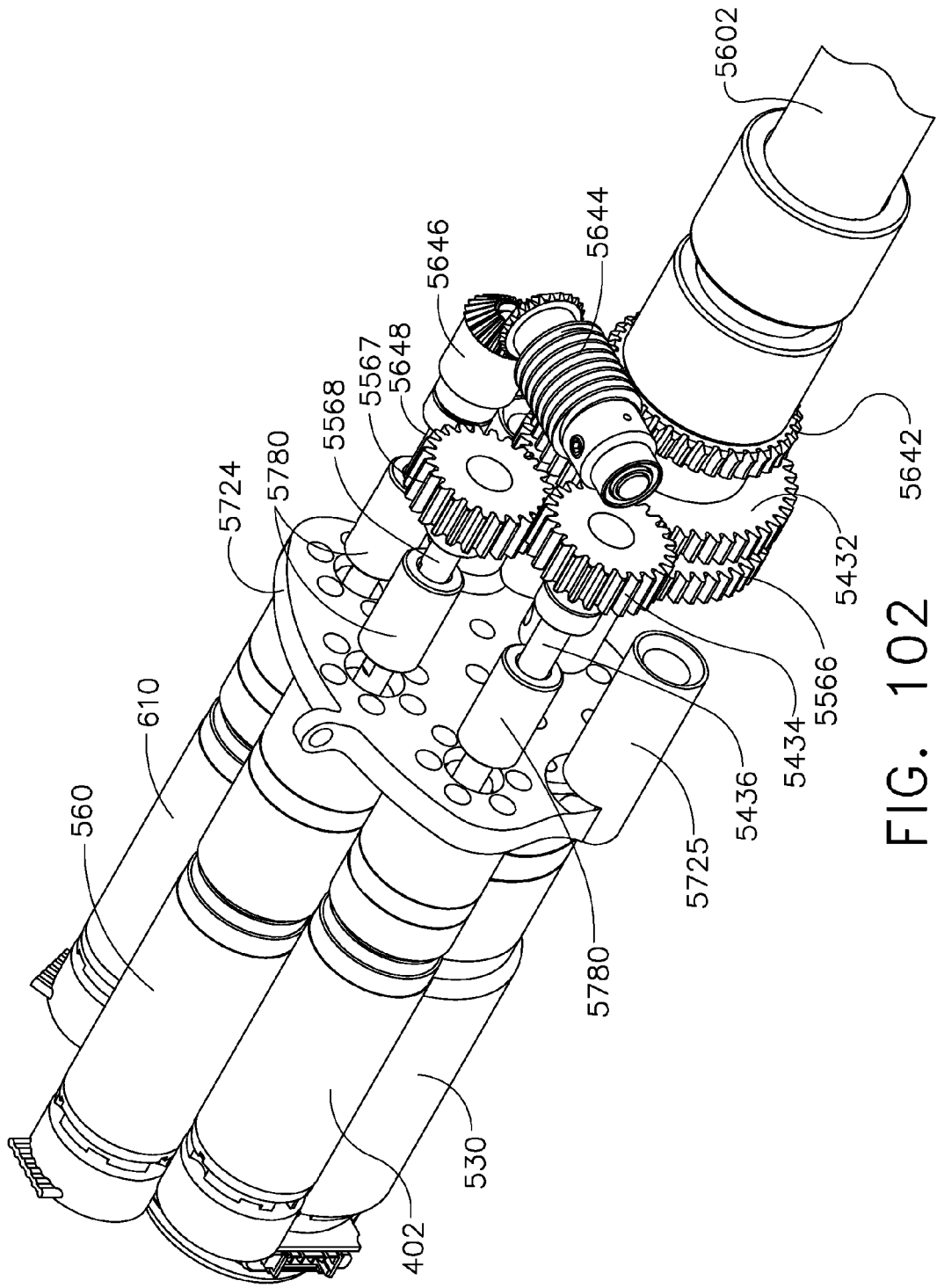
FIG. 102 is another perspective view of the motor mounting assembly of FIGS. 100 and 101.
Figure 103:
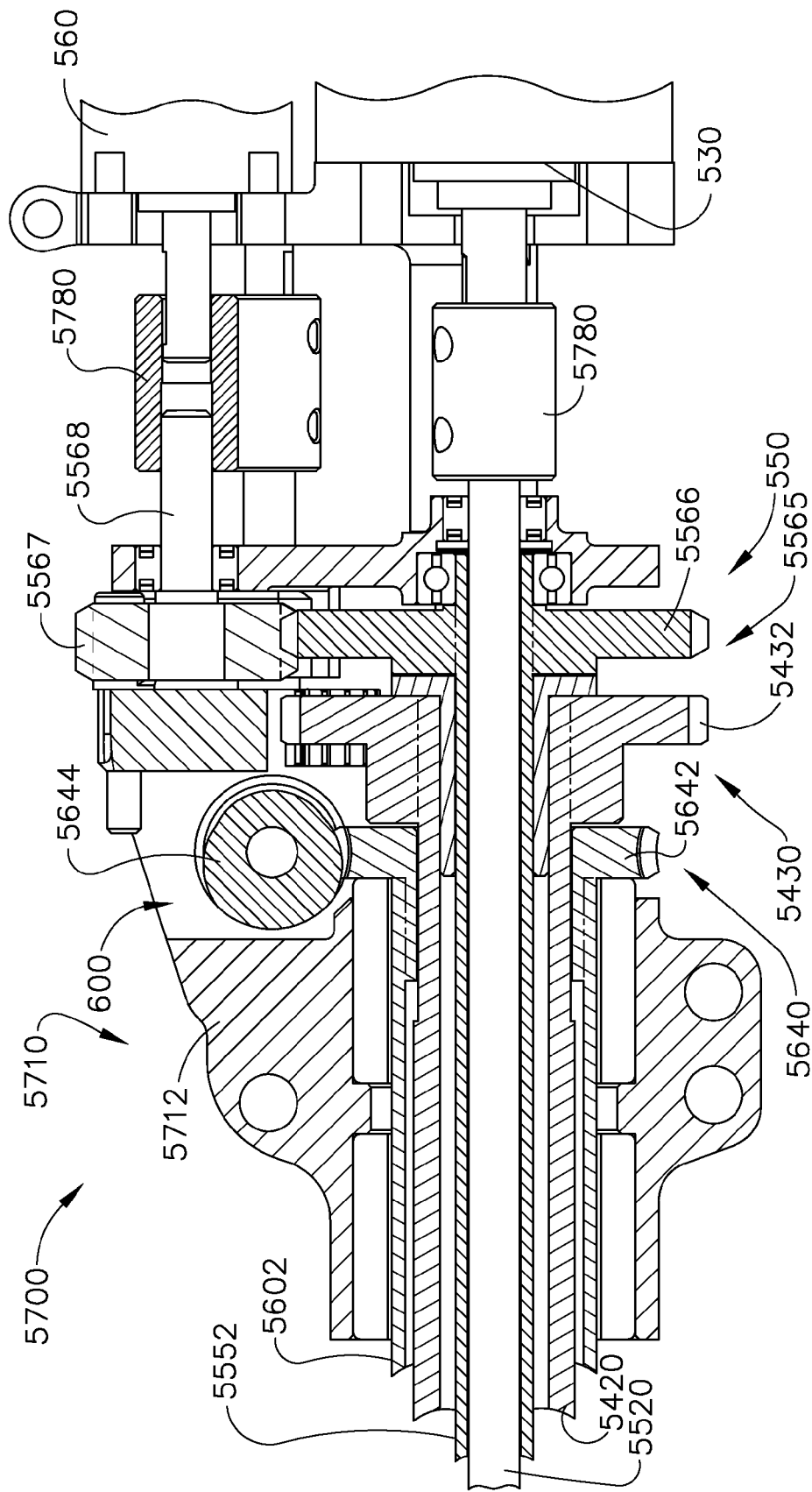
FIG. 103 is a cross-sectional view of the motor mounting assembly of FIGS. 100-102.
Figure 104:
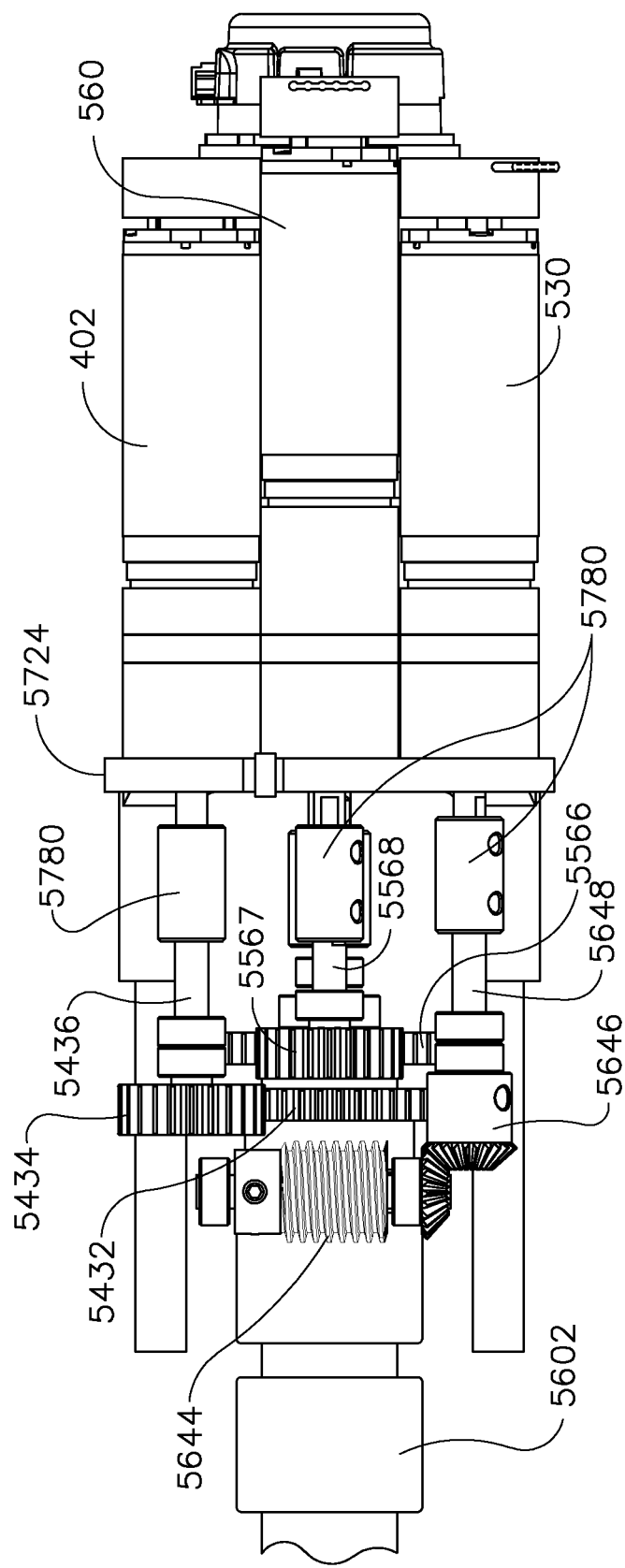
FIG. 104 is a top view of the motor mounting assembly of FIGS. 100-103.

FIGS. 100-103 illustrate an alternative drive mount 5700 that employs a collection of gear drives for transmitting drive motions from the motors to their respective shafts. As can be seen in FIG. 100, the drive mount 5700 may include a distal shaft housing assembly 5710 that includes a distal shaft housing 5712 that operably supports a plurality of gear train arrangements. The distal shaft housing 5712 is configured to be removably mounted to the proximal coupler bulkhead plate 5724 that has a pair of mounting sockets 5725 for receiving corresponding mounting lugs 5713 protruding from the distal shaft housing 5712 as can be seen in FIG. 100. As in the above described arrangements, the shaft of the firing or transection motor 530 is directly coupled to the proximal firing shaft segment 5520 by a coupler assembly 5780 as can be seen in FIG. 103. The proximal rotational shaft segment 5552 of the end effector rotation system 550 is rotated by a gear train, generally depicted as 5565. In at least one form, for example, the gear train 5565 includes a driven gear 5566 that is attached to the proximal rotational shaft segment 5552 and is supported in meshing engagement with a drive gear 5567. As can be most particularly seen in FIG. 103, the drive gear 5567 is mounted to a spur shaft 5568 that is rotatably supported in the distal shaft housing 5712. The spur shaft 5568 is coupled to the shaft of the end effector rotation or distal roll motor 560 by a coupler assembly 5780.

The proximal articulation shaft segment 5420 is rotated by a gear train, generally depicted as 5430. In at least one form, for example, the gear train 5430 includes a driven gear 5432 that is attached to the proximal articulation shaft segment 5420 and is supported in meshing engagement with a drive gear 5434. As can be most particularly seen in FIG. 102, the drive gear 5434 is mounted to a spur shaft 5436 that is rotatably supported in the distal shaft housing 5712. The spur shaft 5436 is coupled to the shaft of the articulation control motor 402 by a coupler assembly 5780.

The proximal outer shaft segment 5602 is rotated by a gear train, generally depicted as 5640. In at least one form, for example, the gear train 5640 includes a driven gear 5642 that is attached to the proximal outer shaft segment 5602 and is supported in meshing engagement with a compound bevel gear 5644 that is rotatably supported within the distal shaft housing 5712. The compound bevel gear 5644 is in meshing engagement with a drive bevel gear assembly 5646 that is mounted to a spur shaft 5648 that is also rotatably supported in the distal shaft housing 5712. The spur shaft 5648 is coupled to the shaft of the shaft rotation or proximal roll motor 610 by a coupler assembly 5780. See FIG. 101. The alternative drive mount 5700 motors and gear trains may be used to power and control the surgical instrument in the manners herein described.

Power and Control Systems

In various forms, the surgical instrument 10 may employ a control system generally designated as 800 for controlling the various motors employed by the instrument. The motors 402, 530, 560 and 610 and their related control components may also be referred to herein as a "drive system", generally designated as 398. In one form, the drive system 398 serves to "electrically generate" a plurality of control motions. The term "electrically generate" refers to the use of electrical signals to actuate a motor or other electrically powered device and may be distinguished from control motions that are manually or otherwise mechanically generated without the use of electrical current. In one form, the drive system 398 may be operably supported within a handle assembly that may be held in the hand or hands of the clinician. In other forms, however, the drive system 398 may comprise a part of and/or be operated by and/or be supported by a robotic system.

In one form, the motors 402, 530, 560 and 610 and their related control components may receive power from a battery 802 that is housed within the pistol grip portion 26 of the handle assembly 20. In other arrangements, the battery may be supported by a robotic system, for example. In other embodiments, however, the handle assembly 20 may have a power cord (not shown) protruding therefrom for supplying power from another source electrical power. In still other arrangements, the motors and electrical components may receive power and control signals from a robotic system. The control system 800 may comprise various control system components that may include, for example, a distal circuit board 810 that is supported on the detachable drive mount 700. The distal circuit board 810 may include electrical connectors 812 and/or electrical components that can be sterilized utilizing conventional steam sterilization techniques as well as by other lower temperature sterilization methods. The control system 800 may further include a proximal circuit board 820 that is supported in the portion of the handle assembly 20 formed by the handle housings segments 23 and 24. The proximal circuit board 820 is configured to be electrically coupled to the distal circuit board 810 when the detachable drive mount 700 has been coupled to the motor mounting assembly 750.

Figures 36, 37:
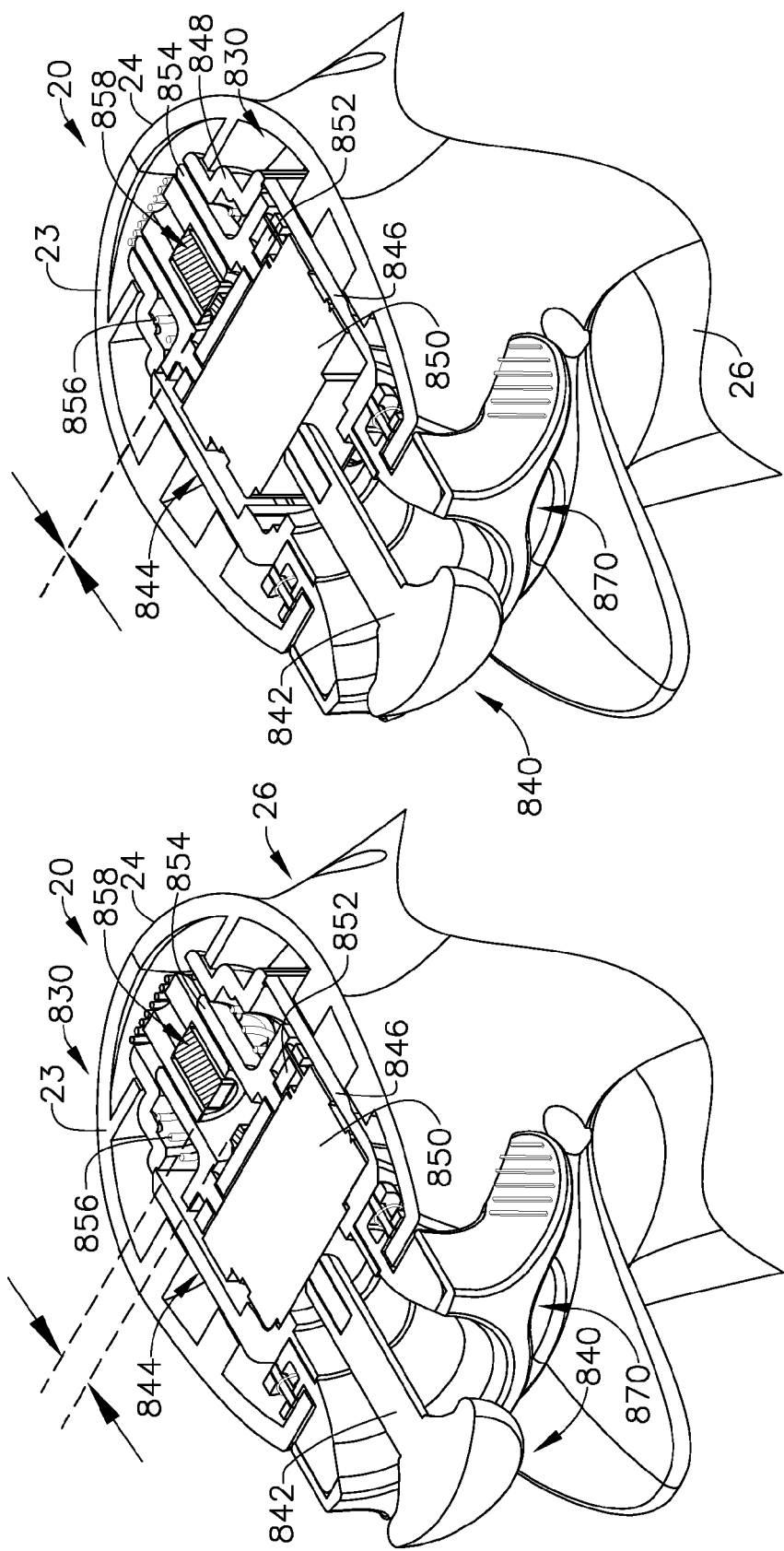
FIG. 36 is a cross-sectional view of portion of the switch arrangement of FIGS. 34 and 35 mounted with the handle assembly wherein the joy stick control portion is in an unactuated position.
FIG. 37 is another cross-sectional view of the switch arrangement of FIG. 36 with the joy stick control portion in an actuated position.
Figures 38, 39:
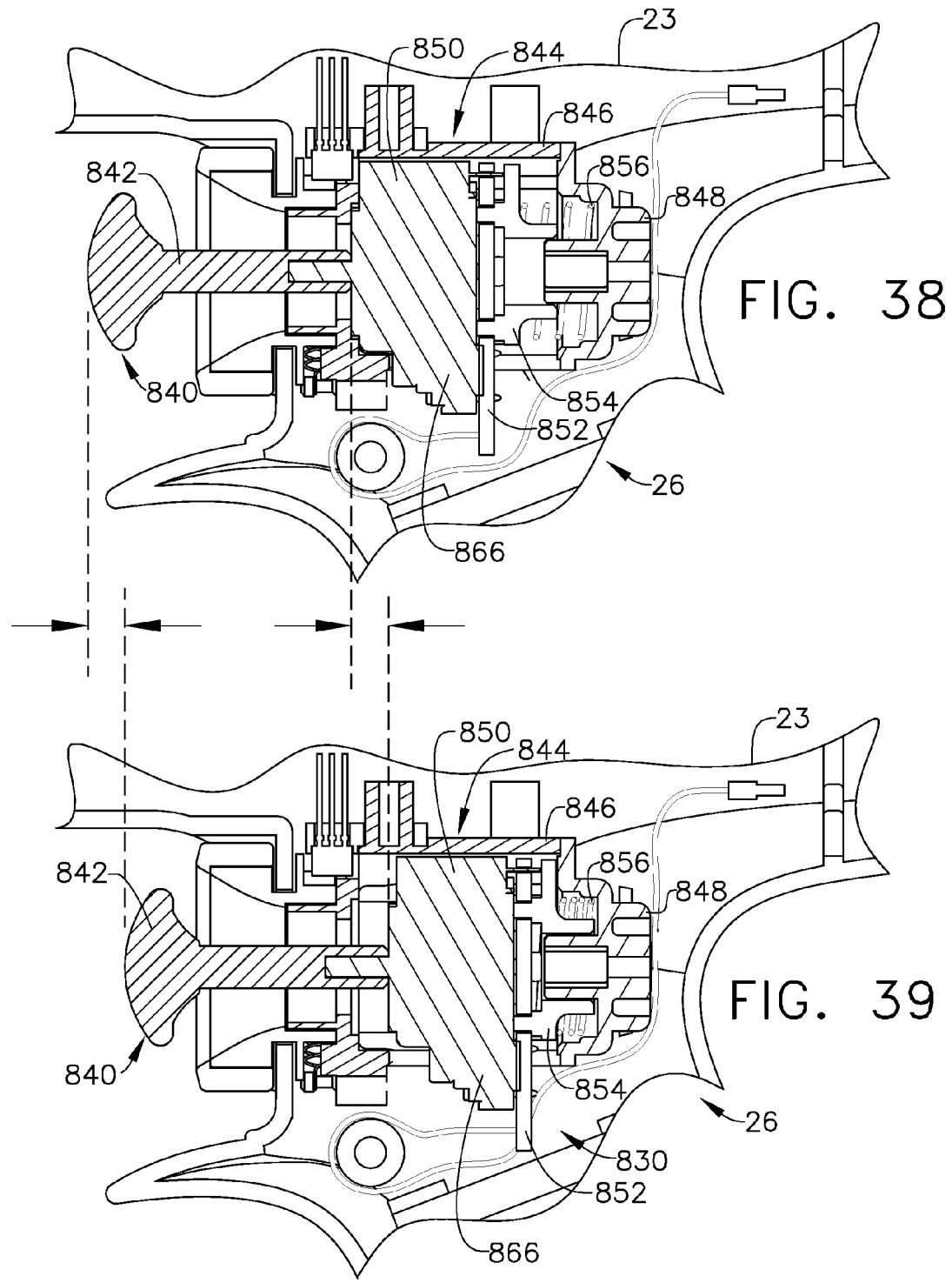
FIG. 38 is a side cross-sectional view of the switch arrangement of FIG. 36.
FIG. 39 is a side cross-sectional view of the switch arrangement of FIG. 37.
Figure 40:
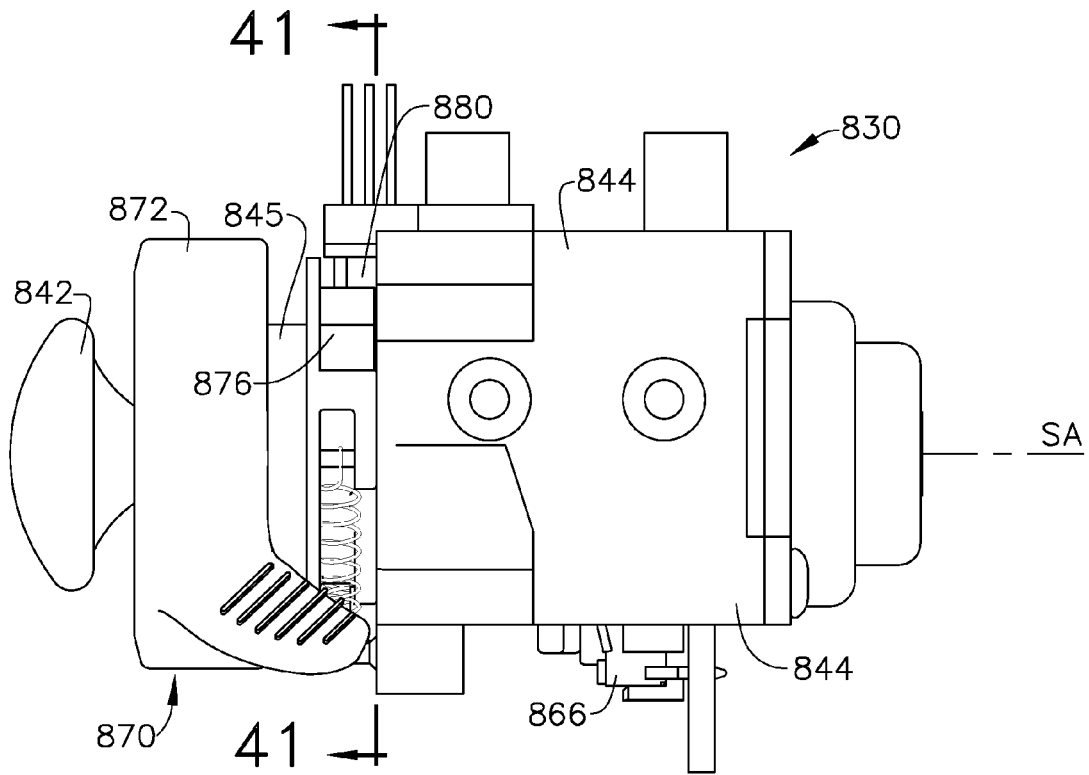
FIG. 40 is a side elevational view of the switch arrangement of FIGS. 34-39.

Various forms of the surgical instrument 10 may employ a unique and novel control switch arrangement 830 that may be operably housed within or supported by the pistol grip portion 26 of the handle assembly 20. For example, in at least one form, the control switch arrangement 830 may include a unique and novel joystick control 840 that enables the user to maximize functional control of various aspects of the surgical instrument 10 through a single interface. More specifically and with reference to FIGS. 33-39, one form of joystick control 840 may include a joystick control rod 842 that is operably attached to a joystick switch assembly 850 that is movably housed within a switch housing assembly 844. The switch housing assembly 844 may be mounted within the pistol grip portion 26 of the handle assembly 20. In at least one form, for example, the switch housing assembly 844 may include a housing body 846 and a rear housing plate 848. As can be most particularly seen in FIGS. 35-39, a joystick printed circuit board 852 may be operably supported on the joystick switch assembly 850 by a rear mounting plate 854. The rear mounting plate 854 may be configured to move as a unit with the joystick switch assembly 850 and joystick printed circuit board 852 within the switch housing 844. A joystick spring 856 may be supported between the rear housing plate 848 and the rear mounting plate 854 to bias the joystick switch assembly 850 and joystick control rod 842 in the forward or distal direction. See FIGS. 36 and 38.

The joystick control 840 may be electrically coupled to the proximal circuit board 820 and battery 802 of the control system 800 through various connector cables 864 for providing control power to the various motors 402, 530, 560, and 610 of the surgical instrument 10. For example, by rocking or otherwise actuating the joystick control rod 842, the user may control the articulation control motor 402 and/or the distal roll motor 560 and/or the proximal roll motor 610.

The joystick control switch assembly 850 may be referred to herein as a "first switch" for controlling one or more of the motors of the drive system. The joystick control 840 may further include a first sensor 860 which may comprise, for example, a magnet, that may be mounted to the joystick printed circuit board 852 for movable travel therewith. In addition, a second or stationary sensor 862 may be mounted within the rear housing plate 848. The second sensor 862 may comprise, for example, a "hall effect" sensor or similar sensing device. In at least one arrangement for example, the sensor 862 may be configured to communicate with the firing motor 530. The first and second sensors, 860, 862 may be referred to herein as a "second switch" generally designated as 858. The above-described arrangement allows the joystick switch assembly 850 to axially move in and out when the user depresses the joystick control rod 842. By leveraging the in and out motion of the entire joystick switch assembly 850, in at least one form, the design essentially consists of a switch within a switch. In an unactuated position, the joystick spring 856 biases the joystick switch assembly 850 in the forward (distal) direction. When the clinician pushes the joystick 842 inwardly (proximally), the first sensor 860 is moved closer to the second sensor 862. Moving the first sensor 860 closer to the second sensor 862 may result in the actuation of the so-called second switch 858 which may result in the actuation of the transection or firing motor 530.

When performing a procedure using an end effector 102, the clinician may wish to open and close the anvil assembly 190 to manipulate the target tissue into a desired position without transecting or cutting the tissue. In one form, as the clinician initially depresses the joystick control rod 842, the second switch 858 causes the firing motor 530 to be activated to thereby cause the tissue cutting member 160 to start to move distally. In various forms, the tissue cutting member 160 is arranged within the end effector 102 such that initial movement of the tissue cutting member 160 in the distal direction causes the anvil assembly 190 to close (i.e., pivot toward the staple cartridge 130 without cutting the tissue or firing the surgical staples). When the clinician releases the joystick control rod 842, the joystick spring 856 will bias the joystick assembly 850 distally to thereby move the first sensor 860 away from the second sensor 862. Movement of the sensor 860 away from the second sensor 862 may reduce the rotational speed of the firing motor 530 until the firing motor 530 is eventually stopped or deactivated. In at least one form, this second switch arrangement 858 may be configured such that the rotational speed of the firing motor 530 is directly proportional to the speed at which the user depresses the joystick control rod 842.

Once the clinician has positioned and captured the desired tissue within the end effector 102, the end effector 102 may be actuated or "fired" by fully depressing the joystick control rod 842. In various forms, the joystick switch assembly 850 may also have a third compression switch 866 integrally formed therein and which also communicates with the control system 800. Full depression of the joystick control rod 842 may result in the activation of the third switch 866. In at least one form, when the third switch 866 is activated, the firing motor 530 will remain activated even when the clinician releases the joystick control rod 842. After the firing stroke has been completed (i.e., the tissue cutting member 160 has been driven to its distal-most position in the end effector 102), the user may again fully depress the joystick control rod 842 to release the third switch 866 and thereby return control of the firing motor 530 to the second switch 858. Thus, if the clinician releases the joystick control rod 842 after completely depressing it for the second time, the joystick spring 856 will bias the joystick switch assembly 850 to the starting position. The control system 800 will cause the firing motor 530 to rotate in an opposite direction until the tissue cutting member 160 has been returned to its starting position whereby the anvil assembly 190 is once again moved to an open position to enable the end effector 102 to release the transected tissue.

Figure 41:
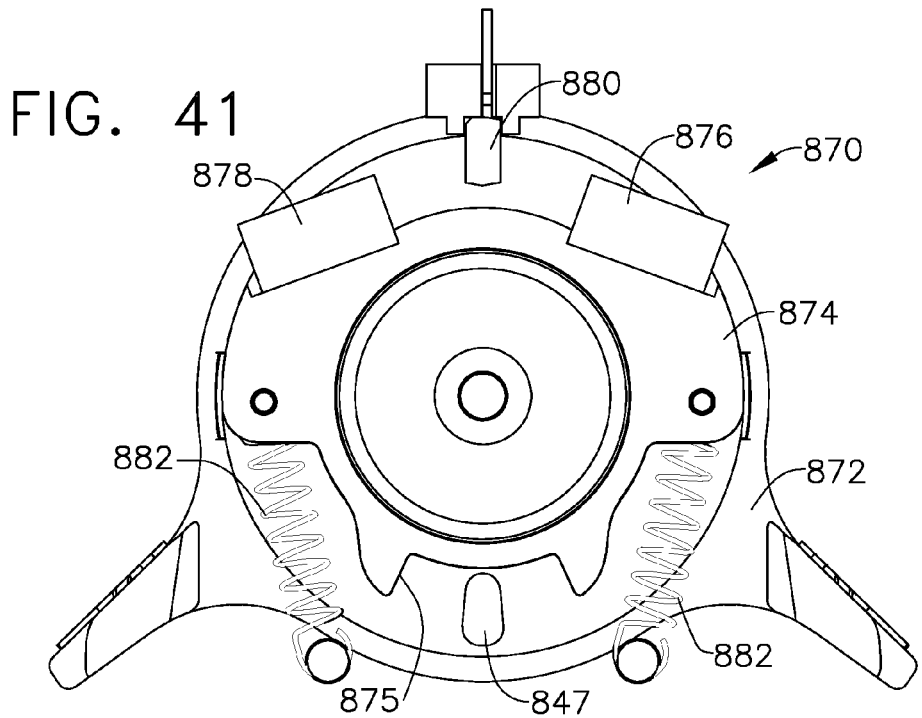
FIG. 41 is a front elevational view of the switch arrangement of FIGS. 34-40.
Figure 42:
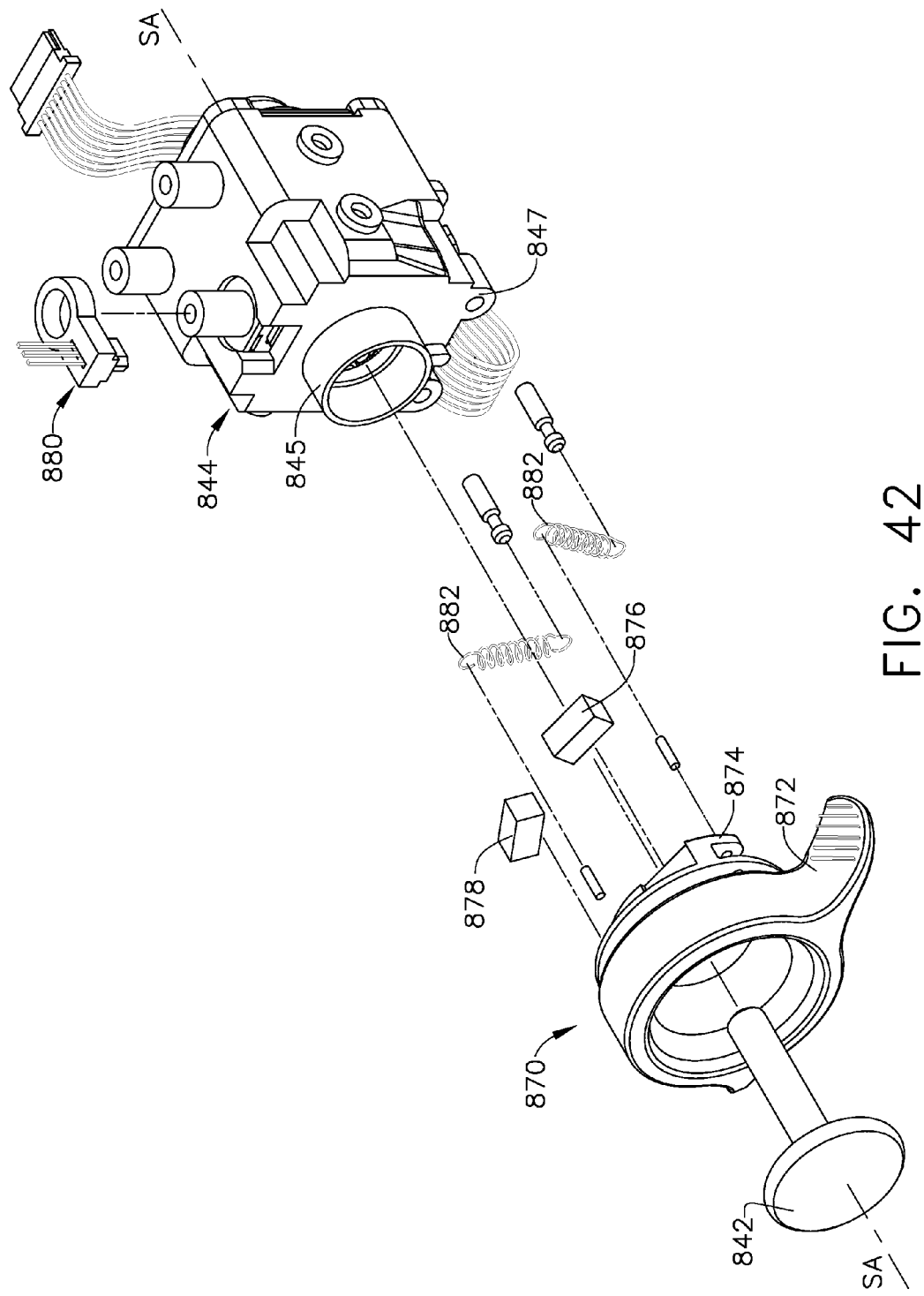
FIG. 42 is another exploded assembly view of the switch arrangement of FIGS. 34-41.

In various forms, the switch arrangement 830 may also employ a unique and novel thumbwheel control assembly 870. As can be seen in FIG. 42, the thumbwheel control assembly 870 may be rotatably mounted on a distally protruding hub portion 845 of the switch housing assembly 844 such that the thumbwheel control assembly 870 is pivotable about a switch axis SA-SA. Such position conveniently places a thumbwheel actuator member 872 of the thumbwheel control assembly 870 in a position wherein the clinician can pivot it with a thumb and/or index finger while grasping the pistol grip portion 26 of the handle assembly 20. The thumbwheel actuator member 872 may be attached to a thumbwheel collar 874 that is received on the hub portion 845 and may be rotatably retained in position by a mounting flange 27 formed by the handle segments 23 and 24. A left sensor (magnet) 876 and a right sensor (magnet) 878 are mounted to the thumbwheel collar 874 as shown in FIG. 41. The sensors 876 and 878 may have opposing polarities. A stationary sensor 880 may be mounted to the switch housing assembly 844 such that it is centrally disposed between the left sensor 876 and the right sensor 878. The stationary sensor 880 may comprise, for example, a "hall effect" sensor and be coupled to the proximal circuit board 820 of the control system 800 for controlling one of the control motors. For example, the thumbwheel control assembly 870 may be used to control, for example, the proximal roll or shaft rotation motor 610. In other arrangements, the thumbwheel control assembly 870 may be used to control the distal roll motor 560 to rotate the end effector about the shaft axis relative to the elongate shaft assembly. A pair of centering springs 882 may be employed to bias the thumbwheel collar 874 into a central or neutral position. When the thumbwheel collar 874 is in the neutral position as shown in FIG. 41, the shaft rotation or proximal roll motor 610 (or distal roll motor 560—whichever the case may be) is deactivated.

Figure 43:
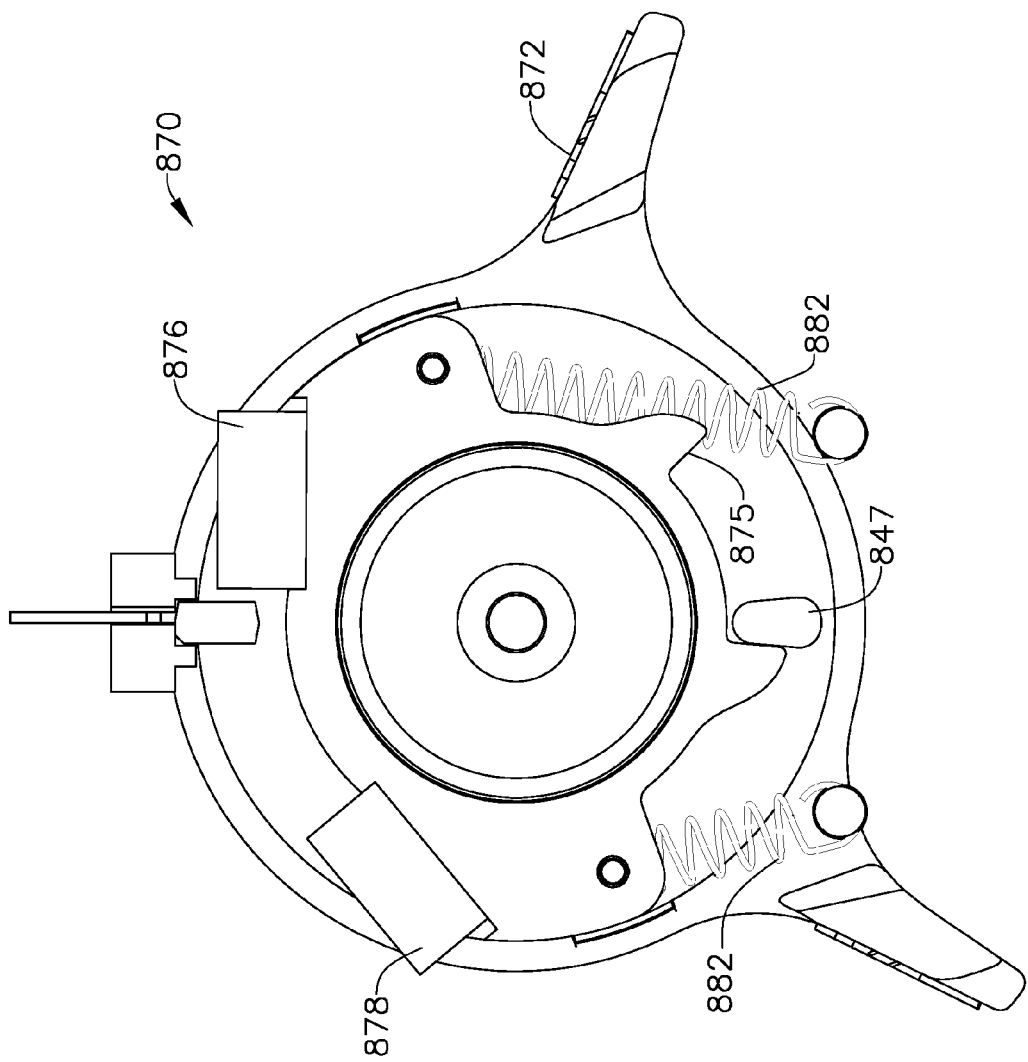
FIG. 43 is a rear elevational view of a thumbwheel paddle control assembly arrangement in an actuated position.
Figure 44:
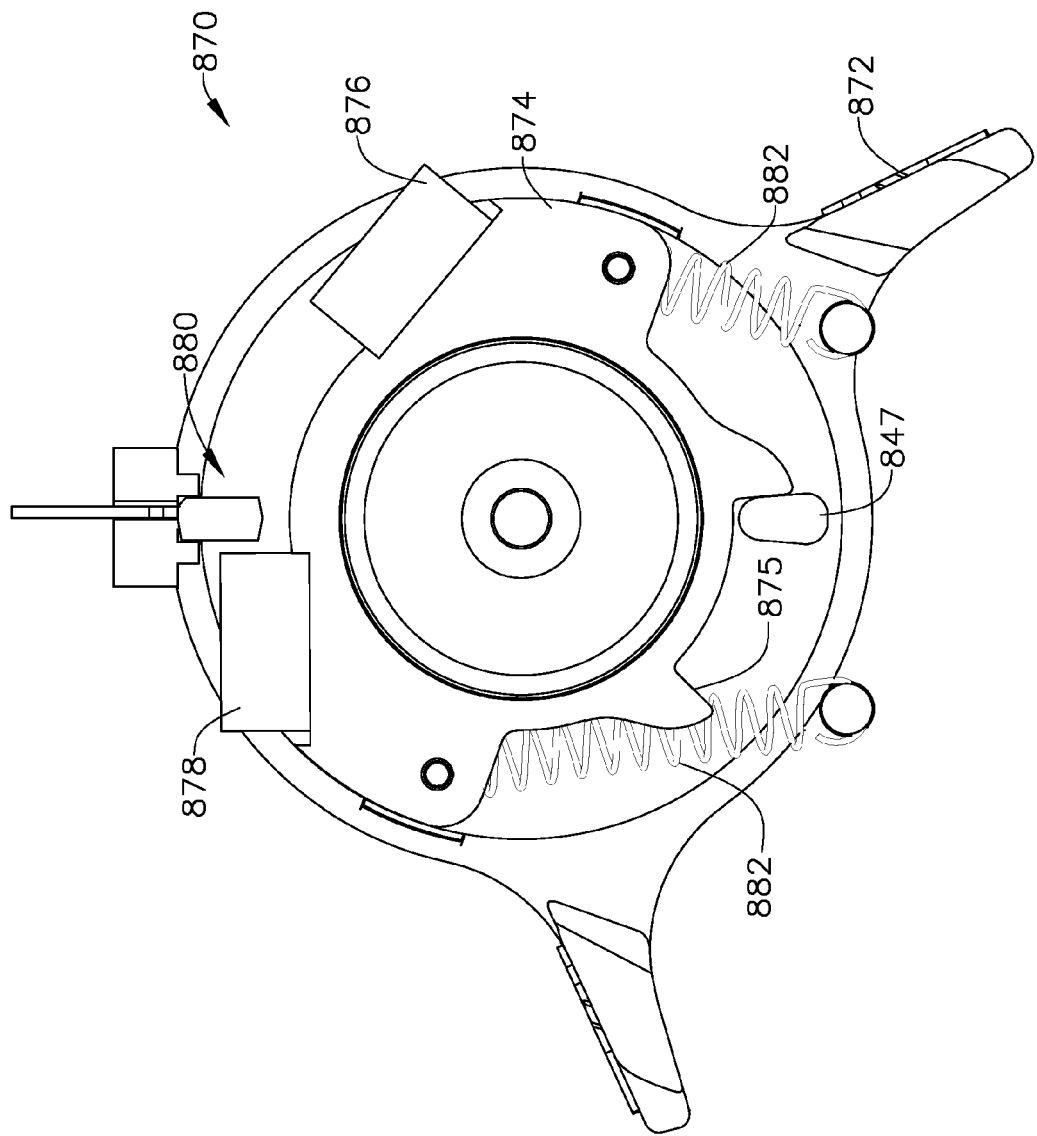
FIG. 44 is another rear elevational view of the thumbwheel paddle control assembly arrangement in another actuated position.

As the user pivots the thumbwheel actuator 872 in a clockwise direction to a position shown in FIG. 43, the control system 800 may cause the shaft rotation motor 610 to rotate the elongate shaft assembly 30 about the shaft axis A-A in a clockwise direction. Likewise, when the user pivots the thumbwheel actuator 872 in a counterclockwise direction to the position shown in FIG. 44, the control system 800 may cause the shaft rotation motor 610 to rotate the elongate shaft assembly 30 in the counterclockwise direction about the shaft axis A-A. Stated another way, as the user pivots the thumbwheel actuator 872 clockwise or counterclockwise, the stationary sensor 880 controls the rotational direction of the elongate shaft assembly 30 based upon the proximity of the left and right sensors 876, 878 in relationship to the stationary sensor 880. The response of the stationary sensor 880 can be configured so that, as the user increases rotation of the thumbwheel actuator 872, the relative speed that the motor 610 rotates the elongate shaft assembly 30 increases. As can be seen in FIGS. 41-44, a stop lug 847 may be formed on the switch housing assembly 844 to cooperate with a notch 875 in the thumbwheel collar to prevent contact between the movable sensors 876, 878 and the stationary sensor 880. Those of ordinary skill in the art will understand that the thumbwheel control assembly 870 may be used to control any of the other motors of the surgical instrument 10. Similarly, the joy stick control 840 may be configured to control any one or more of the motors in the surgical instrument 10. The unique and novel thumbwheel control assembly arrangements disclosed herein enable the user to have functional control through rotation of an ergonomic thumbwheel actuator interface. In alternative forms, the movable sensors 876, 878, may comprise hall effector sensors that each communicate with the motor. The stationary sensor 880 may comprise a magnet.

Figure 29:
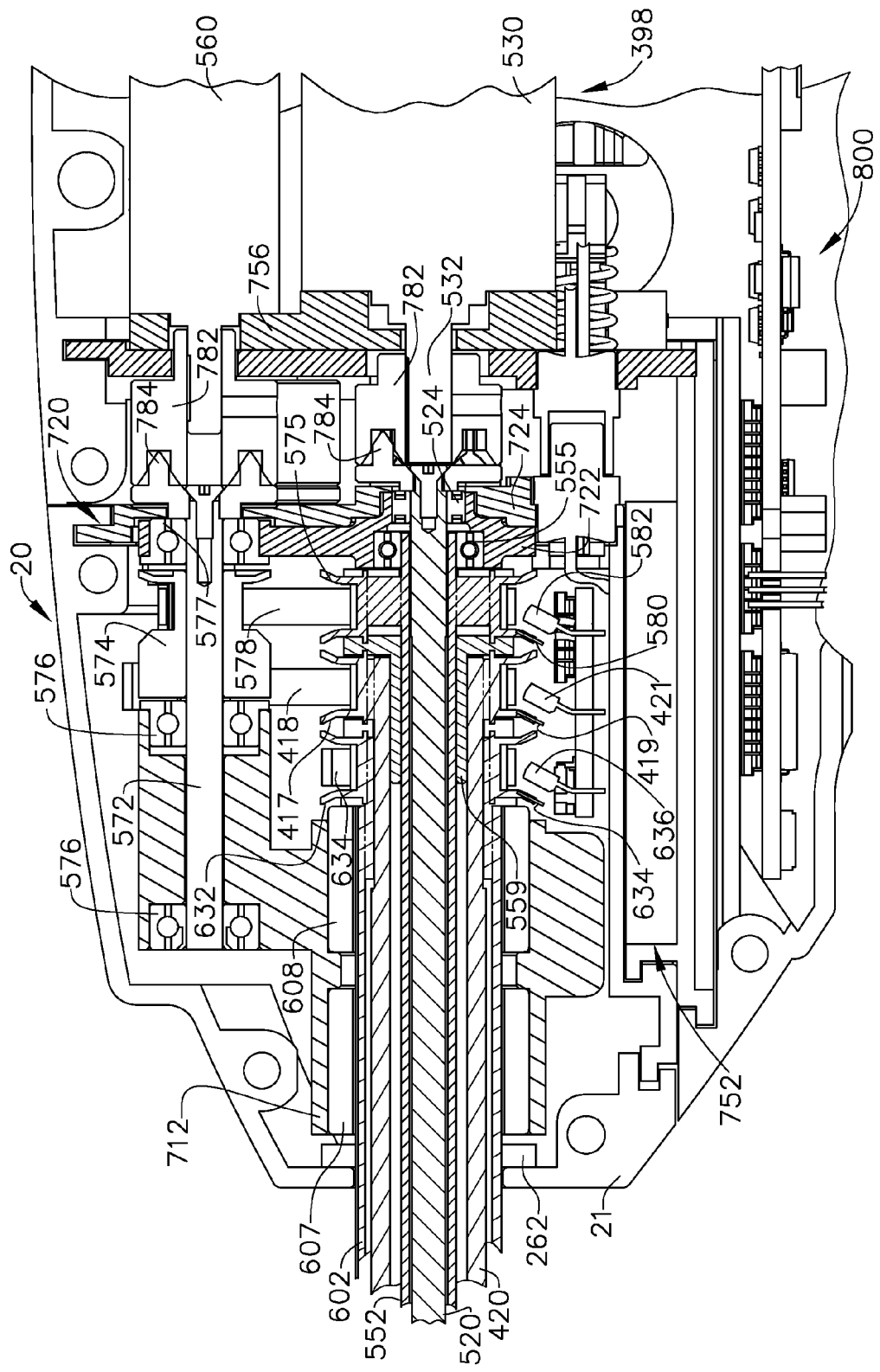
FIG. 29 is a cross-sectional view of a portion of a handle assembly arrangement.

In various forms, each of the motors of the surgical instrument 10 may be provided with a corresponding encoder that communicates with a microprocessor chip on the proximal circuit board 820. For example, the articulation control motor 402 may have an encoder 404 operably coupled thereto that communicates with the proximal circuit board 820. The firing or transection motor 530 may have an encoder 534 operably coupled thereto that communicates with the proximal circuit board 820. The end effector rotation or distal roll motor 560 may have an encoder 564 operably coupled thereto that communicates with the proximal circuit board 820. The shaft rotation or proximal roll motor 610 may have an encoder 614 operably coupled thereto that communicates with the proximal circuit board 820. The encoders may serve to provide the corresponding microprocessor chips with feedback regarding the number of rotations and direction of rotation for each of the motors. In some forms, in addition to the encoders, the rotation drive assembly 570 may employ sensor arrangements to track the rotation of the various shaft segments. For example, as can be seen in FIGS. 15, 28, and 29, the articulation drive pulley 417 may have a first articulation sensor 419 mounted thereto that is adapted to be detected by a second articulation sensor 421 which may comprise, for example, a hall effect sensor, that is mounted to the distal circuit board 810. The first and second articulation sensors 419, 421 serve to provide an additional means of feedback for tracking the rotatable position of the proximal articulation shaft 420. Likewise, the distal roll pulley 575 of the rotation drive assembly 570 may have a first distal roll sensor 580 mounted thereto that is adapted to be detected by a second distal roll sensor 582 that is mounted to the distal circuit board 810. See FIGS. 24, 28, and 29. The first and second distal roll sensors 580, 582 serve to provide an additional means of feedback for tracking the rotatable position of the proximal rotation shaft segment 552. In addition, the pulley 632 of the proximal roll drive assembly 620 may have a first proximal roll sensor 634 that is adapted to be detected by a second proximal roll sensor 636 mounted to the distal circuit board 810. See FIGS. 26, 28, and 29. The first and second proximal roll sensors 634, 636 serve to provide an additional means of feedback for tracking the rotatable position of the proximal outer shaft segment 602.

Conductive Pathways from End Effector to Handle Assembly

As discussed herein, various forms of the surgical instrument 10 may be effectively employed with a variety of different end effectors or surgical implements that require or employ rotary or other motions for end effector/implement operation/manipulation. For example, one form of the end effector 102 requires rotary control motions to open and close the anvil assembly 190, drive the surgical staples and transect tissue. One form of the end effector 102 may also be equipped with a distal sensor arrangement for sensing a degree or amount of closure attained by the anvil assembly 190 relative to the surgical staple cartridge 130. For example, the anvil assembly 190 may include a first anvil sensor 890 that is mounted in the distal end thereof. See FIG. 3. The anvil sensor 890 may comprise, for example, a hall effector sensor that is configured to detect a second staple cartridge sensor (magnet) 892 mounted in the distal end of the surgical staple cartridge 130. In at least one form, the first anvil sensor 890 may communicate with at least one an end effector conductor 894 that is mounted on the anvil assembly 190 as shown. In one form for example, the end effector conductor 894 comprises a flat metal strip that has a flexible hook 896 formed on the proximal end thereof. As generally used herein, the terms "conductor" or "conductive" refer to a member or component that is capable of conducting electricity therethrough. A conductor, for example, may comprise wire or wires, flexible conductive strips or metal traces, multi-channel conductive ribbon cable, etc. As used herein, the terms "electrically contacts" and "electrically communicates with" means that the components are configured to pass electrical current or signals therebetween.

Figure 45:
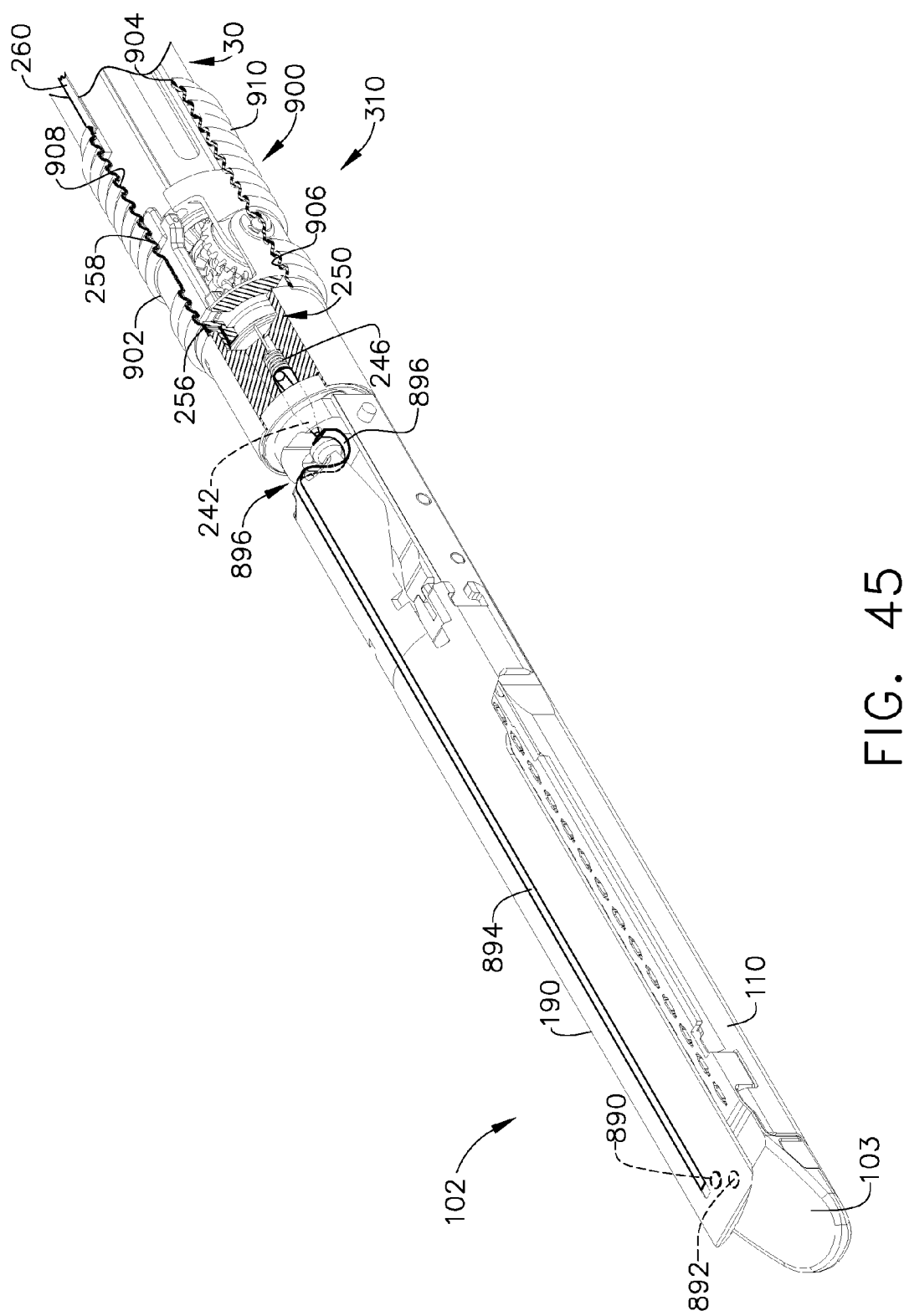
FIG. 45 is another partial cross-sectional view of an end effector and elongate shaft assembly arrangement.
Figure 46:
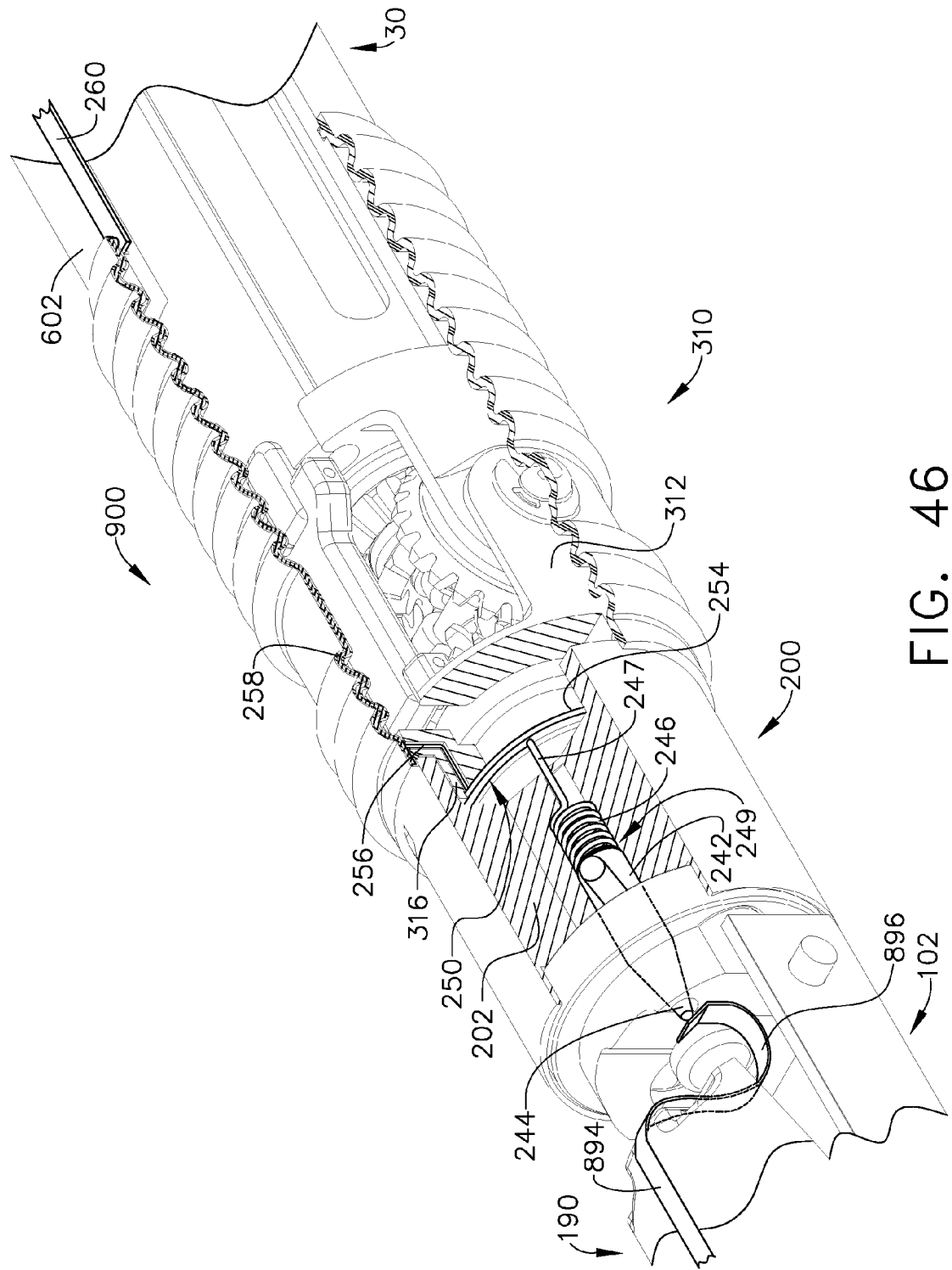
FIG. 46 is an enlarged cross-sectional view of a portion of an articulation joint arrangement and coupler assembly arrangement with an end effector coupled thereto.

Referring now to FIGS. 45 and 46, it can be seen that the flexible hook 896 may be oriented for contact with the distal end 244 of the locking pin 242. The locking pin 242 may, for example, be constructed from electrical conductive material and be coated with an insulative coating (e.g., polymer, etc.) to electrically insulate the locking pin 242 from the coupler housing segment 202 but have an exposed tip configured to make electrical contact with the hook 896. In addition, the locking spring 246 may also be fabricated from an electrical conductive material (e.g., metal). The locking spring 246 may be attached (e.g., soldered, etc.) to the locking pin 242 such that the locking pin 242 and locking spring 246 form an electrically conductive coupler pathway for conducting electrical current through the coupler assembly 200. The locking spring 246 may also be coated with an insulative coating to electrically insulate it from the coupler housing segment 202. The locking pin 242 and the locking spring 246 may be collectively referred to herein as a "locking pin assembly" 249. The locking spring 246 may terminate in a proximal end 247 that is configured for slidable electrical contact with a proximal conductor assembly 250 that is mounted to the distal clevis 312 of the articulation joint 310.

Figure 8:
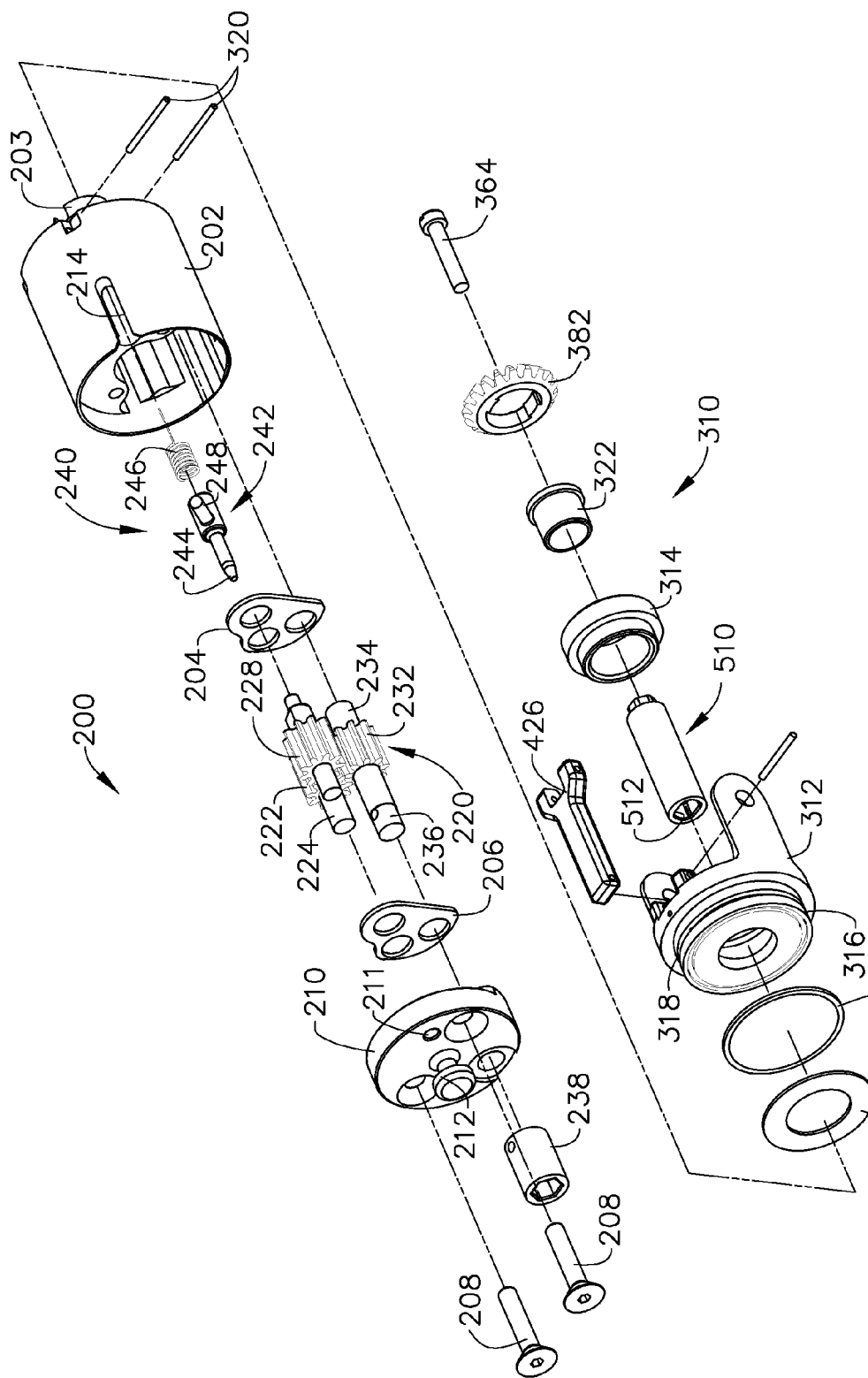
FIG. 8 is an exploded assembly view of the coupler assembly of FIG. 7.

As can be seen in FIG. 8, one form of proximal conductor assembly 250 may include conductor wire/wires/trace 252 and an annular electrical conductor in the form of, for example, a conductive washer 254. As can be seen in FIG. 46, the conductor 252 communicates with a proximal conductor portion 256 that protrudes out through the distal clevis 312 to communicate with an articulation joint conductor 258 supported by a flexible joint cover 900 that extends over the articulation joint 310. In at least one form, the joint cover 900 includes a hollow body 902 that has an open proximal end 904 and an open distal end 906 and a joint receiving passage 908 extending therebetween. The hollow body 902 may contain a plurality of ribs 910 and be fabricated from a polymer or similar non-electrically-conductive material that is omni-directionally stretchable to accommodate movement of the articulation joint components. However, the joint cover 900 could also be fabricated from other suitable materials and arrangements such as flexible micro-cut tubing, etc. The articulation joint conductor 258 may comprise for example, a conductive ribbon cable, wire, wires, trace, etc. As can be further seen in FIG. 46, a proximal end of the articulation joint conductor 258 is electrically coupled to a shaft conductor 260 on the proximal outer shaft segment 602.

Figure 47:
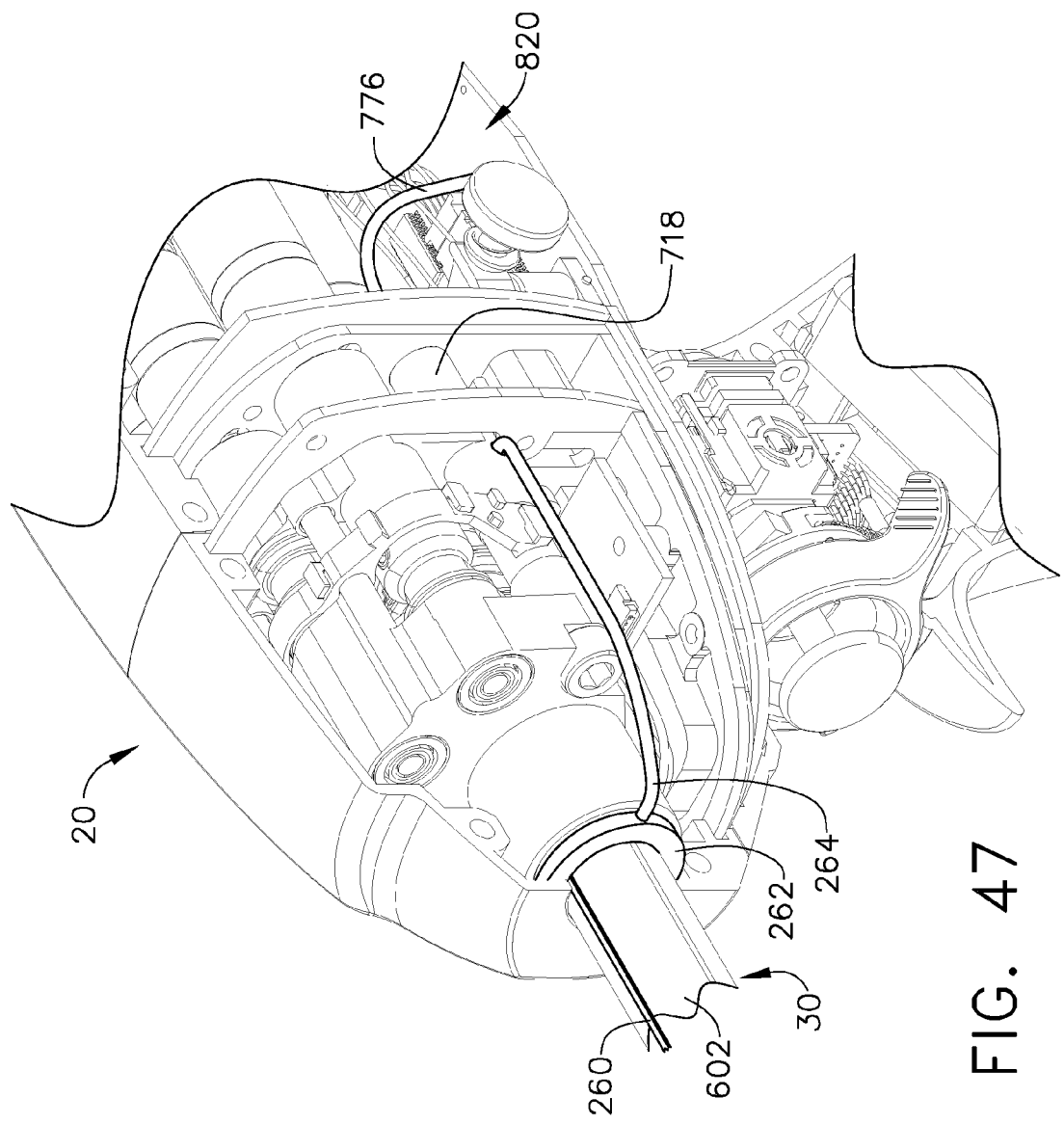
FIG. 47 is a perspective view of a portion of the handle assembly arrangement with a portion of the handle housing removed.
Figure 48:
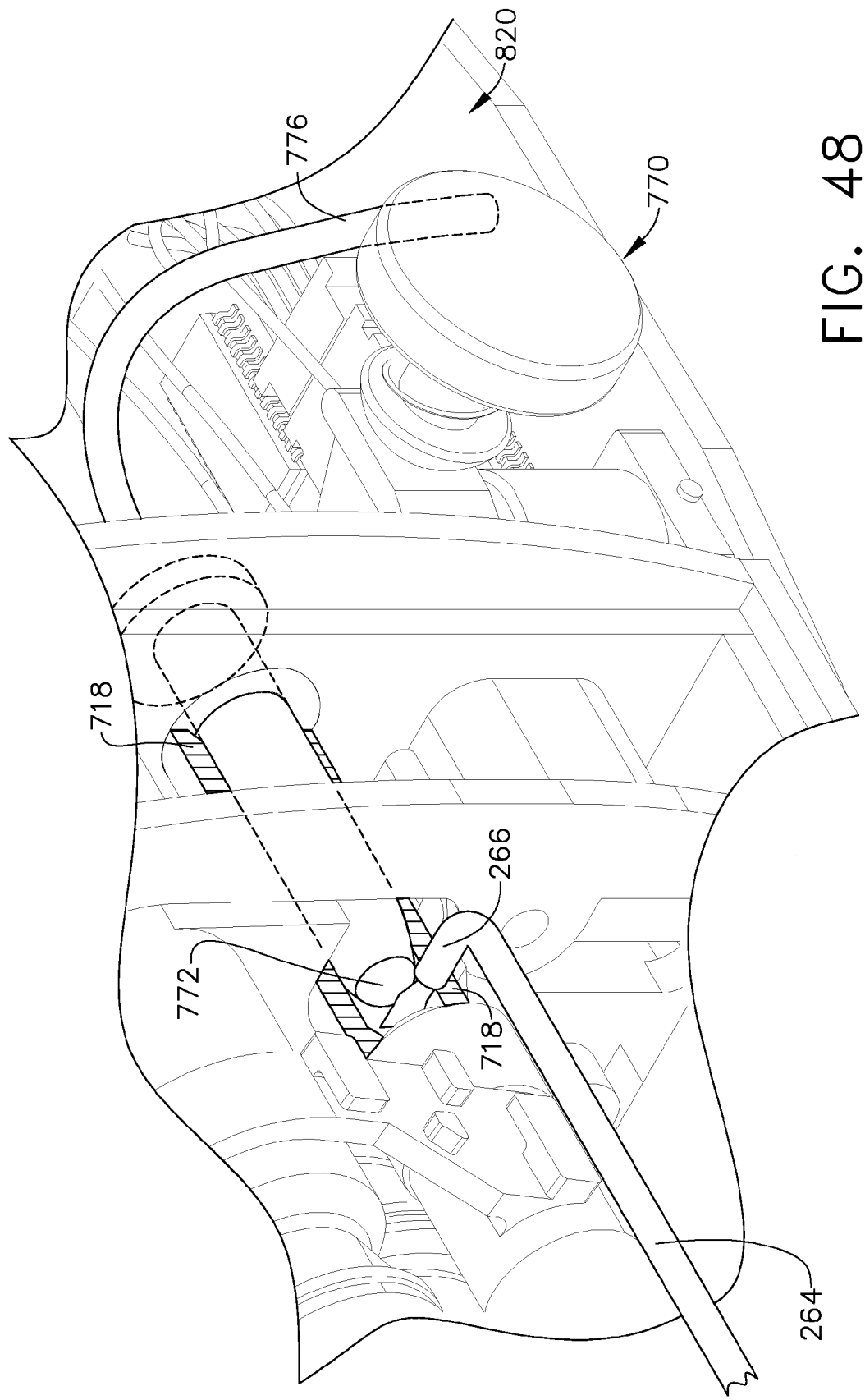
FIG. 48 is an enlarged perspective view of a portion of a handle assembly illustrating a conductor coupling arrangement.

Referring now to FIGS. 47 and 48, in at least one form, the proximal end of the shaft conductor 260 may be oriented for sliding contact with an annular conductor ring 262 that is mounted in the handle assembly 20. Such arrangement may enable electrical current to flow between the shaft conductor 260 and the conductor ring 262 as the elongate shaft assembly 30 is rotated about the shaft axis A-A relative to the handle assembly 20. As can be further seen in FIGS. 47 and 48, a conductor 264 is coupled to the conductor ring 262 and extends proximally through the handle housing 20. The conductor 264 may comprise a wire or other suitable electrical conductor and have a proximal end 266 that is configured to flexibly contact the tip of the left locator pin 774. In particular, for example, the proximal end 266 may extend through the wall of the left locator socket 718 such that when the left locator pin 774 is inserted therein, the proximal end portion 266 of the conductor 264 makes contact with the left locator pin 774. In at least one form, the left locator pin 774 is fabricated from electrically conductive material (metal) such that when the proximal end 266 of the conductor 264 makes contact therewith, electrical current can flow between those components. In addition, an attachment conductor 776 serves to electrically couple the left locator pin 774 to the proximal circuit board assembly 820 to facilitate transfer of electrical current therebetween.

The above-described arrangement facilitates the passage of electrical current between the end effector or surgical implement that has been attached to the elongate shaft assembly 30 of the surgical instrument 10 and the control system components located in the handle assembly 20 of the surgical instrument 10. This conductive pathway is maintained while also maintaining the ability to rotate the end effector relative to the elongate shaft assembly, articulate the end effector relative to the elongate shaft assembly and rotate the end effector and elongate shaft assembly as a unit. The joint cover 900 may provide an electrical communication path between the elongate shaft and the end effector. The joint cover 900 may contain an electrical flex strip, wire, trace, etc. to conduct more than one signal for electrical communication. Thus, a plurality of different sensors or electrical components may be employed in the end effector to provide various forms of feedback to the user. For example, sensors may be employed determine the number of use cycles, track the progress of the cutting instrument within the end effector during firing, provide feedback to the control system to automatically control the various motors in the handle assembly, etc.

Figure 49:
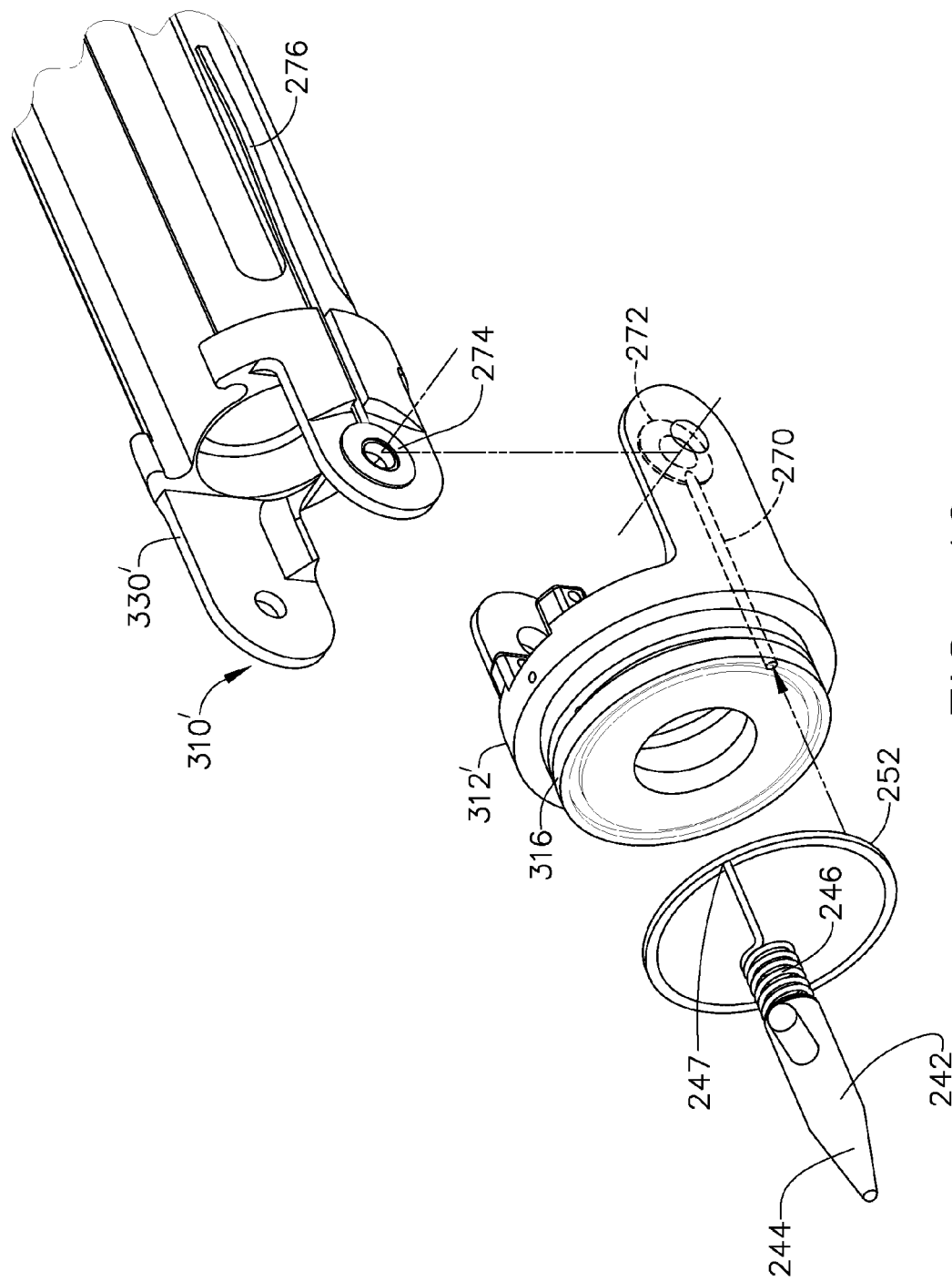
FIG. 49 is an exploded perspective view of a portion of another coupler assembly arrangement and articulation joint arrangement.
Figure 50:
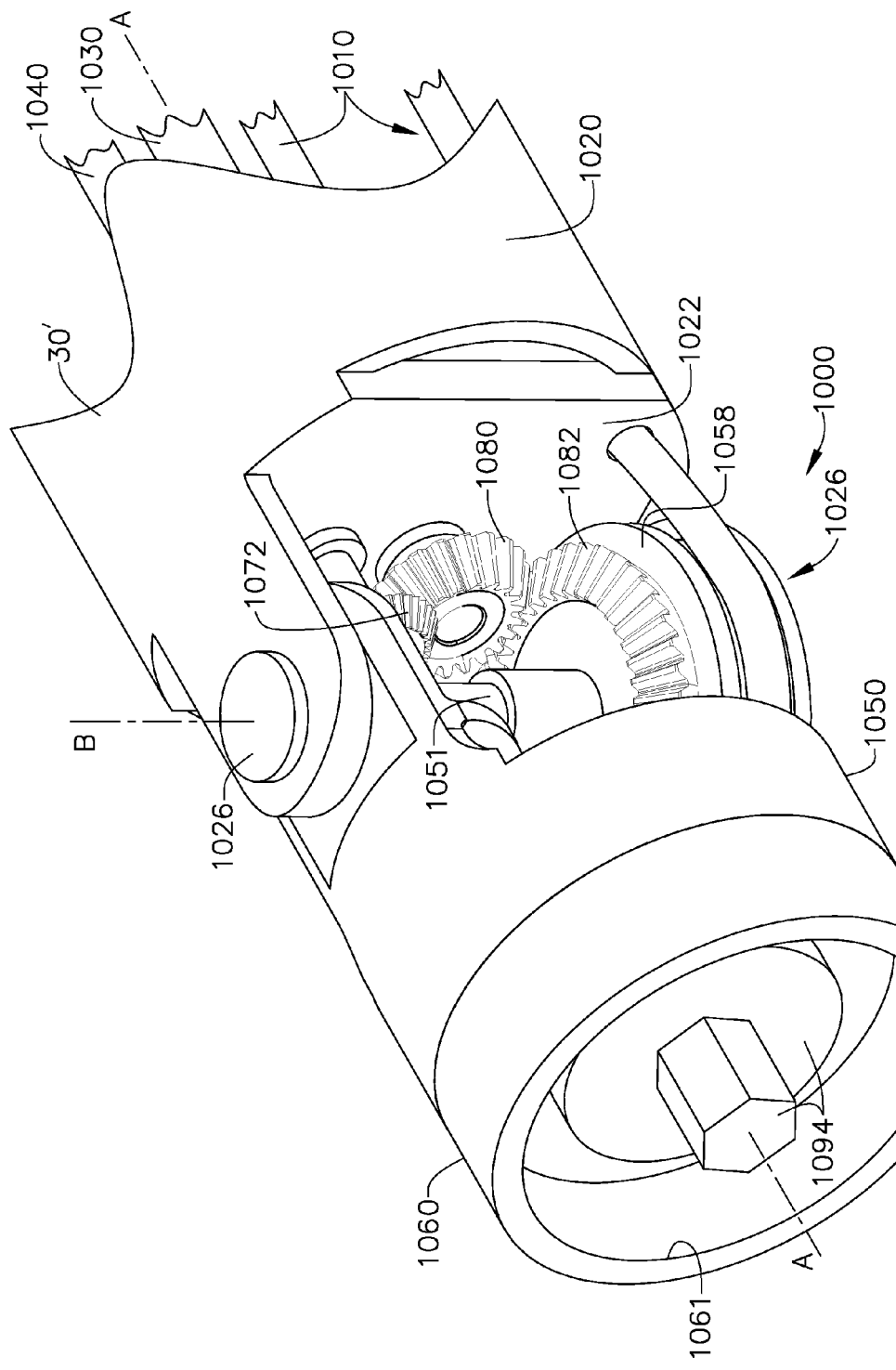
FIG. 50 is a perspective view of another articulation joint arrangement of the present invention.
Figure 51:
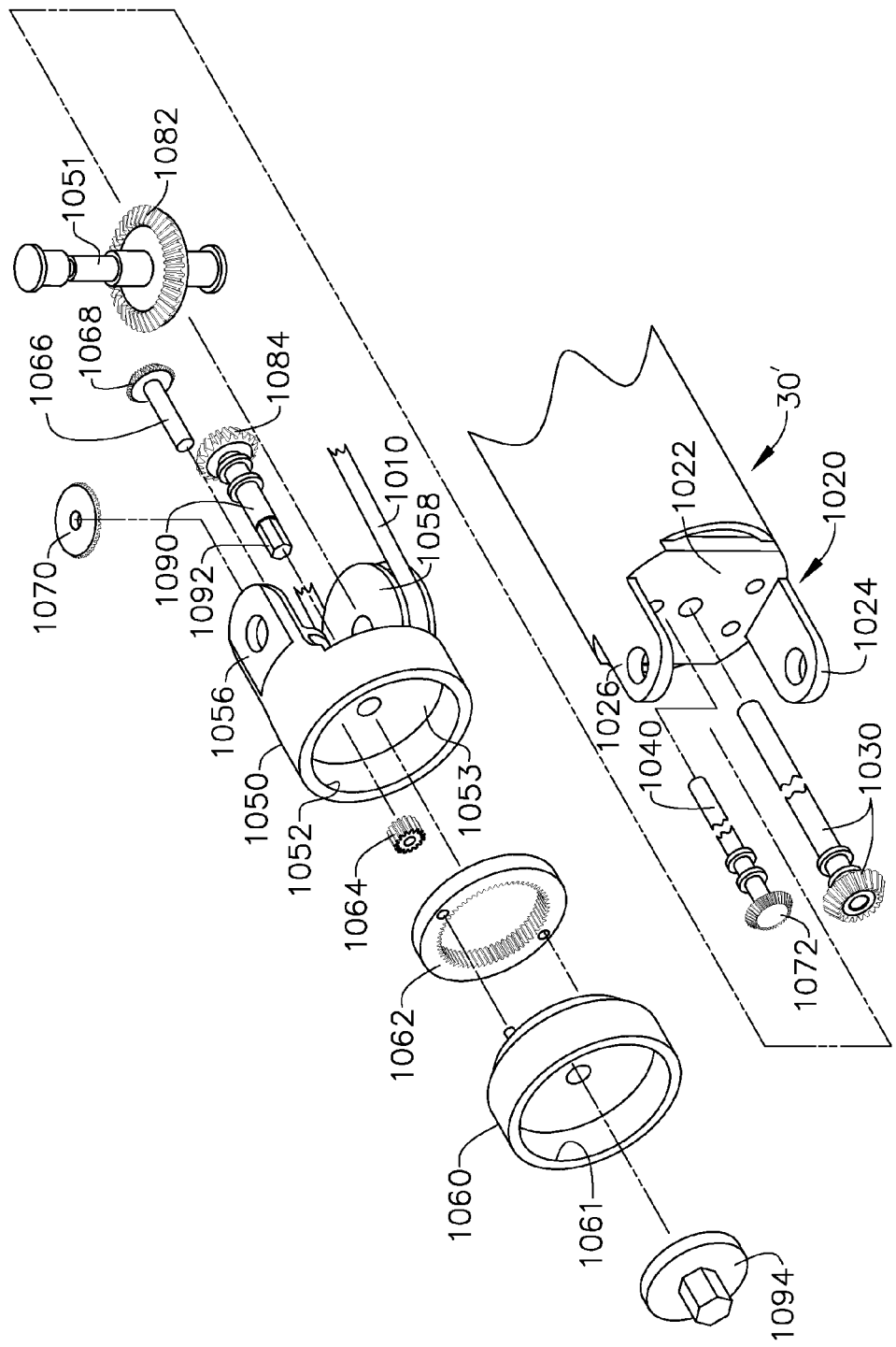
FIG. 51 is an exploded assembly view of the articulation joint arrangement of FIG. 50.

FIG. 49 illustrates an alternative articulation joint 310' that is configured to permit the passage of electrical current or signals therethrough. In this form, a distal electrical joint conductor 270 is provided through the distal clevis 312' to contact a distal metal washer 272 embedded therein as shown. The proximal clevis 330' may have a proximal metal washer 274 mounted thereto for rotational contact with the distal metal washer 272 when the distal clevis 312' is coupled to the proximal clevis 330'' in the manner described above. The proximal metal washer 274 may be curved or beveled to maintain sliding contact between the washers 272, 274. A proximal electrical joint conductor 276 in the form of, for example, a contactor strip, wire or trace is attached to the washer 274 and is configured for electrical contact with the shaft conductor 260 on the proximal outer shaft segment 602. Thus, such arrangement facilitates the passage of electrical current/signals from the end effector 102 through the locking pin 242, locking spring 242 (i.e., the locking pin assembly 249), conductor ring 252, distal electrical joint conductor 270, washers 272, 274 and the proximal electrical joint conductor 276 to the shaft conductor 260.

Alternative Articulation Joint Arrangements

Another form of articulation joint 1000 is shown in FIGS. 50-53. Such articulation joint 1000 can facilitate the articulation and rotation of an end effector or surgical implement coupled thereto relative to the shaft axis A-A of the elongate shaft to which the articulation joint 1000 is attached. The articulation joint may also facilitate such movement of the end effector or surgical implement while also providing a rotary control motion to the end effector/implement for actuation or manipulation thereof. The articulation joint 1000 may be coupled to an elongate shaft assembly that is similar in construction to the elongate shaft assembly 30 described above or it may be coupled to other suitable shaft assemblies. The elongate shaft assembly may be coupled to a handle assembly that houses a plurality of motors. One motor may be used to apply control motions to a flexible cable member 1010 that extends through the elongate shaft assembly and which is operably coupled to the articulation joint 1000. For example, the flexible cable 1010 may be attached to a sheave or pulley assembly that is operably attached to or communicates with the shaft of a corresponding motor such that operation of the motor causes the cable 1010 to be actuated. The handle assembly may also include a firing motor that is operably attached to a proximal firing shaft 1030 that extends through the elongate shaft assembly to interface with the articulation joint 1000 as will be discussed in further detail below. The handle assembly may also include a motor that operably interfaces with an end effector or distal roll shaft 1040 that transmits a rotary control motion to the articulation joint 1000 which may be used to rotate the end effector or surgical implement about the shaft axis A-A relative to the elongate shaft. The handle assembly may also include a proximal roll motor that is employed to rotate the elongate shaft assembly about the shaft axis A-A in the manner described above.

In at least one form, the articulation joint 1000 may include a proximal clevis assembly 1020 that is attached to or formed on the end of the elongate shaft assembly. In the arrangement shown in FIGS. 50-53, the proximal clevis assembly 1020 is formed on a distal end of the elongate shaft assembly 30'. As can be seen in those Figures, the proximal clevis assembly 1020 has a distal end wall 1022 and a pair of spaced clevis arms 1024, 1026. The proximal clevis 1020 is configured to be pivotally coupled to a distal clevis 1050 by a pivot shaft 1051 which serves to define articulation axis B-B. Articulation axis B-B may be substantially transverse to shaft axis A-A.

Figure 53:
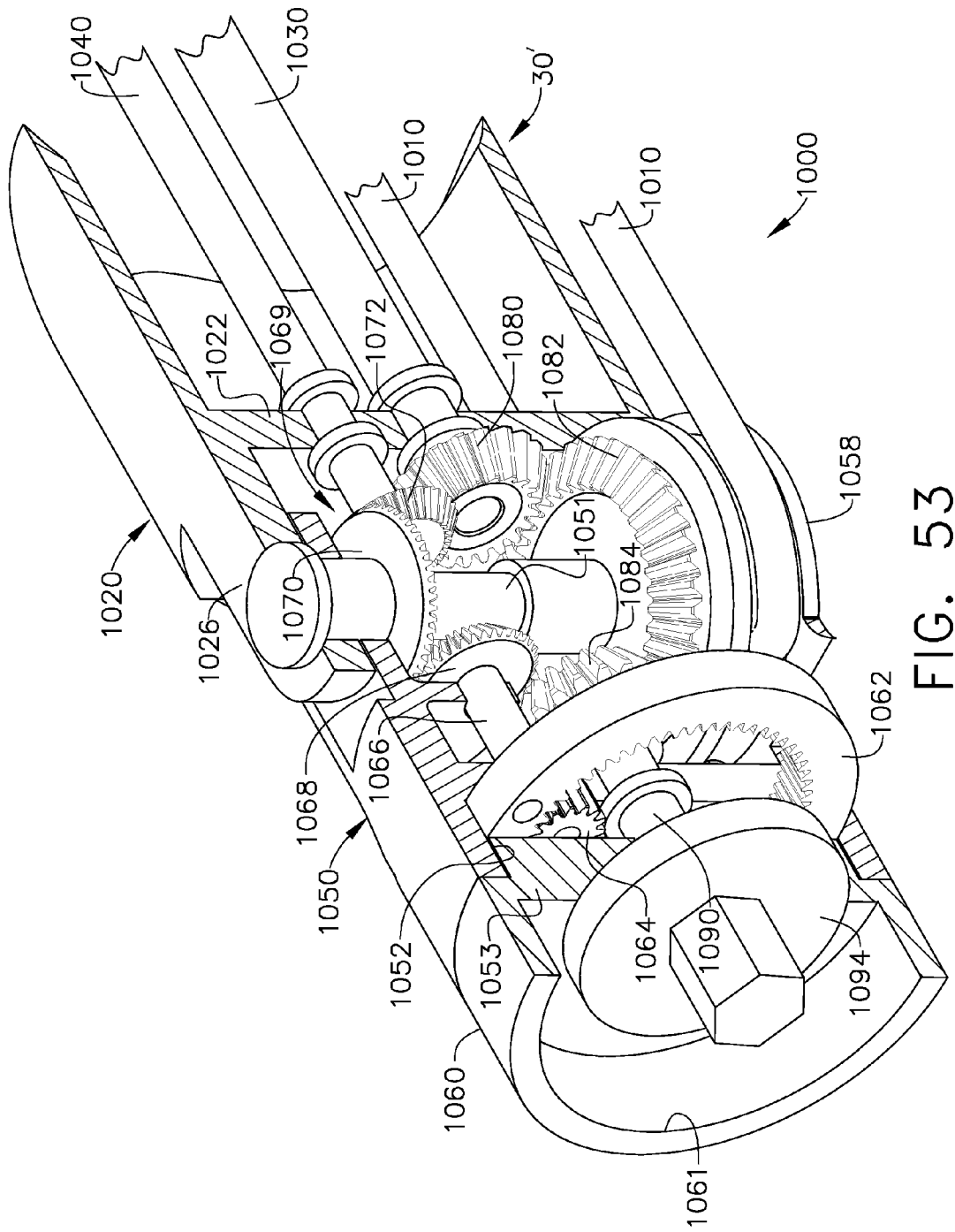
FIG. 53 is another cross-sectional perspective view of the articulation joint arrangement of FIGS. 50-52.
Figure 54:
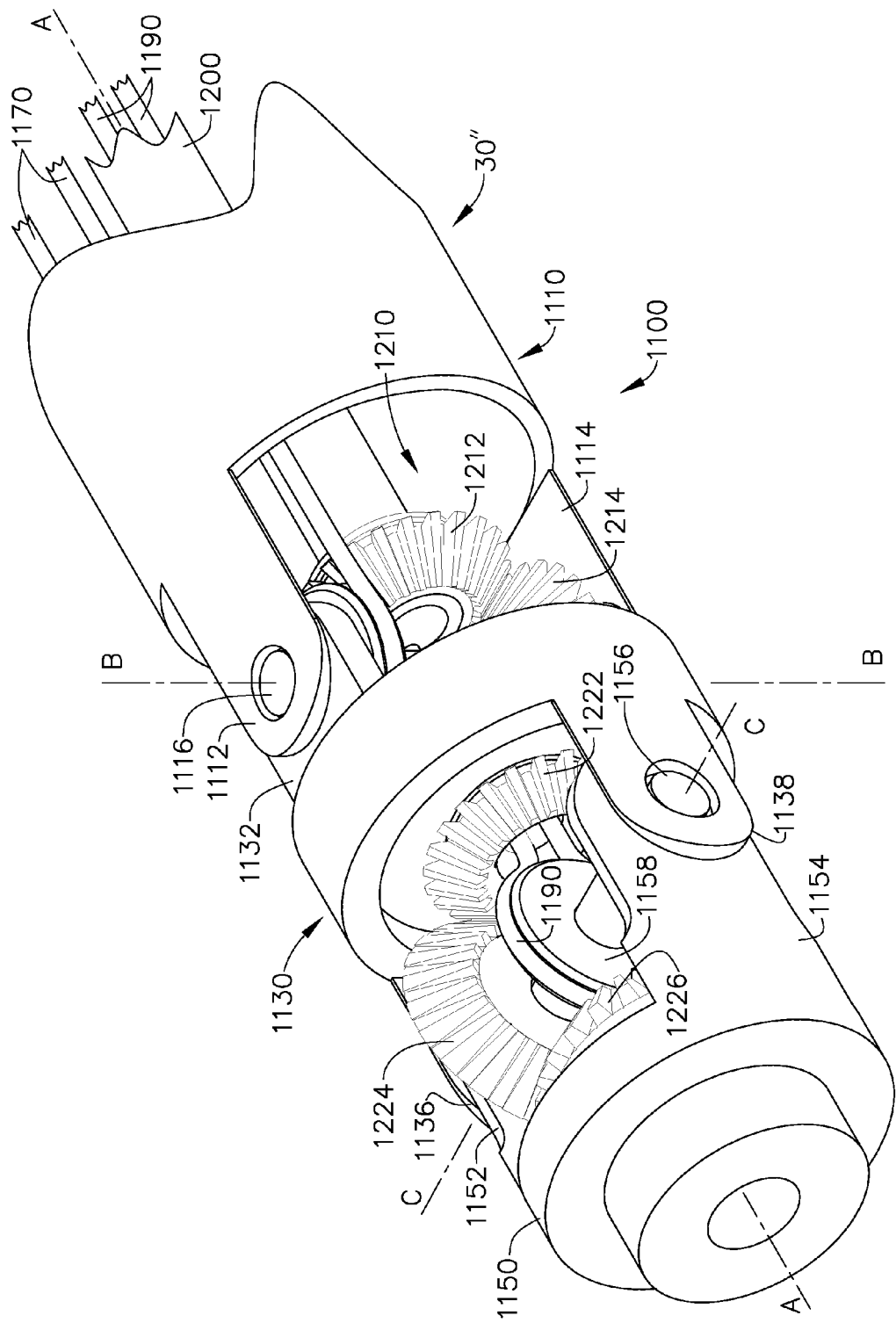
FIG. 54 is a perspective view of another articulation joint arrangement of the present invention.
Figure 55:
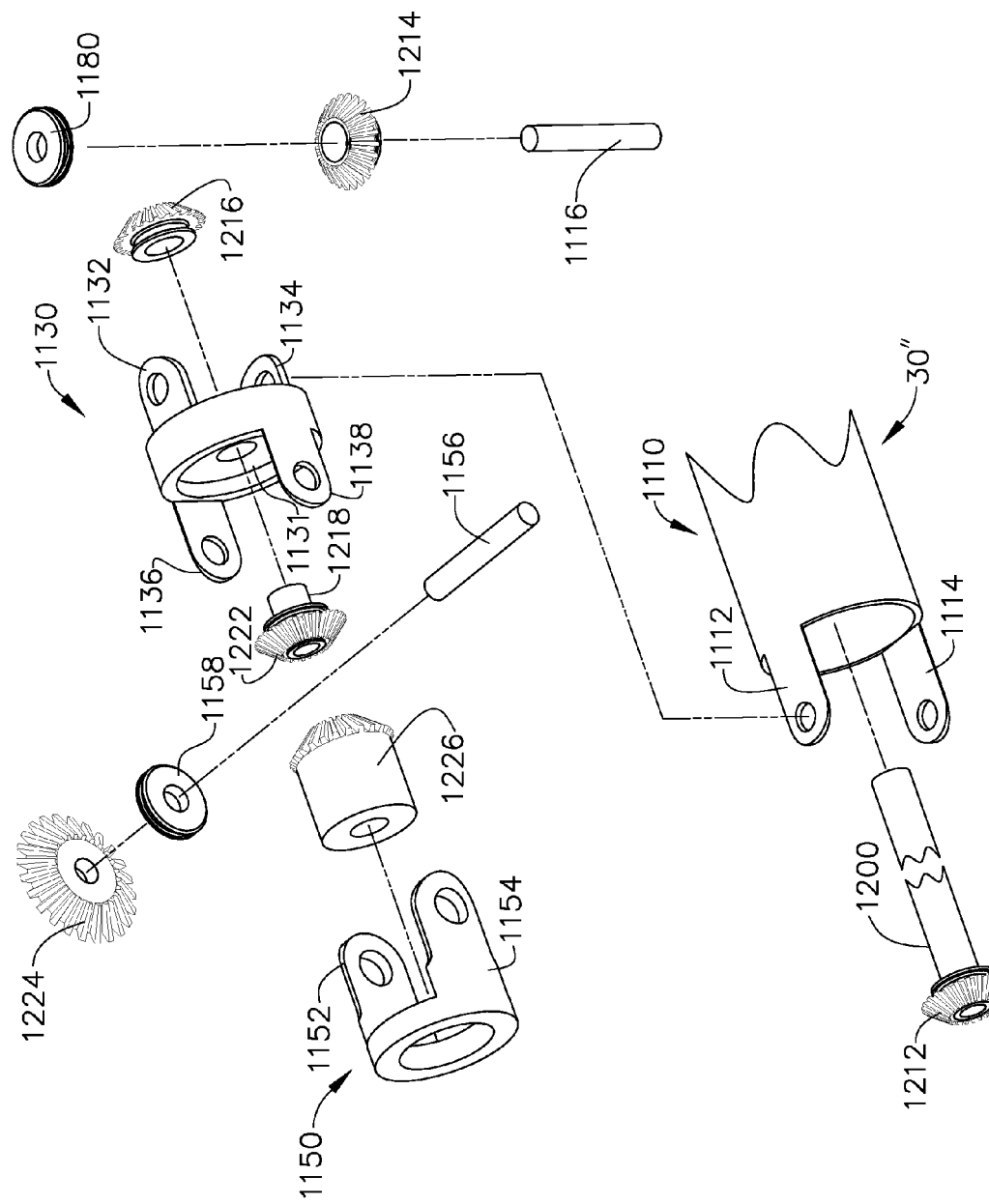
FIG. 55 is an exploded assembly view of the articulation joint arrangement of FIG. 54.
Figure 56:
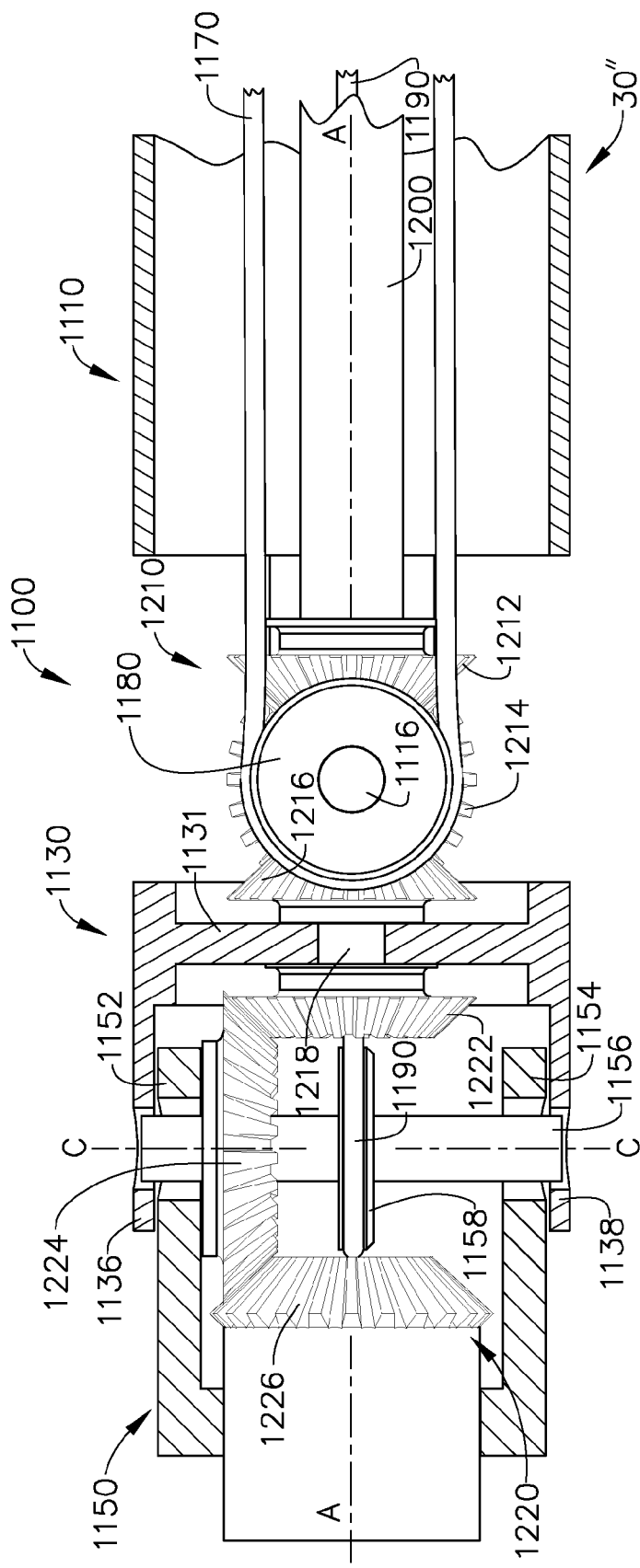
FIG. 56 is a partial cross-sectional view of the articulation joint arrangement of FIGS. 54 and 55.
Figure 57:
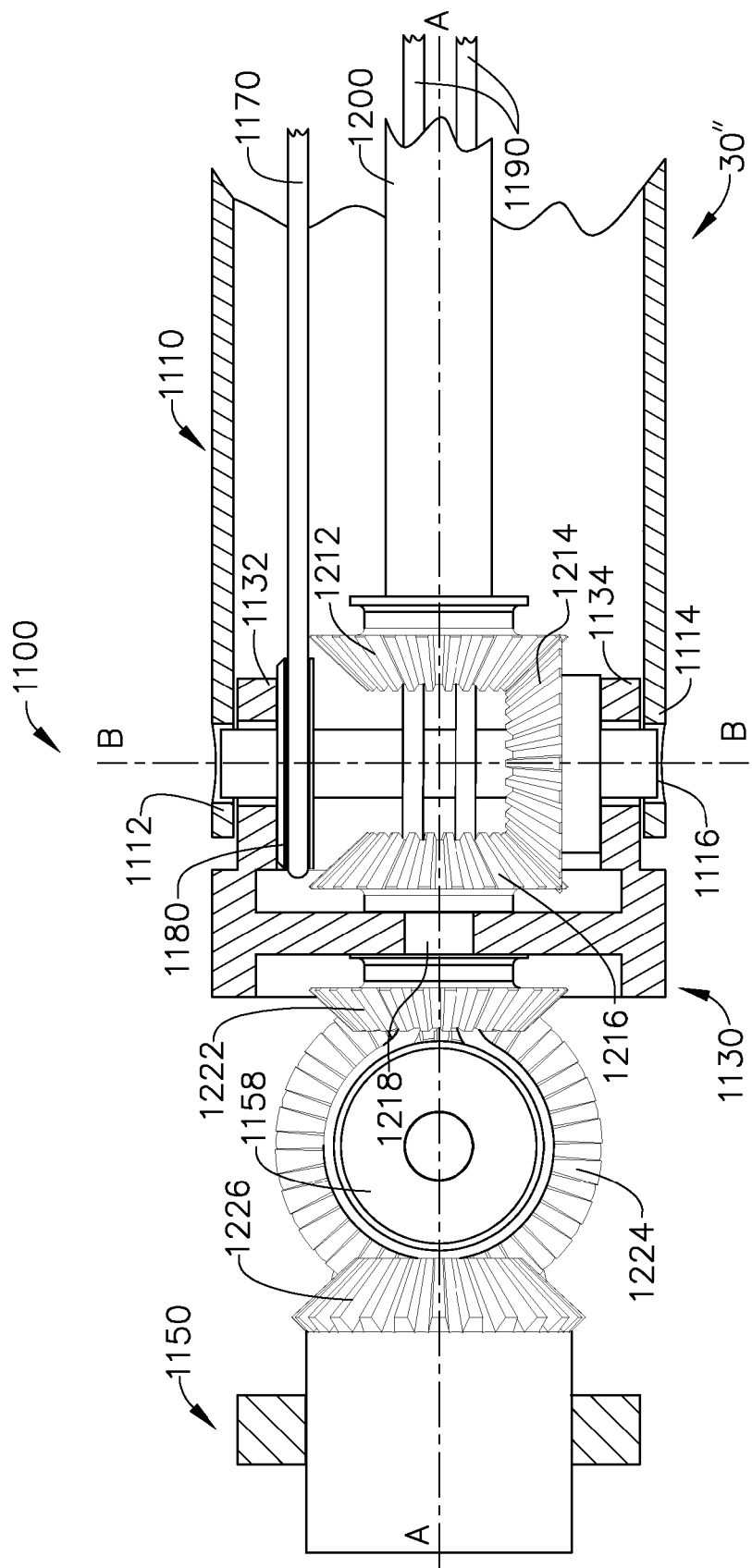
FIG. 57 is another partial cross-sectional view of the articulation joint arrangement of FIGS. 54-56.
Figure 58:
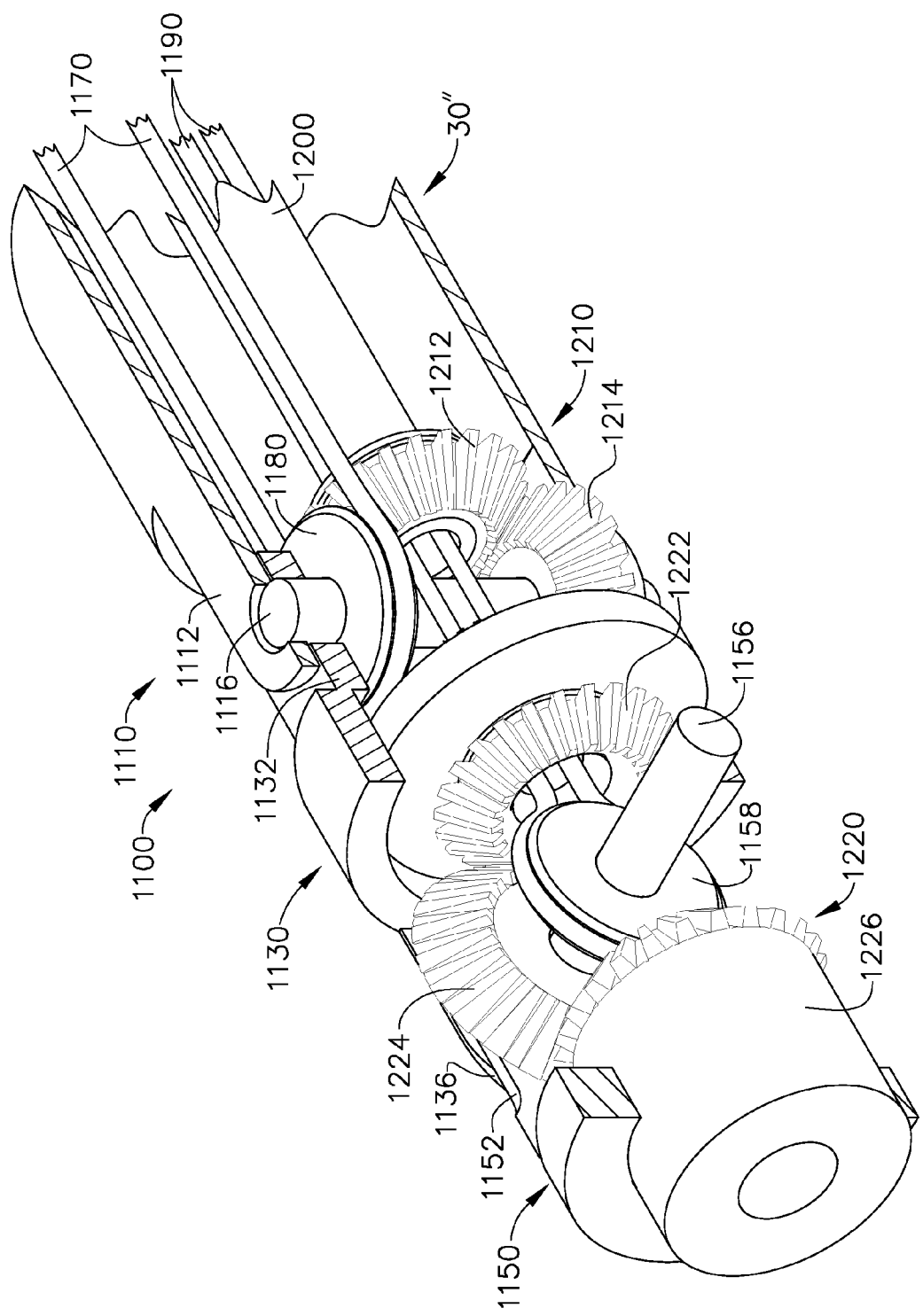
FIG. 58 is another partial perspective cross-sectional view of the articulation joint arrangement of FIGS. 54-57.
Figure 59:
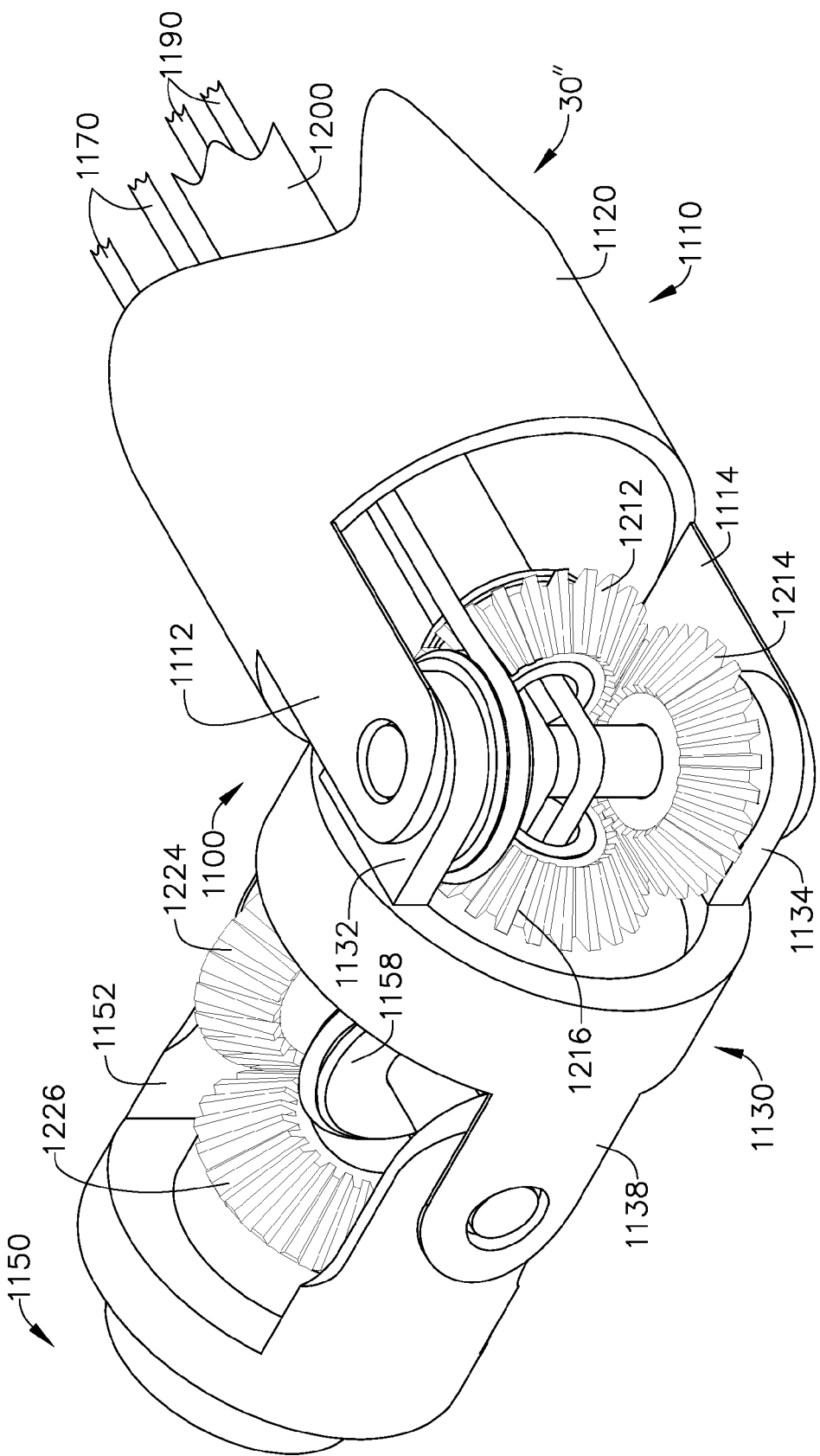
FIG. 59 is another partial perspective cross-sectional view of the articulation joint arrangement of FIGS. 54-58 with the joint in an articulated orientation.
Figure 60:
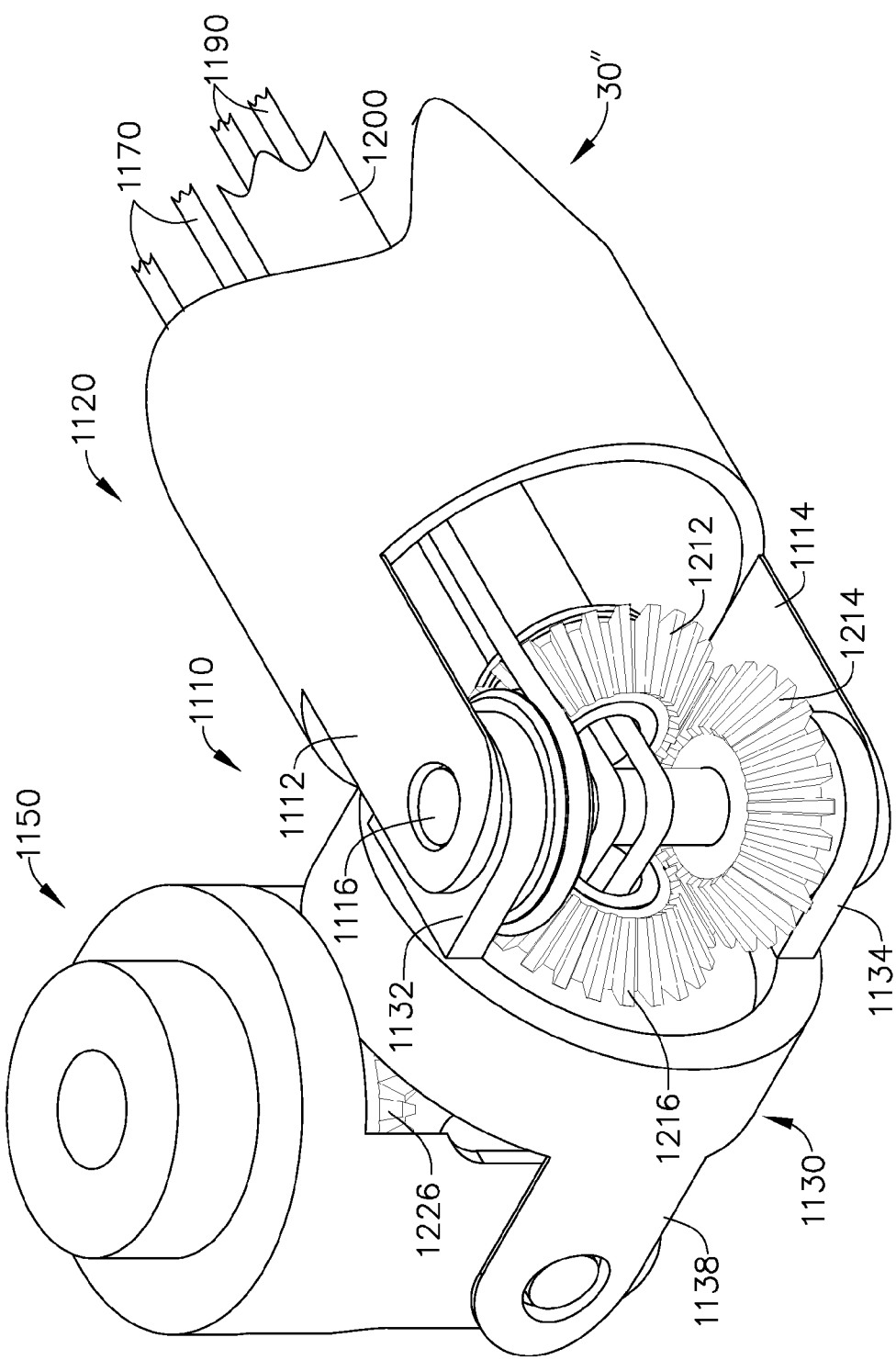
FIG. 60 is another partial perspective cross-sectional view of the articulation joint arrangement of FIGS. 54-59 with the joint in another articulated orientation.
Figure 61:
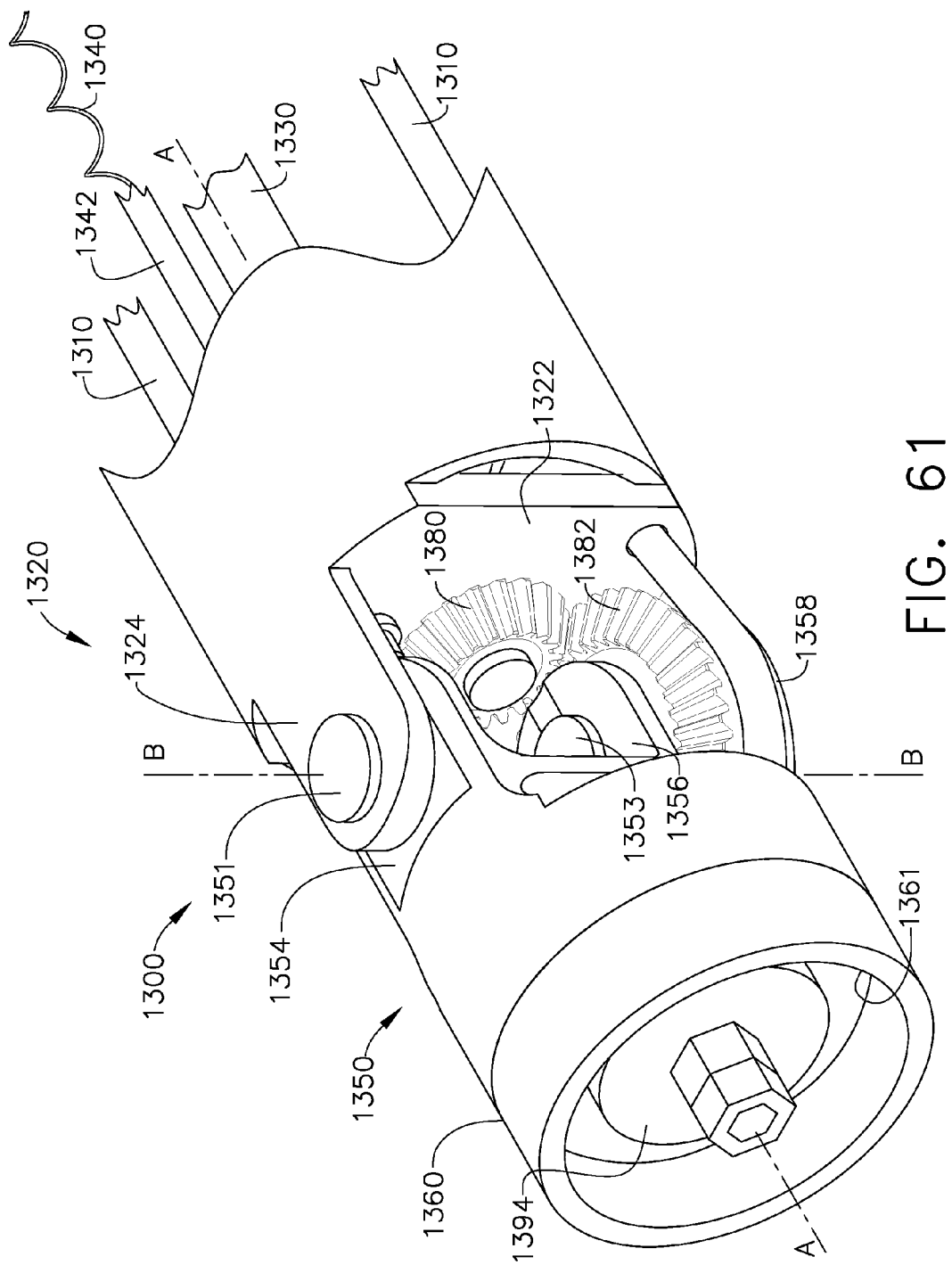
FIG. 61 is a perspective view of another articulation joint arrangement of the present invention.
Figure 62:
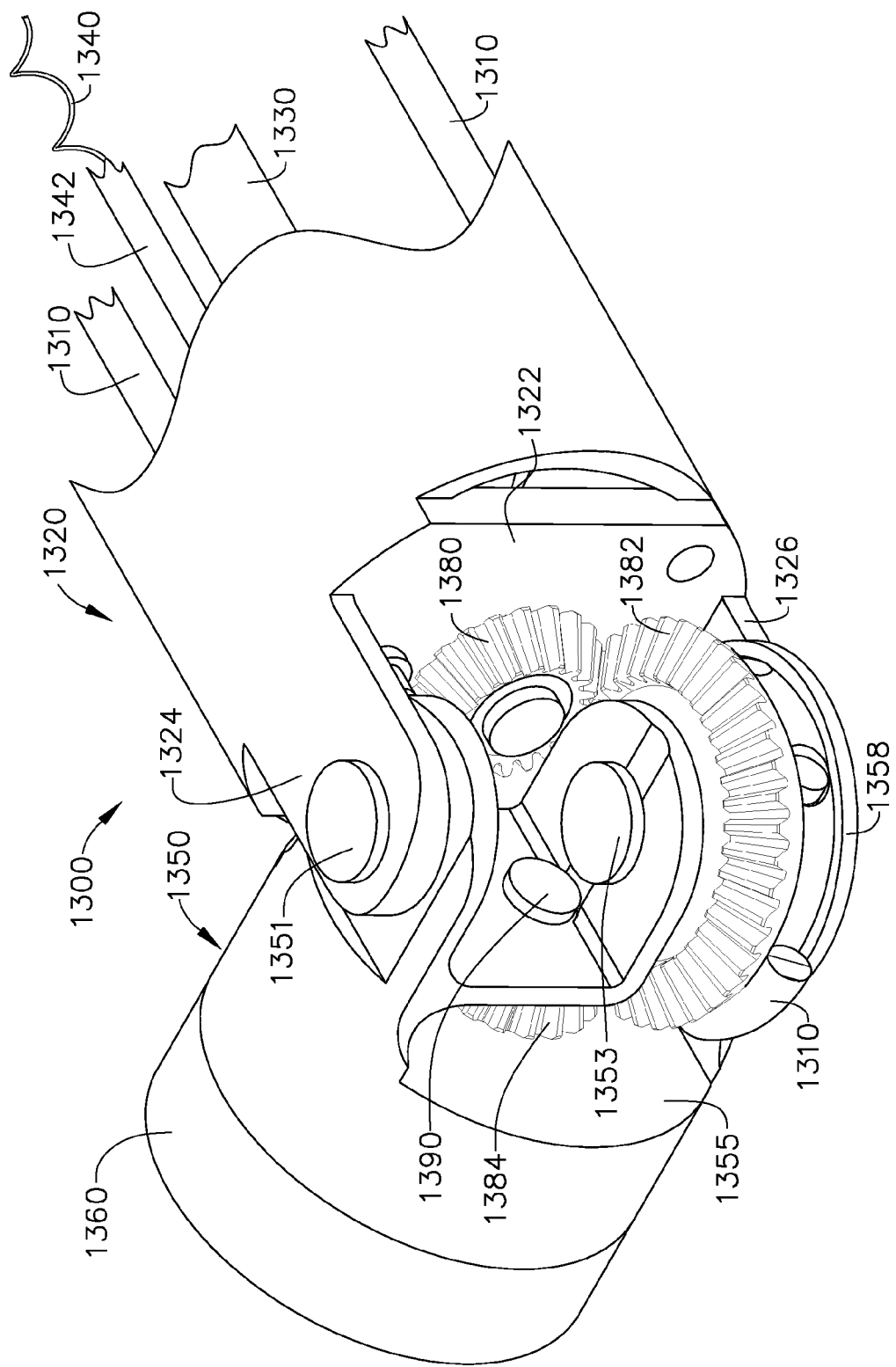
FIG. 62 is another perspective view of the articulation joint arrangement of FIG. 60 in an articulated orientation.

The distal clevis 1050 has a socket 1052 formed thereon and a pair of distal clevis arms 1054, 1056. The pivot shaft 1051 extends centrally through the clevis arms 1024, 1054, 1056, and 1026 as shown in FIG. 53. The clevis arm 1054 may have a cable pulley 1058 formed thereon to which the flexible cable 1010 is attached. Thus, rotation of the cable 1010 by its corresponding motor will result in rotation of the distal clevis 1050 relative to the proximal clevis 1020 about the articulation axis B-B.

In various forms, the articulation joint 1000 may further include a rotatable mounting hub 1060 that is rotatably received within the socket 1052. The mounting hub 1060 may have a ring gear 1062 attached thereto that is adapted for meshing engagement with a distal roll pinion gear 1064. The distal roll pinion gear 1064 is attached to a pinion shaft 1066 that is rotatably supported in an end wall 1053 of the distal clevis 1050. The pinion shaft 1066 has a distal roll output gear 1068 attached thereto. The distal roll output gear 1068 is supported in meshing engagement with distal roll transfer gear 1070 that is rotatably journaled on the pivot shaft 1051 and is in meshing engagement with a distal roll input gear 1072. The distal roll input gear 1072 is mounted to the distal roll shaft 1040. The distal roll output gear 1068, the distal roll transfer gear 1070 and the distal roll input gear 1072 are referred to herein as the "distal roll gear train", generally designated as 1069. The distal roll transfer gear 1070 is "free-wheeling" on the pivot shaft 1051 such that rotation of the distal roll shaft 1040 ultimately results in the rotation of the of the distal roll pinion gear 1064 without rotating the pivot shaft 1051. Rotation of the distal roll pinion gear 1064 within the ring gear 1062 results in the rotation of the mounting hub 1060 about the shaft axis A-A. In various forms, an end effector or surgical implement may be directly coupled to the mounting hub 1060 such that rotation of the mounting hub 1060 results in rotation of the end effector/implement. For example, the mounting hub 1060 may be formed with a hub socket 1061 that is sized to retainingly receive a portion of the end effector/implement therein. In alternative arrangements, the mounting hub 1060 may comprise an integral part of the end effector or the end effector may be attached to the mounting hub 1060 by other fastener arrangements. For example, the mounting hub 1060 may be attached to a coupling assembly of the type and construction described above and then the end effector/implement may be detachably attached to the coupling assembly.

Figure 52:
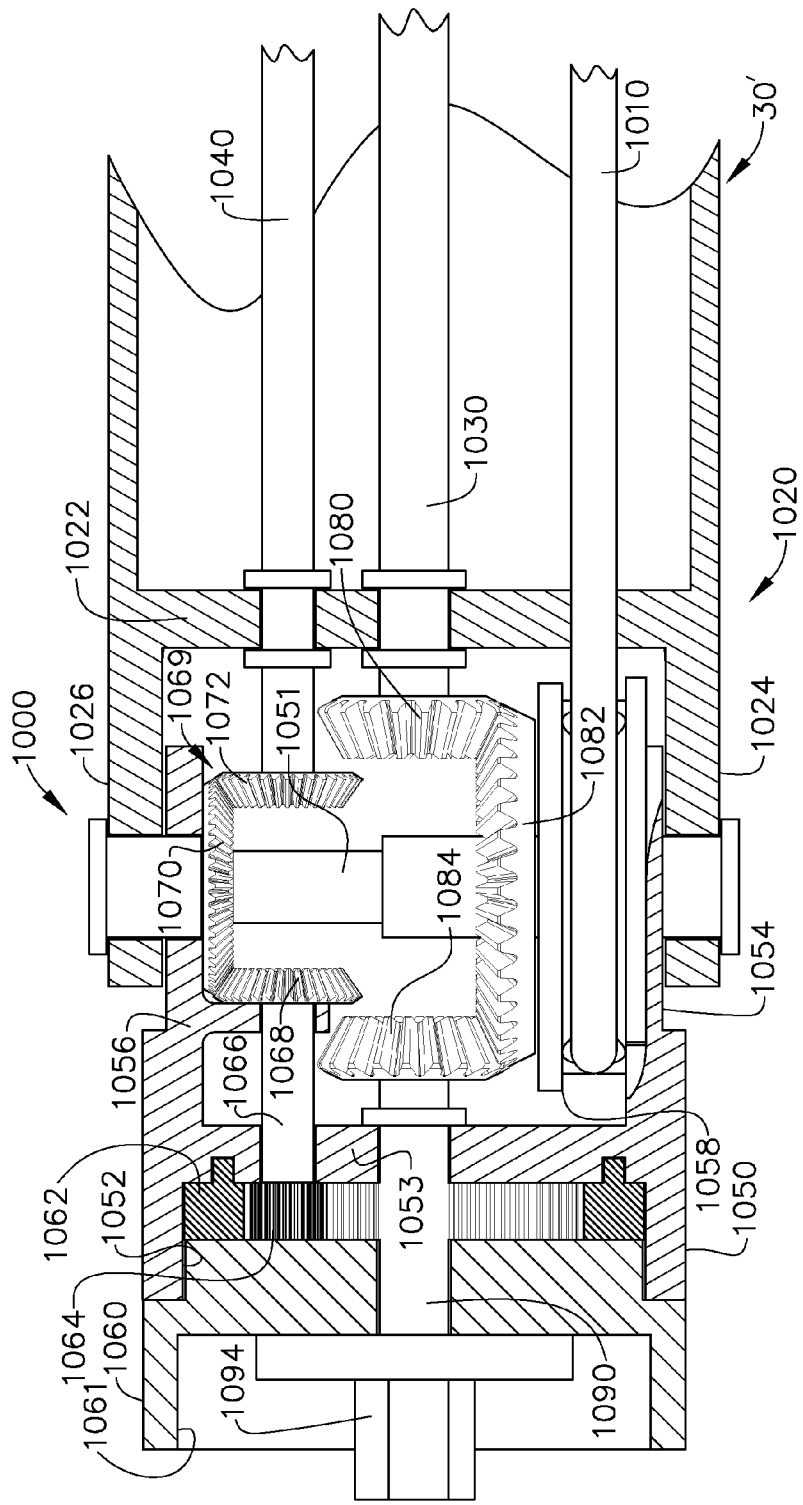
FIG. 52 is a cross-sectional view of the articulation joint arrangement of FIGS. 50 and 51.

The articulation joint 1000 may also facilitate transfer of a rotary control motion through the joint 1000 to the end effector/implement attached thereto. As can be seen in FIGS. 52 and 53, a distal end of the proximal firing shaft 1030 is rotatably supported by the distal end wall 1022 of the proximal clevis assembly 1020 and has an input firing gear 1080 attached thereto. The input firing gear 1080 is in meshing engagement with a firing transfer gear 1082 that is journaled on the pivot shaft 1051. The firing transfer gear 1082 is in meshing engagement with a firing output gear 1084 that is mounted on a firing output shaft 1090 that is mounted in the end wall 1053 of the distal clevis 1050. The firing output shaft 1090 may be configured for driving engagement with a corresponding drive member or shaft on the end effector/implement. For example, the distal end 1092 of the firing output shaft 1090 may be formed with a hexagonal shape so that it may be received in a corresponding hexagonal socket formed in a mounting flange 1094 that may be configured to be attached to the drive shaft of the end effector/implement. The firing input gear 1080, the firing transfer gear 1082, and the firing output gear 1084 are referred to herein as the "firing shaft gear train", generally designated as 1081. The firing transfer gear 1082 is "free-wheeling" on the pivot shaft 1051 such that rotation of the proximal firing shaft 1030 ultimately results in the rotation of the of the firing output shaft 1090 without rotating the pivot shaft 1051. The distal roll gear train 1069 and the firing shaft gear train 1081 are essentially "nested" together facilitate articulation of the end effector/implement relative to the elongate shaft assembly while facilitating the transfer of rotary control motions to the end effector and while facilitating the rotation of the end effector about the shaft axis A-A.

FIGS. 54-60 illustrate another alternative articulation joint arrangement 1100. In at least one form, the articulation joint 1100 may include a proximal clevis 1110, a central clevis 1130 and a distal clevis 1150. The articulation joint 1100 may be configured to facilitate the articulation of an end effector or surgical implement coupled thereto about two different articulation axes B-B and C-C that are substantially transverse to each other as well as to the shaft axis A-A of an elongate shaft assembly 30" to which it is attached. For example, the articulation joint 1100 may be configured such that the central clevis 1130 may be pivoted about the first articulation axis B-B relative to the first clevis 1110 and the distal clevis 1150 may be selectively pivoted about a second articulation axis C-C relative to the central clevis 1130. The articulation joint 1100 may also facilitate such articulation of the end effector or surgical implement while also providing a rotary control motion to the end effector/implement for actuation or manipulation thereof.

The articulation joint 1100 may be coupled to an elongate shaft assembly that is similar in construction to the elongate shaft assembly 30 described above or it may be coupled to other suitable shaft assemblies. In one arrangement, the proximal clevis 1110 is integrally formed with the outer tube of the elongate shaft assembly 30". As can be seen in FIGS. 54-60, the proximal clevis 1110 has an upper proximal clevis arm 1112 and a lower proximal clevis arm 1114. The central clevis 1130 also has an upper central clevis arm 1132 and a lower central clevis arm 1134. The upper proximal clevis arm is pivotally coupled to the upper central clevis arm 1132 by a proximal pivot pin 1116. The proximal pivot pin 1116 also pivotally couples the lower proximal clevis arm 1114 to the lower central clevis arm 1134. The proximal pivot pin 1116 serves to define the first articulation axis B-B.

Also in at least one arrangement, the central clevis 1130 has a right central clevis arm 1136 and a left central clevis arm 1138. The distal clevis 1150 has a right distal clevis arm 1152 and a left distal clevis arm 1154. The right central clevis arm 1136 is pivotally coupled to the right distal clevis arm 1152 by a distal pivot pin 1156. The left central clevis arm 1138 is pivotally coupled to the left distal clevis arm 1154 by the distal pivot pin 1156. The distal pivot pin 1156 defines the second articulation axis C-C. In one arrangement, the distal pivot pin 1156 is non-pivotally attached to the right and left distal clevis arms 1152, 1154 such that the distal pivot pin 1156 rotates with the distal clevis 1150 relative to the central clevis 1130.

The elongate shaft assembly 30" may be coupled to a handle assembly that houses a plurality of motors. One motor may be used to apply control motions to a first flexible cable member 1170 that extends through the elongate shaft assembly 30" and which is operably coupled to the articulation joint 1100. For example, the first flexible cable 1170 may be attached to a first sheave or pulley assembly that is operably attached to or communicates with the shaft of a corresponding motor such that operation of the motor causes the first cable 1170 to be actuated.

In one arrangement, the first flexible cable 1170 may be employed to selectively pivot the central clevis 1130 relative to the proximal clevis 1110 about the first articulation axis B-B. In such arrangement, for example, the first cable 1170 extends around a first pulley or sheave 1180 that is attached to the central clevis 1130. For example, the first pulley 1180 is attached to the upper central clevis arm 1132 and pivotally journaled on the proximal pivot pin 1116. Actuation of the first cable 1170 will cause the central clevis 1130 to pivot relative to the proximal clevis 1110 about the first articulation axis B-B.

The articulation joint 1100 may also employ a second flexible cable 1190 that is received on a sheave or pulley assembly that is operably attached to or communicates with the shaft of a corresponding motor within the handle assembly such that operation of the motor causes the second cable 1190 to be actuated. The second cable 1190 may be employed to selectively pivot the distal clevis 1150 relative to the central clevis 1130 about the second articulation axis C-C. In such arrangement, for example, the second cable 1190 extends around a second pulley or sheave 1158 that is non-rotatably attached to the distal pivot pin 1156. Actuation of the second cable 1190 will result in the rotation of the distal pivot pin 1156 and the distal clevis 1150 attached thereto about the second articulation axis C-C relative to the central clevis 1130.

The articulation joint 1100 may also facilitate transfer of a rotary control motion through the joint 1100 to the end effector/implement attached thereto. A proximal rotary firing shaft 1200 may extend through the elongate shaft assembly 30" and be operably coupled to a firing motor in the handle assembly for applying a rotary firing motion thereto. In one arrangement, the proximal firing shaft 1200 may be hollow such that the second cable 1190 may extend therethrough. The proximal firing shaft 1200 may operably interface with a proximal firing gear train 1210 operably supported in the articulation joint 1100. For example, in one arrangement, the first firing gear train 1210 may include a proximal input firing gear 1212 that is attached to the proximal firing shaft 1200. The proximal input firing gear 1212 is oriented in meshing engagement with a proximal firing transfer gear 1214 that is journaled on the proximal pivot shaft 1116 such that it can freely rotate thereon. The proximal firing transfer gear 1212 is oriented in meshing engagement with a proximal firing output gear 1216 that is coupled to a central firing shaft 1218 that rotatably passes through a central web 1131 of the central clevis 1130.

The articulation joint 1100 may further include a distal firing gear train 1220 that cooperates with the proximal firing gear train 1210 to transfer the rotary firing or control motion through the articulation joint 1100. The distal firing gear train 1220 may include a distal firing input gear 1222 that is mounted to the central firing shaft 1216. The distal firing input gear 1222 is in meshing engagement with a distal firing transfer gear 1224 that is rotatably mounted to the distal pivot pin 1156 such that it may freely rotate thereon. The distal firing transfer gear 1224 is in meshing engagement with a distal firing output gear 1226 that is rotatably supported within the distal clevis 1150. The distal firing output gear 1226 may be configured for driving engagement with a corresponding drive member or shaft on the end effector/implement.

Another form of articulation joint 1300 is shown in FIGS. 61-66. Such articulation joint 1300 can facilitate the articulation and rotation of an end effector or surgical implement coupled thereto relative to the shaft axis A-A of the elongate shaft to which the articulation joint 1300 is attached. The articulation joint may also facilitate such movement of the end effector or surgical implement while also providing a rotary control motion to the end effector/implement for actuation or manipulation thereof. The articulation joint 1300 may be coupled to an elongate shaft assembly that is similar in construction to the elongate shaft assembly 30 described above or it may be coupled to other suitable shaft assemblies. The elongate shaft assembly may be coupled to a handle assembly that houses a plurality of motors. One motor may be used to apply control motions to a flexible cable 1310 that extends through the elongate shaft assembly and which is operably coupled to the articulation joint 1300. For example, the flexible cable 1310 may be attached to a sheave or pulley assembly that is operably attached to or communicates with the shaft of a corresponding motor such that operation of the motor causes the cable 1310 to be actuated. The handle assembly may also include a firing motor that is operably attached to a proximal firing shaft 1330 that extends through the elongate shaft assembly to interface with the articulation joint 1300 as will be discussed in further detail below. The handle assembly may also include a motor that operably interfaces with a flexible distal roll shaft 1340 that transmits a rotary control motion to the articulation joint 1300 which may be used to rotate the end effector or surgical implement about the shaft axis A-A relative to the elongate shaft. The handle assembly may also include a proximal roll motor that is employed to rotate the elongate shaft assembly about the shaft axis A-A in the manner described above.

In at least one form, the articulation joint 1300 may include a proximal clevis assembly 1320 that is attached to or formed on the end of the elongate shaft assembly. In the arrangement shown in FIGS. 61-66, the proximal clevis assembly 1320 is formed on a distal end of an outer tube forming a portion of the elongate shaft assembly 30". As can be seen in those Figures, the proximal clevis assembly 1320 has a distal end wall 1322 and a pair of spaced clevis arms 1324, 1326. The proximal clevis 1320 is configured to be pivotally coupled to a distal clevis 1350 by an upper pivot shaft 1351 and a lower pivot shaft 1353 which serve to define articulation axis B-B. Articulation axis B-B is substantially transverse to shaft axis A-A.

Figure 64:
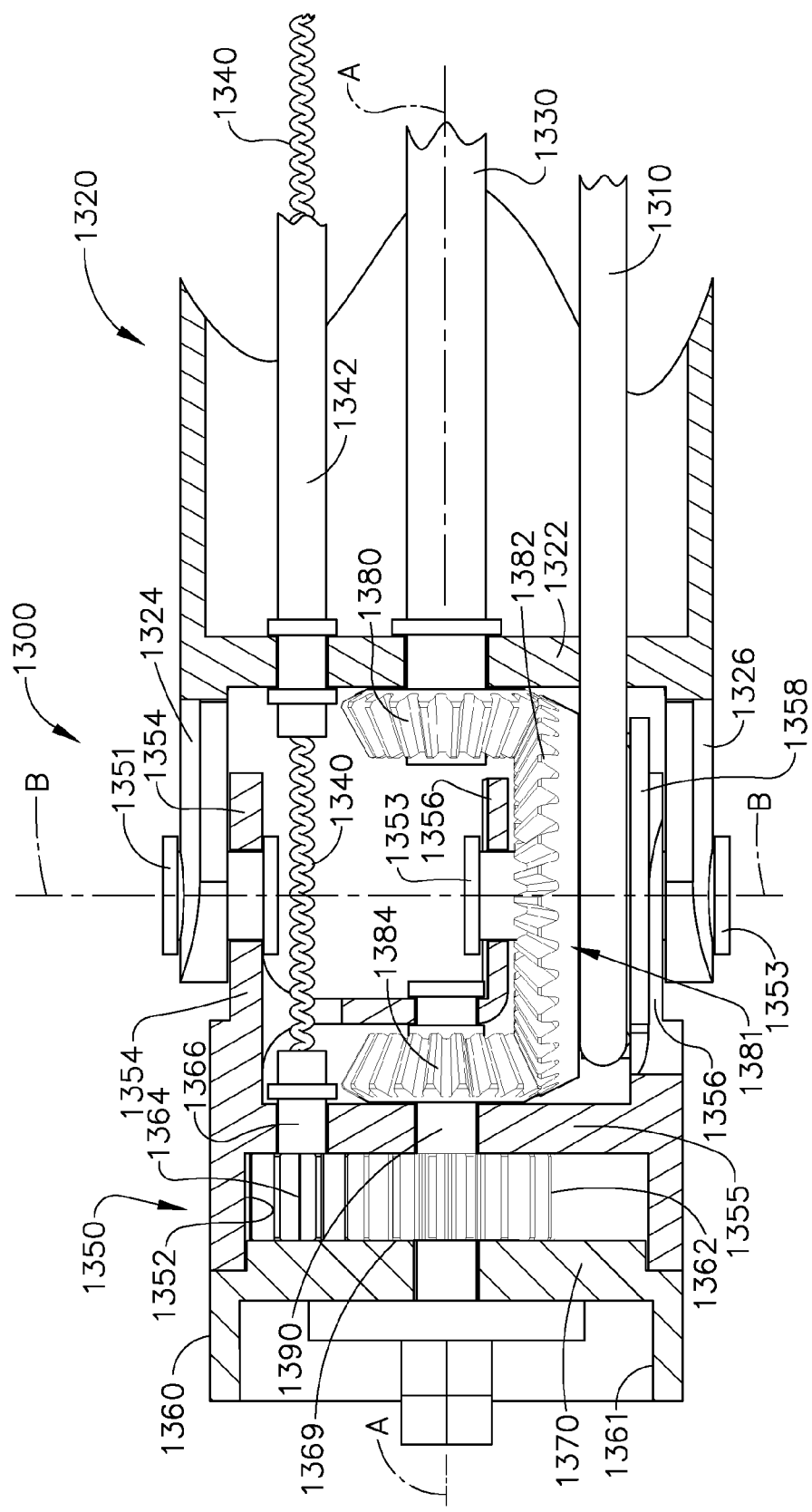
FIG. 64 is a cross-sectional view of the articulation joint arrangement of FIGS. 61-63.
Figure 65:
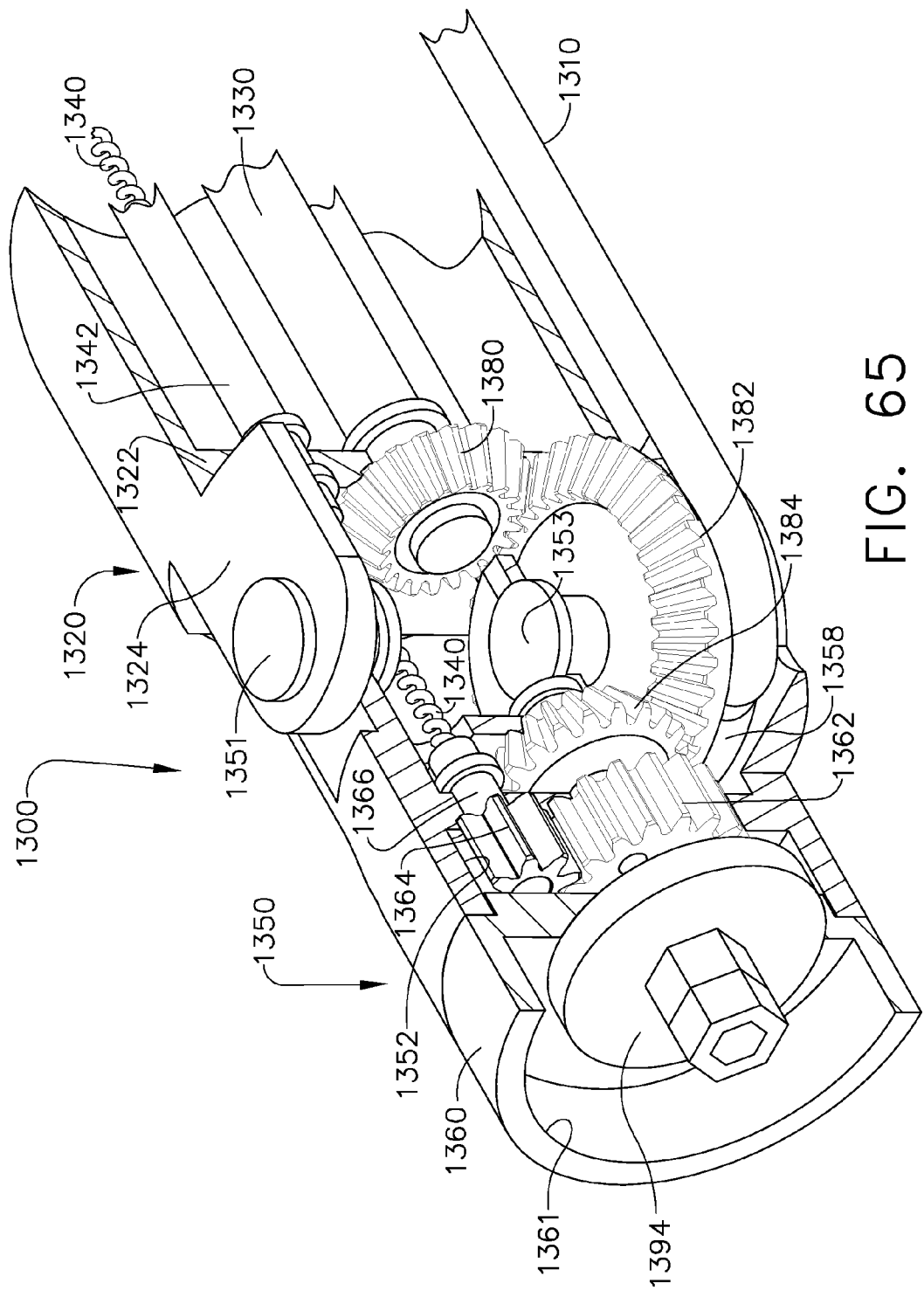
FIG. 65 is another cross-sectional perspective view of the articulation joint arrangement of FIGS. 61-64.
Figure 66:
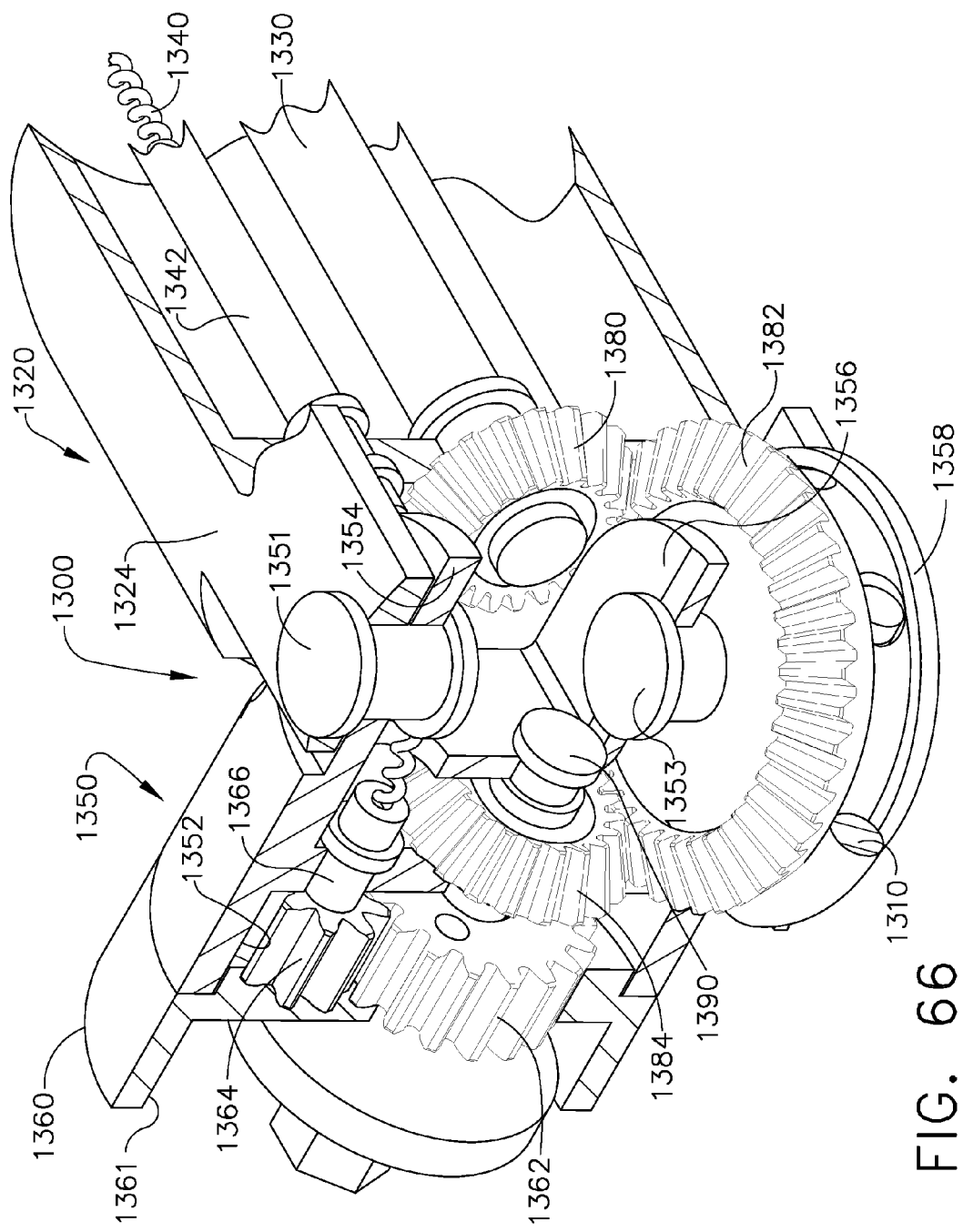
FIG. 66 is another cross-sectional perspective view of the articulation joint arrangement of FIGS. 61-65 with the articulation joint in an articulated orientation.

The distal clevis 1350 has a socket 1352 formed thereon and a pair of distal clevis arms 1354, 1356. The upper pivot shaft 1351 extends centrally through the clevis arms 1324 and 1354. The lower pivot shaft 1353 extends through the clevis arms 1356, and 1026 as shown in FIG. 64. The clevis arm 1356 further has a cable pulley 1358 formed thereon or attached thereto. The flexible cable 1310 is attached to the cable pulley 1358 such that actuation of the cable 1310 will result in articulation of the distal clevis 1350 about the articulation axis B-B relative to the proximal clevis 1320.

In various forms, the articulation joint 1300 may further include a rotatable mounting hub 1360 that is rotatably received within the socket 1052. The mounting hub 1060 may have a driven gear 1362 attached thereto that is adapted for meshing engagement with a distal roll pinion gear 1364. The distal roll pinion gear 1364 is attached to a pinion shaft 1366 that is rotatably supported in an end wall 1355 of the distal clevis 1350. In at least one arrangement, the distal roll pinion gear 1364 is operated by the flexible distal roll shaft 1340 that extends through a proximal support shaft 1342 extending through the elongate shaft assembly 30". In various forms, an end effector or surgical implement may be directly coupled to the mounting hub 1360 such that rotation of the mounting hub 1360 results in rotation of the end effector/implement. For example, the mounting hub 1360 may be formed with a hub socket 1361 that is sized to retainingly receive a portion of the end effector/implement therein. In alternative arrangements, the mounting hub 1360 may comprise an integral part of the end effector or the end effector may be attached to the mounting hub 1360 by other fastener arrangements. For example, the mounting hub 1360 may be attached to a coupling assembly of the type and construction described above and then the end effector/implement may be detachably attached to the coupling assembly.

Figure 63:
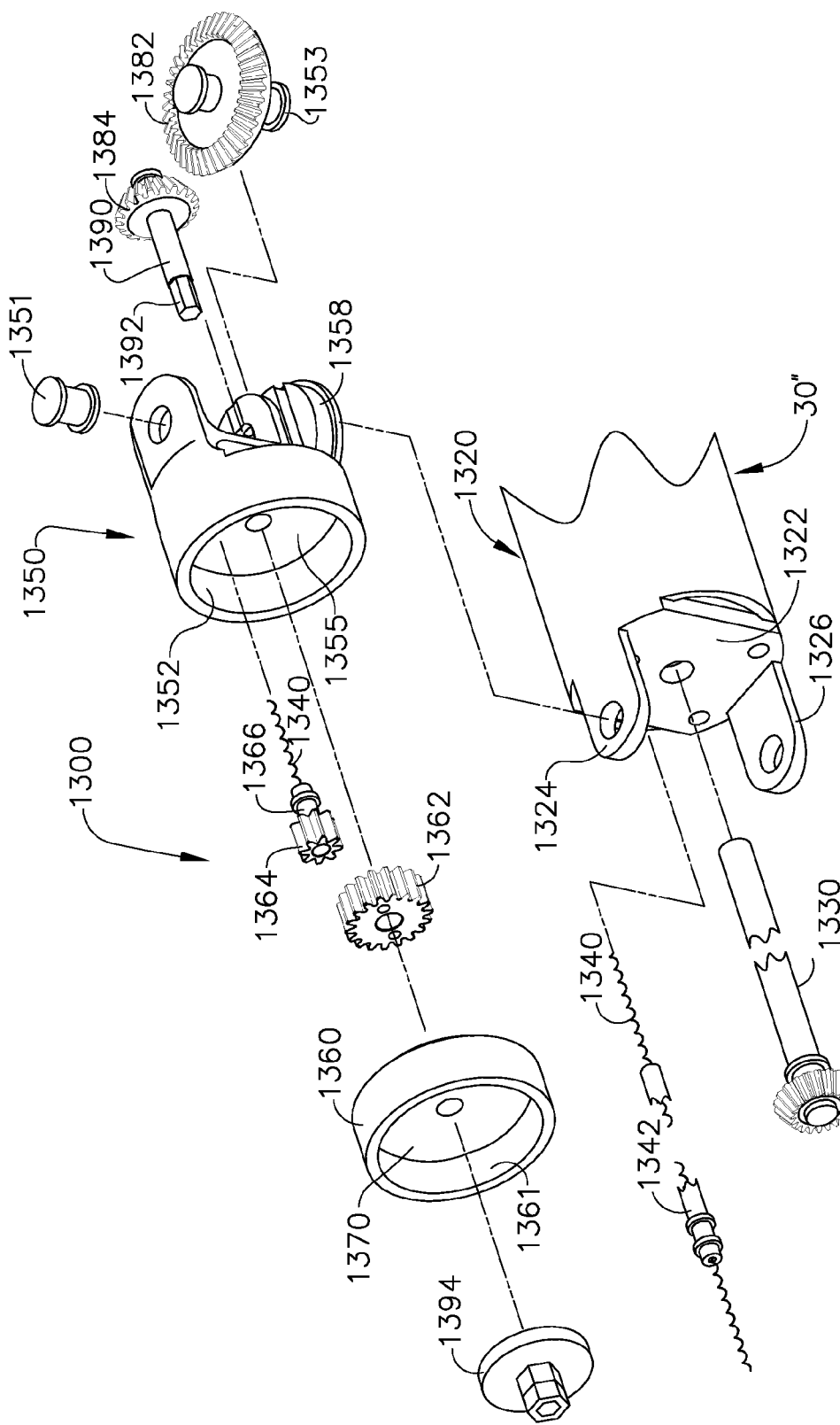
FIG. 63 is an exploded assembly view of the articulation joint of FIGS. 61 and 62.

The articulation joint 1300 may also facilitate transfer of a rotary control motion through the joint 1300 to the end effector/implement attached thereto. As can be seen in FIGS. 63 and 64, a distal end of the proximal firing shaft 1330 is rotatably supported by the distal end wall 1322 of the proximal clevis assembly 1320 and has a firing input gear 1380 attached thereto. The input firing gear 1380 is in meshing engagement with a firing transfer gear 1382 that is journaled on the lower pivot shaft 1353. The firing transfer gear 1382 is in meshing engagement with a firing output gear 1384 that is mounted on a firing output shaft 1390 that extends through the end wall 1355 of the distal clevis 1350 and the end wall 1370 of the mounting hub 1360. The firing output shaft 1390 may be configured for driving engagement with a corresponding drive member or shaft on the end effector/implement. For example, the distal end 1392 of the firing output shaft 1390 may be formed with a hexagonal shape so that it may be received in a corresponding hexagonal socket formed in a mounting flange 1394 that may be configured to be attached to the drive shaft of the end effector/implement. The firing input gear 1380, the firing transfer gear 1382, and the firing output gear 1384 are referred to herein as the firing shaft gear train, generally designated as 1381. The firing transfer gear 1382 is "free-wheeling" on the lower pivot shaft 1353 such that rotation of the proximal firing shaft 1330 ultimately results in the rotation of the of the firing output shaft 1390 without rotating the lower pivot shaft 1353. The distal roll gear train 1369 and the firing shaft gear train 1381 facilitate articulation of the end effector/implement relative to the elongate shaft assembly while facilitating the transfer of rotary control motions to the end effector and while facilitating the rotation of the end effector about the shaft axis A-A.

Alternative Motor Mounting Assemblies

Figure 67:
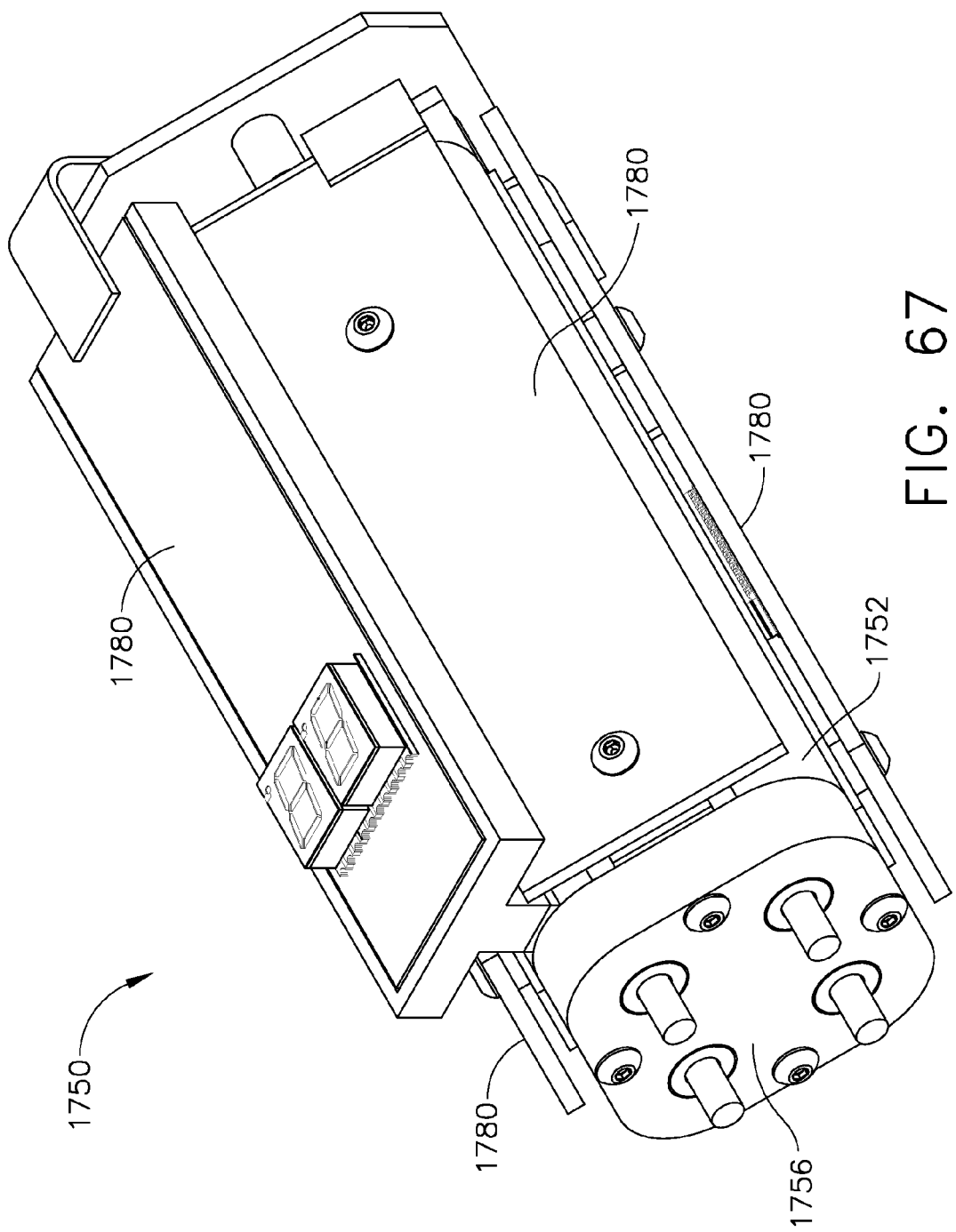
FIG. 67 is a perspective view of another motor mounting assembly arrangement of the present invention.
Figure 68:
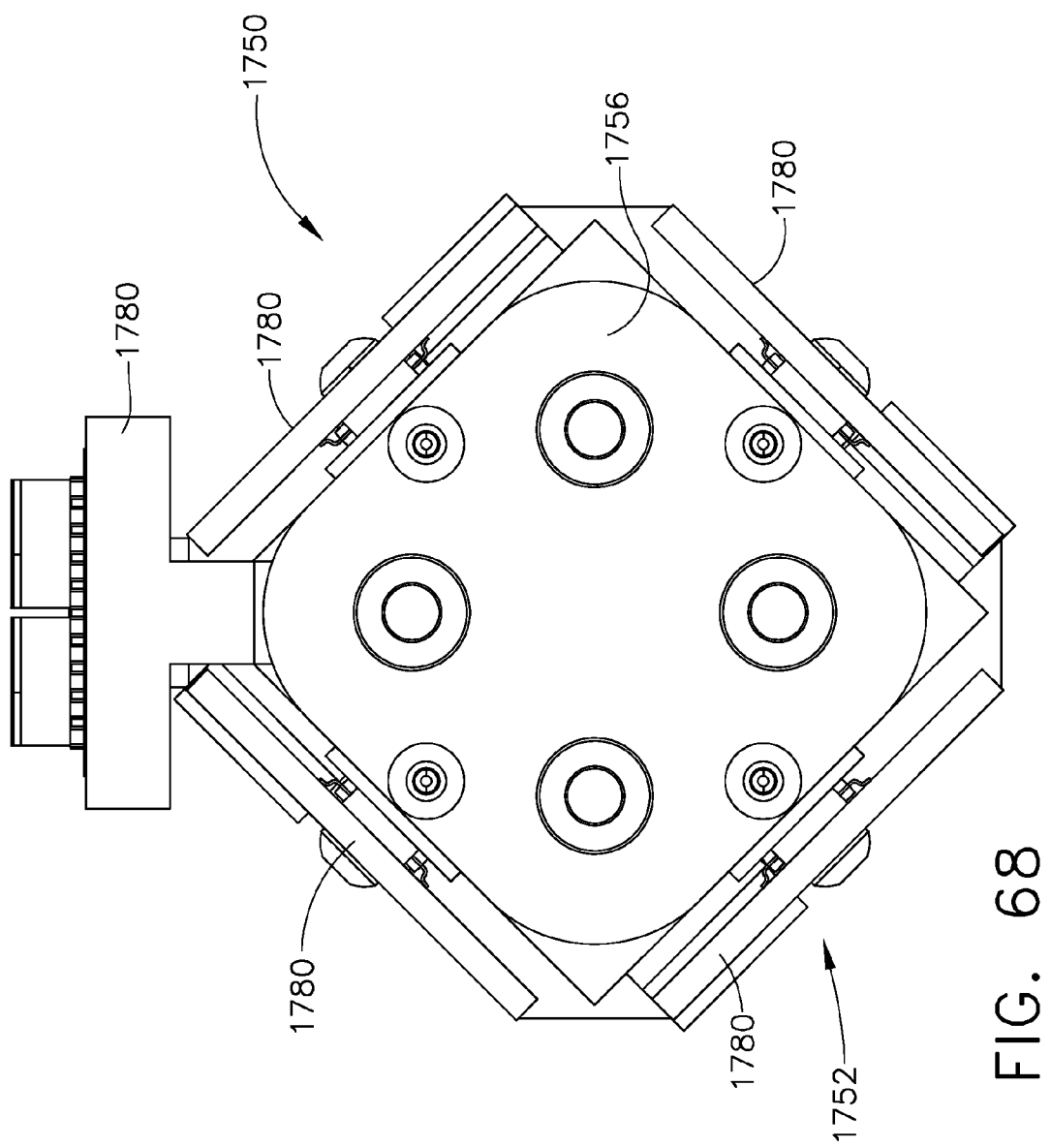
FIG. 68 is a front elevational view of the motor mounting assembly arrangement of FIG. 67.
Figure 69:
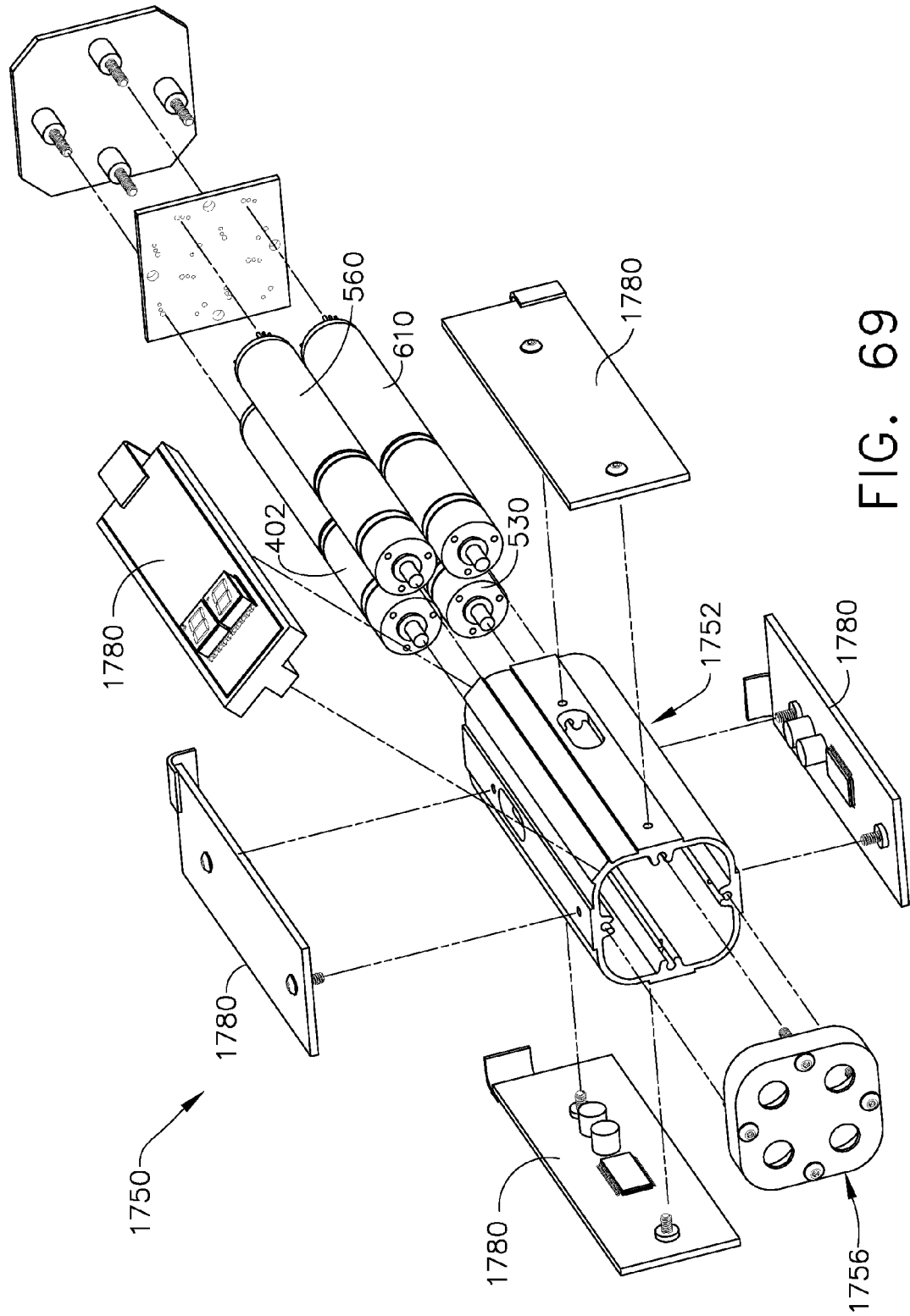
FIG. 69 is an exploded assembly view of the motor mounting assembly arrangement of FIGS. 67 and 68.

FIGS. 67-69 illustrate an alternative motor mounting assembly generally designated as 1750. The motor mounting assembly 1750 may be supported within handle housing segments 23 and 24 that are couplable together by snap features, screws, etc. and serve to form a pistol grip portion 26 of the handle assembly 20. In at least one form, the motor mounting assembly 1750 may comprise a motor housing 1752 that is removably supported within the handle housing segments 23 and 24. In at least one form, for example, the motor housing 1752 has a motor bulkhead assembly 1756 attached thereto. The motor housing 1752 serves to support motors 402, 530, 560 and 610. Each motor has its own circuit control board 1780 attached thereto for controlling the operation of each motor in the various manner described herein.

In some forms, the implement portion 100 may comprise an electrosurgical end effector that utilizes electrical energy to treat tissue. Example electrosurgical end effectors and associated instruments are described in U.S. patent application Ser. No. 13/536,393, entitled "Surgical End Effector Jaw and Electrode Configurations," now U.S. Patent Application Publication No. 2014/0005640, and U.S. patent application Ser. No. 13/536,417, entitled "Electrode Connections for Rotary Drive Surgical Tools," now U.S. Pat. No. 9,101,385, both of which are incorporated by reference herein in their entireties. FIGS. 70-73 illustrate an example end effector 3156 making up an alternate implement portion 100. The end effector 3156 may be adapted for capturing and transecting tissue and for the contemporaneously welding the captured tissue with controlled application of energy (e.g., radio frequency (RF) energy). The first jaw 3160A and the second jaw 3160B may close to thereby capture or engage tissue about a longitudinal axis 3194 defined by an axially moveable member 3182. The first jaw 3160A and second jaw 3160B may also apply compression to the tissue.

Figure 70:
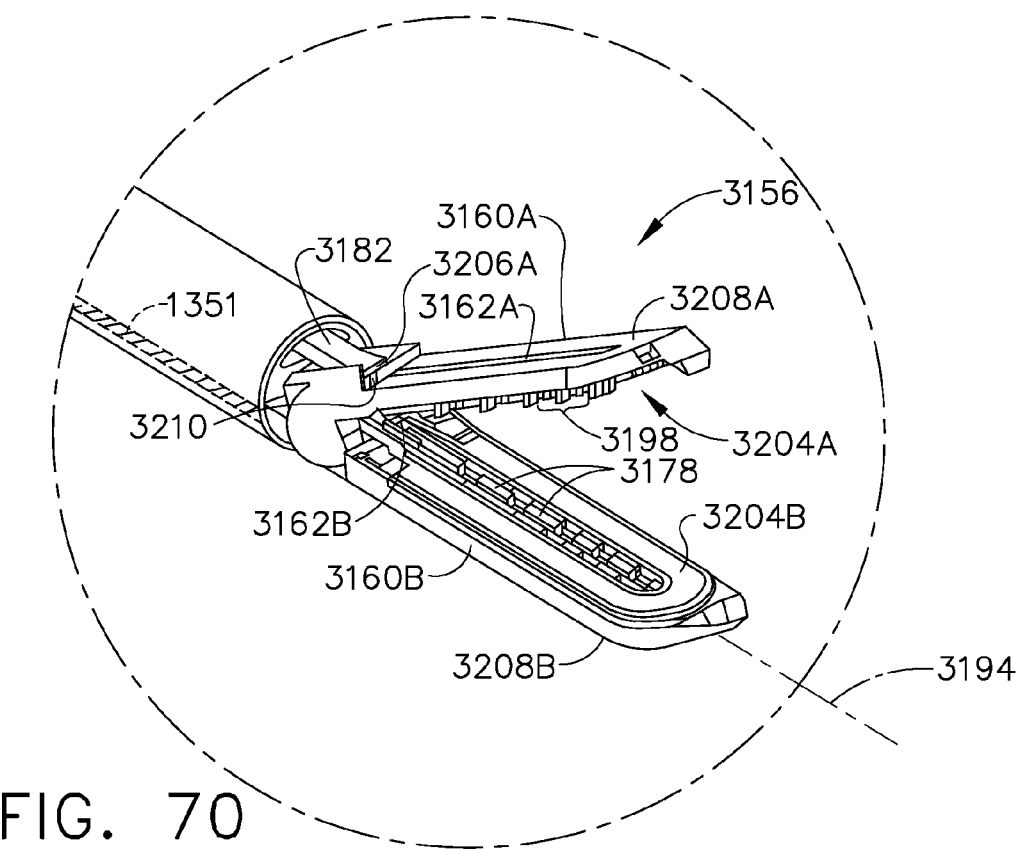
FIG. 70 shows a perspective view of some forms of an electrosurgical end effector for use with the surgical instrument.
Figure 71:
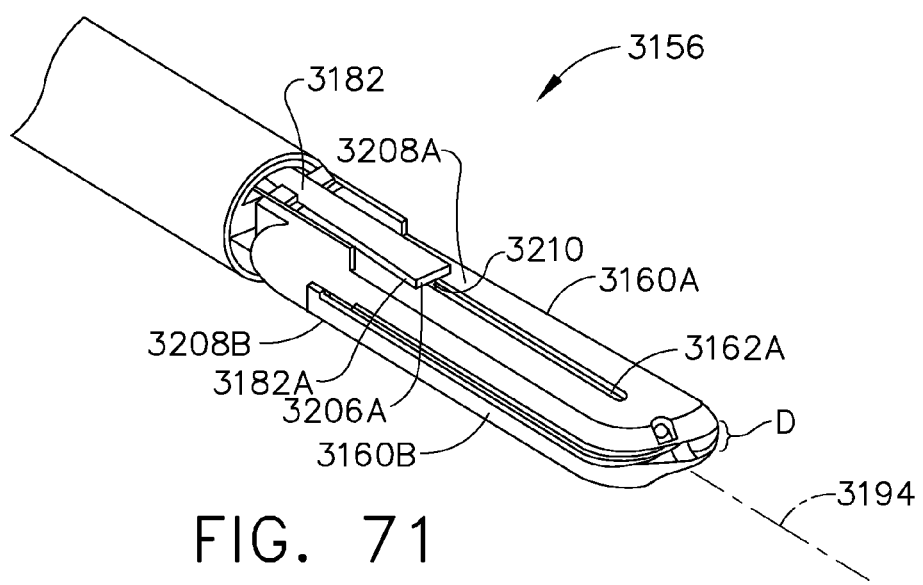
FIG. 71 shows a perspective view of some forms of the end effector of FIG. 70 with the jaws closed and the distal end of an axially movable member in a partially advanced position.

FIG. 70 shows a perspective view of some forms of an electrosurgical end effector 3156 for use with the surgical instrument 10. FIG. 70 shows the end effector 3156 with the jaws 3160A, 3160B open. FIG. 71 shows a perspective view of some forms of the end effector 3156 with the jaws 3160A, 3160B closed. As noted above, the end effector 3156 may comprise the upper first jaw 3160A and the lower second jaw 3160B, which may be straight or curved. The first jaw 3160A and the second jaw 3160B may each comprise an elongate slot or channel 3162A and 3162B (FIG. 70), respectively, disposed outwardly along their respective middle portions. Further, the first jaw 3160A and second jaw 3160B may each have tissue-gripping elements, such as teeth 3198, disposed on the inner portions of first jaw 3160A and second jaw 3160B. The first jaw 3160A may comprise an upper first jaw body 3200A with an upper first outward-facing surface 3202A and an upper first energy delivery surface 3204A. The second jaw 3160B may comprise a lower second jaw body 3200B with a lower second outward-facing surface 3202B and a lower second energy delivery surface 3204B. The first energy delivery surface 3204A and the second energy delivery surface 3204B may both extend in a "U" shape about the distal end of the end effector 3156. It will be appreciated that the end effector 3156 may be rotatable and articulable in a manner similar to that described herein with respect to the end effector 102.

Figure 72:
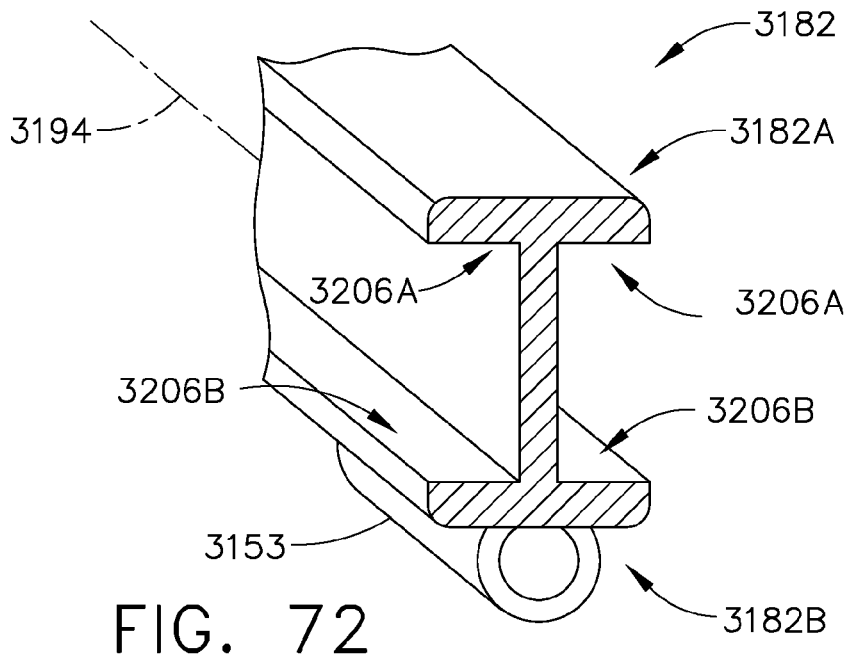
FIG. 72 is a perspective view of some forms of the axially moveable member of the end effector of FIG. 70.

FIG. 72 shows one form of an axially movable member 3182 of the end effector 3156. The axially movable member 3182 is driven by a threaded drive shaft 3151. (FIG. 70) A proximal end of the threaded drive shaft 3151 may be configured to be non-rotatably coupled to the output socket 238 and thereby receive rotational motion provided by the motor 530. The axially movable member 3182 may comprise a threaded nut 3153 for receiving the threaded drive shaft 3151 such that rotation of the threaded drive shaft 3151 causes the axially movable member 3182 to translate distally and proximally along the axis 3194. (FIG. 72) The axially moveable member 3182 may comprise one or several pieces, but in any event, may be movable or translatable with respect to the elongate shaft 158 and/or the jaws 3160A, 3160B. Also, in at least some forms, the axially moveable member 3182 may be made of 17-4 precipitation hardened stainless steel. The distal end of axially moveable member 3182 may comprise a flanged "I"-beam configured to slide within the channels 3162A and 3162B in jaws 3160A and 3160B. The axially moveable member 3182 may slide within the channels 3162A, 3162B to open and close first jaw 3160A and second jaw 3160B. The distal end of the axially moveable member 3182 may also comprise an upper flange or "c"-shaped portion 3182A and a lower flange or "c"-shaped portion 3182B. The flanges 3182A and 3182B respectively define inner cam surfaces 3206A and 3206B for engaging outward facing surfaces of first jaw 3160A and second jaw 3160B. The opening-closing of jaws 3160A and 3160B can apply very high compressive forces on tissue using cam mechanisms which may include movable "I-beam" axially moveable member 3182 and the outward facing surfaces 3208A, 3208B of jaws 3160A, 3160B.

More specifically, referring now to FIGS. 70-72, collectively, the inner cam surfaces 3206A and 3206B of the distal end of axially moveable member 3182 may be adapted to slidably engage the first outward-facing surface 3208A and the second outward-facing surface 3208B of the first jaw 3160A and the second jaw 3160B, respectively. The channel 3162A within first jaw 3160A and the channel 3162B within the second jaw 3160B may be sized and configured to accommodate the movement of the axially moveable member 3182, which may comprise a tissue-cutting element 3210, for example, comprising a sharp distal edge. FIG. 71, for example, shows the distal end of the axially moveable member 3182 advanced at least partially through channels 3162A and 3162B (FIG. 70). The advancement of the axially moveable member 3182 may close the end effector 3156 from the open configuration shown in FIG. 70. In the closed position shown by FIG. 71, the upper first jaw 3160A and lower second jaw 3160B define a gap or dimension D between the first energy delivery surface 3204A and second energy delivery surface 3204B of first jaw 3160A and second jaw 3160B, respectively. In various forms, dimension D can equal from about 0.0005" to about 0.040", for example, and in some forms, between about 0.001" to about 0.010", for example. Also, the edges of the first energy delivery surface 3204A and the second energy delivery surface 3204B may be rounded to prevent the dissection of tissue.

Figure 73:
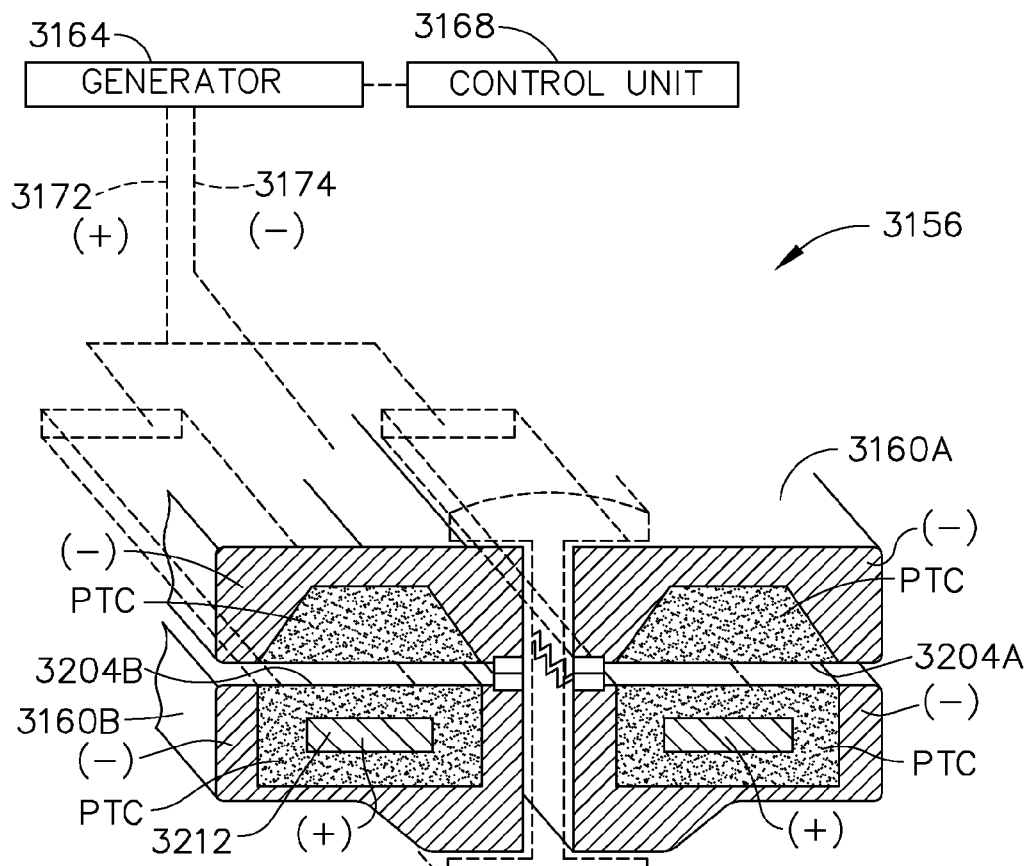
FIG. 73 is a section view of some forms of the end effector of FIG. 70.

FIG. 73 is a section view of some forms of the end effector 3156. The engagement, or tissue-contacting, surface 3204B of the lower jaw 3160B is adapted to deliver energy to tissue, at least in part, through a conductive-resistive matrix, such as a variable resistive positive temperature coefficient (PTC) body. At least one of the upper and lower jaws 3160A, 3160B may carry at least one electrode 3212 configured to deliver the energy from a generator 3164 to the captured tissue. The engagement, or tissue-contacting, surface 3204A of upper jaw 3160A may carry a similar conductive-resistive matrix (e.g., a PTC material), or in some forms the surface may be a conductive electrode or an insulative layer, for example. Alternatively, the engagement surfaces of the jaws can carry any of the energy delivery components disclosed in U.S. Pat. No. 6,773,409, filed Oct. 22, 2001, entitled ELECTROSURGICAL JAW STRUCTURE FOR CONTROLLED ENERGY DELIVERY, the entire disclosure of which is incorporated herein by reference.

The first energy delivery surface 3204A and the second energy delivery surface 3204B may each be in electrical communication with the generator 3164. The generator 3164 is connected to the end effector 3156 via a suitable transmission medium such as conductors 3172, 3174. In some forms, the generator 3164 is coupled to a controller, such as a control unit 3168, for example. In various forms, the control unit 3168 may be formed integrally with the generator 3164 or may be provided as a separate circuit module or device electrically coupled to the generator 3164 (shown in phantom to illustrate this option). The generator 3164 may be implemented as an external piece of equipment and/or may be implemented integral to the surgical instrument 10.

The first energy delivery surface 3204A and the second energy delivery surface 3204B may be configured to contact tissue and deliver electrosurgical energy to captured tissue which are adapted to seal or weld the tissue. The control unit 3168 regulates the electrical energy delivered by electrical generator 3164 which in turn delivers electrosurgical energy to the first energy delivery surface 3204A and the second energy delivery surface 3204B. The control unit 3168 may regulate the power generated by the generator 3164 during activation.

As mentioned above, the electrosurgical energy delivered by electrical generator 3164 and regulated, or otherwise controlled, by the control unit 3168 may comprise radio frequency (RF) energy, or other suitable forms of electrical energy. Further, the opposing first and second energy delivery surfaces 3204A and 3204B may carry variable resistive positive temperature coefficient (PTC) bodies that are in electrical communication with the generator 3164 and the control unit 3168. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506, all of which are incorporated herein in their entirety by reference and made a part of this specification.

A suitable generator 3164 is available as model number GEN11, from Ethicon Endo-Surgery, Inc., Cincinnati, Ohio. Also, in some forms, the generator 3164 may be implemented as an electrosurgery unit (ESU) capable of supplying power sufficient to perform bipolar electrosurgery using radio frequency (RF) energy. In some forms, the ESU can be a bipolar ERBE ICC 350 sold by ERBE USA, Inc. of Marietta, Ga. In some forms, such as for bipolar electrosurgery applications, a surgical instrument having an active electrode and a return electrode can be utilized, wherein the active electrode and the return electrode can be positioned against, adjacent to and/or in electrical communication with, the tissue to be treated such that current can flow from the active electrode, through the positive temperature coefficient (PTC) bodies and to the return electrode through the tissue. Thus, in various forms, the surgical instrument 10 utilizing the end effector 3156 creates a supply path and a return path, wherein the captured tissue being treated completes, or closes, the circuit. In some forms, the generator 3164 may be a monopolar RF ESU and the surgical instrument 10 may utilize comprise a monopolar end effector in which one or more active electrodes are integrated. For such a system, the generator 3164 may utilize a return pad in intimate contact with the patient at a location remote from the operative site and/or other suitable return path. The return pad may be connected via a cable to the generator 3164.

During operation of electrosurgical instrument 150, the user generally grasps tissue, supplies energy to the captured tissue to form a weld or a seal, and then drives a tissue-cutting element 3210 at the distal end of the axially moveable member 3182 through the captured tissue. According to various forms, the translation of the axial movement of the axially moveable member 3182 may be paced, or otherwise controlled, to aid in driving the axially moveable member 3182 at a suitable rate of travel. By controlling the rate of the travel, the likelihood that the captured tissue has been properly and functionally sealed prior to transection with the cutting element 3210 is increased.

Figure 74:
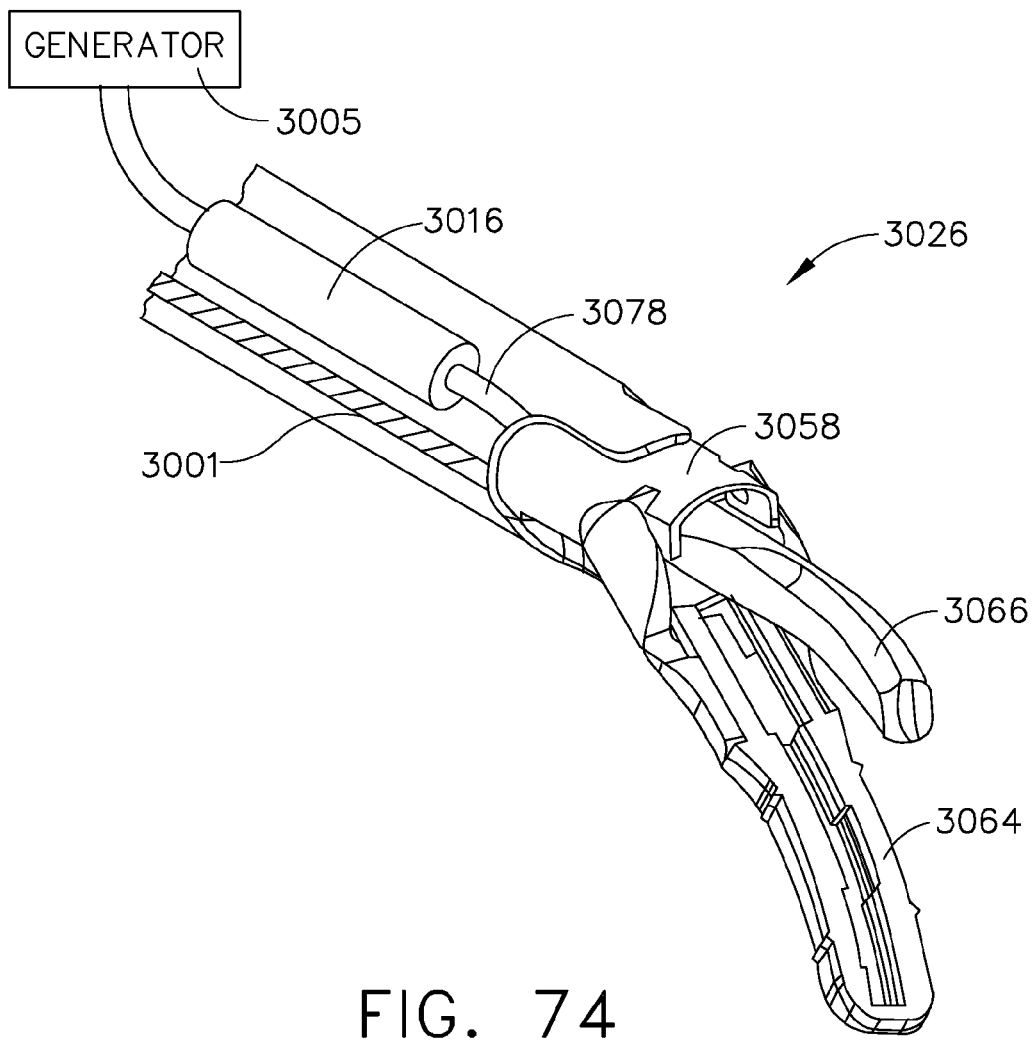
FIG. 74-75 illustrates one form of an ultrasonic end effector for use with the surgical instrument.

In some forms, the implement portion 100 may comprise an ultrasonic end effector that utilizes harmonic or ultrasonic energy to treat tissue. FIG. 74 illustrates one form of an ultrasonic end effector 3026 for use with the surgical instrument 10. The end effector assembly 3026 comprises a clamp arm assembly 3064 and a blade 3066 to form the jaws of the clamping mechanism. The blade 3066 may be an ultrasonically actuatable blade acoustically coupled to an ultrasonic transducer 3016 positioned within the end effector 3026. Examples of small sized transducers and end effectors comprising transducers are provided in co-pending U.S. application Ser. No. 13/538,601, entitled Ultrasonic Surgical Instruments with Distally Positioned Transducers and U.S. Application Publication No. 2009/0036912. The transducer 3016 may be acoustically coupled (e.g., directly or indirectly mechanically coupled) to the blade 3066 via a waveguide 3078.

Figure 75:
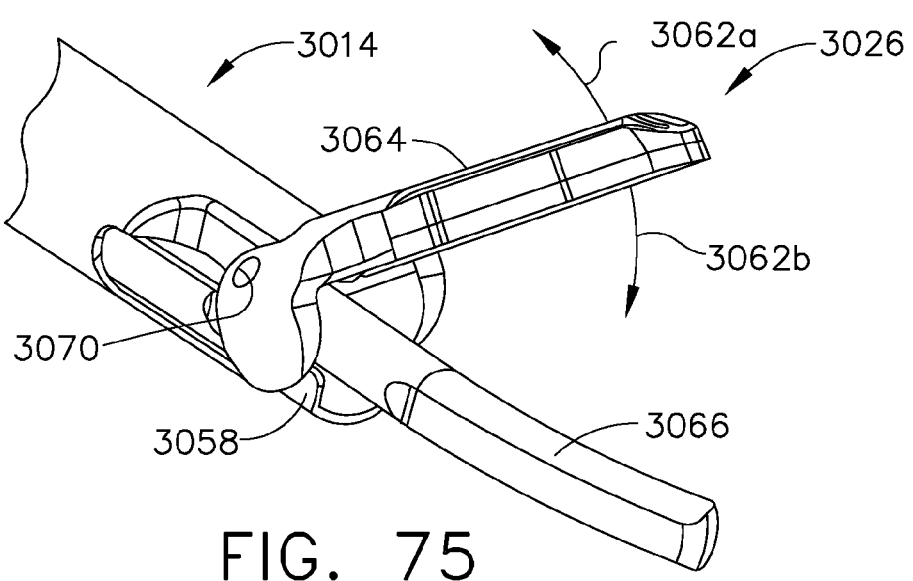

A tubular actuating member 3058 may move the clamp arm assembly 3064 to an open position in direction 3062A wherein the clamp arm assembly 3064 and the blade 3066 are disposed in spaced relation relative to one another and to a clamped or closed position in direction 3062B wherein the clamp arm assembly 3064 and the blade 3066 cooperate to grasp tissue therebetween. The distal end of the tubular reciprocating tubular actuating member 3058 is mechanically engaged to the end effector assembly 3026. In the illustrated form, the distal end of the tubular reciprocating tubular actuating member 3058 is mechanically engaged to the clamp arm assembly 3064, which is pivotable about the pivot point 3070, to open and close the clamp arm assembly 3064. For example, in the illustrated form, the clamp arm assembly 3064 is movable from an open position to a closed position in direction 3062B about a pivot point 3070 when the reciprocating tubular actuating member 3058 is retracted proximally. The clamp arm assembly 3064 is movable from a closed position to an open position in direction 3062A about the pivot point 3070 when the reciprocating tubular actuating member 3058 is translated distally. (FIG. 75)

Figure 76:
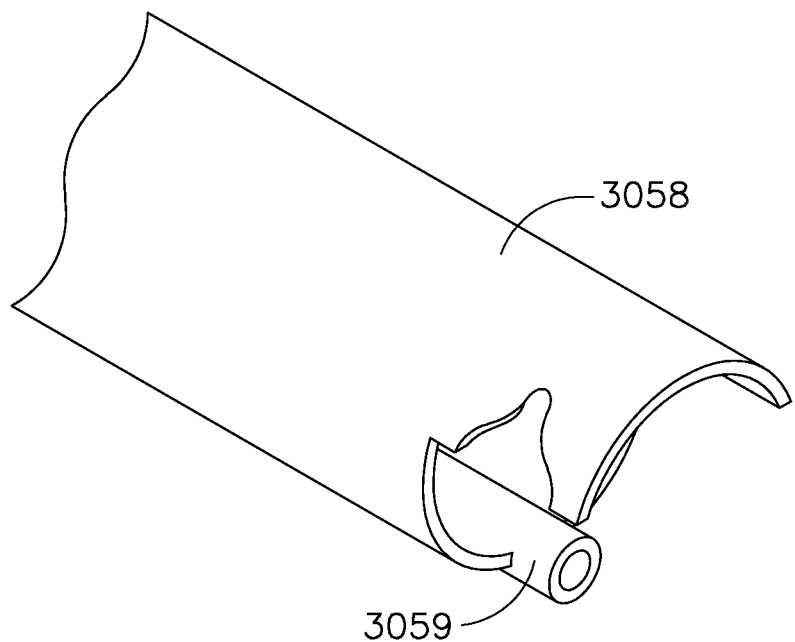
FIGS. 76-77 show additional views of one form of the axially movable member of the end effector of FIG. 74.
Figure 77:
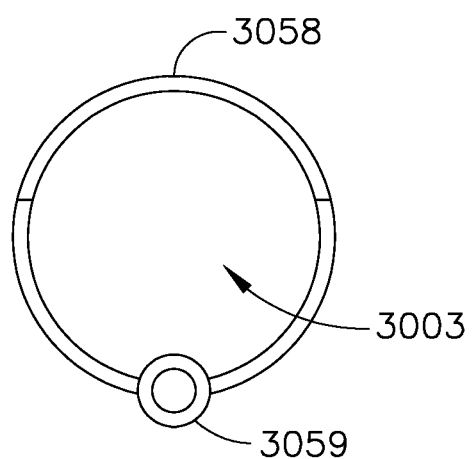

The tubular actuating member 3058 may be translated proximally and distally due to rotation of a threaded drive shaft 3001. A proximal end of the threaded drive shaft 3001 may be configured to be non-rotatably coupled to the output socket 238 and thereby receive rotational motion provided by the motor 530. The tubular actuating member 3058 may comprise a threaded nut 3059 for receiving the threaded drive shaft 3001 such that rotation of the threaded drive shaft 3001 causes the tubular actuating member 3058 to translate distally and proximally. FIGS. 76-77 show additional view of one form of the axially movable member 3058 and tubular nut 3059. In some forms, the tubular actuating member 3058 defines a cavity 3003. The waveguide 3078 and/or a portion of the blade 3066 may extend through the cavity 3003, as illustrated in FIG. 74.

In one example form, the distal end of the ultrasonic transmission waveguide 3078 may be coupled to the proximal end of the blade 3066 by an internal threaded connection, preferably at or near an antinode. It is contemplated that the blade 3066 may be attached to the ultrasonic transmission waveguide 3078 by any suitable means, such as a welded joint or the like. Although the blade 3066 may be detachable from the ultrasonic transmission waveguide 3078, it is also contemplated that the single element end effector (e.g., the blade 3066) and the ultrasonic transmission waveguide 3078 may be formed as a single unitary piece.

The ultrasonic transducer 3016, which is known as a "Langevin stack", generally oscillates in response to an electric signal provided by a generator 3005 (FIG. 74). For example, the transducer 3016 may comprise a plurality of piezoelectric elements or other elements for converting an electrical signal from the generator 3005 to mechanical energy that results in primarily a standing acoustic wave of longitudinal vibratory motion of the ultrasonic transducer 3016 and the blade 3066 portion of the end effector assembly 3026 at ultrasonic frequencies. The ultrasonic transducer 3016 may, but need not, have a length equal to an integral number of one-half system wavelengths ($n\lambda/2$; where "n" is any positive integer; e.g., n=1, 2, 3 . . . ) in length. A suitable vibrational frequency range for the transducer 3016 and blade 3066 may be about 20 Hz to 32 kHz and a well-suited vibrational frequency range may be about 30-10 kHz. A suitable operational vibrational frequency may be approximately 55.5 kHz, for example.

The generator 3005 may be any suitable type of generator located internal to or external from the surgical instrument 10. A suitable generator is available as model number GEN11, from Ethicon Endo-Surgery, Inc., Cincinnati, Ohio. When the transducer 3016 is energized, a vibratory motion standing wave is generated through the waveguide 3078 and blade 3066. The end effector 3026 is designed to operate at a resonance such that an acoustic standing wave pattern of predetermined amplitude is produced. The amplitude of the vibratory motion at any point along the transducer 3016, waveguide 3078 and blade 3066 depends upon the location along those components at which the vibratory motion is measured. A minimum or zero crossing in the vibratory motion standing wave is generally referred to as a node (i.e., where motion is minimal), and a local absolute value maximum or peak in the standing wave is generally referred to as an anti-node (e.g., where local motion is maximal). The distance between an anti-node and its nearest node is one-quarter wavelength ($\lambda/4$).

In one example form, the blade 3066 may have a length substantially equal to an integral multiple of one-half system wavelengths ($n\lambda/2$). A distal end of the blade 3066 may be disposed near an antinode in order to provide the maximum longitudinal excursion of the distal end. When the transducer assembly is energized, the distal end of the blade 3066 may be configured to move in the range of, for example, approximately 10 to 500 microns peak-to-peak, and preferably in the range of about 30 to 64 microns at a predetermined vibrational frequency of 55 kHz, for example.

In one example form, the blade 3066 may be coupled to the ultrasonic transmission waveguide 3078. The blade 3066 and the ultrasonic transmission waveguide 3078 as illustrated are formed as a single unit construction from a material suitable for transmission of ultrasonic energy. Examples of such materials include Ti6Al4V (an alloy of Titanium including Aluminum and Vanadium), Aluminum, Stainless Steel, or other suitable materials. Alternately, the blade 3066 may be separable (and of differing composition) from the ultrasonic transmission waveguide 3078, and coupled by, for example, a stud, weld, glue, quick connect, or other suitable known methods. The length of the ultrasonic transmission waveguide 3078 may be substantially equal to an integral number of one-half wavelengths ($n\lambda/2$), for example. The ultrasonic transmission waveguide 3078 may be preferably fabricated from a solid core shaft constructed out of material suitable to propagate ultrasonic energy efficiently, such as the titanium alloy discussed above (i.e., Ti6Al4V) or any suitable aluminum alloy, or other alloys, for example.

In some forms, the surgical instrument 10 may also be utilized with other stapler-type end effectors. For example, FIG. 78 illustrates one form of a linear staple end effector 3500 that may be used with the surgical instrument 10. The end effector 3500 comprises an anvil portion 3502 and a translatable staple channel 3514. The translatable staple channel 3514 is translatable in the distal and proximal directions, as indicated by arrow 3516. A threaded drive shaft 3506 may be coupled to the output socket 238, for example, as described herein above to receive rotational motion provided by the motor 530. The threaded drive shaft 3506 may be coupled to a threaded nut 3508 fixedly coupled to the staple channel 3514 such that rotation of the threaded drive shaft 3506 causes translation of the staple channel 3514 in the directions indicated by arrow 3516. The nut 3508 may also be coupled to a driver 3510, which may, in turn, contact a staple cartridge 3512. As it translates distally, the driver 3510 may push staples from the staple cartridge 3512 against the anvil 3502, thus driving the staples through any tissue positioned between the staple channel 3514 and the anvil 3502.

Also, in some forms, the surgical instrument may be utilized with a circular staple end effector. FIG. 79 illustrates one form of a circular staple end effector 3520 that may be used with the surgical instrument 10. The end effector 3520 comprises an anvil 3522 and a staple portion 3524. A threaded drive shaft 3530 extends from the anvil 3522 through the staple portion 3524. The threaded drive shaft 3530 may be coupled to the output socket 238, for example, as described herein above to receive rotational motion provided by the motor 530. A threaded nut 3532 may be coupled to the staple portion 3524 such that rotation of the threaded drive shaft 3530 alternately translates the staple portion 3524 distally and proximally as indicated by arrow 3534. The threaded shaft may also be coupled to a driver 3528 such that distal motion of the staple portion 3524 pushes the driver 3528 distally into a staple cartridge 3526 to drive staples from the cartridge 3526 into any tissue positioned between the anvil 3522 and the staple portion 3524. In some embodiments, the end effector 3520 may also comprise a knife or cutting implement 3535 for cutting tissue prior to stapling.

In addition to different end effectors, it will be appreciated that other implement portions may be interchangeable with respect to the surgical instrument 10. For example, some forms of the surgical instrument 10 utilize different power cords. FIG. A illustrates several example power cords 3540, 3542, 3544 for use with the surgical instrument. Each of the power cords 3540, 3542, 3544 comprises a socket 3546 for coupling to the surgical instrument 10. The power cords 3540, 3542, 3544 may be utilized to connect the surgical instrument 10 to various power sources. For example power cords 3540 and 3542 comprise sockets 3550, 3552 to be received by generators, such as the model number GEN11 generator, from Ethicon Endo-Surgery, Inc., in Cincinnati, Ohio. Such a generator may provide power to the instrument 10 and/or may provide a signal to drive an electrosurgical and/or ultrasonic end effector. Power cord 3544 comprises a plug 3548 that may be plugged into a wall socket to provide power to the instrument 10 (e.g., in lieu of the battery 802).

In some forms, the surgical instrument may also comprise interchangeable implement portions that include different shafts. FIG. 81 illustrates several example shafts 3554, 3556, 3558 that can be used with the surgical instrument 10. Each shaft 3554, 3556, 3558 comprises a detachable drive mount portion 700', 700'', 700''' similar to the detachable drive mount portion 700 that may be received by the instrument 10 as described herein above. Each shaft 3554, 3556, 3558 also comprises a coupler assembly 3557 for receiving an end effector similar to the coupler assembly 200 described herein above. In some embodiments, different shafts are configured to receive different types of end effectors at the coupler assembly 3557. The shafts 3554, 3556, 3558 may each comprise different characteristics including, for example, different lengths, the presence or absence of articulation, passive or active articulation, different degrees of articulation, different diameters, different curvatures, etc. For example, the shaft 3554 defines a curve 3559 off the center axis of the shaft. The shaft 3558 defines an articulation joint 3560 that may be articulated in a manner similar to that described herein above with respect to the articulation joint 310.

It will be appreciated that different kinds of implement portions 100 (e.g., power cords, shafts, end effectors, etc.) require the various motors and other components of the surgical instrument 10 to operate in different ways. For example, powered end effectors, such as the electrosurgical end effector 3156 and ultrasonic end effector 3026, require an energy signal for powering electrodes and/or ultrasonic blades. Different end effectors may also require different motion of the various motors 402, 560, 530, 610 for actuation, including, for example, the actuation of different motors, the provision of different amounts of torque, etc. In various forms, the implement portions 100 may provide the surgical instrument 10 with control parameters.

Figure 82:
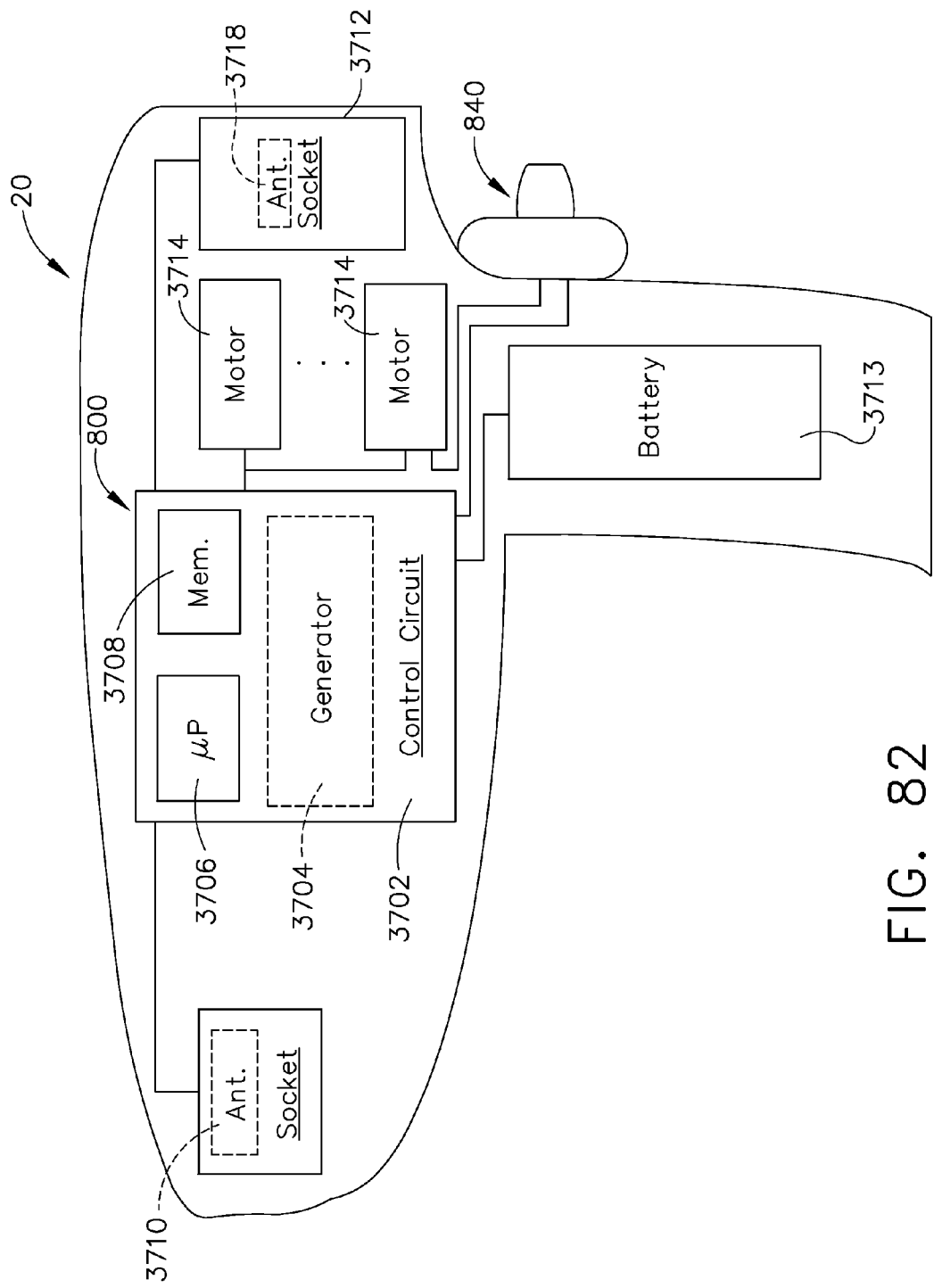
FIG. 82 is a block diagram of the handle assembly of the surgical instrument showing various control elements.

FIG. 82 is a block diagram of the handle assembly 20 of the surgical instrument 10 showing various control elements. The control elements shown in FIG. 82 are configured to receive control parameters from various implement portions and control the surgical instrument 10 based on the received control parameters and based on one or more input control signals received from the clinician (e.g., via the joystick control 840 or other suitable actuation device). The control elements may comprise a control circuit 3702 for controlling the surgical instrument 10. In various forms, the control circuit 3702 may execute a control algorithm for operating the surgical instrument 10 including any installed implement portions. In some forms, the control circuit 3702 is implemented on the proximal circuit board 820 described herein above. The control circuit 3702 comprises a microprocessor 3706 and associated memory and/or data storage 3708. In some forms the control circuit 3702 may also comprise a generator circuit 3704 for providing a power signal to an ultrasonic and/or electrosurgical device. The generator circuit 3704 may operate as a stand-alone component or in conjunction with an external generator.

FIG. 82 also shows motors 3714, which may correspond to the motors 402, 560, 530, 610 described above. A battery 3713 may correspond to the battery 802 described herein above. Input to the control circuit 3702 may be provided by the joystick control 840 or other suitable actuation device. The various surgical implement portions 100 described herein may be coupled to the handle 20 at respective sockets 3710, 3712. The socket 3712 may receive a shaft, such as the shafts 3554, 3556, 3558. For example, the socket 3712 may receive a shaft in a manner similar to the way that the handle 20 receives the detachable derive mount 700 as described herein above. The socket 3710 may be configured to receive a cord socket, such as the sockets 3546 described herein above.

Figure 83:
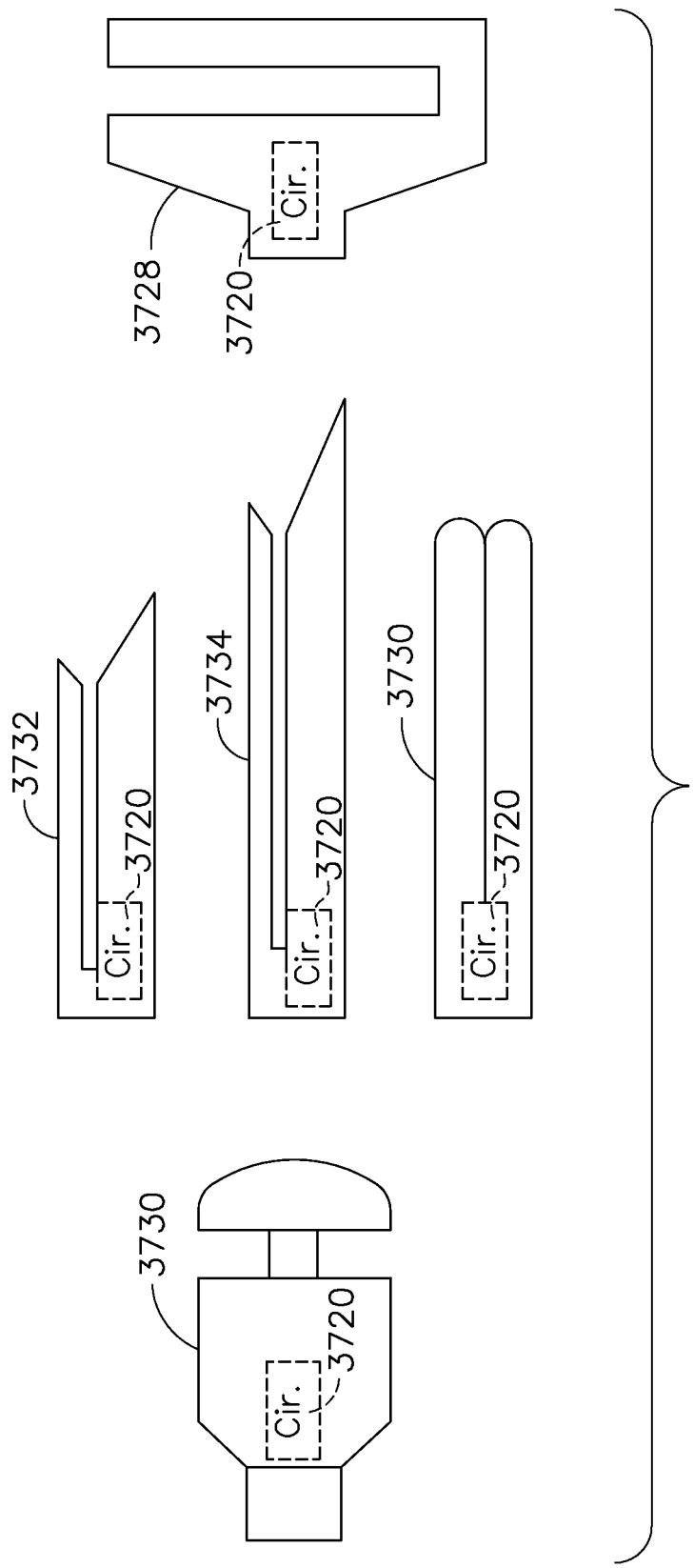
FIG. 83 illustrates one form of various end effector implement portions comprising circuits as described herein.

The control circuit 3702, in conjunction with various other control elements such as the sockets 3710, 3712, may receive control parameters from various installed implement portions. Control parameters may comprise, for example, data describing properties of the implement portions, data describing algorithms for operating the instrument 10 with the implement portions installed, etc. Sockets 3710, 3712 may mechanically and communicatively couple to the various implement portions. For example, various implement portions may comprise circuits 3720 for storing control parameters. Such circuits 3720 are shown in conjunction with the power cords 3540, 3542, 3544 in FIG. 80 and in conjunction with the shafts 3554, 3556 3558 of FIG. 81. Also, FIG. 83 illustrates one form of various end effector implement portions 3730, 3732, 3734, 3736, 3738 comprising circuits 3720 as described herein. The circuits 3720 may comprise one or more data storage components for storing control parameters for provision to the control circuit 3702. Such data storage components can include any suitable type of memory device (e.g., electrically erasable programmable read only memory (EEPROM), digital register, any other type of memory, etc.). Memory devices may also include coils or other hardware components configured to modulate predetermined control parameters, for example, in response to a radio frequency identification (RFID) interrogation signal. In some forms, the circuits 3720 make a direct wired connection to the control circuit 3702, for example, via respective sockets 3710, 3712. Accordingly, the control circuit 3702 may directly communicate with the various circuits 3720 to receive control parameters.

In some forms, the circuits 3720 comprise passive or active RFID devices. The handle 20 may comprise one or more antennas 3716, 3718, which may be positioned at or near the respective sockets 3710, 3712. Utilizing the antennas 3716, 3718, the control circuit 3702 may interrogate the circuits 3720 on installed implement portions to retrieve the control parameters. In some forms, the control circuit 3702 is programmed to interrogate the various implement portions upon start-up and/or upon an indication that an implement portion has been installed and/or removed. In response the control circuit 3702 may receive a reflected signal from the RFID device. The reflected signal may indicate the relevant control parameters. In some forms, the circuits 3720 may comprise active RFID devices that transmit the data describing their associated implement portions, for example, upon installation.

As illustrated in FIG. 81, some shaft forms may comprise antennas 3719 at distal portions. The antennas 3719 may be in communication with the control circuit 3702 via conductors (not shown) extending through the respective shafts allowing the control circuit 3702 to interrogate RFID device circuits 3720 on end effectors, such as end effectors 3730, 3732, 3734, 3736, 3738. In some forms, antennas 3718 positioned in the handle may receive and transmit sufficient power so as to interrogate an RFID device circuit 3720 on an end effector without the requiring a separate antenna 379 in the shaft. In some arrangements, the circuits 3720 may be configured to make a wired connection to the control circuit 3702. For example, antennas 3716, 3718, 3719 may be omitted.

Figure 84:
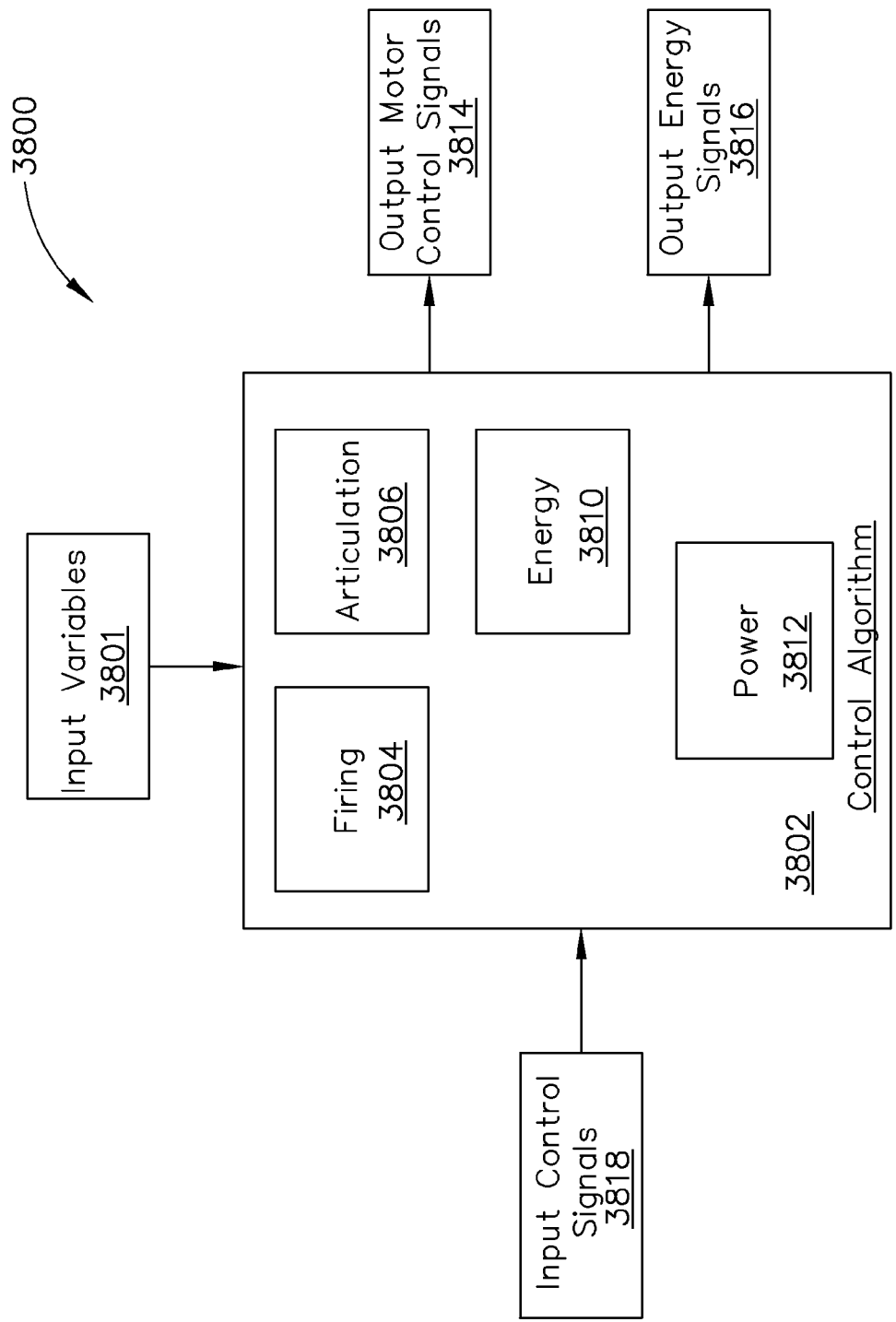
FIG. 84 is a block diagram showing one form of a control configuration to be implemented by the control circuit to control the surgical instrument.

FIG. 84 is a block diagram showing one form of a control configuration 3800 to be implemented by the control circuit 3702 to control the surgical instrument 10. According to the configuration 3800, the control circuit 3702 is programmed with a control algorithm 3802. The control algorithm 3802 receives control parameters from installed implement portions in the form of input variables 3801. The input variables 3801 may describe properties of installed implement portion. The control algorithm 3802 also receives one or more input control signals 3818 (e.g., from the joystick control 840, a robotic system, or other suitable actuation device operated by a clinician). Based on the input variables 3801, the control algorithm 3802 may operate the surgical instrument 10 by translating the one or more input control signals 3818 to an output motor control signal 3814 for controlling the motors 3714 and an optional output energy control signal 3816 for controlling an ultrasonic and/or electrosurgical end effector. It will be appreciated that not all forms of the surgical instrument 10 need receive input variables from all of the listed implement portions. For example, some forms of the surgical instrument comprise a single shaft and/or a fixed end effector. Also, some forms of the surgical instrument (or configurations thereof) may omit a power cord.

The control algorithm 3802 may implement a plurality of functional modules 3804, 3806, 3810, 3812 related to different aspects of the surgical instrument 10. A firing module 3804 may translate the one or more input control signals 3818 to one or more output motor control signals 3814 for controlling the respective motors 3714 to fire the instrument 10. An articulation module 3806 may translate the one or more input control signals 3818 to one or more output motor control signals 3814 for articulating the shaft of the instrument 10. The power module 3812 may route power to the various components of the surgical instrument 10, as required by an installed power cord. For forms of the instrument 10 utilizing energy at the end effector (e.g., ultrasonic and/or electrosurgical instruments), an energy module 3810 may translate the one or more input control signals 3818 into output energy signals 3816 to be provided to the end effector. The energy signals 3816 may be produced by the generator 3704 and/or by an external generator (not shown in FIG. 84) and may be provided to a transducer 3016 and/or energy delivery surfaces 3204A, 3204B at the end effector.

The various modules 3804, 3806, 3810, 3812 of the control algorithm 3802 may utilize control parameters in the form of input variables 3801 to translate the one or more input control signals 3818 into output signals 3814, 3816. For example, input variables 3801 received from different implement portions may affect the control algorithm 3802 in different ways. Input variables 3801 received from power cord, such as 3540, 3542, 3544 may include, for example, a cord type, whether the cord is connected to an external object such as a generator or power socket, the identity of the external object to which the cord is connected, etc. One type of power cord, such as cord 3544, may be configured to receive power from an external power socket, such as a wall outlet. When the control circuit 3702 determines that a cord of this type is installed (e.g., at socket 3710), the power module 3812 may be programmed to configured the control circuit 3702 to power the motors 3714 and/or energy elements from power provided through the installed cord implement. Power provided through the installed cord implement may be used in addition to or instead of power provided by the battery 3713.

Another type of cord, such as 3540 and 3542, may be configured to communicate with an external generator. The power module 3812 and/or energy module 3810 may configured the control circuit 3702 to power the energy element based on an energy signal received via the installed power cord. In addition, the energy module 3810 may configure the control circuit 3702 to provide input to the generator via the installed power cord. Such input may include, for example, an input control signal 3818 indicating that the clinician has requested energy. In some forms, the input variables 3801 received from the power cord may also indicate a type of generator that the power cords is configured to (and/or is) coupled to. Example generators may include stand-alone electrosurgical generators, stand-alone ultrasonic generators, combined electrosurgical/ultrasonic generators, etc. In some forms, the input variables 3801 received from the cord may also indicate a type of generator with which the cord is configured to couple. In some forms, the type of generator indicated may affect the operation of the control algorithm 3802. For example, different generator types may have different control interfaces and expect different forms of instructions from the surgical instrument 10 and/or provide outputs in different forms.

When the shaft, such as one of shafts 3554, 3556, 3558, is a removable implement portion, input variables 3801 received from the shaft may indicate various properties of the shaft. Such properties may include, for example, a length of the shaft, a position and degree of curvature of the shaft (if any), parameters describing an articulation joint of the shaft (if any), etc. The length of the shaft and the position and degree of curvature of the shaft may be utilized, for example, by the firing module 3804 and/or by the articulation module 3806 of the control algorithm 3802 to determine torque requirements and/or tolerances. The parameters describing the articulation joint of the shaft may indicate, or allow the articulation module 3806 to derive, various motor motions required to articulate the shaft in different directions. In some embodiments, the input variables 3801 may also indicate a degree of allowable articulation, which the articulation module 3806 may translate into a maximum allowable motor movement. In some forms, input variables 3801 received from the shaft may also indicate whether the installed shaft supports shaft rotation and/or end effector rotation. Such variables 3801 may be utilized by the control algorithm 3802 to derive which motor or motors 3714 are to be actuated for shaft and/or end effector rotation, the torque and number of rotations indicated for each motor 3714, etc.

Input variables 3801 received from end effector implement portions may be of different forms based on the type of end effector used. For example, endocutters and other stapler end effectors, such as the end effector 102 described herein above, may provide variable values indicating the length of the end effector (e.g., 45 mm or 60 mm staple line), whether the anvil and elongate channel are straight or curved, the motor 3714 to which a drive shaft, such as drive shaft 180, is coupled, etc.

Such input variables 3801 may be utilized by the firing module 3804 to translate input control signals 3818 requesting firing of the instrument 10 to output motor control signals 3814. For example, the length, curvature, etc. of the end effector may determine the motor 3714 to be activated, the amount of force or torque required to be provided, the number of motor rotations required to fire, etc. Similarly, input variables 3818 received from linear or circular stapler end effectors, such as 3500 and 3520, may be utilized by the firing algorithm 3804 to determine the motor 3714 to be actuated to fire, the amount of force or torque required to be provide in response to different levels of the input control signal 3818 related to firing, the number of motor rotations required to fire, etc.

When the end effector is an energy end effector, such as the electrosurgical end effector 3156 or the ultrasonic end effector 3026, the received input variables 3801 may describe information relating to the closure motion of the end effector, as well as information describing the energy elements including, for example, the timing of energy provision in the context of the firing stroke. The information describing the closure motion may be utilized, for example, by the firing module 3804 to determine which motor or motors 3714 are to be actuated for firing and/or retraction, the torque and number of rotations indicated for each motor 3714, etc. Information describing the energy elements may be utilized, for example, by the energy module 3810 to generate the output energy signal 3816. For example, the energy module 3810 may determine what type of output energy signal 3816 is required (e.g., voltage, current, etc.), whether the signal can be generated by an internal generator 3704, whether there are any lock-outs to be implemented with the signal. Example lock-outs may prevent the firing motion from taking place unless energy is being provided and/or may prevent energy from being provided unless the firing motion is taking place. In some embodiments, the energy module 3810 may also derive the timing of the output energy signal 3816 in the context of the instrument's firing stroke. For example, referring to the electrosurgical end effector 3156, the energy module 3810 may derive how long the energy delivery surfaces 3204A, 3204B should be activated before the tissue cutting element 3210 is advanced.

Figure 85:
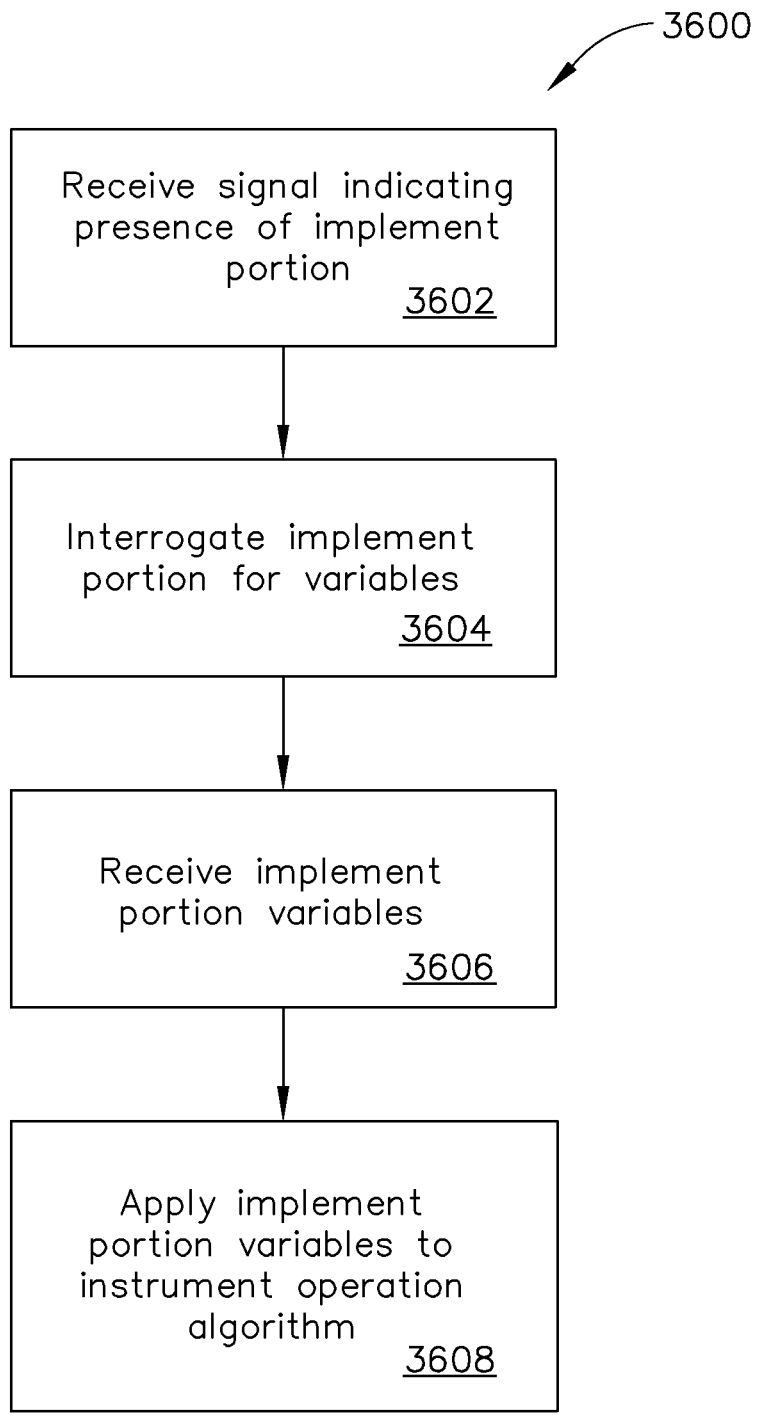
FIG. 85 is a flowchart showing one example form of a process flow for implementing the control algorithm of FIG. 84.

FIG. 85 is a flowchart showing one example form of a process flow 3600 for implementing the control algorithm 3802 with the control circuit 3702. At 3602, the control circuit 3702 may receive an indication of the presence of an implement portion (e.g., a power cord, shaft, end effector, etc.). The indication may be generated automatically upon installation of the implement portion. For example, in forms where the implement portion comprises an active RFID, the indication of the presence of the implement portion may be provided by the active RFID. Also, in some embodiments, the socket 3710, 3712 by which the implement portion is connected to the instrument 10 may comprise a switch that indicates the presence of the implement portion. At 3604, the control circuit 3702 may interrogate the implement portion for input variables 3801. When the implement portion comprises a passive RFID device, the interrogation may comprise illuminating the RFID device with a radio frequency signal. When the implement portion is in wired communication with control circuit, 3702, the interrogation may comprise sending a request to a memory device associated with the implement portion.

At 3606, the control circuit 3702 may receive input variables 3801 from the implement portion. The input variables 3801 may be received in any suitable manner. For example, when the implement portion comprises a passive RFID device, the input variables 3801 may be derived by demodulating a return signal from the RFID device. When there is a wired connection between the implement portion and the circuit 3702, the input variables 3801 may be received directly from a memory device at the implement portion, etc. At 3608, the control circuit 3702 may apply the input variables 3801 to the control algorithm 3802, for example, as described herein above. This may have the effect of configuring the pre-existing algorithm 3802 to operate the instrument 10 with whatever implement portion or portions are installed.

Figure 86:
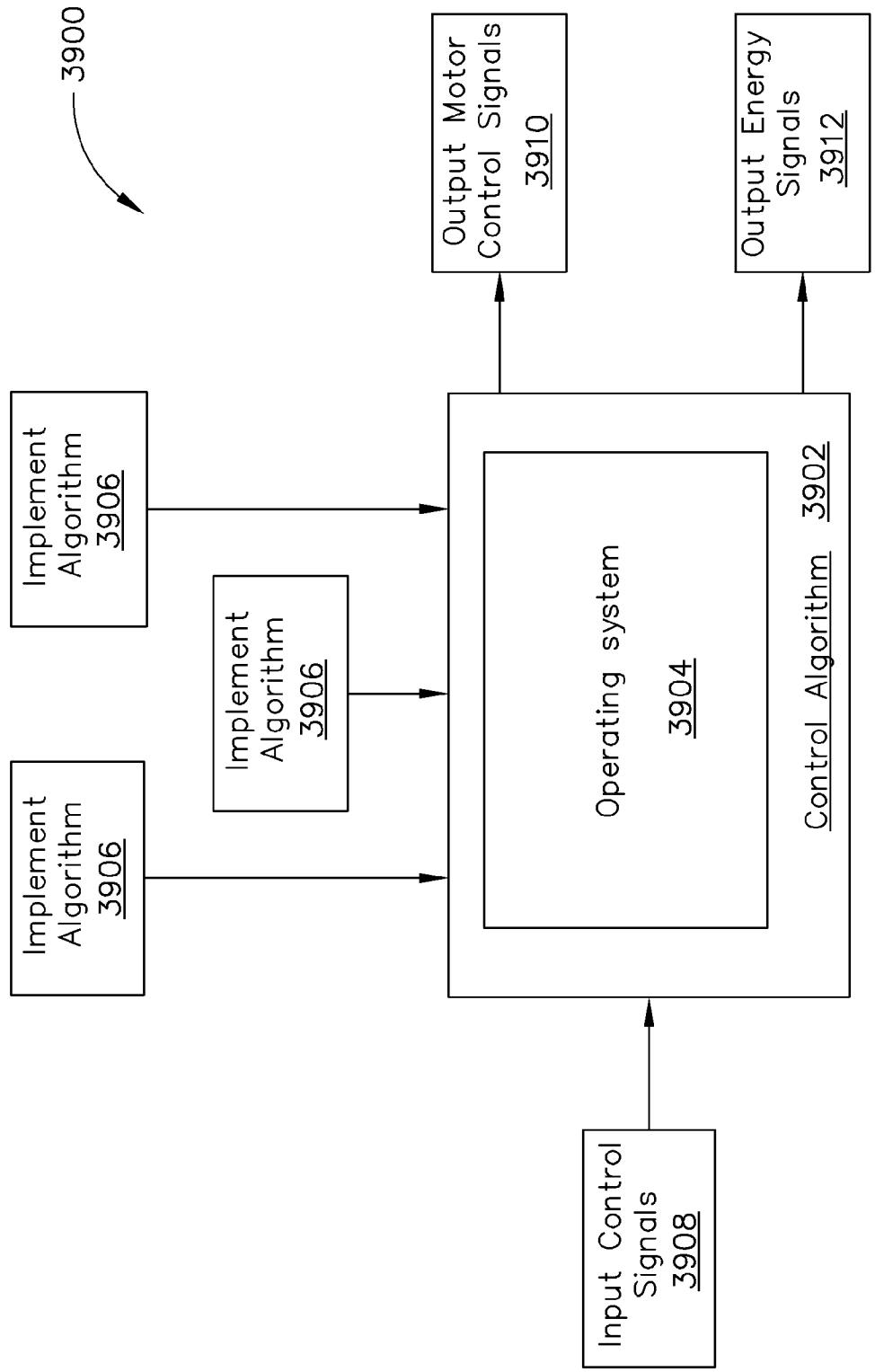
FIG. 86 is a block diagram showing another form of a control configuration to be implemented by the control circuit to control the surgical instrument.

FIG. 86 is a block diagram showing another form of a control configuration 3900 to be implemented by the control circuit 3702 to control the surgical instrument 10. In the configuration 3900, the control parameters received from the various implement portions comprise algorithms for controlling the respective implement portions. The control circuit 3702 implements a shell control algorithm 3902 comprising an operating system 3904. The operating system 3904 is programmed to interrogate installed implement potions to receive control parameters, in the form of implement algorithms 3906. Each implement algorithm 3906 may describe a manner of translating input control signals 3908 into output motor control signals 3910 and output energy signals 3912. Upon receiving the implement algorithms 3906, the operating system 3904 may execute the algorithms 3906 to operate the instrument 10.

In some embodiments, the operating system 3904 may also reconcile the various algorithms 3906. For example, an implement algorithm 3906 received from an energy end effector may take different configurations based on whether the instrument is in communication with an external generator, or utilizing the internal generator 3704. Accordingly, the operating system 3904 may configure an implement algorithm 3906 for an energy end effector based on whether an implement algorithm 3906 has been received from a corresponding power cord configured to couple with an external generator. Also, in some forms, the tolerances and/or number of rotations necessary for firing an end effector may depend on the configuration of the shaft. Accordingly, the operating system 3904 may be configured to modify the implement algorithm 3906 received from an end effector based on a corresponding implement algorithm 3906 received from a shaft.

Figure 87:
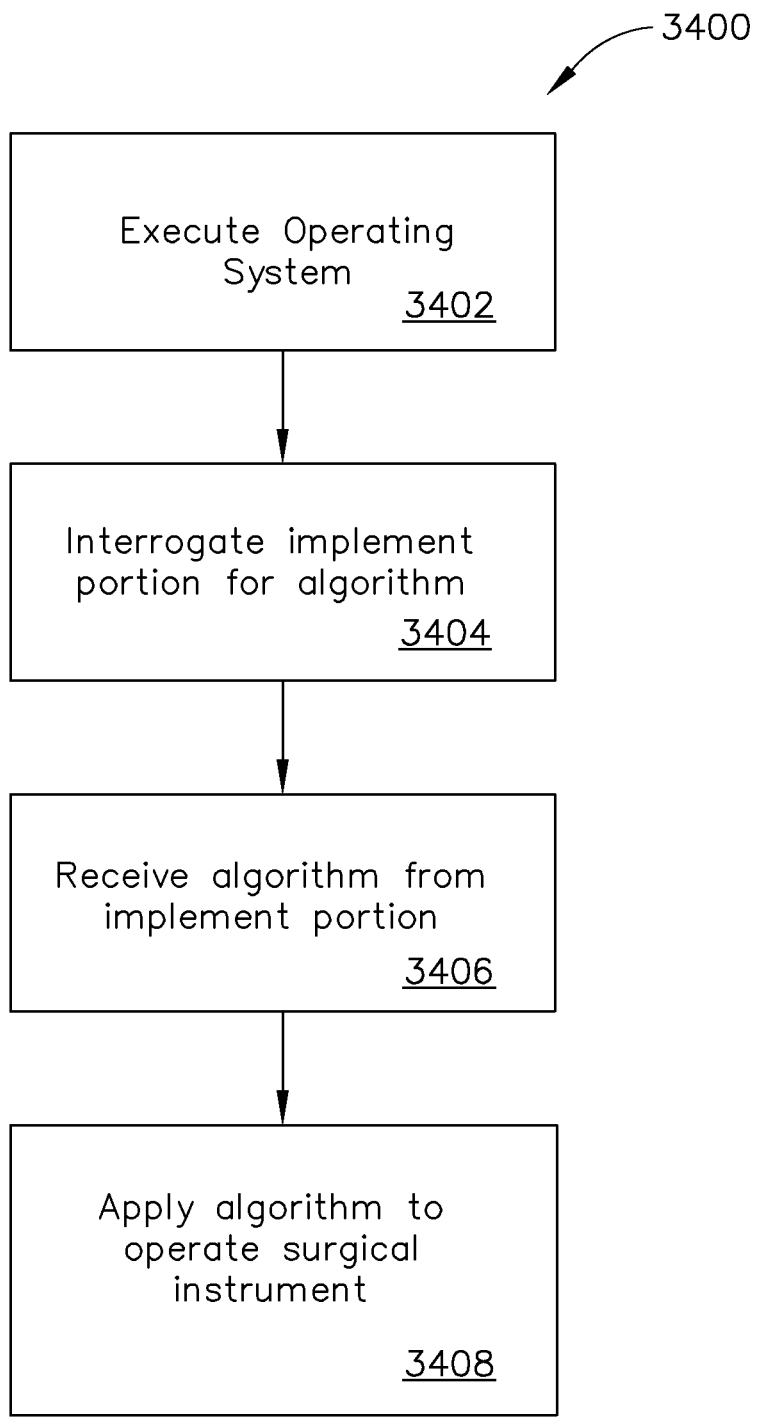
FIG. 87 is a flowchart showing one example form of a process flow for implementing the control algorithm of FIG. 86.

FIG. 87 is a flowchart showing one example form of a process flow 3400 for implementing the control algorithm 3902 utilizing the control circuit 3702. At 3402, the control circuit 3702 may execute the operating system 3904. The operating system 3904 may program the control circuit 3702 to take various other actions described herein with respect to the control configuration 3900. At 3404, the control circuit 3702 may interrogate one or more implement portions installed with the surgical instrument 10, for example, as described herein. At 3406, the control circuit 3702 may receive implement algorithms 3906, as described herein. At 3408, the control circuit 3702 may apply the received algorithms 3906 to operate the surgical instrument. Applying the received algorithms 3906 may include, for example, reconciling the algorithms 3906, as described herein above.

Figure 88:
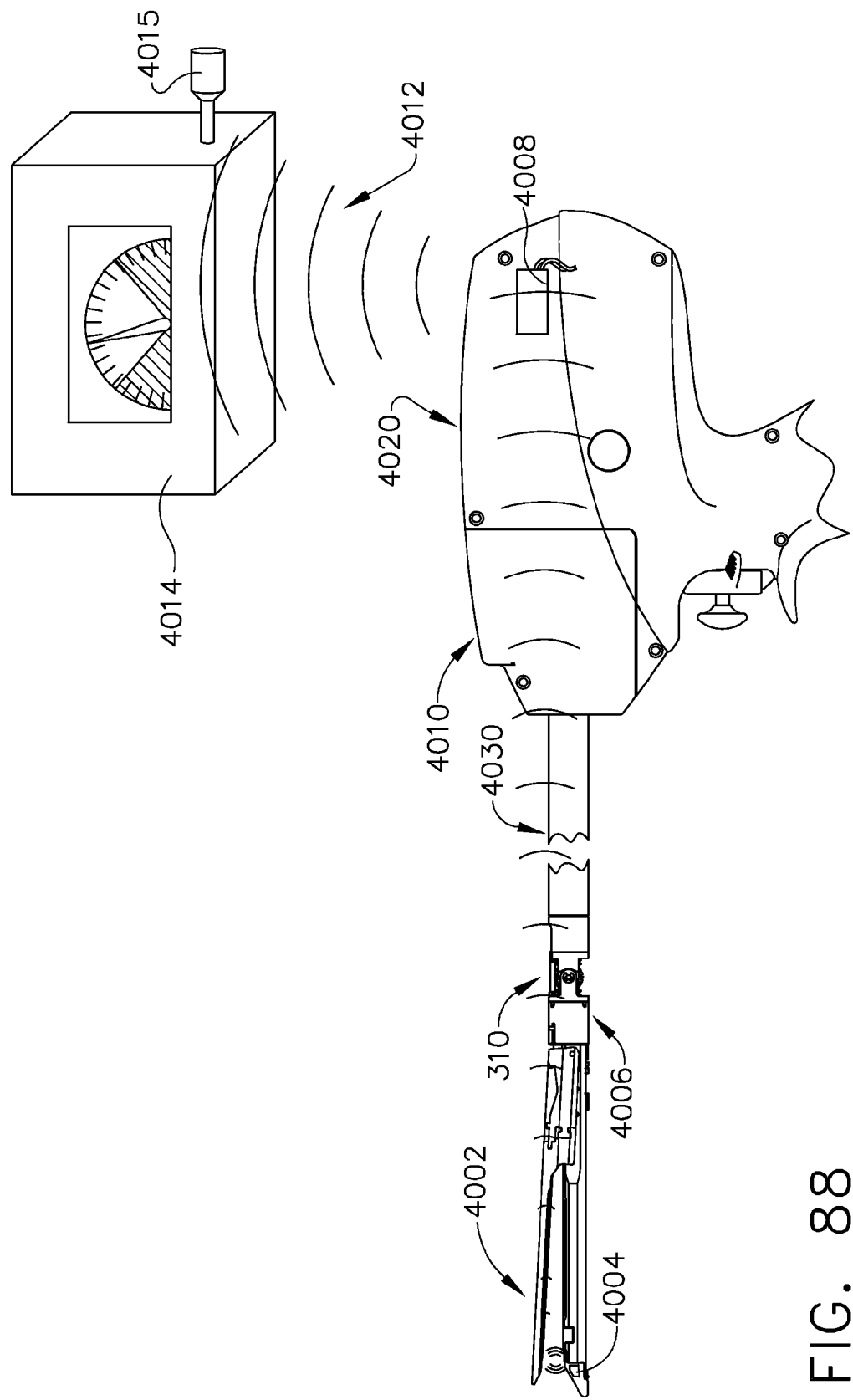
FIG. 88 illustrates one form of a surgical instrument comprising a relay station in the handle.
Figure 89:
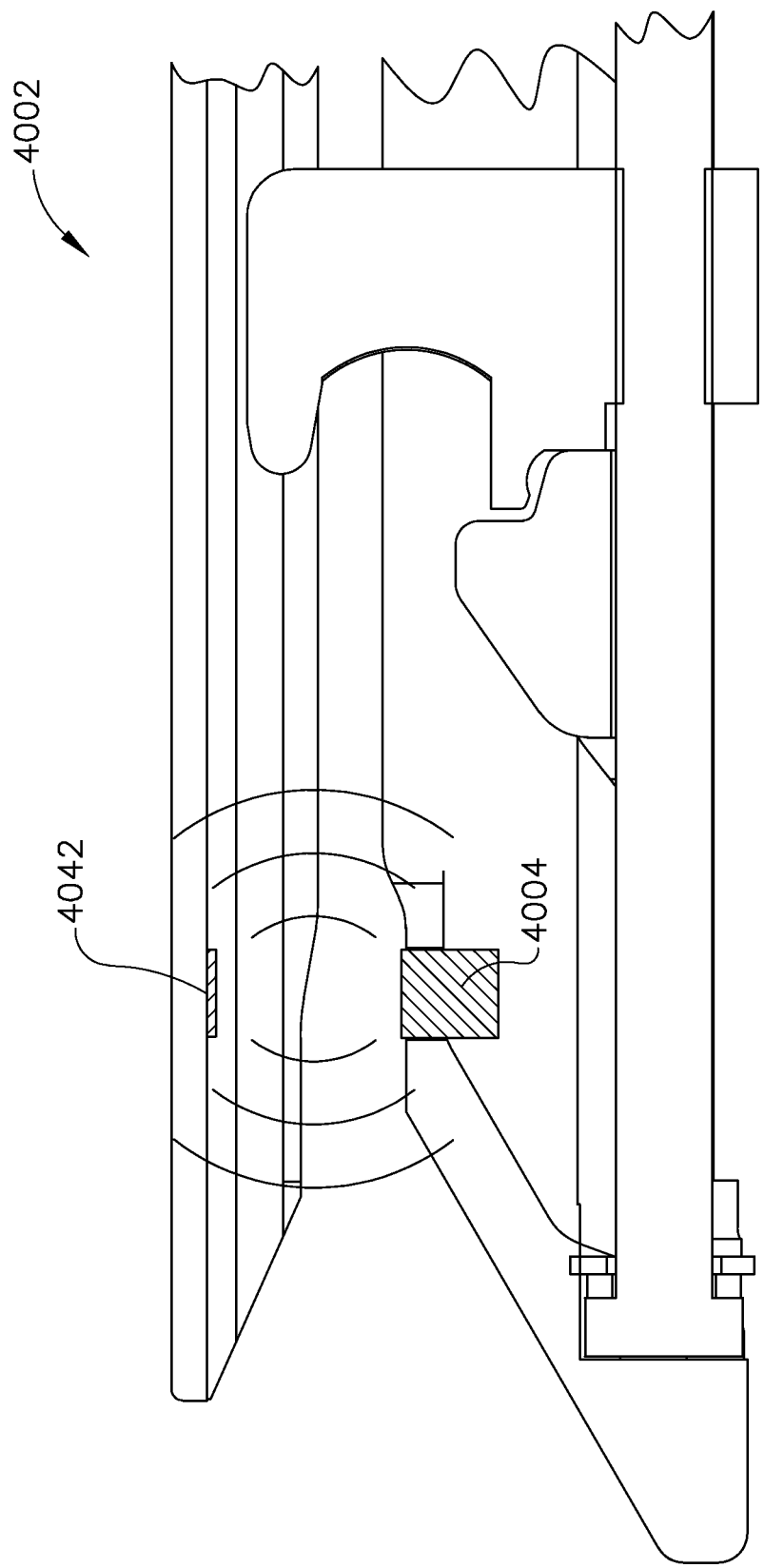
FIG. 89 illustrates one form of an end effector with a sensor module configured to transmit a signal disposed therein.

FIGS. 88 and 89 illustrate one form of a surgical instrument 4010 comprising a sensing module 4004 located in the end effector 4002. In some forms, the surgical instrument 4010 may be similar to the surgical instrument 10 and the end effector 4002 may be similar to the end effector 102 described above. The sensing module 4004 may be configured to measure one or more conditions at the end effector 4002. For example, in one arrangement, the sensing module 4004 may comprise a tissue-thickness sensing module that senses the thickness of tissue clamped in the end effector 4002 between the staple cartridge 130 and the anvil assembly 190. The sensing module 4004 may be configured to generate a wireless signal indicative of the one or more measured conditions at the end effector 4002. According to one arrangement shown in FIG. 89, the sensing module 4004 may be located at a distal end of the end effector 4002, such that the sensing module 4004 is out of the way of the staples of the staple cartridge 130 when the staples are fired. In various forms, the sensing module 4004 may comprise a sensor, a radio module, and a power source. See FIG. 90. The sensor may be disposed in the distal end of the end effector 4002 (as shown in FIG. 89), at the powered articulation joint 310, or any other suitable portion of the implement portion 100.

In various arrangements, the sensor may comprise any suitable sensor for detecting one or more conditions at the end effector 4002. For example, and without limitation, a sensor located at the distal end of the end effector 4002 may comprise a tissue thickness sensor such as a Hall Effect Sensor or a reed switch sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. As another example, and without limitation, a sensor located at the powered articulation joint 310 may comprise a potentiometer, a capacitive sensor (slide potentiometer), piezo-resistive film sensor, a pressure sensor, a pressure sensor, or any other suitable sensor type. In some arrangements, the sensing module 4004 may comprise a plurality of sensors located in multiple locations in the end effector 4002. The sensing module 4004 may further comprise one or more visual markers to provide a visual indication, such as through a video feed, to a user of the current condition at the end effector 4002.

The sensing module 4004 may comprise a radio module configured to generate and transmit a wireless signal indicative of the measured condition at the end effector 4002. See FIG. 90. The radio module may comprise an antenna configured to transmit the wireless signal at a first frequency. The transmission power of the sensing module 4004 may be limited by the size of the antenna and the power source locatable in the sensing module 4004. The size of the end effector 4002 may reduce the available space for placing an antenna or a power source powerful enough to transmit a signal from the sensing module 4004 to a remote location, such as, for example, a video monitor 4014. Due to the constrained size of the antenna and the low power delivered by the power source to the sensing module 4004, the sensing module 4004 may produce a low-power signal 4006 capable of transmission over short distances. For example, in some forms the sensing module 4004 may transmit a signal from the end effector 4002 to the relay station 4008 located proximally from the end effector 4002. For example, the relay station 4008 may be located at the handle 4020 of the instrument 4010, in the shaft 4030 (e.g., a proximal portion of the shaft 4030), and/or in an implantable device positioned on or within the patient.

The relay station 4008 may be configured to receive the low-power signal 4006 from the sensing module 4004. The low-power signal 4006 is limited by the size of the antenna and the power source that may be located in the end effector 4002 as part of the sensing module 4004. The relay station 4008 may be configured to receive the low-power signal 4006 and retransmit the received signal as a high-power signal 4012. The high-power signal 4012 may be transmitted to remote network or device, such as a video monitor 4014 configured to display a graphical representation of the measured condition at the end effector 4002. Although the sensing module 4004 and the relay station 4008 have generally been described in relation to the surgical instrument 4010, those skilled in the art will recognize that the sensing module 4004 and relay station 4008 arrangement may be used with any suitable surgical system, such as, for example, a robotic surgical system. For example, the relay station 4008 may be positioned in a shaft and/or instrument portion of the robotic surgical instrument. A suitable robotic surgical system is described in U.S. patent application Ser. No. 13/538,700, entitled "Surgical Instruments with Articulating Shafts," now U.S. Patent Application Publication No. 2014/0005703, which is herein incorporated by reference in its entirety.

In some forms, the video monitor 4014 may comprise a stand-alone unit for displaying the measured condition at the end effector 4002, a standard viewing monitor for use in endoscopic, laparoscopic, or open surgery, or any other suitable monitor. The displayed graphical representation may be displayed overtop of a video feed or other information displayed on the video monitor. In some forms, the high-power signal 4012 may interrupt the video monitor 4014 display and may cause the video monitor to display only the graphical representation of the measured condition at the end effector 4002. A receiver module 4015 may be interfaced with the video monitor 4014 to allow the video monitor 4014 to receive the high-power signal 4012 from the relay station 4008. In some arrangements, the receiver module 4015 may be formed integrally with the video monitor 4014. The high-power signal 4012 may be transmitted wirelessly, through a wired connection, or both. The high-power signal 4012 may be received by a wide-area network (WAN), a local-area network (LAN), or any other suitable network or device.

In some forms, the video monitor 4014 may display images based on data contained in the received high-power signal 4012. For example, the clinician may see real-time data regarding the thickness of the clamped tissue throughout a procedure involving the surgical instrument 4010. The video monitor 4014 may comprise a monitor, such as a cathode ray tube (CRT) monitor, a plasma monitor, a liquid-crystal display (LCD) monitor, or any other suitable visual display monitor. The video monitor 4014 may display a graphical representation of the condition at the end effector 4002 based on the data contained in the received high-power signal 4012. The video monitor 4014 may display the condition at the end effector 4002 in any suitable manner, such as, for example, overlaying a graphical representation of the condition at the end effector over a video feed or other data displayed on the video monitor 4014. In some forms, the video monitor 4014 may be configured to display only data received from the high-power signal 4012. Similarly, the high-powered signal 4012 may be received by a computer system (not shown). The computer system may comprise a radio-frequency module (such as, for example, receiver module 4015) for communication with the relay station 4008. The computer system may store the data from the high-power signal 4012 in a memory unit (e.g., a ROM or hard disk drive) and may process the data with a processor.

In some forms, the relay station 4008 amplifies the power of the low-power signal 4006 to a high-power signal 4012 but does not otherwise alter the low-power signal 4006. The relay station 4008 may be configured to retransmit the high-power signal 4012 to a remote network or device. In some arrangements, the relay station 4008 may alter or process the received low-power signal 4006 before retransmitting the high-power signal 4012. The relay station 4008 may be configured to convert the received signal from a first frequency transmitted by the sensing module 4004 into a second frequency receivable by a remote network or device, such as the video monitor 4014. For example, in one arrangement, the sensing module 4004 may transmit the low-power signal 4006 using a first frequency comprising a human-tissue permeable frequency. A human-tissue permeable frequency may comprise a frequency configured to pass through human tissue with minimal attenuation of the signal. For example, a frequency may be chosen outside of a water absorption band to limit the attenuation of the signal by human tissue (which may comprise a high percentage of water). For example, the sensing module 4004 may use the Medical Implant Communication Service (MICS) frequency band (402-405 MHz), a suitable industrial, scientific, and medical (ISM) radio band (such as 433 MHz center frequency or 915 MHz center frequency), a near field communication band (13.56 MHz), a Bluetooth communication band (2.4 GHz), an ultrasonic frequency, or any other suitable, human-tissue permeable frequency or frequency band. The relay station 4008 may receive the low-power signal 4006 in the first frequency. The relay station 4008 may convert the low-power signal 4006 from the first frequency to a second frequency that is suitable for transmission through air over long ranges. The relay station 4008 may use any suitable frequency to transmit the high-power signal 4012, such as, for example, a Wi-Fi frequency (2.4 GHz or 5 GHz).

In some forms, the relay station 4008 may convert the received low-power signal 4006 from a first communication protocol to a second communication protocol prior to transmission of the high-power signal 4012. For example, the sensing module 4004 may transmit the low-power signal 4006 using a first communication protocol, such as, for example, a near field communication (NFC) protocol, a Bluetooth communication protocol, a proprietary communication protocol, or any other suitable communication protocol. The relay station 4008 may receive the low-power signal 4006 using the first communication protocol. The relay station 4008 may comprise a protocol conversion module to convert the received signal from the first communication protocol to a second communication protocol, such as, for example, TCP/IP, UDP, or any other suitable communication protocol.

Figure 90:
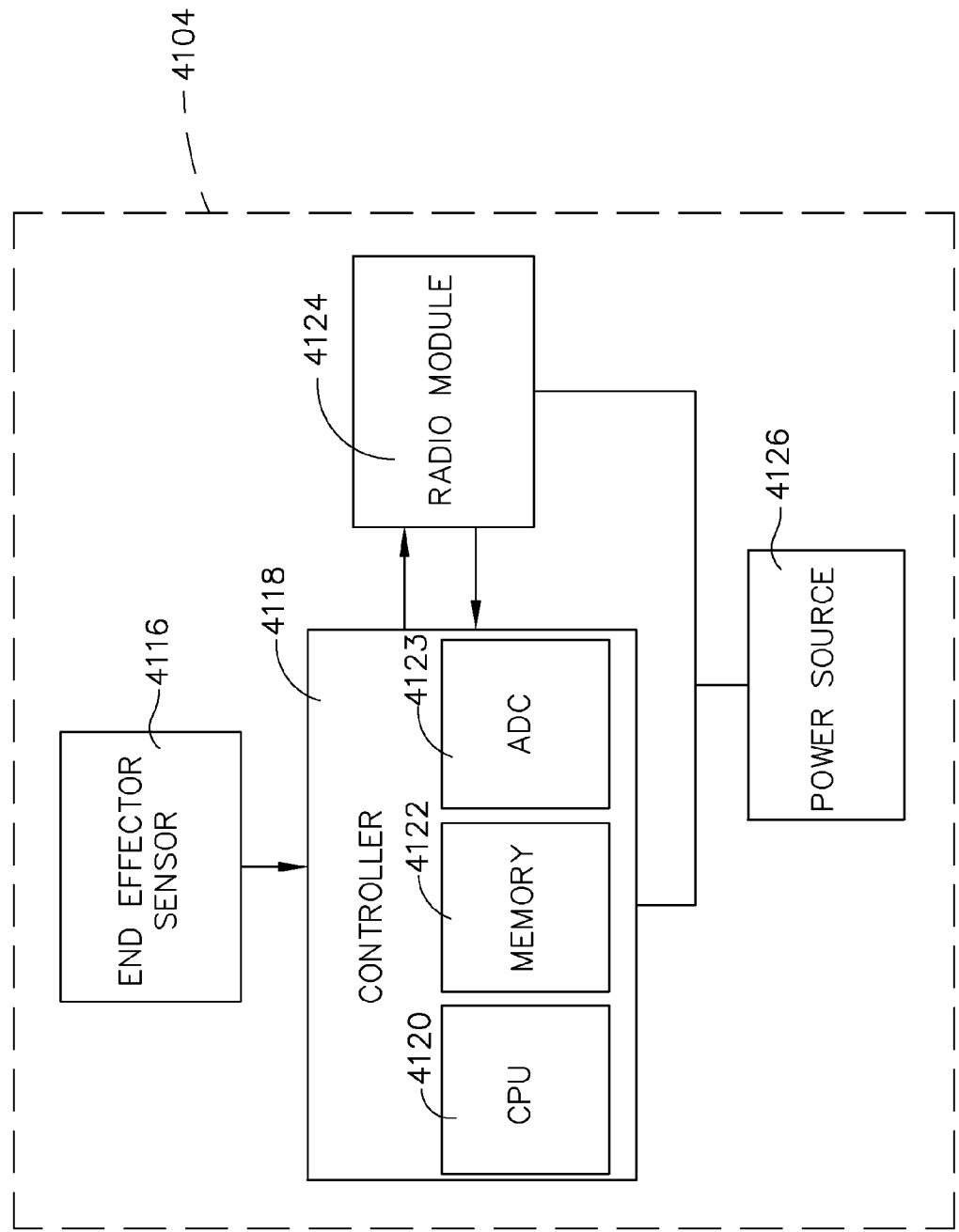
FIG. 90 is a block diagram showing one form of a sensor module.

FIG. 90 is a block diagram showing a sensing module 4104, which represents an example arrangement of the sensing module 4004 described herein above. The sensing module 4104 may comprise a sensor 4116, a controller 4118, a radio module 4124, and a power source 4126. The controller 4118 may comprise a processor unit 4120 and a memory unit 4122. The sensor 4116 may be disposed in the distal end of the end effector 4002 (as shown in FIG. 89), at articulation joint 310, or any other suitable portion of the implement portion 100. In various forms, the sensor 4116 may comprise any suitable sensor for detecting one or more conditions at the end effector.

In some arrangements, the sensor 4116 may comprise a tissue thickness sensor, such as, for example, a Hall Effect sensor. The tissue thickness sensor may detect the thickness of tissue clamped in the end effector 4002 based on a magnetic field generated by a magnet 4042 located, for example, at a distal end of the anvil assembly 190. See FIG. 89. When the clinician closes the anvil assembly 190, the magnet 4042 rotates downwardly closer to the sensing module 4004, thereby varying the magnetic field detected by the sensing module 4004 as the anvil assembly 190 rotates into the closed (or clamped) position. The strength of the magnetic field from the magnet 4042 sensed by the sensing module 4004 is indicative of the distance between the channel 130 and the anvil assembly 190, which is indicative of the thickness of the tissue clamped between the channel 130 and the anvil assembly 190 when the end effector 4002 is in the closed (or clamped) position.

The sensing module 4104 may be configured to generate a wireless signal indicative of the measured condition at the end effector. The wireless signal may be generated by the radio module 4124. In some forms, the transmission power of the radio module 4124 is limited by the size of an antenna included in the radio module 4124 and the size of a power source 4126 located in the sensing module 4104. The size of the end effector 4002 may reduce the available space for placing an antenna or a power source 4126 powerful enough to transmit a signal from the sensor 4116 to a remote location, such as, for example, a video monitor 4014. Due to the limitations on the antenna and the low power delivered by the power source 4126, the radio module 4124 may only produce a low-power signal 4006 capable of transmission over short distances, such as the distance to the proximal end of the shaft 4030. For example, in one form, the radio module 4124 may transmit the low-power signal 4006 from the end effector 4002 to the handle 4020 of the surgical instrument 4010. In some arrangements, a power source 4126 capable of delivering higher power levels may generate a low-power signal 4006 to prolong operation of the surgical instrument 4010.

The memory unit 4122 of the controller 4118 may comprise one or more solid state read only memory (ROM) and/or random access memory (RAM) units. In various arrangements, the processor 4120 and the memory unit(s) 4122 may be integrated into a single integrated circuit (IC), or multiple ICs. The ROM memory unit(s) may comprise flash memory. The ROM memory unit(s) may store code instructions to be executed by the processor 4120 of the controller 4118. In addition, the ROM memory unit(s) 4122 may store data indicative of the cartridge type of the cartridge 130. That is, for example, the ROM memory unit(s) 4122 may store data indicating the model type of the staple cartridge 130. In some arrangements, a controller in the handle 4020 of the surgical instrument 4010 may utilize the condition information and model type of the staple cartridge 130 to detect proper operation of the surgical instrument 4010. For example, the sensing module 4004 may be configured to measure tissue thickness. The tissue thickness information and the cartridge model type may be used to determine if the tissue clamped in the end effector 4002 is too thick or too thin, based on the specified tissue thickness range for the particular staple cartridge 130. The radio module 4124 may be a low power, 2-way radio module that communicates wirelessly, using a wireless data communication protocol, with the relay station 4008 in the handle 4020 of the surgical instrument 4010. The radio module 4124 may comprise any suitable antenna for transmission of the low-power signal 4006. For example, the radio module 4124 may comprise a dipole antenna, a half-wave dipole antenna, a monopole antenna, a near field communication antenna, or any other suitable antenna for transmission of the low-power signal 4006. The size of the antenna, and therefore the available transmission power and frequencies, may be limited by the size of the end effector 4002.

According to various forms, the radio module 4124 may communicate with the relay station 4008 using a human-tissue permeable frequency. For example, the communications between the radio module 4124 and the relay station 4008 may use the Medical Implant Communication Service (MICS) frequency band (402-405 MHz), a suitable industrial, scientific, and medical (ISM) radio band (such as 433 MHz center frequency or 915 MHz center frequency), a Near Field communication band (13.56 MHz), a Bluetooth communication band (2.4 GHz), an ultrasonic frequency, or any other suitable, human-tissue-permeable frequency or frequency band. The power source 4126 may comprise a suitable battery cell for powering the components of the sensing module 4004, such as a Lithium-ion battery or some other suitable battery cell.

In some forms, the components of the sensing module 4104 may be located in the end effector 4002, on the shaft 4030, or in any other suitable location of the surgical instrument 4010. For example, the sensor 4116 may be located in the distal end of the end effector 4002. The controller 4118, the radio module 4124, and the power source 4126 may be located on the shaft 4030. One or more wires may connect the sensor 4116 to the controller 4118, the radio module 4124, and the power source 4126. In some forms, the functions of the end effector 4002 and the shaft 4030 may limit the placement of the sensing module 4104. For example, in the illustrated form, the end effector 4002 is articulable and rotatable through the powered articulation joint 310. Placing wires over the powered articulation joint 310 may result in twisting or crimping of the wires and may interfere with the operation of the powered articulation joint 310. The placement of the sensing module 4004 components may be limited to a location distal of the powered articulation joint 310 to prevent operational issues of the articulation joint 310 or of the sensing module 4004.

In some arrangements, the sensing module 4104 may comprise an analog to digital convertor (ADC) 4123. The sensor 4116 may generate an analog signal representative of a condition at the end effector 4002. Transmission of the signal representative of a condition at the end effector 4002 wirelessly may require conversion of the analog signal to a digital signal. The analog signal produced by the sensor 4116 may be converted into a digital signal by the ADC 4123 prior to the generation and transmission of the low-power signal 4006. The ADC 4123 may be included in the controller 4118 or may comprise a separate controller, such as, for example, a microprocessor, a programmable gate-array, or any other suitable ADC circuit.

Figure 91:
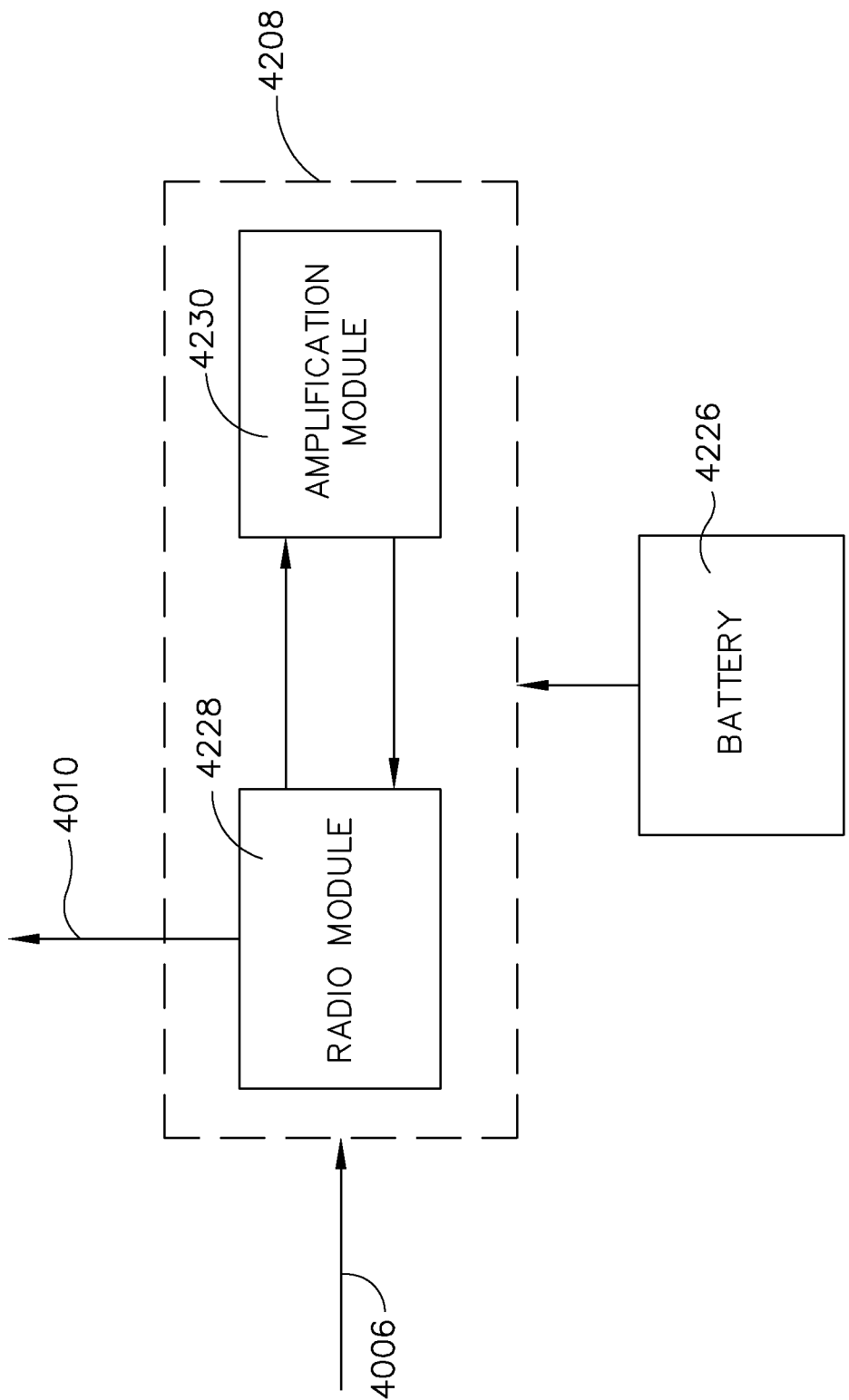
FIG. 91 is a block diagram showing one form of a relay station.

FIG. 91 is a block diagram showing a relay station 4208, which represents one example arrangement of the relay station 4008 described herein above. The relay station 4208 may be located proximal to the shaft, such as, for example, in close proximity with a battery 4226, and spaced away from the sensing module 4004 in the end effector 4002 by, for example, the shaft 4030. For example, the relay station 4208 may be located in the handle 4020 of the surgical instrument 4010. As such, the relay station 4208 may receive a wireless signal from the sensing module 4004. The relay station 4208 may comprise a releasable module that may be selectively interfaced with the handle 4020 of the surgical instrument 4002.

As shown in FIG. 91, the relay station 4208 may comprise a radio module 4228 and an amplification module 4230. In some arrangements, the radio module 4228 is configured to receive the low-power signal 4006. The low-power signal 4006 may be transmitted from the sensing module 4004 and is indicative of a condition at the end effector 4002. The radio module 4228 of the relay station 4208 receives the low-power signal 4006 and provides the low-power signal 4006 to an amplification module 4230. The amplification module 4230 may amplify the low-power signal 4006 to a high-power signal 4012 suitable for transmission over a longer range than the low-power signal 4006. After amplifying the received low-power signal 4006 to the high-power signal 4012, the amplification module 4230 may provide the high-power signal 4012 to the radio module 4228 for transmission to a remote network or device, such as, for example, the video monitor 4014. The amplification module 4230 may comprise any suitable amplification circuit, for example, a transistor, an operational amplifier (op-amp), a fully differential amplifier, or any other suitable signal amplifier.

Figure 92:
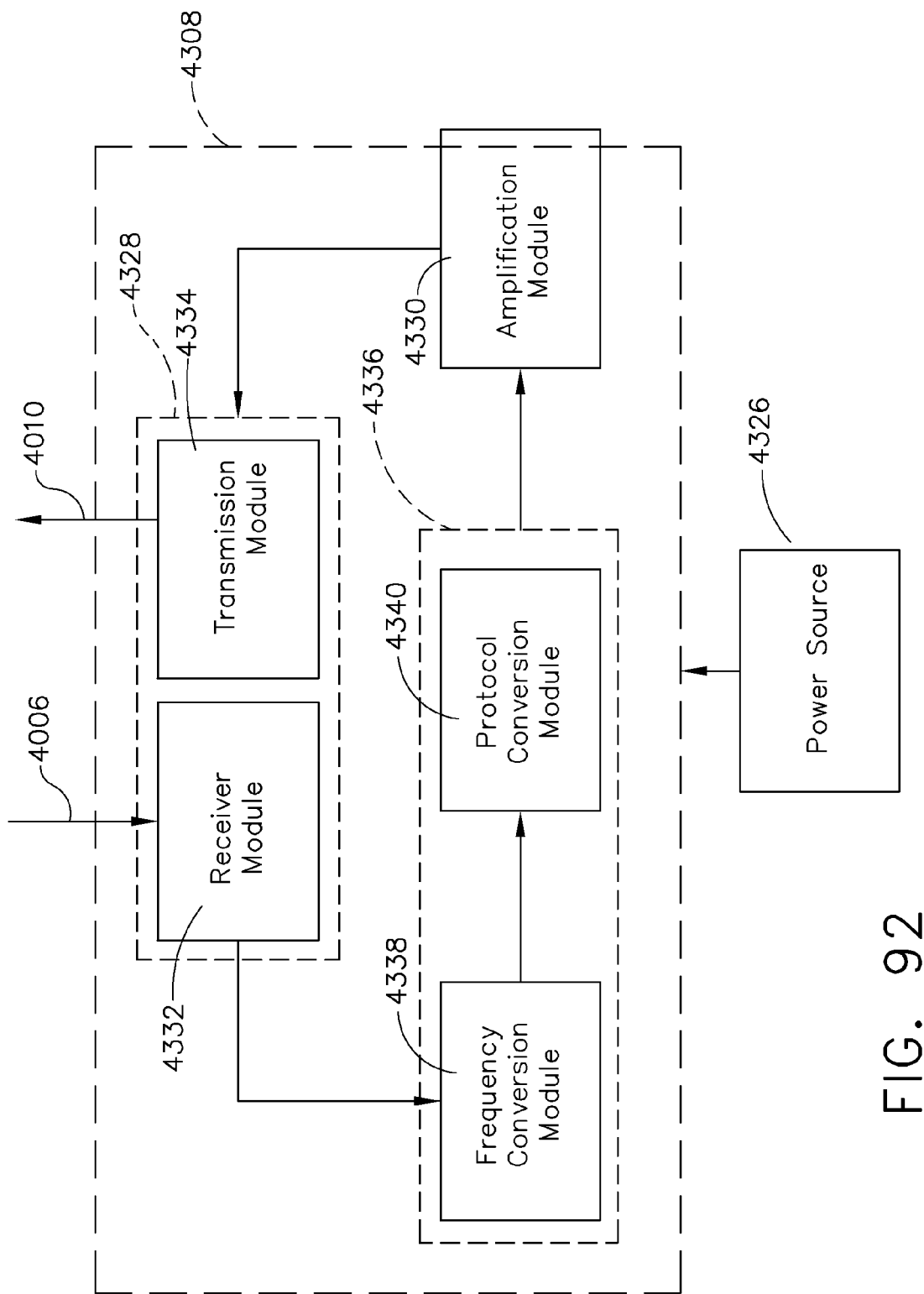
FIG. 92 is a block diagram showing one form of a relay station configured to convert a received low-power signal.

FIG. 92 is a block diagram showing a relay station 4308, which represents another example arrangement of the relay station 4008 described herein above. In the illustrated form, the relay station 4308 comprises a radio module 4328, an amplification module 4330, and a processing module 4336. The amplification module 4330 may amplify the received low-power signal 4006 prior to processing by the processing module 4336, after the processing module 4336 has processed the received low-power signal 4006, or both prior to and after processing by the processing module 4336. The radio module 4328 may comprise a receiver module 4332 and a transmitter module 4334. In some forms, the receiver module 4332 and the transmitter module 4334 may be combined into a signal transceiver module (not shown). The receiver module 4332 may be configured to receive the low-power signal 4006 from the sensing module 4004. The receiver module 4332 may provide the received low-power signal 4006 to the processing module 4336.

In the illustrated arrangement, the processing module 4336 comprises a frequency conversion module 4338 and a protocol conversion module 4340. The frequency conversion module 4338 may be configured to convert the received low-power signal 4006 from a first frequency to a second frequency. For example, the sensing module 4004 may transmit the low-power signal 4006 using a first frequency that is suitable for transmission through human tissue, such as a MICS or an ISM frequency. The receiver module 4332 may receive the low-power signal 4006 in the first frequency. The frequency conversion module 4338 may convert the low-power signal 4006 from the first frequency to a second frequency that is suitable for transmission through air over long ranges. The frequency conversion module 4338 may convert the received low-power signal 4006 into any suitable frequency for transmission of the high-power signal, such as, for example, a Wi-Fi frequency (2.4 GHz or 5 GHz frequencies).

The protocol conversion module 4340 may be configured to convert the received signal from a first communication protocol to a second communication protocol. For example, the sensing module 4004 may transmit the low-power signal 4006 using a first communication protocol, such as, for example, a near field communication (NFC) protocol, a Bluetooth communication protocol, a proprietary communication protocol, or any other suitable communication protocol. The relay station 4308 may receive the low-power signal 4006 using the first communication protocol. The relay station 4308 may comprise a protocol conversion module 4340 to convert the received low-power signal 4006 from the first communication protocol to a second communication protocol, such as, for example, a TCP/IP protocol, a Bluetooth protocol, or any other suitable communication protocol. The processing module 4336, including the frequency conversion module 4338 and the protocol conversion module 4340, may comprise one or more microprocessors, programmable gate-arrays, integrated circuits, or any other suitable controller or any combination thereof.

In some forms, the frequency conversion module 4338 and/or the protocol conversion module 4340 may be programmable. Networks, video monitors, or other receiving equipment may be configured to receive signals at a specific frequency and in a specific protocol. For example, a local-area network (LAN) may be configured to receive a wireless signal using the 802.11 wireless standard, requiring a transmission at a frequency of 2.4 GHz or 5 GHz and using a TCP/IP communication protocol. A user may select the 802.11 wireless communication standard from a plurality of communication standards stored by the relay station 4308. A memory module may be included in the relay station 4308 to store the plurality of communication standards. A user may select a communication standard for the high-power signal 4012 from the plurality of communication standards stored by the memory module. For example, a user may select the 802.11 communication standard as the communication standard for the transmission of the high-power signal 4012. When a communication standard is selected by a user, the frequency conversion module 4338 or the protocol conversion module 4340 may be programmed by the memory module to convert the received low-power signal 4006 into the selected communication standard by converting the frequency or communication protocol of the received low-power signal 4006. In some arrangements, the relay station 4308 may automatically detect the proper frequency and communication protocol for receiving the low-power signal 4006 or transmitting the high-power signal 4012. For example, the relay station 4308 may detect a hospital wireless communication network. The relay station 4308 may automatically program the frequency conversion module 4338 and protocol conversion module 4340 to convert the received low-power signal 4006 into the proper frequency and protocol for communication of the high-power signal 4012 to the hospital wireless communication network.

In the illustrated form, the processing module 4336 may provide the processed signal to an amplification module 4330 for amplification of the processed signal to a high-power signal 4012 prior to transmission. The amplification module 4330 may amplify the processed signal to a suitable level for transmission by a transmission module 4334. The amplification module 4330 may comprise any suitable amplification circuit, for example, a transistor, an operational amplifier (op-amp), a fully differential amplifier, or any other suitable electronic amplifier. The amplification module 4330 may comprise a battery (not shown) or may be connected to a power source 4326 located within the handle 4020 of the surgical instrument 4010. The amplification module 4330 may be programmable to provide one or more amplification levels in response to the selection of a specific communication type.

The amplification module 4330 may provide the high-power signal 4012 to the transmission module 4334 for transmission. Although the radio module 4328, the processing module 4336, and the amplification module 4330 are shown as separate modules, those skilled in the art will recognize that any or all of the illustrated modules may be combined into a signal integrated circuit or multiple integrated circuits.

Figure 93:
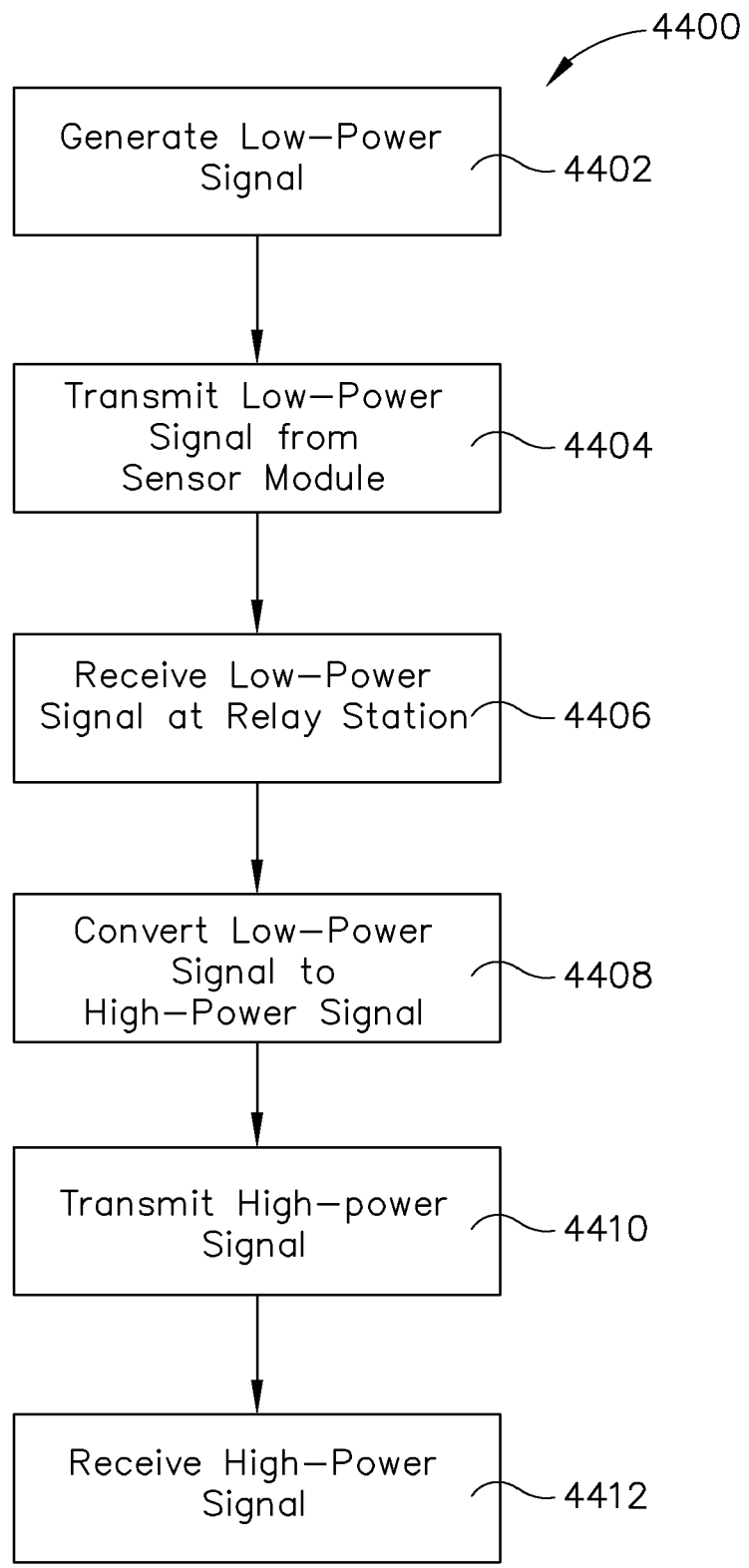
FIG. 93 is a flow chart of one form of a method for relaying a signal indicative of a condition at an end effector.

FIG. 93 illustrates one embodiment of a method for relaying a signal indicative of a condition at an end effector 4400. The method 4400 may comprise generating 4402, by a sensing module (e.g., the sensing module 4004 described herein), a signal indicative of a condition at an end effector, such as end effector 4002. The signal may represent any measurable condition at the end effector 4002, such as, for example, the thickness of tissue clamped in the end effector 4002. The sensing module may generate the signal using a sensor, such as, for example, the sensor 4116 of the sensing module 4104 shown in FIG. 90. The method 4400 may further comprise, transmitting 4404, by a radio module the generated signal as a low-power signal. For example, the radio module 4124 shown in FIG. 90 may transmit a low-power signal 4006. In practice, the transmission power of the radio module may be limited by the size of the antenna and power source that may be disposed in the end effector 4002. Given the limited space, the transmission power of the radio module may be limited to a low-power signal 4006. The low-power signal 4006 may be transmitted using the radio module at a power-level that allows the low-power signal 4006 to be received by a relay station 4008 in the handle 4020 of the surgical instrument 4010.

The method for relaying the signal indicative of a condition at an end effector 4400 may further comprise receiving 4406 the low-power signal by a relay station, such as, for example, relay station 4008. After receiving the low-power signal, the relay station may convert 4408 the low-power signal to a high-power signal, such as, for example, the high-power signal 4012. The conversion of low-power signal to high-power signal may comprise amplification of the low-power signal by an amplification module, such as the amplification module 4230 shown in FIG. 91. Conversion of the low-power signal to high-power signal may also comprise converting the communication standard of the low-power signal to a communication standard suitable for transmission of the high-power signal. For example, the method 4400 may comprise converting 4408, using a processing module, the received low-power signal from a first frequency to a second frequency.

After converting 4408 the low-power signal to the high-power signal, the method 4400 may further comprise transmitting 4410, by the relay station, the high-power signal to a remote location, such as, for example, an operating room viewing screen or a hospital network. The high-power signal may be received 4412 by the viewing screen, which may display a graphical representation of the condition at the end effector to a user. In some arrangements, the method may comprise, selecting, by a user, a frequency and/or a communication protocol for the high-power signal prior to the conversion of the low-power signal. The frequency and the communication protocol may be selected from a plurality of frequencies stored in a memory module of the relay station.

Electromechanical Soft Stop

In various forms, the surgical instrument may employ a mechanical stop adapted to stop or decelerate a motor driven element at or near an end of a drive stroke. According to various forms, the mechanical stop may comprises a hard stop structured to abruptly terminate movement of the motor driven element and/or a soft stop structured to decelerate the motor driven element at or near an end of stroke. As described in more detail below, in certain forms, such instruments may include an electromechanical stop comprising the mechanical stop and a control system configured to measure and/or monitor current provided to a motor used to drive the motor driven element. In one form, the control system is configured to terminate power to the motor or otherwise disengage the drive motion of the motor driven element upon determining the occurrence of a current meeting predetermined parameters.

It is to be appreciated that for brevity and ease of understanding the various aspects of the mechanical and electromechanical stops described herein are generally described with respect to surgical instruments and associated drive members comprising cutting and fastening devices. However, those having skill in the art will appreciate that the present disclosure is not so limited and that the various mechanical stops and related electromechanical features disclosed herein may find use in a variety of other devices known to the art. For example, while additional uses will become more apparent below, various mechanical stops disclosed herein may be employed in any device comprising an electrically controlled motor and/or control or drive system, for example, as well as non-endoscopic surgical instruments, such as laparoscopic instruments. Referring again to FIGS. 1-6, which illustrate an electromechanical surgical instrument 10 equipped with on form of a mechanical stop according to one aspect. The handle assembly 20 is operatively coupled to the elongate shaft assembly 30, a distal portion of which is operatively attached to the end effector 102. The end effector 102 comprises a proximal end 103 and a distal end 104. As described above, the elongate channel member 110 may be configured to operably and removably support the staple cartridge 130, and the anvil assembly 190 may be selectively movable relative to the staple cartridge 130 between an open position (see FIG. 4) and an open position (see FIG. 6) to capture tissue therebetween.

In certain forms, the instrument 10 comprises a drive member, which may be any portion or component of the instrument 10 that is movable by action of a motor. In various forms, the drive member may include the elongate shaft assembly 30, the end effector 102, or one or more portions or components thereof, such as the sled 170 or tissue cutting member 160, the body portion 162 of which may be threadably journaled on the end effector drive screw 180 such that it is rotatably mounted within the elongate channel 110. As described above, the sled 170 may be supported for axial travel relative to the end effector drive screw 180 and may be configured to interface with the body portion 162 of the tissue cutting member 160. The end effector drive screw 180 may be rotatably supported within the elongate channel 110 as described above. Rotation of the end effector drive screw 180 in a first direction causes the tissue cutting member 160 to move in the distal direction through a drive stroke. As the tissue cutting member 160 is driven distally through the drive stroke, the sled 170 is driven distally by the tissue cutting member 160. In various forms, the staple cartridge 130 may be fitted with a mechanical stop comprising a soft stop. According to one aspect, the soft stop comprises one or more bumpers 174 to cushion the sled 170 as it reaches its end of stroke near the distal-most position within the elongate channel 110. The bumpers 174 may each be associated with a resistance member 175, such a spring 176, to provide the bumper with a desired amount of cushion.

As described in greater detail above, the sled 170 and tissue cutting member 160 are movable through a drive stoke along shaft axis A-A extending between the proximal end 103 of the end effector 102 and the distal end 104 of the end effector 102 to simultaneously cut and fasten tissue. While the illustrated end effector 102 is configured to operate as an endocutter for clamping, severing and stapling tissue, in other aspects, different types of end effectors may be used, such as end effectors for other types of surgical devices, such as graspers, cutters, staplers, clip appliers, access devices, drug/gene therapy devices, ultrasound, RF or laser devices, etc.

Figure 94:
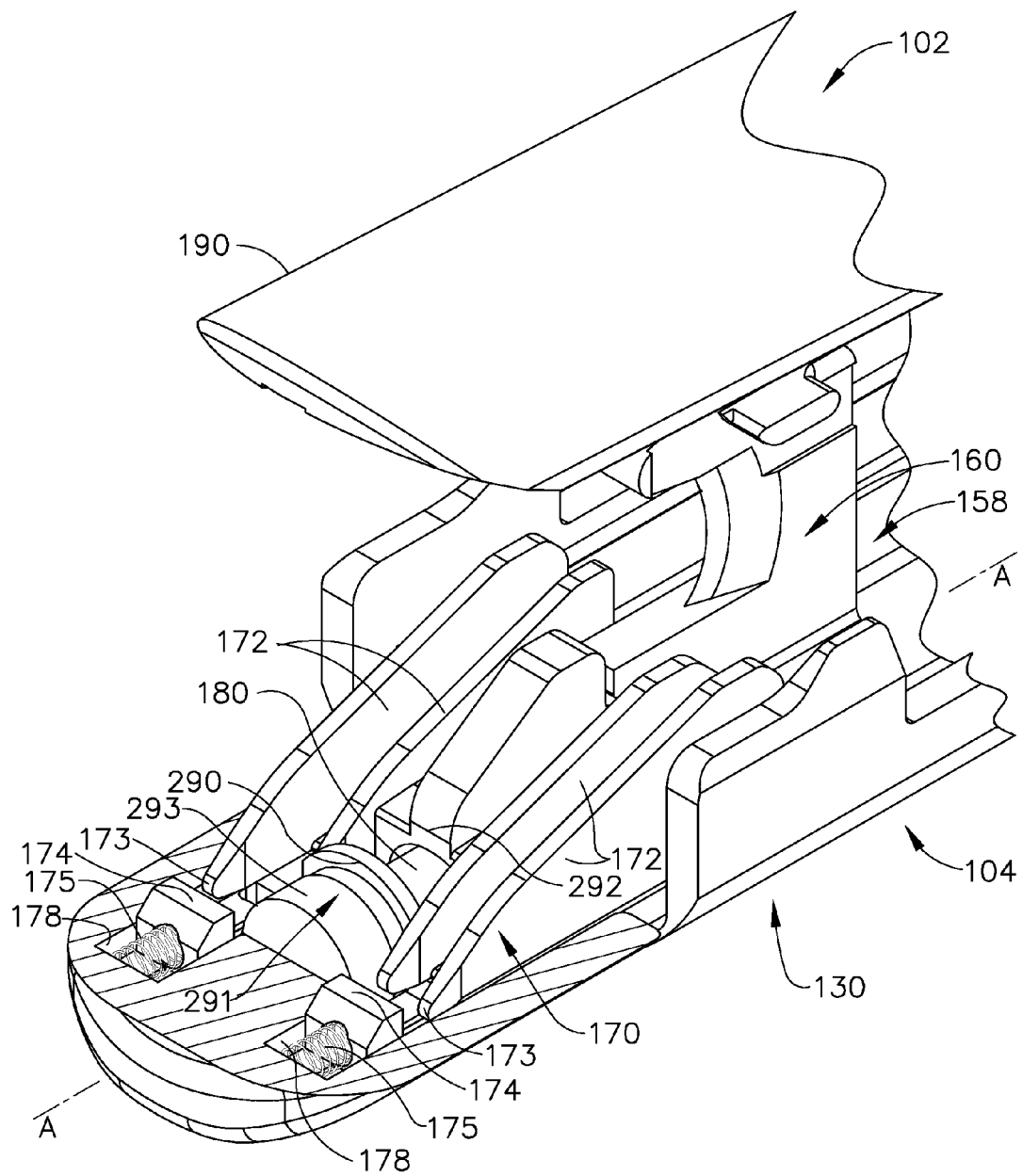
FIG. 94 illustrates a distal portion of an instrument comprising a mechanical stop as illustrated in FIG. 1 according to certain aspects described herein.

Referring to FIG. 94, which illustrates the distal end 104 of the end effector 102 shown in FIGS. 1-6, a drive member 158 comprising the sled 170 and cutting member 160 is movable through a drive stroke defined along the shaft axis A-A between a proximal home position and a distal end of stroke position. In one aspect, the end of stroke position is defined between a first and second position $S_1$, $S_2$ (see FIGS. 97 and 78). In various forms, at least one of the home position and the end of stroke includes a mechanical stop, such as a hard stop or soft stop, which may physically impede, e.g., block or limit, additional longitudinal movement beyond a respective stop position. In one form, both the home position and the end of stroke comprise a mechanical stop. As illustrated, the drive member 158 is distally disposed prior to or adjacent to the end of stroke.

Figure 95:
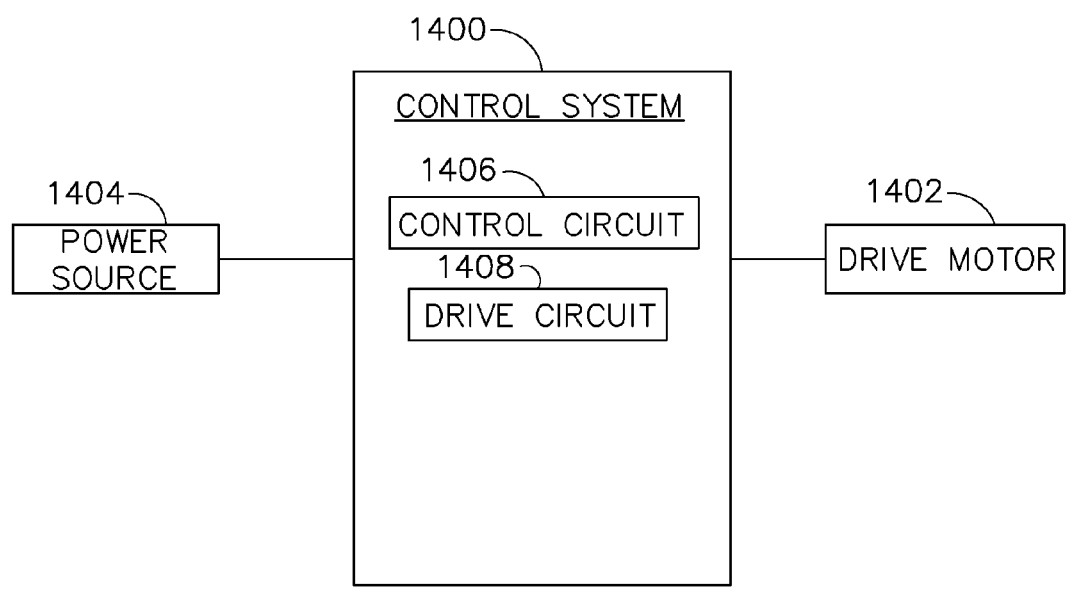
FIG. 95 is a diagram of a system adaptable for use with an electromechanical stop comprising a power source, a control system, and a drive motor according to according to certain aspects described herein.

As described above, the surgical instrument 10 may employ a control system for controlling one or more motors and related drive components as described above. FIG. 95 is a diagram depicting one form of a system comprising a control system 1400, drive motor 1402, and power source 1404 for use with a surgical instrument employing an electromechanical stop, which may include a mechanical soft or hard stop according to various aspects. The surgical system comprises a power source 1404 operatively coupled to the drive motor 1402 via the control system 1400. The power source 1404 may be configured to supply electric power to the drive motor 1402 to drive a drive member, such as drive member 158. In certain aspects, the power source 1404 may comprise any convenient source of power such as a battery, a/c outlet, generator, or the like. The control system 1400 may comprise various modules or circuits and may be operative to control various system components, e.g., the drive member 158, power source 1404, or a user interface. The control system 1400 may be configured to control, monitor, or measure various instrument 10 operations, signals, inputs, outputs, or parameters, for example.

In various forms, the control system 1400 may be similar to control system 800 described above. For example, in various aspects, the control system 1400 may be configured to "electrically generate" a plurality of control motions. The term "electrically generate" refers to the use of electrical signals to actuate or otherwise control a motor 1402, for example motors 402, 530, 560, and 610, or other electrically powered device and may be distinguished from control motions that are manually or mechanically generated without the use of electrical current. For example, the control system 1400 may electrically generate a control motion, such as a rotary control motion, comprising delivering power to the drive motor, which may be in response to a user instruction, such as an electrical signal given to the control system via actuation of an actuator, such a drive or firing trigger associated with the handle assembly 20. In certain aspects, the control system 1400 may electrically generate a rotary control motion comprising termination of power delivery to the drive motor 1402, which may be in response to a user or biasing mechanism returning the actuator or firing trigger to an open position. In at least one aspect, the control system 1400 may electrically generate a rotary control motion comprising termination or reduction of power delivery to the drive motor 1402 due to a measured electrical parameter reaching a predetermined value. For example, the control system 1400 may terminate power delivery to the drive motor 1402 when measured current reaches a predetermined threshold.

Referring generally to FIG. 1 and FIGS. 94 and 95, in various forms, the surgical instrument 10 comprises a handle assembly 20 equipped with a user interface configured to transmit an actuation signal from the user, e.g., a clinician, to the control system 1400 to electrically generate a control motion with respect to the elongate shaft assembly 30, the end effector 102, or the drive member 158. For example, in certain aspects, the user interface comprises a trigger assembly comprising an actuator or trigger operative to provide an input signal to the control system 1400 to control a supply of power to the drive motor 1402, such as firing motor 530 (see FIG. 23). The assembly may comprise a closure trigger for closing and/or locking the anvil assembly 190 and a firing trigger for actuating the end effector 102, e.g., driving the drive member 158 through the drive stroke. In operation, the closure trigger may be actuated first, thereby bringing the anvil assembly 190 to the closed position, e.g., capturing tissue between the staple cartridge 130 and the anvil assembly 190. Once the clinician is satisfied with the positioning of the end effector 102, the clinician may draw back the closure trigger to its fully closed, locked position. The firing trigger may then be actuated from an open position to a closed position to actuate the drive member 158 through the drive stroke. In various aspects, the firing trigger may return to the open position when the clinician removes pressure or may be mechanically resettable to the open position via operative connection to the actuation of the drive member 158 or a separate mechanism. In one aspect, the firing trigger may be a multi-position trigger whereby once the drive member 158 has reached a position at or near the end of stroke, the firing trigger may be actuated from a second open position to a second closed position to actuate the drive member 158 proximally toward the home position. In some such aspects, the first and second open and closed positions may be substantially the same. Depending on the desired configuration, in certain aspects, a release button or latch may be configured to release the closure trigger from the locked position. As explained in more detail below, following actuation of the firing trigger from the open position to the closed position, the firing trigger may be operatively disengaged, e.g., actuation of the firing trigger may provide an initial actuation input signal that may be routed to the control system 1400 to instruct the control system 1400 to initiate actuation of the drive member 158. In certain configurations, absent a user override feature, actuation of the drive member 158 will terminate at or near the end of stroke by action initiated by the control system, e.g., disengaging or interrupting power delivery to drive motor, even when the firing trigger is in the closed position.

In one form, the trigger assembly comprises a joystick control, which may be similar to the joystick control 840 described above. For example, as shown in FIGS. 33-39, the joystick control may beneficially enable the user to maximize functional control of various aspects of the surgical instrument 10 through a single interface. In one aspect, the joystick control rod 842 may be operably attached to the joystick switch assembly 850 that is movably housed within the switch housing assembly 844 such that the switch housing assembly 844 is mounted within the pistol grip 26 of the handle assembly 20. The switch housing assembly 844 may include a biasing member 856 to bias the joystick switch assembly 850 and the joystick control rod 842 in a desired position when not subject to external positioning, for example, by a user. The joystick control 840 may be electrically coupled to the control system 1400 to provide control instructions to the control system 1400. For example, manipulation of the joy stick control rod 842, such as depressing or directional movement, may allow the user may control various control movements associated with the surgical instrument 10, which may include actuation of the drive member 158.

As described above, various forms of the surgical instrument 10 comprise one or more electrically operated or powered motors, such as motors 402, 530, 560, and 610. The one or more motors may, for example, be located in a portion of the handle assembly 20 or elongate shaft assembly 30 of the instrument 10 and be operative to drive the drive member 158 between the home position and the end of stroke. In one form, the motor may include a brushless motor, a cordless motor, a synchronous motor, a stepper motor, or any other suitable electric motor. In certain arrangements, the motor may operate in a rotary or linear actuation mode, e.g., a linear actuator, and may include a transmission coupling between the drive motor 1402 and drive member 158 to convert rotary motion of the drive motor 1402 to linear motion or to couple rotary motion between multiple components. In various forms, a transmission coupling comprising one or more gears or interlocking elements such as belts or pulleys is operative to transmit rotary motion from the drive motor 1400 to one or more segments of the elongate shaft assembly 30 to actuate the end effector 102. For example, rotation of the end effector drive screw 180 in a first direction causes the drive member 158 to move in a first direction, e.g., a distal direction, along shaft axis A-A. In various aspects, rotation of the end effector drive screw 180 in a second direction, opposite of the first, causes the drive member 158 to move in a second direction, e.g., a proximal direction, along shaft axis A-A. In one aspect, the drive motor 1400 drives the drive member 158 distally toward the end of stroke and is reversible to drive the drive member 158 proximally toward the home position. For example, the drive motor 1402 may be reversible, by, for example, reversing the polarity of the voltage supply, thereby producing reverse rotation or motion of the motor and, hence, reverse movement of the drive member 158. As such, the drive member 158 may be moved between positions along the drive stroke in both proximal and distal directions by conventional methods, or methods such as those disclosed in U.S. patent application Ser. No. 12/235,782, which is incorporated herein by reference in its entirety. Notably, although the instruments 10 described herein generally refer to handheld instruments comprising a handle, in various forms, instruments 10 comprising mechanical stops, that may operate as part of an electromechanical stop, may be adapted for use in robotic or similar devices used by robotic systems.

In certain aspects, the surgical instrument 10 comprises a reversible motor and includes a proximal mechanical stop and a distal mechanical stop. In various aspects, as described above, actuating the firing trigger signals actuation of the drive member 158 through the drive stroke. When the drive member 158 reaches the end of the drive stroke, for example, when a cutting member 160 reaches the distal end of its cutting stroke, an end of stroke or direction switch, for example, may be switched to a closed position, reversing the polarity of the voltage applied to the motor 1402 to thereby reverse the direction of rotation of the motor 1402. Such a switch may be associated with the control system 1400 and may be in addition to or in the alternative to termination of power delivery to the drive motor 1402. Notably, however, in other aspects a manual return switch may be provided to reverse the motor 1402 and return the drive member 158 to its original or home position.

A mechanical stop is disposed at or near the end of stroke and is structured to increase resistance to movement of the drive member 158 through the end of stroke. The mechanical stop includes a soft stop comprising a pair of bumpers 174 each operatively coupled to a resistance member 175. The bumpers 174 are configured to contact the drive member 158 at or near the end of stroke. For example, the bumpers 174 shown in FIG. 94 are structured to contact a contact surface 173 of at least one wedge 172. In various aspects, the bumpers 174 may be dimensioned to complement a dimension of the contact surface 173. For example, in at least on aspect, the bumpers 174 may be dimensioned to present an angled surface substantially equivalent to the contact surface 173. In this way, stability of the contact between the bumpers 174 and the wedges 172 may be increased and the force applied to the contact surface 173 may be distributed along a larger structural area of the wedges 174. Similarly, in one aspect, the bumpers 174 comprise a flexible, such as an elastic or cushion surface to receive the contact surface 173 and reduce component breakdown. In one form, the resistance members 175 each comprise a spring 176 positioned between a bumper 174 and a hard stop 178 to provide resistance and deceleration of the drive member 158 at or near the end of stroke 158.

It will be appreciated that various aspects of surgical instruments 10 may be fitted with multiple bumpers 174 and resistance members 175 and that bumpers 174 and resistance members 175 may be structured to contact other portions of the drive member 158. For example, the instrument 10 may comprise an additional stop, which may be in addition to or instead of the above hard stop 178 and/or the soft stop arrangements. Thus, in one form, referring to FIG. 94, the drive screw 180 may be fitted with a stop that may include a soft stop comprising a bumper 290 associated with a resistance member 291 positioned along the drive stroke and opposed to a contact surface 292 of the drive member 158. In one form, the resistance member 291 comprises an elastomeric material that may be compressible between the bumper 292 and a hard stop 294 to absorb the longitudinal force of the drive member 158. In certain aspects, multiple soft stops may be configured to contact the drive member 158 at different predetermined positions. For example, in one form, the drive member 158 contacts bumper 290 before bumpers 174, for example, to provide a more identifiable current spike, e.g., to produce a current spike comprising two distinct current spike components, the magnitude and/or temporal separation of which may be used to increase assurance of an occurrence of a current spike.

In various forms, resistance members 175 comprise a compressible portion that may or may not be associated with a hard stop 178. For example, in one aspect a resistance member 175 may be housed between the hard stop 178 and the bumper 174 and may include a compressible portion, such as a spring 176, elastomeric material, such as a polymer, foam, or gel. In operation, the bumper 174 may be accelerated toward the compressible portion upon contact with the drive member 158 whereby the compressible portion compresses by a given degree. In various aspects, the resistance member 175 may comprise a deceleration portion, such as a brake. In one aspect the deceleration member comprises a compressible cell, such as a hydraulic pneumatic cell through which contact with the drive member 158 may compress a piston positioned within the cell to impart an increase in pressure configured to decelerate or brake the drive member 158. In certain aspects, the soft stop may be structured to apply a smooth or gradual resistance and/or deceleration with respect to time and/or distance. For example one or more coiled springs having the same or different compressibility properties may be structured or arranged to precisely control deceleration or braking of the deceleration member, e.g., in a gradual or stepped manner. In one form, the soft stop may be structured to apply a progressive resistance to the distal motion of the drive member 158.

In various forms, a soft stop includes a biasing member configured to bias the contact member away from the hard stop. It will be appreciated that, in some aspects, the biasing member may be the same or share similar components with the resistance members 175. Thus, in some forms, a biasing member may be structured to compress between the bumper 174 and the hard stop 178 by the longitudinal actuation force of the drive member 158 and thereafter return to a precompressed state upon removal of the force. In certain aspects, the biasing member may be actuatable, movable, and/or compressible to counter the actuation motion of the drive member 158. Notably, compressing or otherwise countering a bias associated with the resistance members 175 may result in an energy transfer that may, at least temporarily, be stored or retained by the soft stop in a potential energy position. In one aspect, the resistance members 175 may be maintained in a potential energy position by a latch, hook, or obstruction, for example, which may prevent one or more resistance members 175 from returning to a precompressed state. Beneficially, the stored energy may be released, for example, by the user and/or the control system 1400 whereby at least a portion of the stored energy is applied to return the drive member 158 to the home position.

In various aspects, resistance members 175 may comprise additional configurations. For example, in one aspect, one or more magnets, such as permanent magnets, may be positioned to repel an opposed permanent magnet associated with the drive member 158. For example, one or more magnets may be rotatable or movable to adjust the size of repulsive magnetic fields opposing longitudinal movement. Various other aspects may employ coil magnets electrically coupled to the control system for activation before or after successful deceleration of the drive member 158. Additional resistance members 175 may comprise reciprocating structures including arrangements implementing pulleys and/or gears, for example.

In various aspects, a mechanical stop comprising a soft stop may or may not be associated with a hard stop 178. For example, in some forms the soft stop includes a hard stop 178, while in other forms the soft stop does not include a hard stop or the hard stop 178 may operate as an auxiliary stop. In some forms, the soft stop may comprise a spring loaded hard stop 178 to provide a gradual and/or progressive resistance to the drive stroke or deceleration of the drive member 158. For example, the soft stop may be configured to gradually decrease the velocity of the drive member 158 by providing resistance to the proximal or distal force applied to the drive member 158 by the drive motor 1402 or present in the inertia of the system. In at least one form, the magnitude of resistance provided by the soft stop to counter or decelerate the actuation or drive motion may be selectively adjustable. For example, the instrument 10 may be fitted with one or more soft stops that may be selectively slid or rotated to multiple positions along the drive stroke. As such, a user may customize the position of a soft stop for a particular application. In one form, an electrochemical device comprising a soft stop may include an adjustable dial to adjust the resistance provided by the soft stop along the end of stroke. In some such forms, adjusting the dial may simultaneously adjust the longitudinal distance encompassed by the soft stop and, hence, the end of stoke, as well as threshold values associated with determining a current spike, as explained in more detail below. In one form, a warning signal may be provided to the user when a manual setting is set beyond a predetermined mechanical tolerance.

Referring again to FIG. 95, in various forms, the control system 1400 is configured to formulate and/or respond to feedback information that may, at least in part, be derived from information measured by the control system 1400 or obtained from other system components. For example, in one aspect, the control system 1400 may be configured to initiate power delivery to system components in response to an input signal, such as an instruction provided by a user. In certain aspects, the control system 1400 may generate or provide information, such as a warning or instrument state, to a user via the user interface, such as a visual or audio display. Signals or inputs generated by the control system 1400 may be, for example, in response to other signals or inputs provided by a user, instrument components, or may be a function of one or more measurements associated with the instrument 10. In certain aspects, the control system 1400 may be configured to monitor or receive various measurements and thereafter interpret, calculate, and/or decode the information and respond in a predetermined way.

In one aspect, the control system 1400 includes or may be selectively associated with a semiconductor, computer chip, or memory. As stated above, inputs provided to or from the control system 1400, such as those supplied by the user or produced by the control system 1400 in response to instructions, signals, or measured parameters may be analog or digital. Accordingly, in some forms, the control system 1400 may be configured to send or receive analog or digital inputs or signals to or from instrument components. In various aspects, the control system 1400 may use software that may employ one or more algorithms to further formulate input signals to control and monitor instrument components. Such formulated input signals may be a function of criteria measured and/or calculated by the control system 1400 or, in some instances, provided to the control system 1400 by another instrument component, a user, or a separate system in operative communication with the control system 1400. For example, the control system 1400 may respond by activating or deactivating the drive motor 1402, terminating, initiating power to the drive motor 1402 or to additional system components, or by providing instructions or additional inputs for these or other operations. In various aspects, the control system 1400 may comprise circuitry, for example transistors or switches, configured to monitor electrical parameters associated with the operation of the instrument 10. For example, control system circuitry may be configured to activate or deactivate the drive motor 1402 or open or close a power delivery path to the drive motor 1402 when electrical parameters associated with operation of the instrument 10 reach a threshold value, e.g., a current spike, as determined by the circuitry configuration.

In certain forms, surgical instruments 10 and systems employing a mechanical stop may operate in an open loop. For example, in one form, the instruments may operate without assistance from a position feedback device configured to provide the control system 1400 with information regarding how the instrument 10 is responding to inputs, such that the control system 1400 may modify output. In various aspects, as introduced above, the control system 1400 may monitor power delivery to a drive motor 1402 to determine end of stroke position of the drive member 158. That is, for example, the control system 1400 through various voltage monitory techniques from which current, namely current spikes, may be determined, may, at least in part, be ascertained using a mechanical stop. For example, a control system 1400 may monitor voltage to determine current with respect to power delivery to a drive motor 1402 and, hence, the drive member 158, as described above. Resistance to the drive stroke increases torque on the drive motor 1402 resulting in detectable current spikes with respect to the power delivered to the drive motor 1402. Thus, a large current spike may be measured by the control system 1400 when the drive member 158 contacts a mechanical stop at which time the control system 1400 may respond by terminating power delivery to the drive motor 1402. Hence, the mechanical stop provides the physical force to decelerate the drive member 158 and produce the current spike that may be ascertained by the control system 1400 to initiate disengagement of the drive motor 1400.

As introduced above, in certain aspects, the control system 1400 is configured to control various operations of the instrument 10. For example, in certain aspects, the control system 1400 comprises a control circuit 1406 operatively coupled to a drive circuit 1408. The drive circuit 1408 may be configured to deliver power from the power source 1404 to the drive motor 1402 to drive the drive member 158. The control circuit 1406 may be configured to control the delivery of power to the drive circuit 1408. Hence, the control circuit 1406 may be configured to control the drive motor 1402 via control over power delivery to the drive circuit 1408. The control circuit 1406 may be further configured to monitor, e.g., sample or measure, the power delivered to the drive motor 1402. For example, the control circuit 1406 may sample input/output voltage and/or current at one or more points of the drive circuit 1408 through which the drive motor 1402 receives power to actuate the drive member 158. In various aspects, the control circuit 1406 may include or be coupled to the drive circuit 1408 through which it may monitor input/output voltage, for example across a resistor coupled to a current path associated with the drive circuit 1408, for example. As those skilled in the art will appreciate, the above description is just one manner of measuring and/or monitoring current supplied to the drive motor 1402 and will further recognize that current may similarly be measured and/or monitored by alternate methods known in the art, and, therefore, such methods are within the scope of the present disclosure. In some forms, when the control circuit 1406 detects a spike in the current supplied to the drive motor 1402, the control system 1400 terminates energy delivery to the drive motor 1402 through the drive circuit 1408. In various aspects, the control system 1400 may also disengage operative coupling, e.g., transmission, between the drive motor 1402 and the drive member 158, at least momentarily, in response to a measured current spike.

In certain configurations, when electromechanical stops comprise a hard stop designed to abruptly terminate the drive stroke, the instrument 10 may be susceptible to mechanical failure due to, for example, time lag between detection of the current spike and subsequent relief from the actuation force provided by the drive motor 1402. Additionally, due to the inertia of the system, for example, the drive member 158 may also continue to be actuated or driven after reaching the end of stroke, despite termination of power delivery to the drive motor 1402. In some instances, the delay in relieving the drive member 158 of the actuation force may drive the drive member 158, drive motor 1402, drive screw 180, or other transmission coupling to mechanical failure.

Figure 96:
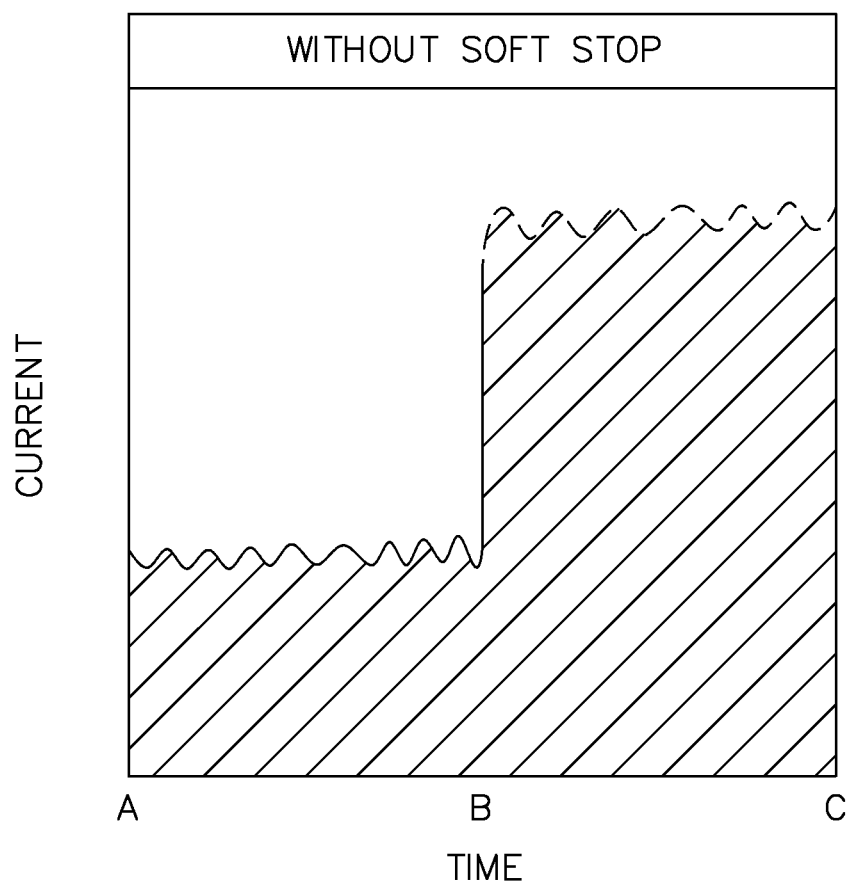
FIG. 96 is a graphical illustration depicting change in current over time associated with an instrument comprising an electromechanical stop without a soft stop according to certain aspects described herein.

FIG. 96 is a graphical illustration depicting current over time of an instrument 10 employing a electromechanical stop comprising a hard stop 178 without a soft stop. The current between time A, corresponding to a position of the drive member 158 proximal to the end of stroke, and time B, corresponding to a position of the drive member 158 upon contact with the hard stop 178 at an end of stroke, is relatively low or steady. However, at time B, the current spikes, representing contact between the drive member 158 and the hard stop that is positioned at the end of stroke. Due to a time lag between detection of the current spike sometime after time B and termination of power delivery to the drive motor 1402, the drive motor 1402 continues to drive the drive member 158, although unsuccessfully, against the hard stop 178 until time C, when power delivery to the drive member 158 is terminated. Although not shown, the inertia of the system may also continue to actuate the drive member 158 against the hard stop 178 for a period of time after time C.

As stated above, while providing the convenience of open loop operation, surgical instruments operating as depicted in FIG. 76 may be susceptible to mechanical failure due to, for example, the time lag between detection of the current spike and subsequent relief from the actuation motion. According to various forms, referring to FIGS. 97 and 98, the instruments 10 disclosed herein may comprise electromechanical stops comprising a soft stop structure to contact and decelerate the drive member 158 prior to reaching the end of stroke to induce an identifiable current spike, thereby increasing the amount of time the control system 1400 has to detect and respond to the current spike. The surgical instrument 10 includes various features similar to those illustrated in FIGS. 1 and 70; thus, like features are identified using like numeric identifiers and, for brevity, will not be described again. The instrument 10 includes an electromechanical stop comprising a soft stop to oppose movement of a drive member 158 at or near the end of the drive stroke or segment thereof, such as at a proximal home position or a distal end of stroke extending between a first soft stop position $S_1$ and a second soft stop position $S_2$ along the shaft axis A-A. The electromechanical stop further comprises a hard stop 178 disposed at position H. The soft stop comprises a bumper 174 and a resistance member 175 disposed at or near the end of stroke, e.g., at least partially within the first soft stop position $S_1$ and second soft stop position $S_2$. The bumper 174 and resistance member 175 function to provide resistance to the drive member 158 within the end of stroke defined between the first soft stop position $S_1$ and second soft stop position $S_2$. In various forms, the bumper 174 and resistance member 175 may also function to decelerate the drive member 158 from the first soft stop position $S_1$ to the second soft stop position $S_2$. In certain forms, a soft stop may be positioned in any preferred location where it is desirable to provide resistance to or begin decelerating the drive member 158.

Figure 97:
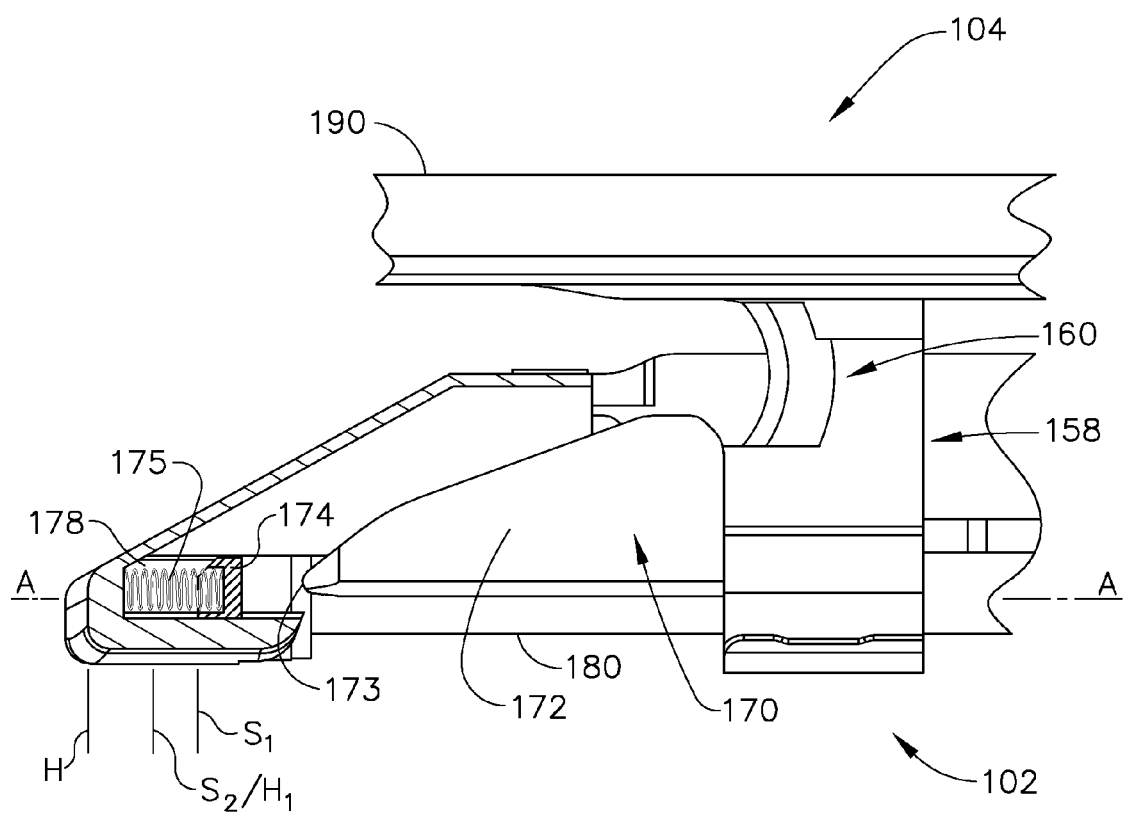
FIG. 97 illustrates a distal portion of an instrument equipped with a mechanical stop comprising a soft stop wherein the drive member is actuated to a position prior to contact with the soft stop at a second position of an end of stroke according to certain aspects described herein.
Figure 98:
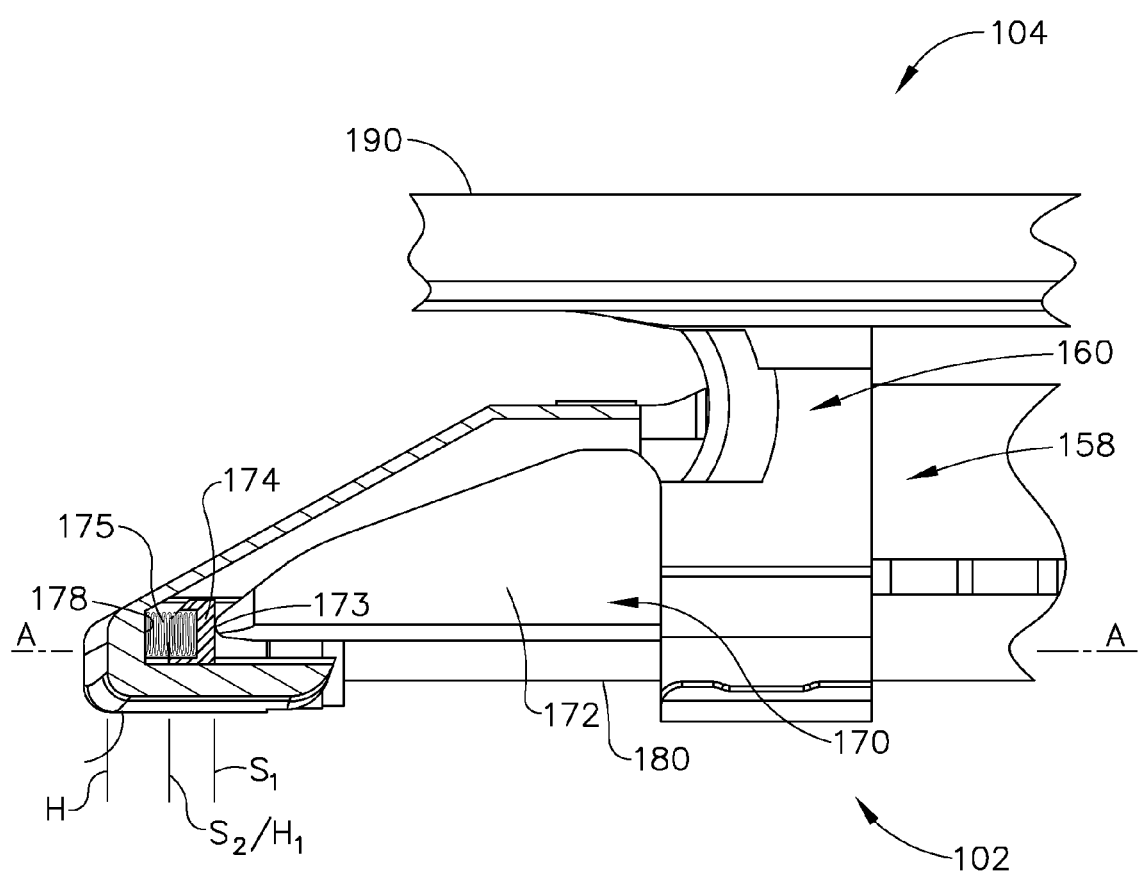
FIG. 98 illustrates the instrument shown in FIG. 97 wherein the drive member is actuated through the first position of the end of stroke to the second position of the end of stroke according to certain aspects described herein.

FIG. 97 depicts the drive member 158 in the process of extending through the drive stroke at a position proximal to the first soft stop position $S_1$. FIG. 98 depicts the drive member 158 after fully extending through the drive stroke beyond the first soft stop position $S_1$ of the end of stroke such that it is positioned at a second soft stop position $S_2$ of the end of stroke. Accordingly, the soft stop is positioned to contact the drive member 158 at the first soft stop position $S_1$ and thereafter compress distally toward the second soft stop position $S_2$ due to compressive interaction with the hard stop at position H. Accordingly, the second soft stop position $S_2$ may effectively comprise a hard stop position H* with respect to the drive member and the extreme distal terminus of the end of stroke. In various aspects, the drive member 158 may completely or appreciably decelerate prior to reaching the hard stop position H* at the second soft stop position $S_2$. Thus, in such aspects, a hard stop, if present, may comprise a redundant or safety feature.

Resistance to the actuation motion provided by the mechanical stop, which may be accompanied by a decelerating or braking force, may be gradual, progressive, or stepped with respect to distance and/or time, for example. That is, in some aspects, a soft stop presents a path of increased resistance between a first soft stop position $S_1$ and the second soft stop position $S_2$. Notably, the end of stroke does not necessarily imply that the functional operation of the drive member continues throughout the entire end of stroke, e.g., to the second soft stop position $S_2$. For example, in one form, the end of stroke is positioned at or slightly proximal to the distal most staple. In another form, the position of initial contact with the soft stop, e.g., at the first soft stop position $S_1$, is distal to the distal most staple. That is, the drive member 158 may not contact or experience significant resistance to longitudinal movement through the drive stroke until the distal most staple has been ejected, at which time increased resistance and/or deceleration may take place. In this way, movement of the drive member will not be prematurely limited by action of the control system 1400.

Figure 99:
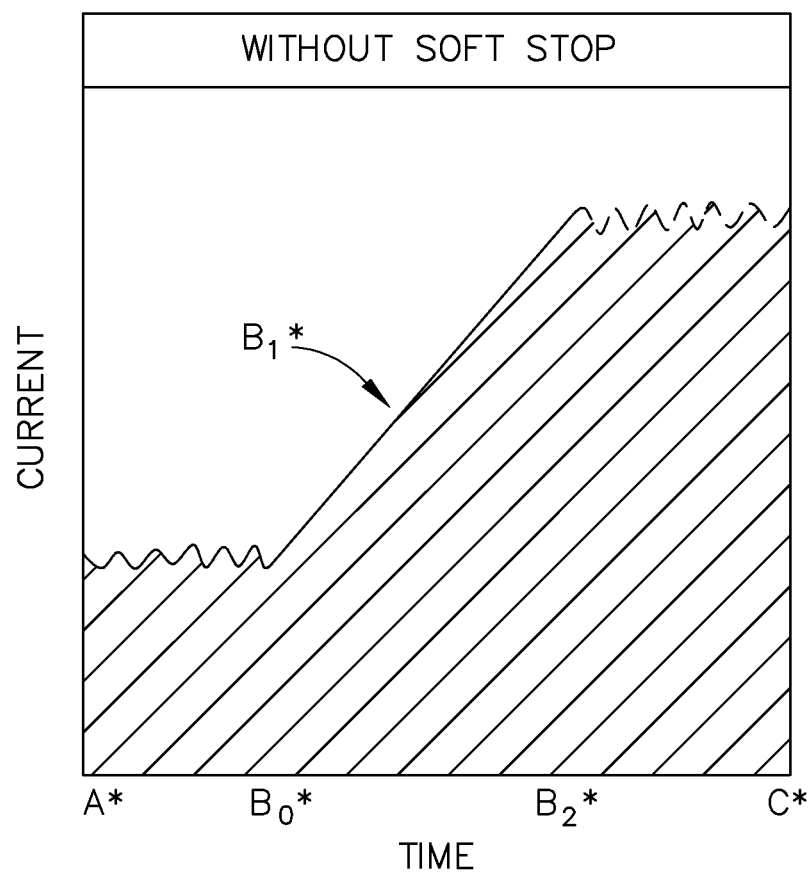
FIG. 99 is a graphical illustration depicting change in current over time associated with an instrument comprising an electromechanical stop with a soft stop according to certain aspects described herein.

FIG. 75 is a graphical illustration depicting current over time of an instrument 10 employing an electromechanical stop comprising a soft stop according to various aspects. The current between time A*, corresponding to a position of the drive member 158 proximal to the end of stroke, and time $B^*_0$, corresponding to a position of the drive member 158 upon contact with the soft stop, for example at a bumper 174, the current is relatively low or steady. However, following time $B^*_0$ the current gradually begins to spike representing increasing resistance to the longitudinal motion of the drive member. In various aspects, the gradual increase in resistance may advantageously increase the time in which the current spike occurs, for example between times $B^*_0$ and $B^*_2$, effectively slowing down response time to give the control system 1400 time to react, thus minimizing the adverse effects of the time lag explained above with respect to FIG. 96. In certain aspects, the control system 1400 may monitor voltage and measure current supplied to the drive motor 1402, as described above. The control system 1400 may be configured to respond in a predetermined way to changes in current. For example, upon reaching a threshold current, for example at time $B^*_1$, the control system 1400 may terminate power supply to the drive motor 1402. In one configuration, the threshold current may comprise a time component. For example, the threshold current may include a current differential over a specific period of time. In certain configurations, a current spike may comprise one of multiple predetermined current thresholds, each defined by a ratio of a current differential over a time period. As can be seen in FIG. 99, the gradual increase in resistance may also advantageously reduce impact loading on the end effector 102 upon contact with a hard stop at time $B^*_2$ as well as reduce the time period $B^*_2$ to C* in which the drive motor 1402 continues to actuate the drive member 158 against the hard stop 178 after distal movement has ceased.

In certain aspects, the control system 1400 may determine that a predetermined current threshold as measured by an increase or slope of current over time, for example, has been achieved and may thereafter terminate a power input signal provided to drive motor 1402. For example, in one configuration, the control system 1400 may monitor current and thereby terminate power delivery to the drive motor 1402 when a magnitude of the current increases a predetermined amount over a given period of time. In various aspects, these or other values, such as threshold values, may be adjusted by a user such as manually or by accessing onboard protocol via an administrative link, such a through a computer. In at least one configuration, the drive circuit 1408 or control circuit 1406 comprises a variable resister such that a user may vary the current supplied to the drive motor 1402 by varying the extent of actuation with respect to the trigger. For example, the rotation of the firing motor 530 may be proportional to the pressure or movement a user applies to the actuator or trigger. In one form the control circuit 1406 may communicate with the drive circuit 1408 such that threshold values may be raised or desensitized.

In certain configurations, a plurality of sensors or electrical components may be employed in the end effector 102 to provide various forms of feedback to the user. In one aspect, sensors may provide feedback to the control system 1400 to automatically control the various motors associated with the instrument. For example, in one aspect the surgical instrument comprises multiple motors, such as motors 402, 530, 560, and/or 610, that are actuatable by one or more control systems, such as control systems 800 and 1400, to electrically generate control motions. The control systems may be configured to operatively control the motors and receive positional feedback from a plurality of sensors configured to monitor positional information. In certain aspects, the control systems may use the positional information to electrical generate altered or modulated control motions via control of power delivery to one or more motors or may provide various positional information to the user, for example. In various aspects, the control systems may be operable in a hybrid open/closed loop system. For example, the control system

1400 may be configured to operate the drive motor 1402, such as firing motor 530 in an open loop as described herein while also operating various other motors, such as shaft rotation motor 610, for example, in a closed loop. In one aspect, the control system 1400 may be configured such that the user may selectively choose which motors the control system 1400 may operate in a closed or open loop to, for example, customize the various operations of the instrument 10 as may be desired.

It will be appreciated that one or more inputs may be provided by a user which may or may not be subject to evaluation by the control system 1400. For example, the control system 1400 may include an override mode in which one or more inputs provided to the control system 1400 by one or more users or other control systems in communication with the control system 1400 may be forwarded and/or provided to the instrument 10. For example, when the drive member 158 is in the home position, the control system 1400 may lockout, prevent, or ignore instructions to couple delivery of power to the drive motor 1402 or otherwise engage the drive motor 1402 to electrically generate the actuation motion of the drive member 158. In at least one aspect, lockout occurs or is the default state or condition of the system until the occurrence of one or more events, such as closure of the anvil 190 or adequate mechanical or electrical feedback, such as, for example, latching of components, user initiated override, change in measured parameter at, near, or along the path or drive member.

In various aspects, one or more mechanical stops including soft stop assemblies according to the present disclosure may be provided in a kit. The kit may have specific application to one or more select devices or may be universal or modifiable for universal application to a number of devices. For example, a soft stop assembly kit may contain a replacement deceleration member, such as resistance members and/or contact members, such as bumpers. In one form, a kit includes replacement or aftermarket bushings that may be used as or be insertable within a housing dimensioned to support a resistance member in order to increase the resistance provided by the soft stop at one or more locations along the drive stroke. In various forms, shims may be provided to adjust clearance between a stop and the body of the device. In some aspects, the contact member may include a permanent or temporary, such as replaceable, modifiable, or upgradable, contact guard structured to be disposed between the drive member and the bumper, the resistance member, and/or the hard stop. The contact guard may be formed from an elastic or other material that is at least partially compressible when contacted by the accelerated mass of the drive member or impacted upon the soft or hard stop. One aspect of a guard may be a polymer that may slip, slide, snap, or be molded onto a portion, such as a contact surface of the drive member 158. In another aspect, a guard may be fitted or fittable onto a face of the bumper 174. In yet other aspects, the bumper 174 may comprise a contact configured to contact and at least partially absorb the force of the accelerated mass of the drive member 158 to prevent or partially limit the extent of physical damage or mechanical failure to the drive member 158, drive motor 1402, drive screw 180, or associated components.

In some forms, removing a surgical instrument, such as the surgical instrument 10 shown in FIGS. 1 and 2, from a patient may be difficult, as the end effector 102 may be in an articulated or rotated position, preventing the end effector 102 from passing through a trocar or other access point into a patient. A clinician may be unaware of the current articulation state of the end effector 102, such as, for example, articulated along the articulation axis B-B, and may attempt to remove the surgical instrument 10 without first straightening the end effector 102. In various forms, a surgical instrument be configured such that its end effector is straightened based on input from a sensor (e.g., the instrument may have a sensor-straightened end effector). In this way, the clinician may ensure that end effector 102 is straight with respect to the articulation axis B-B prior to removing the end effector 102 from a patient, such as, for example, through a trocar. In various forms, a sensor may be configured to trigger a powered straightening event as the end effector is removed from the patient.

Figure 105:
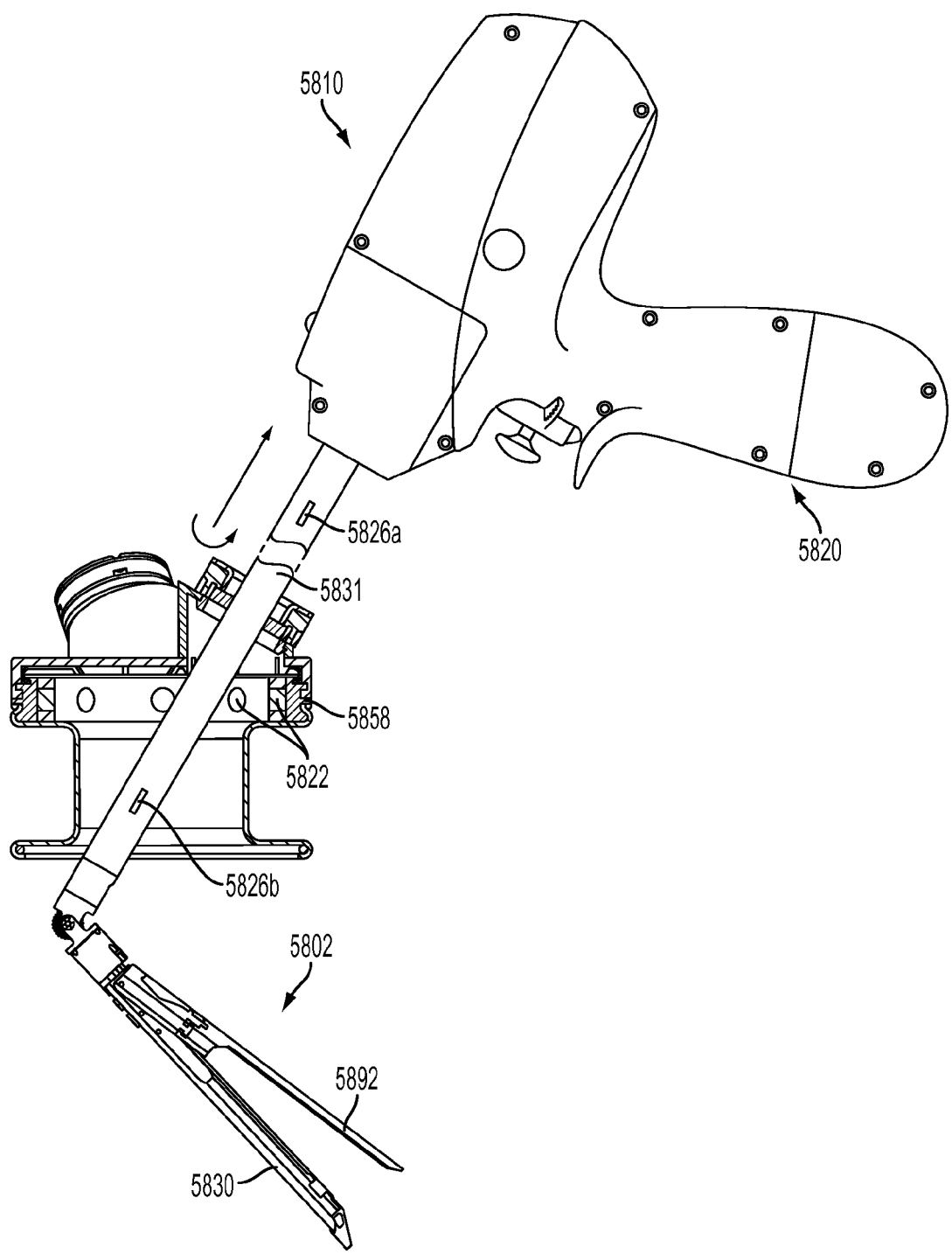
FIG. 105 illustrates one form of a surgical instrument comprising a sensor-straightened end effector in an articulated state.

FIG. 105 illustrates one form of a surgical instrument 5810 comprising a sensor-straightened end effector 5802. A sensor 5826a, 5826b may detect a gross proximal motion of the surgical instrument 5810. The gross proximal motion may indicate that the surgical instrument 5810 is being removed from the patient, such as through a trocar or an overtube. A minimum threshold proximal motion may be set to prevent the end effector 5802 from straightening due to a slight proximal adjustment of the surgical instrument 5810 during treatment. In various forms, when the gross proximal motion of the surgical instrument 5810 exceeds a minimum threshold, the sensor 5826a, 5826b may send a signal to a motor, such as, for example, the articulation control motor 402, to cause the motor to straighten the end effector 5802.

In some forms, the sensor 5826a, 5826b may be located in the shaft 5831, the end effector 5802, the handle 5820, or any other suitable location to detect a gross proximal movement of the surgical instrument 5810. In various forms, the sensor 5826a, 5826b may comprise any suitable sensor for detecting movement of the surgical instrument 5810. For example, the sensor 5826a, 5826b may comprise a sensor configured to measure acceleration, such as an accelerometer. When the accelerometer detects acceleration in a proximal direction above a predetermined threshold, the accelerometer may send a signal to the articulation control motor 402 to activate a straightening process. As another example, the sensor 5826a, 5826b may comprise a proximity sensor, such as a magnetic sensor, a Hall Effect sensor, a reed switch sensor, or any other suitable proximity sensor. In various forms, the proximity sensor may be configured to measure the proximity of the sensor 5826a, 5826b to a fixed point, such as a trocar 5858 or an overtube 5960. As the surgical instrument 5810 is withdrawn in a proximal direction, the proximity between the sensor 5826a, 5826b and the fixed point may decrease, causing the sensor 5826a, 5826b to send a signal to the articulation control motor 402 to activate a powered straightening process of the end effector 5802. In various forms, multiple sensors may be included to provide a redundant check for the straightening process.

In one form, a first sensor 5826a and a second sensor 5826b may be disposed on the surgical instrument 5810. The first sensor 5826a may be located on a proximal portion of the shaft 5831 and the second sensor 5826b may be located on a distal portion of the shaft 5831. Those skilled in the art will recognize that the first and second sensors 5826a, 5826b may be located in any suitable portion of the surgical instrument 5810 such as, for example, the handle 5820, a detachable surgical module, the shaft 5831, or the sensor-straightened end effector 5802. In some forms, the first sensor 5826a may comprise an accelerometer configured to detect a gross proximal movement of the surgical instrument 5810. In some forms, the second sensor 5826b may comprise a proximity sensor configured to detect a distance between the second sensor 5826b and a fixed point, such as, for example, the trocar 5858. In the illustrated form, the trocar 5858 comprises a plurality of magnets 5822. The plurality of magnets 5822 may generate a constant magnetic field. The second sensor

5826b may be configured to detect an increase in intensity of the magnetic field, indicating movement of the second sensor 5826b, and therefore the sensor-straightened end effector 5802, towards the trocar 5858.

In one form, the first sensor 5826a and the second sensor 5826b may be configured to activate a powered straightening process of the sensor-straightened end effector 5802. In operation, the first sensor 5826a may detect a gross proximal movement of the surgical instrument 5810 by detecting a proximal acceleration above a predetermined threshold. The first sensor 5826a may send a first signal to the articulation control motor 402 to activate the powered straightening process. In some forms, the second sensor 5826b may also detect the gross proximal movement of the end effector by detecting a change in the magnetic field intensity between the sensor 5826b and a fixed point, such as the trocar 5858. The second sensor 5826b may send a second signal to the articulation control motor 402 to activate the powered straightening process.

As shown in FIG. 105, the sensor-straightened end effector 5802 has been articulated at the articulation axis B-B (shown in FIG. 1). The sensor-straightened end effector 5802 may be coupled to a shaft 5831. An operator may move the surgical instrument 5810 in a proximal direction, causing the shaft 5831 and the sensor-straightened end effector 5802 to move in a proximal direction. The proximal movement may be detected by a first sensor 5826a. The first sensor 5826a may comprise an accelerometer. The first sensor 5826a may send a signal to an articulation control motor, such as, for example, the articulation control motor 402 to activate a powered straightening process. The proximal movement may also be detected by a second sensor 5826b. The second sensor 5826b may comprise a magnetic proximity sensor, such as, for example, a Hall Effect sensor or a reed switch sensor. The second sensor 5826b may send a signal to the articulation control motor 402 to activate the powered straightening process. The second sensor 5826b may send the signal to the articulation control motor 402 independent of the first sensor 5826a.

Figure 106:
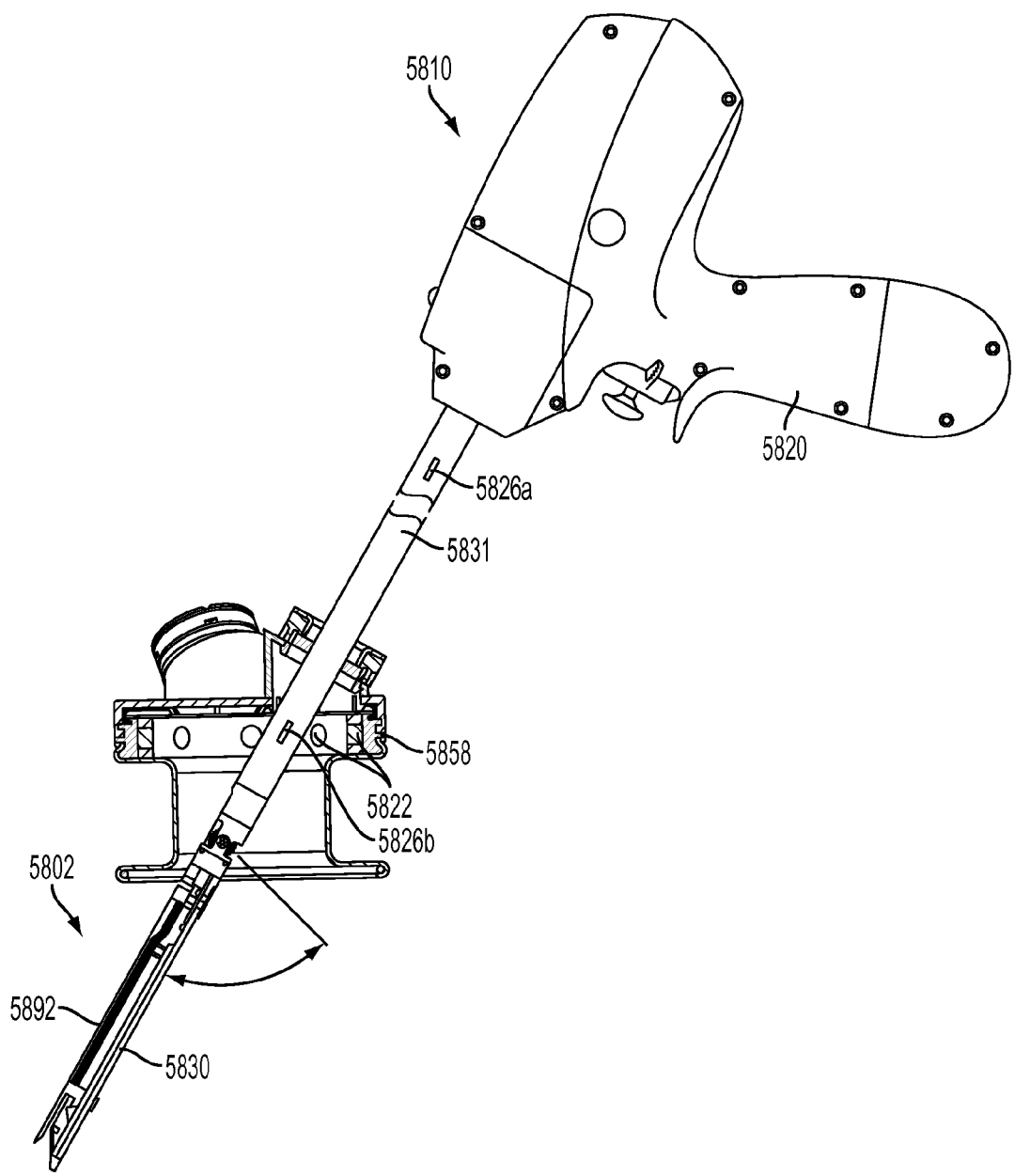
FIG. 106 illustrates the surgical instrument of FIG. 105 in a straightened state.

As the clinician removes the surgical instrument 5810 from the trocar 5858, the powered straightening process straightens the sensor-straightened end effector 5802. After the powered straightening process has completed, the sensor-straightened end effector 5802 is in a straight configuration, as shown in FIG. 106. The straightened sensor-straightened end effector 5802 may be withdrawn through the trocar 5858 without damaging the patient or the trocar 5858 and without the clinician needing to manually straighten the sensor-straightened end effector 5802. In some forms, the surgical instrument 5810 may provide a feedback signal to the user to indicate the activation or progress of a powered straightening process. For example, in some forms, a light-emitting diode (LED) may be located on the handle 5820. The LED may be illuminated during the powered straightening process to provide the user with a visual indication that the powered straightening process is occurring.

In some forms, the first and second sensors 5826a, 5826b may function as redundant checks on the straightening process. For example, in some forms, both the first and second sensors 5826a, 5826b may provide a signal to the articulation control motor 402 to activate the straightening process. A signal from either the first sensor 5826a or the second sensor 5826b may cause the articulation control motor 402 to straighten the sensor-straightened end effector 5802. In some forms, the powered straightening process may not execute until a signal has been received from both the first sensor 5826a and the second sensor 5826b. In some forms, either the first sensor 5826a or the second sensor 5826b may independently activate the powered straightening process but the process may be aborted if a signal is not received from both the first and second sensors 5826a, 5826b within a predetermined time limit. For example, the powered straightening process may be initiated by a signal from the first sensor 5826a. If a signal is not received from the second sensor 5826b within a predetermined time limit, the powered straightening process may be aborted by the surgical instrument 5810.

In some forms, the surgical instrument 5810 may comprise a stop sensor. The stop sensor may detect contact between the sensor-straightened end effector 5802 and a tissue section during the straightening process. If the stop sensor detects contact between the sensor-straightened end effector 5802 and a tissue section, the stop sensor may send a signal to the articulation control motor 402 to deactivate the straightening process to prevent damage to the patient. In some forms, when the stop sensor determines that the sensor-straightened end effector 5802 is no longer in contact with a tissue portion, the stop sensor may send a signal to the articulation control motor 402 to continue the straightening process. In some forms, the stop sensor may send a signal to the operator, for example through a feedback device, to notify the user that the sensor-straightened end effector 5802 has contacted a tissue section and that the straightening process has been deactivated. The stop sensor may comprise, for example, a pressure sensor disposed on the sensor-straightened end effector 5802.

Figure 107:
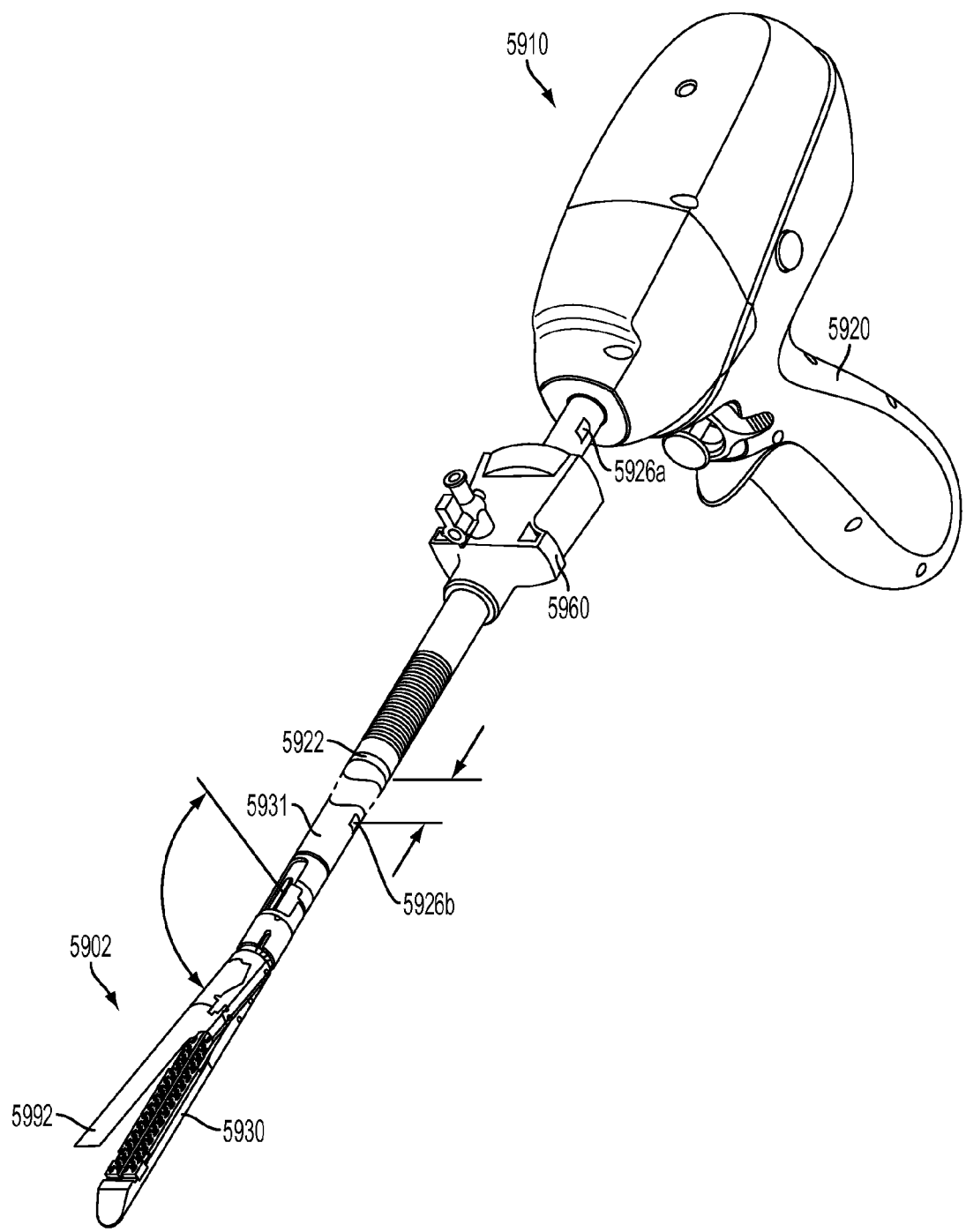
FIG. 107 illustrates one form of a sensor-straightened end effector inserted into a surgical overtube.
Figure 108:
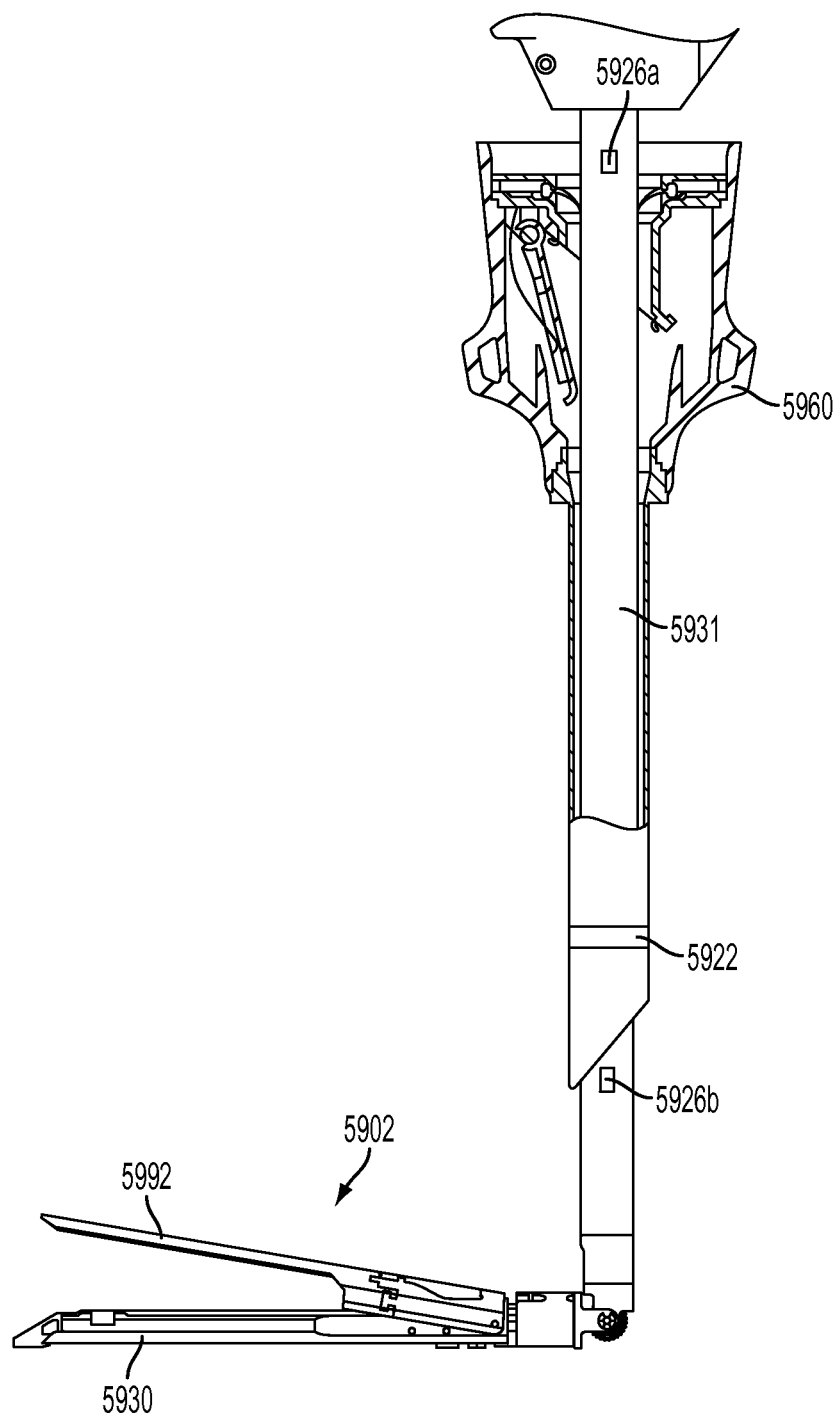
FIG. 108 illustrates one form of a sensor-straightened end effector inserted into a surgical overtube in an articulated state.

FIGS. 107 and 108 illustrate one form of a sensor-straightened end effector 5902. In some forms, the sensor-straightened end effector 5902 may be inserted into a patient through an overtube 5960. The overtube 5960 may comprise a magnetic ring 5922 located on the distal end of the overtube 5960. A first sensor 5926a and a second sensor 5926b may be configured to detect movement of the sensor-straightened end effector 5902 when the shaft 5931 is withdrawn from the overtube 5960. In some forms, the first sensor 5926a may comprise an accelerometer and the second sensor 5926b may comprise a magnetic proximity sensor. The second sensor 5926b may detect a change in a magnetic field strength as the second sensor 5926b is moved in a proximal direction towards the magnetic ring 5922. As the second sensor 5926b approaches the magnetic ring 5922, the second sensor 5926b may generate a signal to initiate a powered straightening process of the end effector 5902. The second sensor 5926b may comprise any suitable sensor for sensing a changing magnetic field, such as, for example, a reed switch sensor or a Hall Effect sensor. As discussed above, the first sensor 5926a and the second sensor 5926b may provide a redundant check for the powered straightening process. Those skilled in the art will recognize that in some forms, only the first sensor 5926a or the second sensor 5926b may be included. In some forms, additional sensors may be included to detect a gross proximal movement of the surgical instrument 5910.

Figure 109:
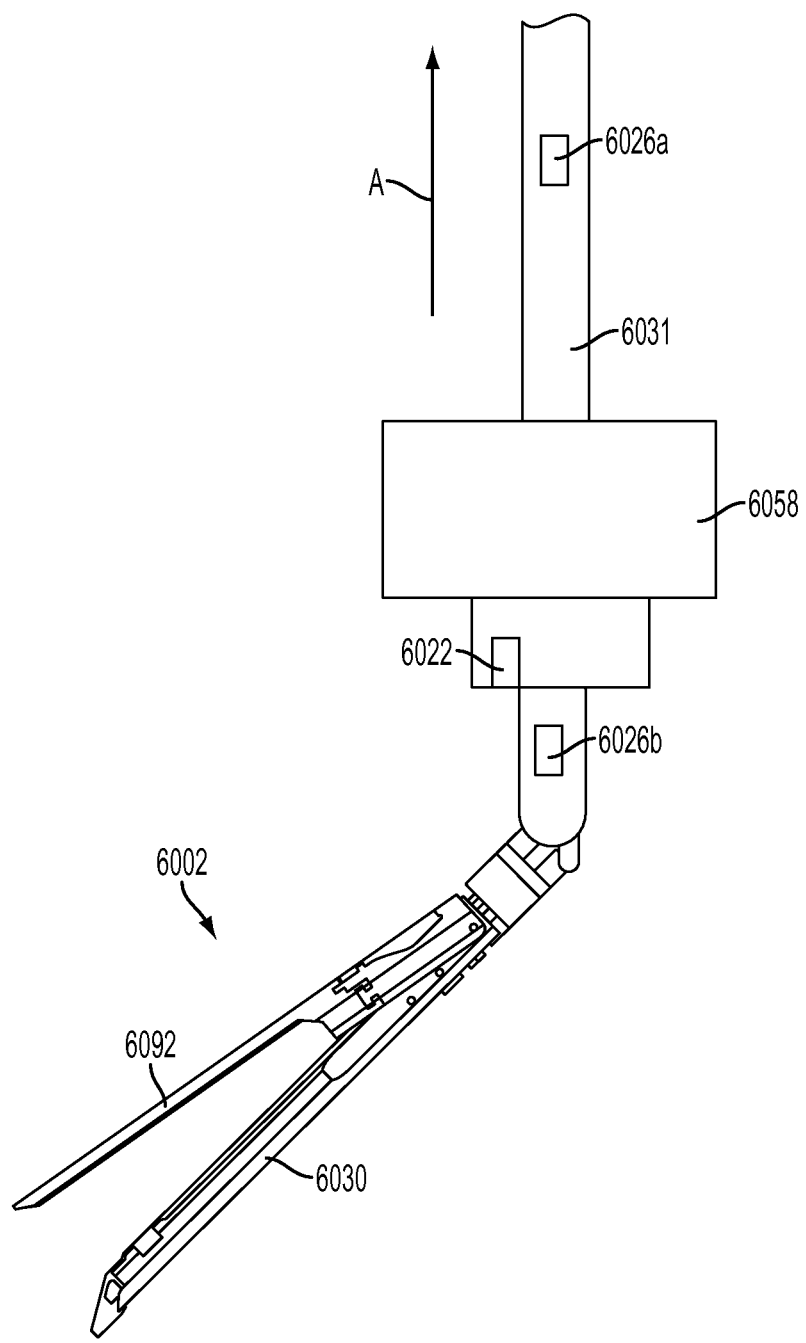
FIG. 109 illustrates one form of a sensor-straightened end effector in an articulated state.
Figure 110:
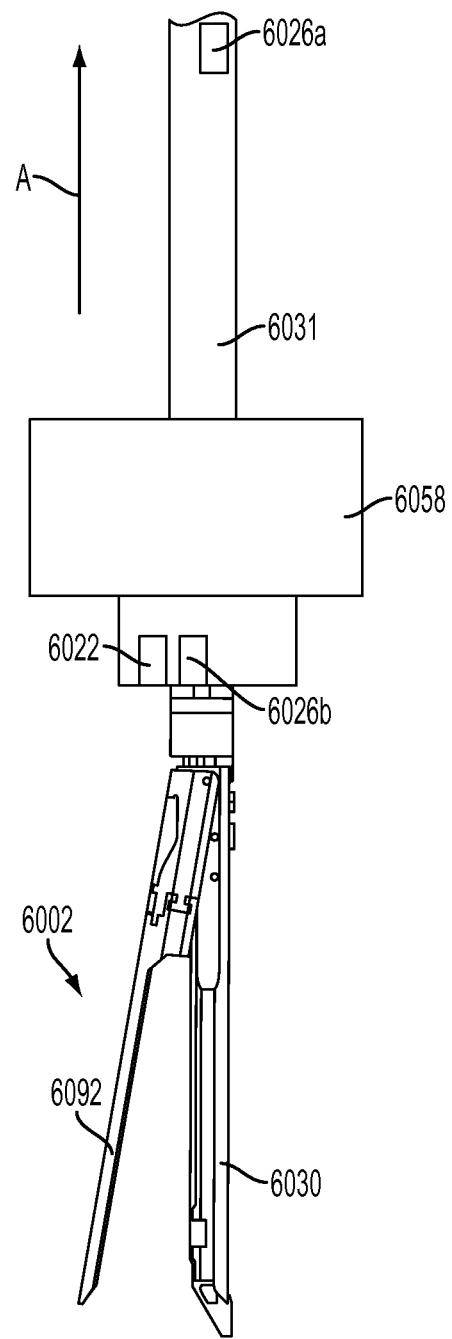
FIG. 110 illustrates one form of the sensor-straightened end effector of FIG. 109 in a straightened state.

FIGS. 109 and 110 illustrate one form of a sensor-straightened end effector 6002 transitioning from an articulated state to a straightened state during removal from a trocar 6058. In FIG. 109, the sensor-straightened end effector 6002 is in an articulated position with respect to the shaft 6031. A clinician may begin to withdraw the sensor-straightened end effector 6002 through the trocar 6058 in a proximal direction, as indicated by arrow 'A.' The proximal movement may be detected by a first sensor 6026a, a second sensor 6026b, or both the first and second sensors 6026a, 6026b. The first sensor 6026a may comprise an accelerometer configured to detect a gross proximal movement of the shaft 6031. The second sensor 6026b may comprise a magnetic sensor configured to detect a change in a magnetic field between the second sensor 6026b and a fixed point, such as, for example, the trocar 6058. The trocar 6058 may comprise a magnet 6022 to generate a magnetic field. As the shaft 6031 is withdrawn through the trocar 6058, the strength of the magnetic field detected by the magnetic sensor 6026b will change proportionally to the distance between the magnetic sensor 6026b and the magnet 6022. The first sensor 6026a or the second sensor 6026b may generate a signal to the articulation control motor 402 to activate a powered straightening process to straighten the sensor-straightened end effector 6002 with respect to the shaft 6831.

After the powered straightening process has completed, the sensor-straightened end effector 6002 is in a straight state as shown in FIG. 110. In the straight state, the sensor-straightened end effector 6002 may be withdrawn through the trocar 6058 without damaging the patient, the trocar 6058, and without the clinician needing to manually straighten the end effector 6002. In some forms, a clinician may be able to override the powered straightening process and maintain the sensor-straightened end effector 6002 in an articulated state during removal from the trocar 6058.

Figure 111:
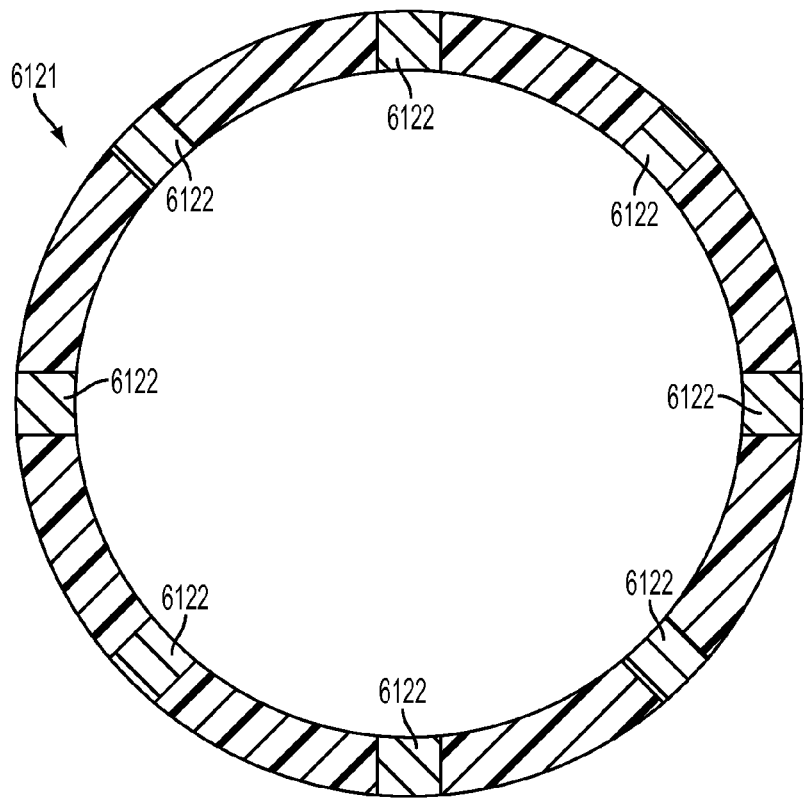
FIG. 111 illustrates one form of a magnetic ring for use with a sensor-straightened end effector.

FIG. 111 illustrates one form of a magnetic ring 6121 that may be attached to a trocar 5858, 6058 or an overtube 5960. The magnetic ring 6121 may comprise a plurality of magnets 6122 that may generate a magnetic field. The magnetic field may be detected by a magnetic sensor disposed on a surgical instrument, such as, for example, the second sensor 6026b. The magnetic sensor 6026b may be configured to maintain a sensor-straightened end effector, such as end effector 6002, in a straightened state when the magnetic sensor detects the magnetic field generated by the magnetic ring 6121. For example, in one form, the magnetic sensor 6026b may be configured to generate a lockout signal that prevents articulation of an end effector if the magnetic sensor 6026b detects a magnetic field above a predetermined threshold. The predetermined threshold may be determined based on the strength of the magnetic field generated by the magnetic ring 6121 at a specific distance corresponding to the articulation axis B-B being located outside of the trocar 5858 or the overtube 5960. In some forms, the magnetic sensor 6026b may activate a powered straightening process when the detected magnetic field strength exceeds the predetermined threshold and may generate a lockout signal to prevent articulation of the sensor-straightened end effector 6002 until the detected magnetic field strength drops below the predetermined threshold.

Figure 112:
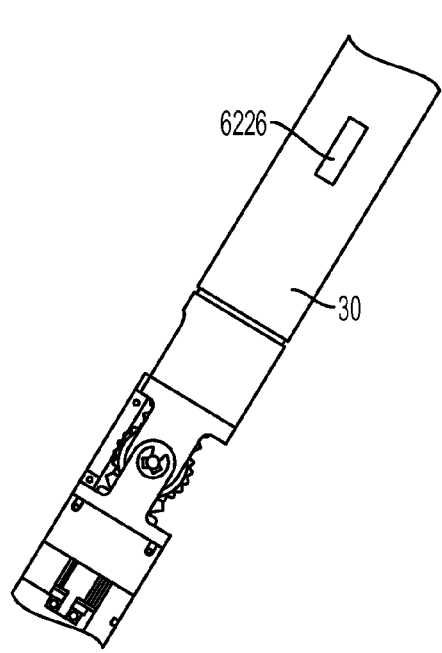
FIG. 112 illustrates one form of a sensor-straightened end effector comprising a magnetic sensor.
Figure 113:
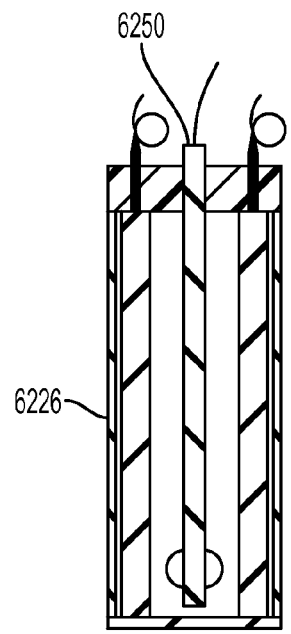
FIG. 113 illustrates one form of a magnetic reed sensor.

FIGS. 112 and 113 illustrate one form of a magnetic sensor 6226 comprising a reed switch sensor. A reed switch may comprise an electrical switch 6250 operated by an applied magnetic field. A pair of contacts may be disposed on ferrous metal reeds in a hermetically sealed glass envelope. The contacts may be normally open, closing when a magnetic field is present, or normally closed and opening when a magnetic field is applied.

With reference now to FIGS. 105 and 106, a method for controlling a sensor straightened end effector is disclosed. Although the method for controlling a sensor straightened end effector is described herein with reference to FIGS. 105 and 106, those skilled in the art will recognize that the method may be used with any of the forms of the sensor-straightened end effector disclosed herein, such as, for example, the forms illustrated in FIGS. 107-113. In one form, the method may comprise detecting, by a first sensor 5826a, a gross proximal movement of a surgical instrument 5810. The surgical instrument 5810 may comprise a sensor-straightened end effector 5802. A clinician may articulate the sensor-straightened end effector 5802 during treatment. Once the treatment is complete, the clinician may begin to withdraw the surgical instrument 5810 from the patient, moving the surgical instrument 5810 in a proximal direction. The proximal movement of the surgical instrument 5810 may be detected by the first sensor 5826a. In some forms, the first sensor 5826a may comprise an accelerometer configured to detect a gross proximal movement of the surgical instrument 5810. The method may further comprise generating, by the first sensor 5826a, a signal indicating that a gross proximal movement has been detected. The signal may be transmitted by the first sensor 5826a to a controller for the articulation control motor 402, such as, for example, a control circuit such as the control circuit 3702 shown in FIG. 82. Additional motor controllers are provided and described with respect to FIGS. 84, 114-116, etc. The method may further comprise receiving, by the articulation control motor 402, the signal from the first sensor 5826a and activating, by the articulation control motor 402, a powered straightening process to straighten the angle of articulation of the sensor-straightened end effector 5802 in response to the received signal. The powered straightening process may return the sensor-straightened end effector 5802 to a zero articulation state.

In some forms, the method may further comprise detecting, by a second sensor 5826b, the gross proximal movement of the surgical instrument 5810. In some forms, the second sensor 5826b may comprise a magnetic proximity sensor, such as, for example, a Hall Effect sensor or a reed switch sensor. The second sensor 5826b may be configured to detect the distance between the second sensor 5826b and a fixed point, such as a trocar 5858 or an overtube 5960. The method for controlling a sensor-straightened end effector 5802 may further comprise generating, by the second sensor 5826b, a signal indicating that the gross proximal movement has been detected. The second signal may be transmitted to the articulation control motor 402. The method may further comprise receiving, by the articulation control motor 402, the second signal and activating, by the articulation control motor 402, the powered straightening process to straighten the angle of articulation of the sensor-straightened end effector 5802. In some forms, the second sensor 5826b may generate the second signal independent of the first sensor 5826a.

In some forms, the first and second sensors 5826a, 5826b may function as redundant checks on the straightening process. For example, in some forms, both the first and second sensors 5826a, 5826b may provide a signal to the articulation control motor 402 to activate the straightening process. A signal from either the first sensor 5826a or the second sensor 5826b may cause the articulation control motor 402 to straighten the sensor-straightened end effector 5802. In some forms, the powered straightening process may not execute until both a signal has been received from both the first and the second sensors 5826a, 5826b. In some forms, either the first sensor 5826a or the second sensor 5826b may independently activate the powered straightening process but the process may be aborted if a signal is not received from both the first and second sensors 5826a, 5826b within a predetermined time limit. For example, the powered straightening process may be initiated by a signal from the first sensor 5826a. If a signal is not received from the second sensor 5826b within a predetermined time limit, the powered straightening process may be aborted by the surgical instrument 5810.

Figure 114:
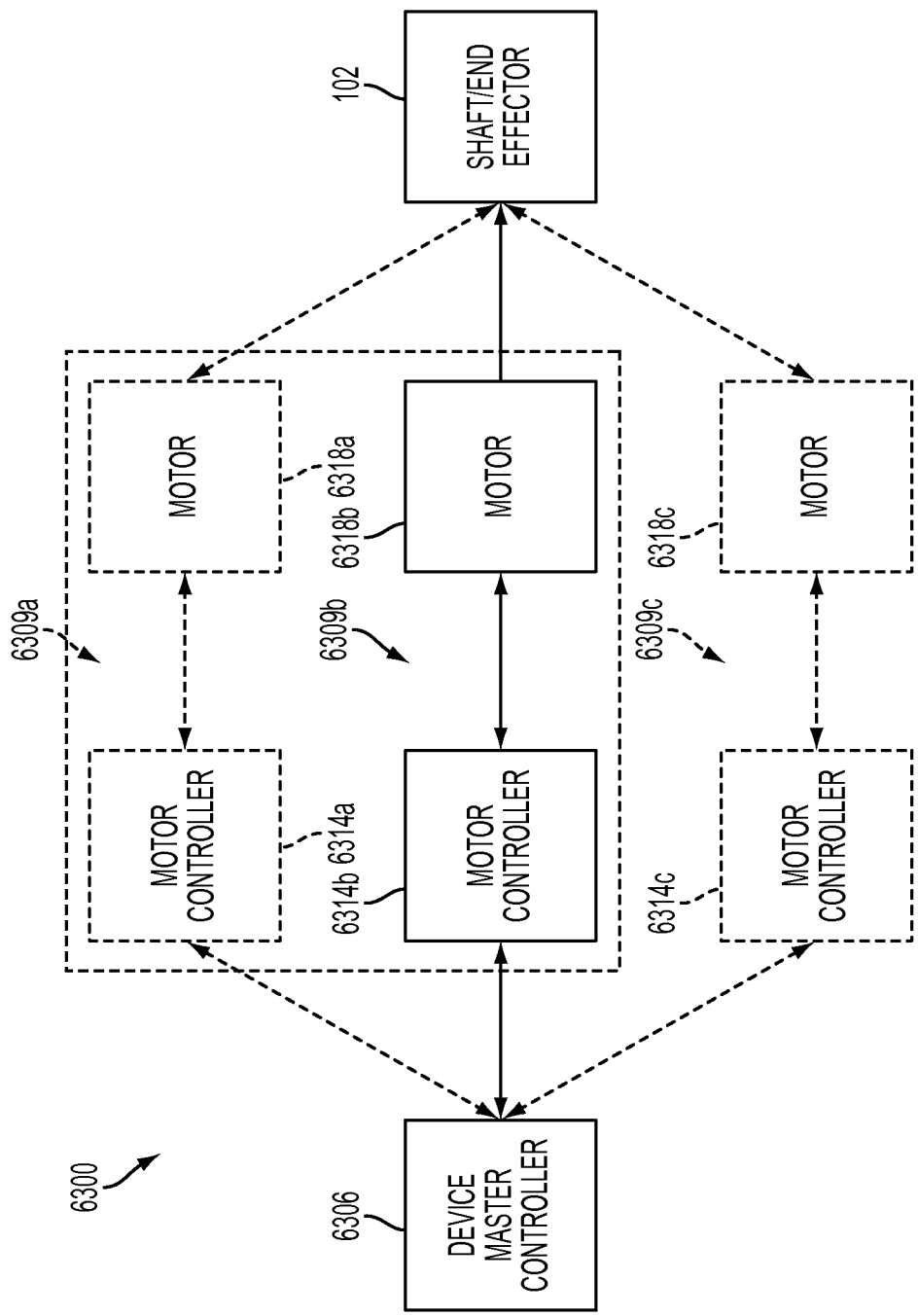
FIG. 114 illustrates one form of a modular motor control platform.

In one form, various surgical instruments may utilize a modular motor control platform. For example, the modular control platform may be implemented by the control circuit 3702. FIG. 114 shows one form of a modular motor control platform 6300 comprising a master controller 6306, one or more motor-controller pairs 6309a-6309c. The platform 6300 may control one or more motors 6318a, 6318b, 6318c. The motors 6318a, 6318b, 6318c may be any motors utilized in a surgical instrument. For example, in some forms one or more of the motors 6318a, 6318b, 6318c may correspond to one or more of the articulation motor 402, the firing motor 530, the end effector rotation motor 560 and/or the shaft rotation motor 610.

In various forms, the respective controllers 6306, 6309a-6309c may be implemented utilizing one or more processors (e.g., processors implemented on the control circuit 3702). The modular motor control platform 6300 may be suitable to control a motor controlled surgical instrument, such as, for example, the surgical instrument 10 illustrated in FIGS. 1 and 2. In various forms, the master controller 6306 may be mounted on the distal circuit board 810 or the proximal circuit board 820. A first motor controller 6314a is operatively coupled to a first motor 6318a to provide one or more control signals to the first motor 6318a. A second motor controller 6314b may be operatively coupled to the second motor 6318b and a third motor controller 6314c may be operatively coupled to the third motor 6318c. The motor controllers 6314a-6314c are in electrical communication with the master controller 6306. The master controller 6306 provides control signals to the motor controllers 6314a-6314c based on a main control process for controlling one or more functions of the end effector 6302. The main control process may be a predefined process, a user-defined process, or a device generated process.

In one form, the main control process may define one or more surgical procedures performable by the surgical instrument 10 comprising one or more functions of the shaft 30 and the end effector 102. For example, in one form, the main control process may define a cutting and sealing operation of the surgical instrument 10. The cutting and sealing operation may comprise multiple functions of the surgical instrument 10, such as, for example, a clamping function, a stapling function, a cutting function, and an unclamping function. A user may indicate the initiation of a cutting and sealing operation in any suitable manner, such as, for example pressing a button or switch on the handle 20. Those skilled in the art will appreciate that any suitable input method may be used to activate one or more functions of the surgical instrument 10.

In one form, when the clinician indicates initiation of the cutting and sealing operation, such as, for example, by pressing a button on the handle 20, the master controller 6306 may generate a series of control signals and provide the control signals to one or more motor controllers 6314a-6314c. For example, at time $t_0$, a cutting and sealing operation may be initiated. The master controller 6306 may generate a first control signal indicating that a clamping function should be performed. The first control signal may be transmitted to a first motor controller 6314a coupled to a first motor 6318a configured to control a clamping motion of the end effector 6302. The first motor controller 6314a may, in turn, provide one or more signals to the first motor 6318a, activating the first motor 6318a to pivot the anvil assembly 190 of the end effector 102 to clamp tissue located between the anvil assembly 190 and the cartridge 130. The master controller 6306 may poll the first motor controller 6314a for a status signal until the first motor controller 6314a indicates the clamping operation has completed. At time $t_1$, the first motor controller 6314a may provide a signal to the master controller 6306 indicating the clamping function has completed.

At time $t_2$, a second control signal may be transmitted from the master controller 6306 indicating that a stapling and cutting operating should be performed. The second control signal may be sent to a second motor controller 6314b coupled to a second motor 6318b. The second motor 6318b may be configured to control proximal and distal movement of the cutting portion 164 and/or the sled 170 disposed within the end effector 102. A stapling and cutting operation control signal may result in the second motor controller 6314b activating the second motor 6318b to advance the cutting portion 164 and/or the sled 170 in a distal direction causing the staple cartridge 130 to fire and the cutting portion 164 to cut tissue clamped by the anvil assembly 190, as discussed in more detail above. At time $t_3$, the cutting portion 164 reaches a distal-most point and the second motor controller 6314b may provide a signal to the master controller 6306 indicating that the stapling and cutting operation has completed. The second motor controller 6314b may automatically generate a control signal for the second motor 6318b to reverse the direction of the cutting portion 164 until the cutting portion 164 has been fully retracted.

After receiving the signal from the second motor controller 6314b at time $t_3$, the master controller 6306 may provide a third control signal to the first motor controller 6314a indicating that a release function should be performed. The first motor controller 6314a may generate a control signal for the first motor 6318a to cause the first motor 6318a to reverse the earlier clamping operation and to unclamp the anvil assembly 190. The release function may be performed by the first motor controller 6314a and first motor 6318a simultaneously with the reversing of the second motor 6318b to retract the cutting portion 164 to its starting position. The use of a master controller 6306 and individual motor controllers 6314a, 6314b allows the surgical instrument 10 to perform multiple operations simultaneously without over stressing any of the individual controllers 6306, 6314a, 6314b.

The motor controllers 6314a-6314c may comprise one or more independent processes for monitoring and controlling surgical operations, such as, for example, movement of a motor. In some forms, the motor controllers 6314a-6314c may be configured to operate one or more control feedback loop mechanisms. For example, in some forms, the motor controllers 6314a-6314c may be configured as closed loop controllers, such as single-input-single-output (SISO) or multiple-input-multiple-output (MIMO) controllers. In some forms, the motor controllers 6314a-6314c may operate as proportional-integral-derivative (PID) controllers. A PID controller may operate a control loop using three tuning terms, a proportional gain term, an integral gain term, and a derivative gain term. A PID controller may comprise a control process configured to measure a specified variable and compare the measured value of the specified variable to an expected value or set-point of the specified variable. The PID controller may adjust a control variable based on the difference between the measured valued and the expected value of the specified variable. In some forms, the motor controllers 6314a-6314c may comprise a PID velocity controller. For example, a first motor controller 6314a may measure a specified variable, such as the position of a motor 6314a. The first motor controller 6314a may adjust a control variable, such as the speed of the motor 6314a, based on the difference between the measured position of the motor 6314a and a set-point or expected position of the motor 6314a.

In some forms, the motor controllers 6314a-6314c may be configured as fault detection controllers. A fault detection controller may operate a fault detection process. In some forms, the fault detection controller may operate a direct pattern recognition fault process comprising monitoring one or more sensors configured to directly indicate a fault, which may be referred to as signal processing based fault detection.

In some forms, a sensor value provided by a sensor is compared to an expected value of the sensor derived from a model of the fault detection controller, which may be referred to as model-based fault detection. Those skilled in the art will recognize that a combination of signal processing and model-based fault detection may be employed by a motor controller.

In some forms, the motor controllers 6314a-6314c may be configured as current/force limiting controllers. A current/force limiting controller may be configured to limit a measured value, such as the current delivered to a motor or the force exerted by a motor, to a predetermined value. For example, in one form, a first motor controller 6314a may be configured to limit the force exerted during a clamping operation to a predetermined value. A force sensor may monitor the force provided by a first motor 6318a configured to control a clamping operation of a surgical instrument. When the force value measured by the force sensor matches the predetermined value, the first motor controller 6314a may cease operation of the first motor 6318a. In some forms, a motor controller 6314a-6314c may be configured to monitor the current delivered to a motor 6318a-6318c. The current drawn by the motor 6318a-6318c may be indicative of one or more functions of the motor 6318a-6318c, such as the speed of the motor or the force exerted by the motor during a surgical operation. If the current drawn by the motor 6318a-6318c exceeds a predetermined threshold, the motor controller 6314a-6314c may cease operation of the motor to prevent damage to a patient and to the surgical instrument.

In some forms, the motor controllers 6314a-6314c may provide independent verification of the main control process executed by the master controller 6306. For example, the motor controllers 6314a-6314c may verify that the action requested by the master controller 6306 is a valid action prior to execution of the requested action. In some forms, the motor controller 6314a-6314c may use state information to verify that the requested action is valid. For example, in one form, a first motor controller 6314a may receive an instruction from the master controller 6306 to perform a cutting and stapling operation. The first motor controller 6314a may check the current state of the surgical instrument, such as, for example, checking whether the anvil assembly 190 is in a clamped position. If the state information matches a valid state for executing a cutting and stapling operation, the first motor controller 6314a may perform the cutting and stapling operation. However, if the state information does not match a valid state for cutting and stapling, the first motor controller 6314a may indicate a fault in the master controller 6306 or the main control process. Those skilled in the art will recognize that the motor controllers 6314a-6314c may comprise one or more control processes and one or more types of control processes.

Figure 115:
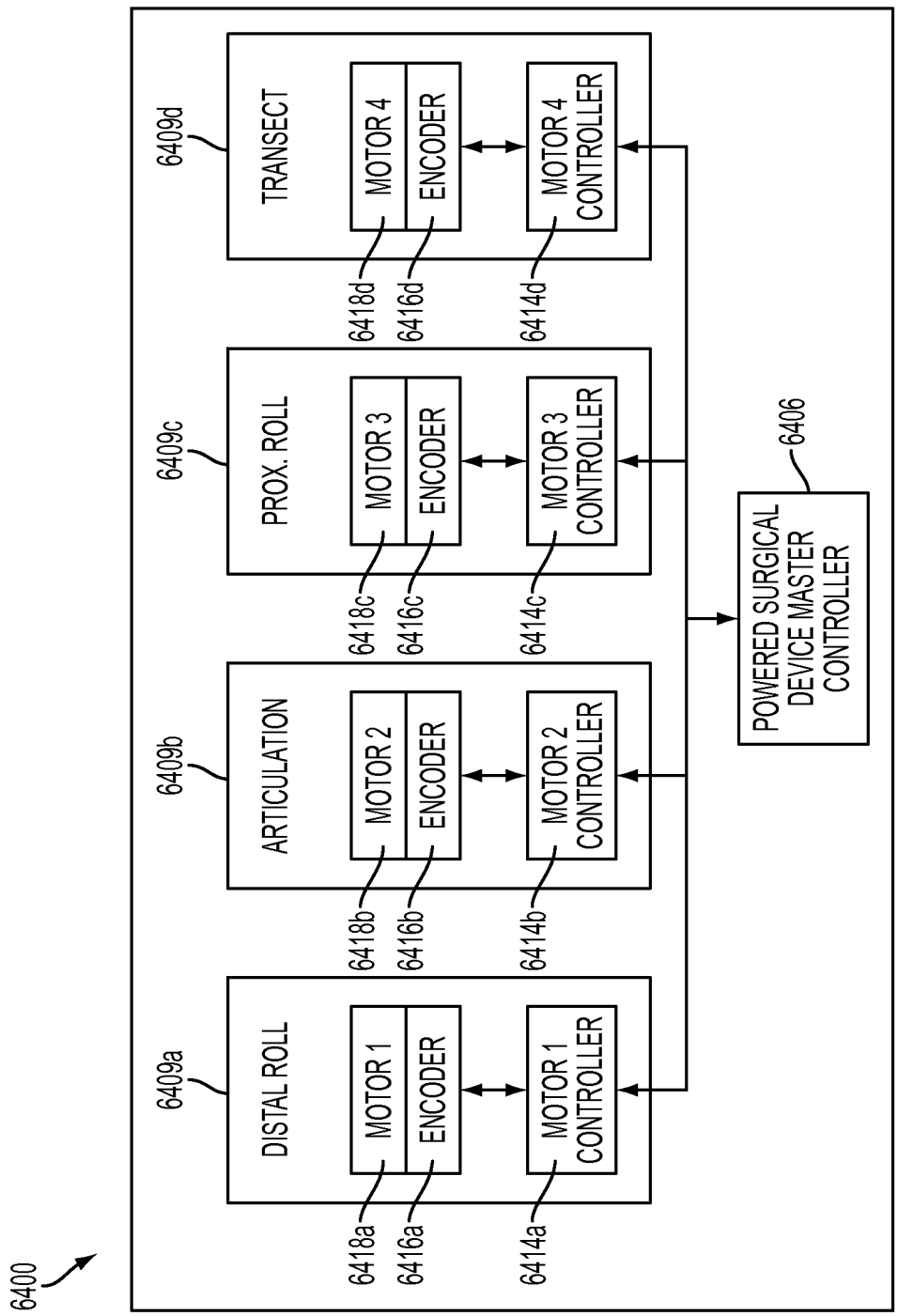
FIG. 115 illustrates one form of a modular motor control platform comprising multiple motor-controller pairs.

FIG. 115 illustrates one form of a modular motor control platform 6400 comprising a master controller 6406 and four motor-controller pairs 6409a-6409d. The modular motor control platform 6400 may also be implemented by the control circuit 3702 described herein above, for example, utilizing one or more processors. The modular motor control platform 6400 may be configured to control various motors. For example, a distal roll motor 6418a may operate in a manner similar to that described herein with respect to the end effector rotation motor 560. An articulation motor 6418b may operate in a manner similar to that described herein with respect to the articulation motor 402. A proximal roll motor 6418c may operate in a manner similar to that described herein with respect to the shaft rotation motor 610. A transaction motor 6418d may operate in a manner similar to that described herein with respect to the firing motor 530.

The master controller 6406 may be electrically coupled to one or more motor controllers 6414a-6414d. The master controller 6406 may be coupled to the one or more motor controllers 6414a-6414d through a wired or wireless connection. In some forms, the motors 6418a-6418d may comprise associated motor encoders 6416a-6416d configured to provide a signal indicative of the position of the motor shaft. In some forms, the motor encoders 6416a-6416d may be omitted. In one form, the master controller 6406 may be configured to communicate with any number of motor controllers 6414a-6414d, such as, for example, one to ten motor controllers. In some forms, the master controller 6406 may be configured to communicate with one or more additional peripheral controllers (not shown) wherein the peripheral controllers are configured to control one or more non-motorized surgical functions, such as, for example, ultrasonic functions, electrosurgical functions, or any other suitable function of the surgical instrument.

In one form, the master controller 6406 may synchronously communicate with the motor controllers 6414a-6414d. The communications from the master controller 6406 may include, for example, providing instructions to execute a specific sub-routine or function of the motor controller 6414a-6414d, querying the motor controller 6414a-6414d for a status update, and receiving feedback information from the motor controllers 6414a-6414d. Synchronous communication may be direct communication between the master controller 6406 and the motor controllers 6414a-6414d where the communications are time synchronized. For example, in the form illustrated in FIG. 114, the master controller 6406 may communicate with each of the motor controllers 6414a-6414d during predefined time windows. In another form, a token may be passed between the motor controllers 6414a-6414d to allow the motor controller 6414a-6414d currently holding the token to communicate with the master controller 6406 during a predetermined time period.

In one form, the master controller 6406 may execute a main control process. The main control process may monitor user inputs, execute operations of the surgical instrument 10, provide feedback to a user, or perform any other functions of the surgical instrument 10. For example, in one form, a master controller 6406 may execute a main control process comprising a cutting and sealing operation. In some forms, the main control process may provide control signals to each of the motor controllers 6414a-6414d. Execution of the individual functions of the motors 6418a-6418d may be controlled by the motor controllers 6414a-6414d. In some forms, the master control process may activate or deactivate one or more of the motors 6418-6418d based on the attachment or removal of a module surgical component, such as a modular shaft 30 or implement portion 100. The master controller 6406 may provide control signals to the motor controllers 6414a-6414d and may receive status signals from the motor controllers 6414a-6414d. The status signals may include, for example, a function completion signal, a fault signal, an idle signal, or a feedback signal.

In some forms, the function signal may indicate the operation or completion status of a function performable by the motor-controller pairs 6409a-6409d. For example, the function signal may indicate that a clamping operation is occurring or has been completed. The function signal may also indicate the success of the operation, such as, for example, indicating the amount of force applied by the tissue clamped during the clamping operation. A motor controller 6414a-6414d may generate a fault signal if the motor controller 6414a-6414d detects an error in an associated motor 6418a-6418d or in the completion of a surgical operation. The fault signal may cause the master controller 6406 to generate a fault signal to the operator, such as, for example, a visual indicator or an audible indicator. The fault signal may also cause the master controller 6406 to send control signals to the motor controllers 6414a-6414d to stop any currently executing functions.

An idle signal may be provided by the motor controllers 6414a-6414d to the master controller 6406 to indicate that an associated motor 6418a-6418d is idle and may be utilized to perform an associated function of the surgical instrument 10. In one form, an idle signal may indicate that a function has been performed by a motor 6418a-6418d. For example, in one form, a first motor controller 6414a may receive a control signal from the master controller 6406 to perform a clamping operation. The first motor controller 6414a may convert the control signal from the master controller 6406 into one or more control signals for the motor 6418a. Once the motor 6418a has performed the indicated function, the motor controller 6414a may transmit an idle signal to the master controller 6406, indicating that the motor 6418a has completed the requested function.

In various forms, a feedback signal may be provided by the motor controllers 6414a-6414d to the master controller 6406. The master controller 6406 may have one or more associated feedback devices (not shown) to provide feedback to an operator. The feedback signals received from the motor controllers 6414a-6414d may be converted to control signals for the feedback devices by the master controller 6406. In some forms, the motor controllers 6414a-6414d may provide feedback signals directly to a feedback device.

In some forms, the synchronous communication between the master controller 6406 and the motor controllers 6414a-6414d may be interrupted by an override signal. The override signal may cause the master controller 6406 to cease synchronous communication and to communicate with the motor controller 6414a generating the override signal. In various forms, the override signal may be generated by a motor controller 6414a as the result of a failure of a motor, an input signal from the user, or based on a predetermined threshold in one or more feedback signals. The override signal may cause the master controller 6406 to send a signal to each of the motor controllers 6414a-6414d to cease all operation of the motors 6418a-6418d until the condition that caused the generation of the override signal has been resolved. In one form, the master controller 6406 may generate a signal for a feedback device to notify the operator of the override signal.

Figure 116:
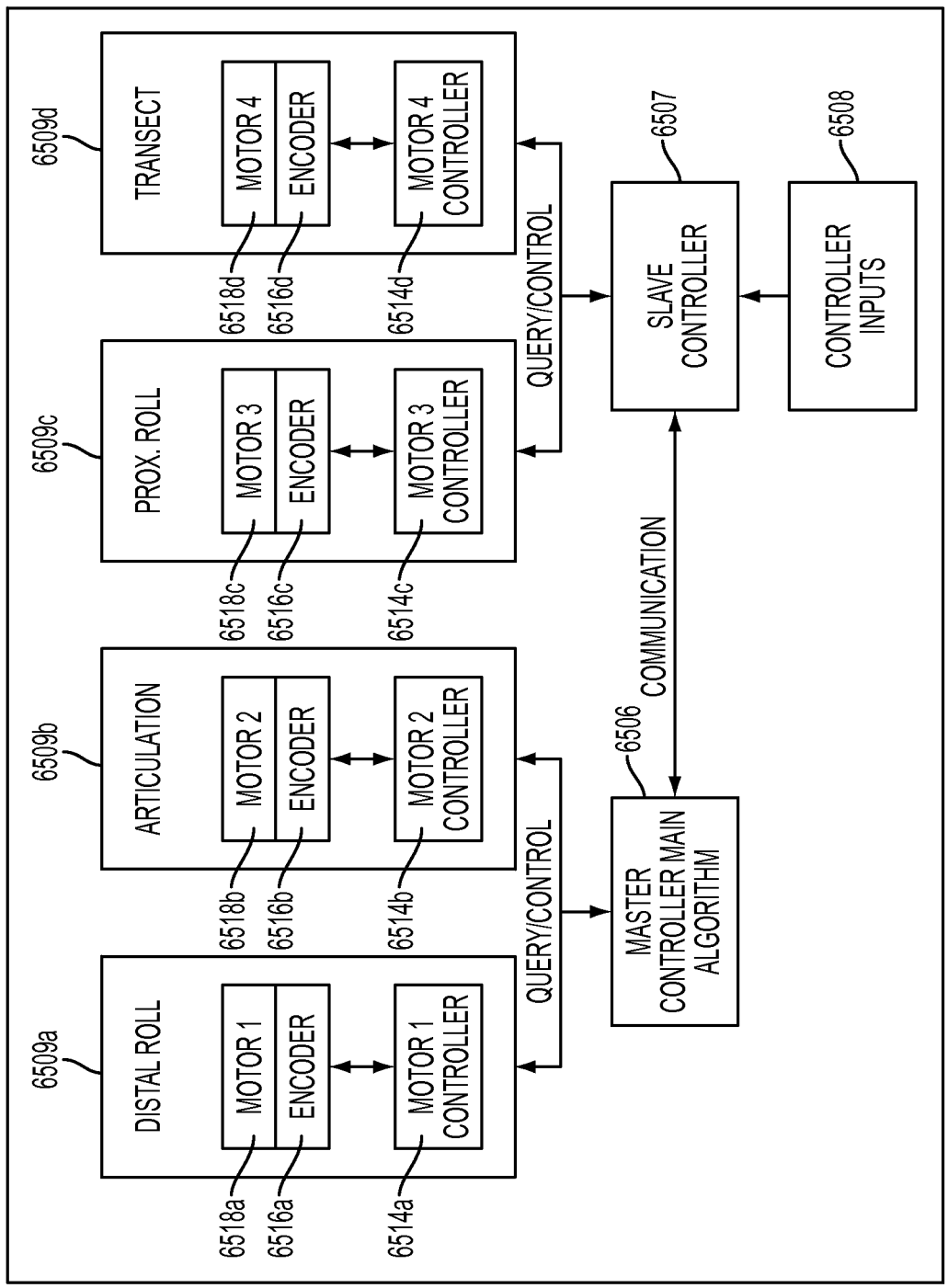
FIG. 116 illustrates one form of a modular motor control platform comprising a master controller and a slave controller.

FIG. 116 illustrates one form of a dual-controller modular motor control platform 6500. The platform 6500 may also be implemented by the control circuit 3702, as described herein. The dual-controller modular motor control platform 6500 comprises a master controller 6506, a slave controller 6507, and four motor-controller pairs 6509a-6509d. The modular motor control platform 6400 may be configured to control motors 6518a, 6518b, 6518c, 6518c. For example, a distal roll motor 6518a may operate in a manner similar to that described herein with respect to the end effector rotation motor 560. An articulation motor 6518b may operate in a manner similar to that described herein with respect to the articulation motor 402. A proximal roll motor 6518c may operate in a manner similar to that described herein with respect to the shaft rotation motor 610. A transaction motor 6518d may operate in a manner similar to that described herein with respect to the firing motor 530.

The modular motor control platform 6400 may be configured to control the articulation motor 402, the firing motor 530, the end effector rotation or "distal roll" motor 560, and the shaft rotation or "proximal roll" motor 610. The master controller 6506 and the slave controller 6507 may each be associated with a subset of the available motor controllers. For example, in the illustrated form, the master controller 6506 is associated with the first and second motor controllers 6526a-6526b and the slave controller 6507 is associated with the third and fourth motor controllers 6526c-6526d. The master controller 6506 and the slave controller 6507 may be in electrical communication. In some forms, the slave controller 6507 may located on the distal circuit board 810 or the proximal circuit board 820. The slave controller 6507 may reduce the load on the master controller 6506 by reducing the number of motor controllers 6526a-6526d that the master controller 6506 must communicate with and control. The master controller 6506 and the slave controller 6507 may receive one or more controller inputs 6508.

In one form, the master controller 6506 may provide control signals directly to a first motor controller 6526a and a second motor controller 6526. The master controller 6506 may also provide control signals to the slave controller 6507. The slave controller may provide control signals to a third motor controller 6526c and a fourth motor controller 6526d. By reducing the number of motor controllers 6526a-6526d that the master controller 6506 must query and control, the dual-controller modular motor control platform 6500 may increase response times or dedicate additional processing load of the master controller 6506 to other tasks. In one form, the master controller 6506 may execute a main control process and the slave controller 6507 may execute a slave control process to generate one or more signals for the motor controllers 6526a-6526d based on input from the master controller 6506. In one form, the slave controller 6507 may receive controller inputs from one or more user controls, such as, for example, a clamping button or a firing switch. In one form, the master controller 6506 may communicate with one or more slave controllers 6507 and may not provide any control signals directly to the motor controllers 6526a-6526d.

In one form, additional slave controllers 6507 may be added to the system to control additional motor controllers or surgical modules. In one form, the slave controller 6507 may only be utilized when a predefined threshold of motor controllers is required. For example, in the form shown in FIG. 115, four motor controllers 6526a-6526d are connected to the dual-controller modular motor control platform 6500. The master controller 6506 and the slave controller 6507 are each associated with two motor controllers 6526a-6526d. Deactivation of one or more motors, such as, for example, by replacing the shaft 30 with a different shaft requiring only to motors for articulation, may result in deactivation of the slave controller 6507, as the additional processing power of the slave controller 6507 is not required to reduce processing load on the master controller 6506. In some forms, deactivation of one or more motor controllers 6526a-6526d may result in the remaining motor controllers being assigned to an idle slave controller 6507. For example, deactivation of the third and fourth motors 6518c, 6518d would result in the slave controller 6507 being idle. The second motor controller 6526b may be disconnected from the master controller 6506 and connected to the slave controller 6507 to lessen the processing load of the master controller 6506. One or more load balancing processes may be executed as part of the main control process to ensure optimized distribution of control between the master controller 6506 and one or more slave controllers 6507.

Referring now back to FIGS. 114-116, a method for controlling a modular surgical instrument 10 comprising multiple motor controllers may be disclosed. Although the method for controlling a modular surgical instrument 10 is discussed with respect to FIGS. 114-116, those skilled in the art will recognize that the method may be employed with respect to any embodiment of the surgical instrument, or the various control platforms described herein. The method may comprise generating, by a master controller 6506, a main control process comprising one or more control signals. The method may further comprise transmitting, from the master controller 6506 to one or more motor controllers 6526a-6526d, the generated control signals. The motor controllers 6526a-6526d may receive the transmitted control signals. In some forms, the subset of the control signals received by a first motor controller 6526a may comprise the control signals transmitted by the master controller 6506 during a specific time period in which the master controller 6506 and the first motor controller 6526a are in synchronous communication. The method may further comprise controlling, by the motor controllers 6526a-6526d, one or more associated motors 6518a-6518d based on the control signals received from the master controller 6506.

In some forms, the method may comprise transmitting, by the master controller 6506, one or more control signals to a slave controller 6507. The slave controller 6507 may be in electrical communication with one or more motor controllers 6526c-6526d. The slave controller 6507 may execute a slave control process comprising generating one or more motor control signals based on input received from the master controller 6506. The slave control process may further comprise transmitting, by the slave controller 6507, the motor control signals to one or more electrically coupled motor controllers 6526c-6526d. The method may further comprise controlling, by the motor controllers 6526c-6526d, one or more associated motors in response to the received motor control signals. In various forms, a subset of the generated motor control signals may be synchronously transmitted to each of the motor controllers 6526c-6526d during a predetermined time period.

Figure 117:
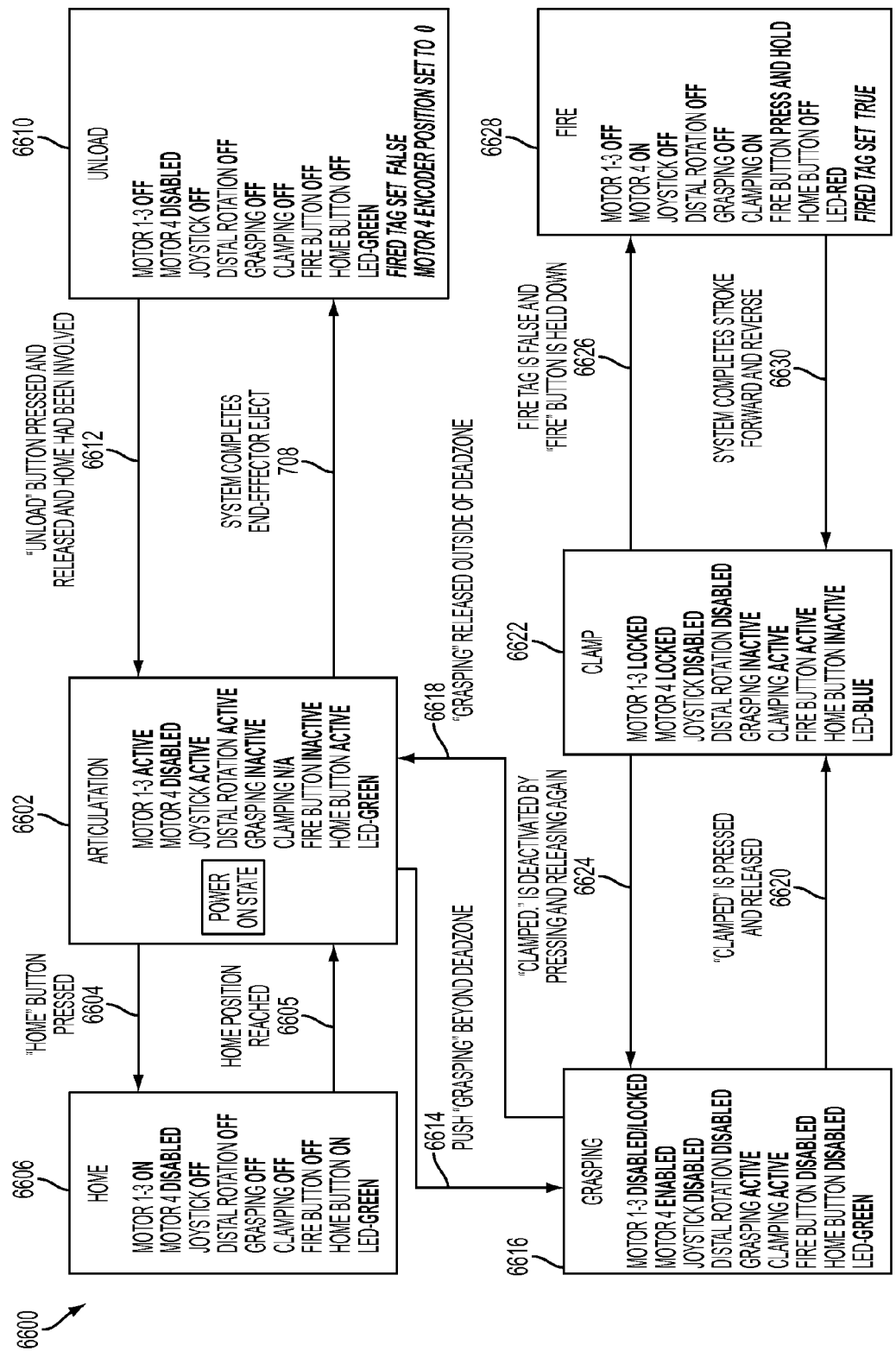
FIG. 117 illustrates one form of a control process implementable by a multiple-motor controlled surgical instrument.

FIG. 117 illustrates one form of a main control process 6600 that may be executed by a master controller, such as, for example, the master controllers shown in FIGS. 114-116 or any other suitable master controller. In one form, the surgical instrument 10 may comprise four motors, such as, for example the articulation motor 402, the firing motor 530, the end effector rotation or "distal roll" motor 560, and the shaft rotation or "proximal roll" motor 610 and a joystick 842. The surgical instrument 10 may be configured to perform a distal rotation function, a grasping function, a clamping function, and a firing function. The surgical instrument 10 may comprise one or more buttons for controlling the various operations of the surgical instrument 10, such as, for example a home button, an unload button, a grasping button, a clamping button, or a fire button. The surgical instrument 10 may further comprise a light-emitting diode (LED) to provide visual feedback to a user regarding the operation of the surgical instrument 10.

In some forms, when the surgical instrument 10 is activated, the master controller 6406 places the device into a default mode. In the illustrated main control process 6600, the default mode is the articulation state 6602. The articulation state 6602 may comprise activation of three of the four available motors. The activated motors may control the rotation of the shaft 30 (e.g., the shaft rotation motor 610), the end effector 102 (e.g., the end effector rotation motor 560), and/or the articulation of the end effector 102 (e.g., the articulation motor 410). In the default articulation mode, the joystick 842 may be active. In the articulation state 6602, the joystick 842 may be used to control the articulation or rotation of the shaft 30 and the end effector 102. The distal rotation function may be active (or available) while the grasping, clamping, and firing functions are unavailable. The home button may also be activated in the default state. The LED may be green to indicate the surgical instrument 10 is in a state during which the surgical instrument 10 may be safely moved.

A user may press the home button 6604 causing the surgical instrument 10 to return to a home state 6606, e.g., a starting state in which the end effector 102 is straightened with respect to the shaft 30 and the shaft 30 and end effector 102 are returned to a zero rotation state. The home state 6606 may be useful for moving from one operation to another or may allow a user to quickly reorient the surgical instrument 10 during operation. Once the home state 6606 has been reached, the master control process 6600 may return 6605 to the default articulation state 6602.

In one form, the end effector 102, illustrated in FIGS. 1 and 2, may be releasably connected to the shaft 30 to allow different implements to be attached to the shaft 30. The shaft 30 may be releasably connected to the handle 20 to allow various shafts to be attached to the surgical instrument 10. In one form, the master controller 6406 may sense the ejection 6608 of an end effector 102 or a shaft 30 from the surgical instrument 10 and may disable operation of the surgical instrument 10 until a new shaft or implement portion has been attached to the surgical instrument 10 and the surgical instrument 10 has been returned to a home state 6606. After the master control process 6600 has detected a new end effector 102 and has returned to the home state 6606, the master control process 6600 may enter the default state 6602.

In one form, the surgical instrument 10 may have an end effector 102 attached. The end effector 102 may be configured to perform a grasping function. The grasping function may comprise grasping an area of tissue between the anvil assembly 190 and the cartridge 130 of the end effector 102. The surgical instrument 10 may comprise a grasping button to activate a grasping function. When a user presses 6614 the grasping button, the surgical instrument 10 may enter a grasping mode 6616, locking out movement of the end effector 102, such as rotation or articulation with respect to the shaft 30. The grasping mode 6616 may activate a fourth motor (e.g., the firing motor 530) to cause a portion of the end effector 102 to grasp a tissue section, such as, for example, moving the anvil assembly 190 from an open position to a closed position. A clamping button may be activated when the surgical instrument 10 enters a grasping state.

In some forms, a clinician may press 6620 a clamping button, causing the surgical instrument 10 to enter a clamp mode 6622. In the clamp mode 6622, the surgical instrument 10 may lock out the fourth motor to prevent release of the tissue section during a subsequent operation. The clamp mode 6622 may activate a fire button located on the handle 20. Once the surgical instrument 10 has entered the clamp mode 6622, the master controller 6406 may change the LED to blue to indicate to the clinician that tissue has been clamped in the anvil assembly 190 and that the surgical instrument 10 may be fired to cause a stapling and cutting operation.

A clinician may press 6626 a fire button to cause the surgical instrument 10 to enter a fire mode 6628. In the fire mode 6628, the surgical instrument 10 may deactivate the motors configured to control movement of the surgical instrument 10, such as, for example, motors 1-3. The fire mode 6628 may activate the fourth motor which may be configurable to control a stapling and cutting operation as described above. The fire button may be held down, causing the master controller 6406 to generate control signals for the motor controller associated with the fourth motor to activate the stapling and cutting operation, causing a cutting portion 164 and/or a sled 170 to advance within a staple cartridge 130 located in the end effector 102. During the firing sequence, the LED may be set to red by the master controller 6406 to alert the clinician that the surgical instrument 10 is firing. A "fired tag" may be set to true by the master controller 6406, indicating that the surgical instrument has been fired and may not be fired again. The master controller 6406 or the motor controller associated with the fourth motor may automatically retract the cutting portion 164 when the cutting portion 164 has reached the distal end of the end effector 102. Once the cutting portion 164 has completed the reverse stroke and returned to its starting position, the master control process 6600 may return 6630 to the clamp state 6622.

A clinician may deactivate 6624 the clamp state 6622 by pressing the clamp button. The master control process 6600 will generate one or more control signals to return to the grasping state 6616 when the clamping state 6622 is deactivated. The clinician may then release 6618 the grasping state 6616 and transition into the articulation state 6602, or any other suitable default state. Those skilled in the art will recognize that the master control process 6600 may be modified to accommodate any surgical operation or function performable by the surgical instrument 10 or any attached surgical module. In some forms, the master control process 6600 may be automatically configured based on the attached shafts, end effectors, or power modules.

In accordance with one general form, there is provided a surgical instrument comprising a handle assembly that is configured to simultaneously and independently electrically generate at least two discrete rotary control motions. The surgical instrument may further include an elongate shaft assembly that operably interfaces with the handle assembly for independently and simultaneously receiving and transmitting the at least two discrete rotary control motions to an end effector operably coupled to the elongate shaft assembly.

In accordance with another general form, there is provided a surgical instrument that comprises a handle assembly that is configured to simultaneously and independently generate at least three discrete rotary control motions. The surgical instrument may further include an elongate shaft assembly that operably interfaces with the handle assembly for independently and simultaneously receiving and transmitting the at least three discrete rotary control motions to an end effector operably coupled to the elongate shaft assembly.

In accordance with another general form, there is provided a surgical instrument that comprises a drive system that is configured to electrically generate a plurality of discrete rotary control motions. The surgical instrument may further include an elongate shaft assembly that is operably coupled to the drive system for receiving a first rotary control motion therefrom for rotating the elongate shaft assembly about a shaft axis. The elongate shaft assembly may be configured to receive and transmit a second rotary control motion from the drive system to a surgical end effector that is operably coupled to the elongate shaft assembly to cause the surgical end effector to rotate about the shaft axis relative to the elongate shaft assembly. The elongate shaft assembly may be further configured to receive and transmit a third rotary control motion from the drive system to an articulation joint that communicates with the elongate shaft assembly and the surgical end effector to articulate the surgical end effector about an articulation axis that is substantially transverse to the shaft axis.

In accordance with still another general form, there is provided an articulation joint for a surgical instrument that includes an elongate shaft assembly and a drive system that is configured to generate and apply a plurality of rotary control motions to the elongate shaft assembly. In at least one form, the articulation joint comprises a proximal joint portion that is coupled to the elongate shaft assembly and a distal joint portion that is movably coupled to the proximal joint portion and is configured to interface with a surgical end effector. A first gear train may operably interface with a proximal firing shaft portion of the elongate shaft assembly. A distal firing shaft may operably interface with the surgical end effector for transmitting a rotary firing motion from the proximal firing shaft to the surgical end effector while facilitating articulation of the distal joint portion relative to the proximal joint portion. A second gear train may operably interface with a proximal rotation shaft portion of the elongate shaft assembly for transmitting a distal rotational control motion to the surgical end effector to cause the surgical end effector to rotate relative to the elongate shaft assembly while facilitating articulation of the distal joint portion relative to the proximal joint portion.

In accordance with another general form, there is provided an articulation joint for a surgical instrument that has an elongate shaft assembly and a drive system that is configured to generate and apply a plurality of rotary control motions to the elongate shaft assembly. In at least one form, the articulation joint includes a proximal clevis that is coupled to the elongate shaft assembly and a distal clevis that is pivotally pinned to the proximal clevis for selective pivotal travel relative thereto about an articulation axis that is substantially transverse to a shaft axis that is defined by the elongate shaft assembly. A first gear train may be supported in a gear area defined between the proximal and distal devises such that no portion of the first gear train extends radially outwardly beyond any portion of the articulation joint. The first gear train may operably interface with a proximal firing shaft portion of the elongate shaft assembly. A distal firing shaft may operably interface with the surgical end effector for transmitting a rotary firing motion from the proximal firing shaft to the surgical end effector while facilitating pivotal travel of the distal clevis relative to the proximal clevis. A second gear train may be supported in the gear area such that no portion of the first gear train extends radially outwardly beyond any portion of the articulation joint. The second gear train may operably interface with a proximal rotation shaft portion of the elongate shaft assembly for transmitting a distal rotational control motion to the surgical end effector to cause the surgical end effector to rotate relative to the elongate shaft assembly while facilitating articulation of the distal clevis relative to the proximal clevis.

In accordance with another general form, there is provided a surgical instrument that includes a drive system that is configured to generate a plurality of rotary control motions. An elongate shaft assembly operably interfaces with the drive system and may comprise an outer shaft segment that operably interfaces with the drive system to receive distal rotational control motions therefrom. An articulation shaft may operably interface with the drive system to receive rotary articulation motions therefrom. The elongate shaft assembly may further include a proximal firing shaft segment that operably interfaces with the drive system to receive rotary firing motions therefrom. The surgical instrument may further include an articulation joint that may include a proximal clevis that is coupled to the elongate shaft assembly and a distal clevis that is pivotally pinned to the proximal clevis for selective pivotal travel relative thereto about an articulation axis that is substantially transverse to a shaft axis defined by the elongate shaft assembly. A coupling assembly may rotatably interface with the distal clevis and be configured for attachment to a surgical end effector. A distal firing shaft segment may be operably supported by the coupling assembly and be configured to interface with a drive shaft portion of the surgical end effector. A first gear train may operably interface with the proximal firing shaft segment and the distal firing shaft segment for transmitting the rotary firing motions from the proximal firing shaft segment to the distal firing shaft segment while enabling the distal clevis to be selectively pivoted relative to the proximal clevis. A second gear train may operably interface with a proximal rotation shaft for transmitting the distal rotational control motions to the coupling assembly while enabling the distal clevis to be selectively pivoted relative to the proximal clevis. An articulation drive link may interface with the articulation shaft and the distal clevis and be constrained to move axially relative to the articulation joint in response to applications of the rotary articulation motions to the articulation shaft.

In accordance with yet another general form, there is provided a cover for an articulation joint that is supported in an elongate shaft assembly of a surgical instrument that is operably coupled to a surgical end effector that has at least one end effector conductor therein. In at least one form, the cover comprises a non electrically-conductive hollow body that has an open distal end and an open proximal end and a joint-receiving passage that extends therebetween for receiving the articulation joint therein. The hollow body is configured to permit portions of the articulation joint to be selectively articulated relative to each other while substantially enclosing the portions within the hollow body. At least one electrically conductive pathway extends from the distal end of the hollow body to the proximal end of the hollow body. Each of the at least one electrically conductive pathways has a distal end portion that is configured to electrically contact a corresponding end effector conductor when the end effector has been coupled to the elongate shaft assembly and a proximal end portion that is configured to electrically contact a corresponding shaft conductor in the elongate shaft assembly.

In accordance with another general form, there is provided a surgical instrument that includes an elongate shaft assembly that has at least one electrical shaft conductor therein and an articulation joint. In at least one form, the articulation joint includes a proximal joint portion that is coupled to the elongate shaft assembly. A distal joint portion is movably coupled to the proximal joint portion for selective articulation relative thereto. A coupler assembly is rotatably coupled to the distal joint portion for selective rotation relative thereto. The coupler assembly may be configured to be detachably coupled to the surgical end effector and form an electrically conductive coupler pathway from an end effector conductor in the end effector to the articulation joint. The surgical instrument may further include an articulation joint conductor that contacts the conductive coupler pathway and traverses the articulation joint to contact the corresponding shaft conductor to form an electrically-conductive path therebetween.

In accordance with another general form, there is provided a surgical instrument that includes a control system that contains at least one electrical control component. The surgical instrument further includes an elongate shaft assembly that has an electrical shaft conductor that operably communicates with at least one of the electrical control components. The surgical instrument may further include an articulation joint that includes a proximal clevis that is coupled to the elongate shaft assembly. A distal clevis is pivotally coupled to the proximal clevis for selective pivotal travel relative thereto. The surgical instrument may further include a coupler assembly that is coupled to the distal clevis and a surgical end effector that is releasably coupled to the coupler assembly. The surgical end effector may include an end effector conductor that is arranged for electrical contact with an electrically conductive coupler pathway formed in the coupler assembly when the surgical end effector has been coupled to the coupler assembly. An articulation joint conductor may traverse the articulation joint and be in electrical contact with the conductive pathway through the coupler assembly and the shaft conductor.

In accordance with yet another general form, there is provided a surgical instrument that includes a handle assembly that has an elongate shaft assembly operably coupled thereto and configured for operably attachment to a surgical end effector. A motor is supported by the handle assembly and is configured to apply a rotary motion to one of the elongate shaft or the surgical end effector coupled thereto. A thumbwheel control assembly is operably supported on the handle assembly and communicates with the motor such that when an actuator portion of the thumbwheel control assembly is pivoted in a first direction, the motor applies a rotary motion to one of the elongate shaft assembly and end effector in the first direction and when the actuator portion is pivoted in a second direction, the motor applies the rotary motion to one of the elongate shaft assembly and end effector in the second direction.

In accordance with another general form, there is provided a surgical instrument that includes a handle assembly that has an elongate shaft assembly rotatably coupled thereto and is configured for operably attachment to a surgical end effector. A motor is supported by the handle assembly and is configured to apply a rotary motion to the elongate shaft assembly for selective rotation about a shaft axis. The surgical instrument further includes a thumbwheel control assembly that includes a thumbwheel actuator member that is pivotally supported relative to the handle assembly. A first magnet is supported on the thumbwheel actuator member and a second magnet is supported on the thumbwheel actuator member. A stationary sensor is centrally disposed between the first and second magnets when the thumbwheel actuator member is in an unactuated position. The stationary sensor communicates with the motor such that when the thumbwheel actuator is pivoted in a first direction, the motor applies a rotary motion to the elongate shaft assembly in the first direction and when the thumbwheel actuator member is pivoted in a second direction, the motor applies the rotary motion to the elongate shaft assembly in the second direction.

In accordance with another general form, there is provided a surgical instrument that includes a handle assembly that has an elongate shaft assembly rotatably coupled thereto and configured for operably attachment to a surgical end effector such that the end effector may be selectively rotated about a shaft axis relative to the elongate shaft assembly. A motor is supported by the handle assembly and is configured to apply a rotary motion to the end effector or coupler portion of the elongate shaft assembly to which the end effector is coupled for selective rotation thereof about the shaft axis. The surgical instrument further includes a thumbwheel control assembly that includes a thumbwheel actuator member that is pivotally supported relative to the handle assembly. First and second magnets are supported on the thumbwheel actuator member. A stationary sensor is centrally disposed between the first and second magnets when the thumbwheel actuator member is in an unactuated position. The stationary sensor communicates with the motor such that when the thumbwheel actuator is pivoted in a first direction, the motor applies a rotary motion to the end effector or coupler position in the first direction and when the thumbwheel actuator member is pivoted in a second direction, the motor applies the rotary motion to the end effector or coupler portion in the second direction.

In accordance with yet another general form, there is provided a surgical instrument that includes a housing that supports a plurality of motors. The surgical instrument further includes a joystick control assembly that includes a first switch assembly that is movably supported by the housing and includes a joystick that is movably mounted thereto such that pivotal movement of the joystick relative to the first switch assembly causes at least one corresponding control signal to be sent to at least one of the motors communicating therewith. The joystick assembly further includes a second switch assembly that comprises a first sensor and a second sensor that is movable with the first switch assembly such that movement of the second sensor relative to the first sensor causes at least one other control signal to be sent to another one of the motors communicating therewith.

In accordance with another general form, there is provided a surgical instrument that includes a handle assembly that has an elongate shaft assembly rotatably supported relative thereto. A proximal roll motor is supported by the handle assembly and is configured to apply proximal rotary motions to the elongate shaft assembly to cause the elongate shaft assembly to rotate relative to the handle assembly about a shaft axis. A surgical end effector is operably coupled to the elongate shaft assembly and is configured to perform a surgical procedure upon application of at least one firing motion thereto. A firing motor is supported by the handle assembly and is configured to apply firing motions to a portion of the elongate shaft assembly for transfer to the surgical end effector. The surgical instrument further includes a joystick control assembly that comprises a first switch assembly that is movably supported by the handle assembly and includes a joystick that is movably mounted thereto such that pivotal movement of the joystick relative to the first switch assembly causes at least one corresponding control signal to be sent to the proximal roll motor. The joystick control assembly further includes a second switch assembly that comprises a first sensor and a second sensor that is movable with the first switch assembly such that movement of the second sensor relative to the first sensor causes at least one other control signal to be sent to the firing motor.

In accordance with another general form, there is provided a surgical instrument that includes a handle assembly that has an elongate shaft assembly rotatably supported relative thereto. The surgical instrument further includes an articulation joint that comprises a proximal joint portion that is coupled to the elongate shaft assembly and a distal joint portion that is movably coupled to the proximal joint portion. An articulation motor is supported by the handle assembly and is configured to apply articulation motions to the articulation joint to cause the distal joint portion to move relative to the proximal joint portion. A surgical end effector is operably coupled to the elongate shaft assembly and is configured to perform a surgical procedure upon application of at least one firing motion thereto. A firing motor is supported by the handle assembly and is configured to apply firing motions to a portion of the elongate shaft assembly for transfer to the surgical end effector. The surgical instrument further includes a joystick control assembly that comprises a first switch assembly that is movably supported by the handle assembly and includes a joystick that is movably mounted thereto such that pivotal movement of the joystick relative to the first switch assembly causes at least one corresponding control signal to be sent to the articulation motor. The joystick assembly further includes a second switch assembly that comprises a first sensor and a second sensor that is movable with the first switch assembly such that movement of the second sensor relative to the first sensor causes at least one other control signal to be sent to the firing motor.

In accordance with another general form, there is provided a surgical instrument for acting on tissue. The instrument comprises at least one processor and operatively associate memory, at least one motor in communication with the processor and at least one actuation device. The processor is programmed to receive from a removable implement portion a first variable describing the removable implement. The processor is also programmed to apply the first variable to an instrument control algorithm. Further, the processor is programmed to receive an input control signal from the actuation device and control the at least one motor to operate the surgical instrument in conjunction with the removable implement in accordance with the instrument control algorithm considering the input control signal.

In accordance with an additional general form, the processor may be programmed to receive from a removable implement an implement control algorithm describing operation of the surgical instrument in conjunction with the removable implement. The processor may also be programmed to receive an input control signal from the actuation device and control the at least one motor to operate the surgical instrument in conjunction with the removable implement in accordance with the implement control algorithm considering the input control signal.

In accordance with another general form, a surgical instrument configured to relay a low-power signal from an end effector to a remote device may be disclosed. The surgical instrument may comprise a handle, a shaft extending distally from the handle, and an end effector attached to the distal end of the shaft. A sensor may be disposed in the end effector. The sensor may generate a signal indicative of a condition at the end effector. A transmitter may be located in the end effector. The transmitter may transmit the signal from the sensor at a first power level. The signal may be received by a relay station located in the handle of the surgical instrument. The relay station is configured to amplify and retransmit the signal at a second power level, wherein the second power level is higher than the first power level.

In accordance with an additional general form, a relay station for relaying a signal from an end effector of a surgical instrument to a remote device may be disclosed. The relay station comprises a receiver configured to receive a signal from a sensor disposed in an end effector. The signal is transmitted at a first power level. The relay station further comprises an amplifier configured to amplify the signal to a second power level. A transmitter is configured to transmit the signal at the second power level. The second power level is higher than the first power level.

In accordance with a general form, a method for relaying a signal received from a sensing module in an end effector may be disclosed. The method comprises generating, by a sensor, a first signal indicative of a condition at a surgical end effector. The sensor is located in the end effector. The method further comprises transmitting, using a transmitter, the first signal at a first power level and receiving the transmitted signal, using a receiver, at a relay station. The first signal is amplified by the relay station using an amplifier to a high-power signal comprising a second power level. The second power level is greater than the first power level. The high-power signal is transmitted, using the relay station, at the second power level. The high-power signal is received by a remote device, such as a video monitor. The video monitor displays a graphical representation of the condition at the surgical end effector.

Some portions of the above are presented in terms of methods and symbolic representations of operations on data bits within a computer memory. These descriptions and representations are the means used by those skilled in the art to most effectively convey the substance of their work to others skilled in the art. A method is here, and generally, conceived to be a self-consistent sequence of actions (instructions) leading to a desired result. The actions are those requiring physical manipulations of physical quantities. Usually, though not necessarily, these quantities take the form of electrical, magnetic or optical signals capable of being stored, transferred, combined, compared and otherwise manipulated. It is convenient, at times, principally for reasons of common usage, to refer to these signals as bits, values, elements, symbols, characters, terms, numbers, or the like. Furthermore, it is also convenient, at times, to refer to certain arrangements of actions requiring physical manipulations of physical quantities as modules or code devices, without loss of generality.

Certain aspects of the present invention include process steps and instructions described herein in the form of a method. It should be noted that the process steps and instructions of the present invention can be embodied in software, firmware or hardware, and when embodied in software, can be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers and computer systems referred to in the specification may include a single processor or may be architectures employing multiple processor designs for increased computing capability.

The methods and displays presented herein are not inherently related to any particular computer or other apparatus. Various general-purpose systems may also be used with programs in accordance with the teachings herein, or it may prove convenient to construct more specialized apparatus to perform the required method actions. The required structure for a variety of these systems will appear from the above description. In addition, the present invention is not described with reference to any particular programming language. It will be appreciated that a variety of programming languages may be used to implement the teachings of the present invention as described herein, and any references above to specific languages are provided for disclosure of enablement and best mode of the present invention.

In various forms, a surgical instrument configured to relay a low-power signal from an end effector to a remote device is disclosed. The surgical instrument may comprise a handle, a shaft extending distally from the handle, and an end effector attached to the distal end of the shaft. A sensor may be disposed in the end effector. The sensor may generate a signal indicative of a condition at the end effector. A transmitter may be located in the end effector. The transmitter may transmit the signal from the sensor at a first power level. The signal may be received by a relay station located in the handle of the surgical instrument. The relay station is configured to amplify and retransmit the signal at a second power level, wherein the second power level is higher than the first power level.

In various forms, a relay station for relaying a signal from an end effector of a surgical instrument to a remote device is disclosed. The relay station comprises a receiver configured to receive a signal from a sensor disposed in an end effector. The signal is transmitted at a first power level. The relay station further comprises an amplifier configured to amplify the signal to a second power level. A transmitter is configured to transmit the signal at the second power level. The second power level is higher than the first power level.

In various forms, a method for relaying a signal received from a sensing module in an end effector is disclosed. The method comprises generating, by a sensor, a first signal indicative of a condition at a surgical end effector. The sensor is located in the end effector. The method further comprises transmitting, using a transmitter, the first signal at a first power level and receiving the transmitted signal, using a receiver, at a relay station. The first signal is amplified by the relay station using an amplifier to a high-power signal comprising a second power level. The second power level is greater than the first power level. The high-power signal is transmitted, using the relay station, at the second power level. The high-power signal is received by a remote device, such as a video monitor. The video monitor displays a graphical representation of the condition at the surgical end effector.

In various forms, a sensor-straightened end effector is disclosed. The sensor-straightened end effector may comprise an end effector coupled to a shaft at an articulation point. The end effector may be articulable at an angle with respect to the shaft. A sensor may be disposed on the sensor-straightened end effector, such as on the shaft or on the end effector. The sensor is configured to detect a gross proximal movement of the surgical instrument. When detecting a gross proximal movement, the sensor may generate a signal to control a motor to straighten the end effector with respect to the shaft.

In various forms, a surgical instrument comprising a sensor-straightened end effector is disclosed. The surgical instrument may comprise a handle. A shaft may extend distally from the handle. A motor may be disposed within the handle for controlling an articulation of the surgical instrument. An articulating end effector is disposed at the distal end of the shaft. A sensor may be disposed in the handle, the shaft, or the end effector. The sensor may be configured to detect a gross proximal movement of the surgical instrument. When the sensor detects the gross proximal movement, the sensor may activate a powered straightening process, causing the motor to straighten the articulated end effector. In some forms, multiple sensors may provide redundant checks for the straightening process.

In various forms, a method for operating a surgical instrument comprising a sensor straightened end effector is disclosed. The method may comprise detecting, by a first sensor, a proximal movement of the surgical instrument. The first sensor may be located in any suitable section of the surgical instrument, such as the handle, shaft, or end effector. The first sensor may be an accelerometer, a magnetic sensor, or any other suitable sensor type. The sensor may generate a signal indicating that a gross proximal movement has been detected. The method may further comprise receiving, by a motor, the generated signal from the first sensor. The motor may straighten an angle of articulation of the motor-controlled articulating end effector in response to the received signal. A second sensor may generate a second signal to provide a redundant check.

In various forms, the present disclosure is directed towards a motor-driven surgical instrument comprising a modular motor control platform. A master controller may execute a main control process for controlling one or more operations of the surgical instrument. A first motor controller and a second motor controller may be operatively coupled to the master controller. The first motor controller may have an associated first motor and the second motor controller may have an associated second motor. The main control process may generate control signals for the first and second motor controllers. The first and second motor controllers may operate the first and second motors in response to the control signals. In some forms, the modular motor control system may comprise a slave controller configured to control one or more of the motor controllers based on one or more control signals received by the slave controller from the master controller.

In various forms, a modular motor control system may comprise one or more motor controllers each having an associated motor. The one or more motor controllers may be in communication with a master controller. The master controller may be configured to provide control signals to the motor controllers as part of a main control process. The motor controllers may control the associated motors in response to the received control signals. In some forms, the one or more motor controllers and the associated motors may be located within a handle adapted to receive a modular shaft, a modular end effector, and a modular power supply. The handle may provide an interface between the motors and the modular shaft and end effector.

In various forms, a surgical instrument may include a modular motor control system. The surgical instrument may comprise a master controller. The surgical instrument may be configured to receive modular surgical components, such as a modular shaft and implement portion. The surgical instrument may have one or more motors and associated motor controllers mounted therein. The motor controllers may be operatively coupled to the motors. The motors may be configured to control one or more movements of an attached shaft or implement portion. The master controller and the motor controllers may be in electrical communication. The master controller may be configured to provide one or more control signals to the motor controllers as part of the main control process. The motor controllers may control the motors in response to the received control signals.

In various forms, a method for controlling a motor-driven surgical instrument is disclosed. The method may comprise generating, by a master controller, one or more control signals. A first control signal may be transmitted to a first motor controller configured to control a first motor. The first motor controller may operate the first motor in response to the first control signal received from the master controller. A second control signal may be transmitted to a second motor controller configured to a control a second motor. The second motor controller may operate the second motor in response to the second control signal received from the master controller. In some forms, the second control signal may be generated by a slave controller.

In accordance with one general form, there is provided a surgical instrument comprising a drive motor and a drive member that is movable by the drive motor through a drive stroke between a home position and an end of stroke position. The end of stroke position extends between a first position and a second position. A mechanical stop may be disposed at or near the end of stroke position and may be structured to increase resistance to the movement of the drive member through the drive stroke from the first position to the second position. The mechanical stop may comprise a bumper and a resistance member. The bumper may be movable from the first position to the second position and be configured to contact the drive member at the first position. The resistance member may be operatively coupled to the bumper and configured to increase resistance to movement of the drive member from the first position to the second position. The resistance member may be configured to decelerate the drive member prior to the drive member actuating to the second position. In one form, the resistance member is structured to be compressible to progressively increase the resistance to the movement of the drive member between the first position and the second position. The resistance member may in one form comprise a spring. The bumpers may comprise contact surfaces that are dimensioned to complement a dimension of a drive member surface contacted at the first position.

In one form, a control system is configured to detect a current spike associated with the increased resistance to the movement of the drive member. The control system may monitor voltage associated with the delivery of power to the drive motor to detect the current spike. The current spike may comprise a predetermined threshold current. The predetermined threshold current may comprise at least one predetermined threshold current differential over at least one defined time period. When the control system detects the current spike, delivery of power to the drive motor may be interrupted. In one form, the mechanical stop may further comprise a hard stop that may prevent movement of the drive member beyond the second position.

In accordance with one general form, there is provided a mechanical stop for use in a surgical instrument to produce a detectable current spike associated with an electromechanical stop. For example, the mechanical stop may be disposed at or near an end of stroke associated with a drive stroke of a drive member. The end of stroke may extend between a first position and a second position. The mechanical stop may comprise one or more bumpers and one or more resistance members. The bumpers may be movable from the first position to the second position and may be configured to contact the drive member at the first position. The resistance members may be operatively coupled to the bumpers and configured to increase resistance to movement of the drive member from the first position to the second position to produce the current spike. The resistance members may be configured to decelerate the drive member prior to the drive member actuating to the second position. One or more of the resistance members may be structured to be compressible to progressively increase the resistance to the movement of the drive member between the first position and the second position. One or more resistance members may also be structured to be compressible and may comprise at least one spring. The bumpers may comprise contact surfaces that are dimensioned to complement a dimension of a drive member surface that is contacted at the first position. The current spike associated with the increased resistance may be detectable by a control system associated with the electromechanical surgical instrument. The control system may be configured to monitor voltage associated with power delivery to a drive motor and to interrupt the delivery of power to the drive motor when the current spike comprises at least one predetermined threshold current. At least one threshold current may comprise a current differential over at least one defined time period. In one form, the mechanical stop further comprises a hard stop for preventing movement of the drive member beyond the second position.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A handheld surgical instrument comprising:
   an end effector;
   a shaft extending proximally from the end effector;
   a handle located proximal to the shaft;
   a sensor disposed in the end effector configured to generate a first signal indicative of a condition at the end effector;
   a transmitter communicatively coupled to the sensor, wherein the transmitter is configured to transmit the first signal at a first power level suitable for wireless transmission within a distance defined by the handheld surgical instrument;
   a relay station located intermediate the end effector and a proximal portion of the handle, wherein the relay station is configured to:
      receive the first signal from the transmitter, convert the first signal to a second signal indicative of the condition at the end effector, and
      transmit the second signal at a second power level to a remote system, wherein the second power level is suitable for transmission over a distance greater than the first power level.

2. The surgical instrument of claim 1, wherein the transmitter comprises an antenna configured to transmit the first signal at a first frequency and at the first power level.

3. The surgical instrument of claim 2, wherein the relay station transmits the second signal at a second frequency.

4. The surgical instrument of claim 3, wherein the first and second frequencies are different.

5. The surgical instrument of claim 3, wherein the relay station comprises a memory module configured to store a plurality of frequencies, wherein the second frequency is selected from the plurality of stored frequencies.

6. The surgical instrument of claim 2, wherein the first frequency is a human-tissue permeable frequency.

7. The surgical instrument of claim 2, wherein the first frequency is 2.4 GHz.

8. The surgical instrument of claim 1, wherein the relay station comprises a transceiver.

9. The surgical instrument of claim 1, wherein the relay station comprises a receiver comprising a first antenna and a transmitter comprising a second antenna.

10. The surgical instrument of claim 1, wherein the sensor comprises an analog to digital converter, wherein the first signal is generated as an analog signal, wherein the first signal is converted into a digital signal by the analog to digital converter prior to transmission of the first signal.

11. The surgical instrument of claim 1, wherein the first signal is transmitted using a first communication protocol and the second signal is transmitted using a second communication protocol.

12. A surgical relay station in a handheld surgical instrument for relaying a signal to a remote location during surgery, the surgical relay station comprising:
   a receiver configured to receive a signal from a sensor located in an end effector of the handheld surgical instrument, wherein the signal is transmitted at a first power level suitable for wireless transmission within a distance defined by the handheld surgical instrument;
   an amplifier configured to increase a transmission power of the signal from the first power level to a second power level;
   a transmitter configured to transmit the signal at the second power level to the remote location, wherein the second power level is suitable for transmission over a distance to the remote location, and wherein the distance to the remote location is greater than the distance defined by the handheld surgical instrument.

13. The surgical relay station of claim 12, comprising:
   a processing module configured to convert the signal from a first frequency to a second frequency, wherein the transmitter is configured to transmit the signal at the second frequency.

14. The surgical relay station of claim 13, wherein the first frequency comprises a frequency outside of a water absorption band.

15. The surgical relay station of claim 13, wherein the signal comprises a digital signal.

16. The surgical relay station of claim 13, comprising:
   a memory module configured to store a plurality of frequencies, wherein the second frequency is selected from the plurality of frequencies.

17. A method for relaying a surgical sensor signal, the method comprising:

generating, by a sensor, a first signal indicative of a condition at a surgical end effector of a handheld surgical instrument;

transmitting, by a transmitter, the first signal at a first power level suitable for wireless transmission within a distance defined by the handheld surgical instrument;

receiving, by a relay station located in the handheld surgical instrument, the first signal;

converting, by the relay station, the first signal to a second signal, wherein the second signal is indicative of the condition at the surgical end effector;

transmitting, by the relay station, the second signal at a second power level, wherein the second power level is suitable for transmission over a distance greater than the first power level.

18. The method of claim 17, wherein the first signal comprises a first frequency and the second signal comprises a second frequency.

19. The method of claim 17, wherein the first signal comprises a first communication protocol and the second signal comprises a second communication protocol.

20. The method of claim 17, comprising:
receiving, by a monitoring device, the second signal.

* * * * *